United States Patent
Bradbury et al.

(10) Patent No.: US 12,359,346 B2
(45) Date of Patent: *Jul. 15, 2025

(54) ANTIBODY LIBRARIES WITH MAXIMIZED ANTIBODY DEVELOPABILITY CHARACTERISTICS

(71) Applicant: RULES-BASED MEDICINE INC., Austin, TX (US)

(72) Inventors: Andrew Raymon Morton Bradbury, Santa Fe, NM (US); Michael Frank Erasmus, Santa Fe, NM (US); Andre Teixeira, Santa Fe, NM (US)

(73) Assignee: RULES-BASED MEDICINE INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/592,456

(22) Filed: Feb. 29, 2024

(65) Prior Publication Data

US 2024/0240360 A1    Jul. 18, 2024

Related U.S. Application Data

(63) Continuation of application No. 17/163,170, filed on Jan. 29, 2021, now Pat. No. 11,920,258, which is a (Continued)

(51) Int. Cl.
*C40B 50/06* (2006.01)
*C12N 15/10* (2006.01)
(Continued)

(52) U.S. Cl.
CPC .......... *C40B 40/10* (2013.01); *C12N 15/1037* (2013.01); *C12N 15/81* (2013.01); *C40B 40/08* (2013.01); *C40B 50/06* (2013.01)

(58) Field of Classification Search
None
See application file for complete search history.

(56) References Cited

U.S. PATENT DOCUMENTS

| 5,888,732 A | 3/1999 | Hartley et al. |
| 2003/0153038 A1 | 8/2003 | Ohlin et al. |

(Continued)

FOREIGN PATENT DOCUMENTS

| WO | WO-0070023 A1 | 11/2000 |
| WO | WO-02083872 A2 | 10/2002 |

(Continued)

OTHER PUBLICATIONS

Knappik et al. (Feb. 11, 2000) Journal of Molecular Biology vol. 296 pp. 57 to 86 (Year: 2000).*

(Continued)

*Primary Examiner* — Christian C Boesen
(74) *Attorney, Agent, or Firm* — Goodwin Procter LLP

(57) ABSTRACT

Antibody libraries comprising a plurality of heavy chain variable domains and/or a plurality of light chain variable domains, which comprise complementary determining regions (CDRs) found in naturally-occurring human antibodies, and methods of making such antibody libraries. The antibody libraries are free of members that comprise one or more liabilities affecting one or more features of such members. Further, the antibody libraries comprise members having heavy chain and/or light chain CDRs not found in the same naturally-occurring human antibody.

8 Claims, 58 Drawing Sheets

Specification includes a Sequence Listing.

Related U.S. Application Data continuation of application No. 16/505,358, filed on Jul. 8, 2019, now Pat. No. 10,954,508.

(60) Provisional application No. 62/822,671, filed on Mar. 22, 2019, provisional application No. 62/695,065, filed on Jul. 8, 2018.

(51) Int. Cl.
*C12N 15/81* (2006.01)
*C40B 40/10* (2006.01)
*C40B 40/08* (2006.01)

(56) References Cited

U.S. PATENT DOCUMENTS

| | | | |
|---|---|---|---|
| 2006/0160178 | A1 | 7/2006 | Rothberg et al. |
| 2012/0077710 | A1 | 3/2012 | Ohlin et al. |
| 2016/0194627 | A1 | 7/2016 | Smider et al. |
| 2017/0362306 | A1 | 12/2017 | Shim et al. |

FOREIGN PATENT DOCUMENTS

| | | |
|---|---|---|
| WO | WO-2009036379 A2 | 3/2009 |
| WO | WO-2019126227 A1 | 6/2019 |

OTHER PUBLICATIONS

Akerstrom et al. "On the interaction between single chain Fv antibodies and bacterial immunoglobulin-binding proteins" J. Immunol. Methods, 177(1-2):151-63, 1994.
Al-Iazikani et al. "Standard conformations for the canonical structures of immunoglobulins" J. Mol. Biol. 273:927-948 (1997).
Almagro, J., "Identification of differences in the specificity-determining residues of antibodies that recognize antigens of different size: implications for the rational design of antibody repertoires" Mol. Recognit. 17:132-143 (2004).
Alves et al. "Small-molecule-based affinity chromatography method for antibody purification via nucleotide binding site targeting" Anal. Chem. 84(18):7721-8, 2012.
Alves et al. "Conjugation of a reactive thiol at the nucleotide binding site for site-specific antibody functionalization" Bioconjug. Chem. 25(7):1198-202, 2014.
Alves et al. "Oriented surface immobilization of antibodies at the conserved nucleotide binding site for enhanced antigen detection" Langmuir, 28(25):9640-8, 2012.
Ayriss et al."High-throughput screening of single-chain antibodies using multiplexed flow cytometry" J Proteome Res. 6(3):1072-82, 2007.
Boder et al. "Engineering antibodies by yeast display" Arch. Biochem. Biophys. 526(2):99-106, 2012.
Boder et al. "Yeast surface display for directed evolution of protein expression, affinity, and stability" Methods Enzymol. 192(2):243-248, 2000.
Briney, B. et al. "Commonality despite exceptional diversity in the baseline human antibody repertoire" Nature 566(7744):393-97 (2019).
Cabantous et al. "Recent Advances in GFP Folding Reporter and Split-GFP Solubility Reporter Technologies. Application to Improving the Folding and Solubility of Recalcitrant Proteins from *Mycobacterium tuberculosis*" J. Struct. Funct. Genomics, 6:113-9; 2005.
Cabantous et al, "New molecular reporters for rapid protein folding assays" PLoS One. 3(6):e2387; 2008.
Chan et al. "Comparison of the efficiency of antibody selection from semi-synthetic scFv and non-immune Fab phage display libraries against protein targets for rapid development of diagnostic immunoassays" Journal of immunological methods, 373(1-2):79-88, 2011.
Charbit et al. "Versatility of a vector for expressing foreign polypeptides at the surface of Gram-negative bacteria" Gene, 70(1):181-9, 1988.
Cherf et al. "Applications of Yeast Surface Display for Protein Engineering" Methods Mol. Biol. 1319: 155-175 (2015).
Cho et al."A yeast surface display system for the discovery of ligands that trigger cell activation" J. Immunol. Methods, 220(1-2):179-188, 1998.
Chothia et al, "Conformations of immunoglobulin hypervariable regions" (1989) Nature 342:877-883.
Chothia, C. et al. "Canonical structures for the hypervariable regions of immunoglobulins" (1987) J. Mol. Biol. 196:901-917.
Clackson et al. "Making Antibody Fragments Using Phage Display Libraries" (1991) Nature 352:624-628.
Close et al. "Using phage display selected antibodies to dissect microbiomes for complete de novo genome sequencing of low abundance microbes" BMC Microbiol. 13:270, 2013.
Corrie, B. D. et al. "iReceptor: a platform for querying and analyzing antibody/B-cell and T-cell receptor repertoire data across federated repositories" Immunol. Rev. 284, 24-41 (2018).
D'Angelo et al. "Filtering "genic" open reading frames from genomic DNA samples for advanced annotation" BMC genomics 12, suppl. 1, S1-S5; 2011.
D'Angelo et al. "The antibody mining toolbox" MAbs. 6(1):160-72, 2014.
De Haard et al. "A large non-immunized human Fab fragment phage library that permits rapid isolation and kinetic analysis of high affinity antibodies" (1999) J. Biol. Chem 274:18218-30.
Enever et al. "Engineering High Affinity Superantigens by Phage Display" Journal of molecular biology, 347(1):107-20, 2005.
Fantini et al. "Assessment of antibody library diversity through next generation sequencing and technical error compensation" PLoS One. 12(5):e0177574, 2017.
Ferrara et al. "Recombinant renewable polyclonal antibodies" MAbs, 7(1):32-41, 2015.
Ferrara et al. "Using Phage and Yeast Display to Select Hundreds of Monoclonal Antibodies: Application to Antigen 85, a Tuberculosis Biomarker" PLoS One, 7(11):e49535, 2012.
Fuchs et al. "Targeting Recombinant Antibodies to the Surface of *Escherichia coli*: Fusion to a Peptidoglycan Associated Lipoprotein" (1991) Bio/Technology 9:1370-1372.
Garrard et al. "FAB Assembly and enrichment in a monovalent phage display system" (1991) Bio/Technology 9:1373-1377.
Glanville et al. "Deep sequencing in library selection projects: what insight does it bring?" Curr. Opin. Struct. Biol. 33:146-60, 2015.
Glanville et al. "Precise determination of the diversity of a combinatorial antibody library gives insight into the human immunoglobulin repertoire" PNAS 106(48):20216-21, 2009.
Graille et al. "Complex between *Peptostreptococcus magnus* Protein L and a Human Antibody Reveals Structural Convergence in the Interaction Modes of Fab Binding Proteins" Structure, 9(8):679-87, 2001.
Gram et al. "In vitro selection and affinity maturation of antibodies from a naïve combinatorial immunoglobulin library" (1992) PNAS 89:3576-3580.
Griffiths et al. "Human anti-self antibodies with high specificity from phage display libraries" (1993) EMBO J 12:725-734.
Griffiths et al. "Isolation of high affinity human antibodies directly from large synthetic repertoires" EMBOJ 13(14):3245-3260, 1994.
Hasenhindl et al. "Stability assessment on a library scale: a rapid method for the evaluation of the commutability and insertion of residues in C-terminal loops of the CH3 domains of IgG1-Fc" Protein Eng. Des. Sel. 26(10):675-82, 2013.
Hawkins et al. "Selection of phage antibodies by binding affinity. Mimicking affinity maturation"(1992) J. Mol. Biol. 226:889-896.
Hay et al. (1992) "Bacteriophage cloning and *Escherichia coli* expression of a human IgM Fab" Hum. Antibod. Hybridomas 3:81-85.
Hillson et al. "The Structural Basis of Germline-encoded V,3 Immunoglobulin Binding to Staphylococcal Protein A" The Journal of experimental medicine. 178(1):331-6, 1993.
Hoogenboom et al. "Multi-subunit proteins on the surface of filamentous phage: methodologies for displaying antibody (Fab) heavy and light chains" (1991) Nuc. Acid Res. 19:4133-4137.
Hoogenboom et al. "Antibody phage display technology and its applications" (1998) Immunotechnology 4:1-20.

(56) References Cited

OTHER PUBLICATIONS

Hoogenboom et al. (2000) "Natural and designer binding sites made by phage display technology" Immunol Today 2:371-8.
Hotzel, I. et al. "A strategy for risk mitigation of antibodies with fast clearance" MAbs 4, 753-760 (2012).
Hugo et al. "VL position 34 is a key determinant for the engineering of stable antibodies with fast dissociation rates" Protein Eng. 16(5):381-6, 2003.
Huse et al. (1989) "Generation of a large combinatorial library of the immunoglobulin repertoire in phage lambda" Science 246:1275-1281.
Jackson et al. "Identifying highly mutated IGHD genes in the junctions of rearranged human immunoglobulin heavy chain genes" J. Immunol. Methods, 324:26-37, 2007.
Jain, T. et al. "Biophysical properties of the clinical-stage antibody landscape" PNAS 114, 944-949 (2017).
Kehoe et al. "Using phage display to select antibodies recognizing post-translational modifications independently of sequence context." Mol. Cell Proteomics, 5(12):2350-63, 2006.
Kelly et al. "High throughput cross-interaction measures for human IgG1 antibodies correlate with clearance rates in mice" MAbs, 7(4):770-7, 2015.
Kelly et al. "Chaperone proteins as single component reagents to assess antibody monospecificity" MAbs. 9(7):1036-40, 2017.
Kohli et al. "A novel screening method to assess developability of antibody-like molecules" MAbs. 7(4):752-8, 2015.
Kovaltsuk, A. et al. "Observed Antibody Space: A Resource for Data Mining Next-Generation Sequencing of Antibody Repertoires" J. Immunol. (2018) 201 (8): 2502-2509.
Lee et al. "Reconsidering the human immunoglobulin heavy-chain locus: 1. An evaluation of the expressed human IGHD gene repertoire" Immunogenetics, 57:917-25, 2006.
Lefranc, M. P. et al. "IMGT unique numbering for immunoglobulin and T cell receptor variable domains and Ig superfamily V-like domains" Dev. Comp. Immunol. 27, 55-77 (2003).
Lillo et al. "Development of Phage-Based Single Chain Fv Antibody Reagents for Detection of Yersinia pestis" PLoS One, 6(12):e27756, 2011.
Lou et al. "Antibodies in haystacks: how selection strategy influences the outcome of selection from molecular diversity libraries" Journal of immunological methods; 253(1-2):233-42, 2001.
Mustafaoglu et al. "Site-specific fab fragment biotinylation at the conserved nucleotide binding site for enhanced ebola detection" Biotechnol. Bioeng. 112(7):1327-34, 2015.
Obrezanova et al. "Aggregation risk prediction for antibodies and its application to biotherapeutic development" MAbs. 7(2):352-63, 2015.
Pavoor, T. V. et al. "An enhanced approach for engineering thermally stable proteins using yeast display" Peds 25(10): 625-630 (2012).
Pepper, L. R. et al. "A decade of yeast surface display technology: Where are we now?" Comb. Chem. High Throughput Screen. 11(2):127-134 (2008).
Perelson et al. "Theoretical studies of clonal selection: Minimal antibody repertoire size and reliability of self-non-self discrimination" J. Theor. Biol. 81(4):645-70, 1979.
Rajagopalan et al. "Novel unconventional binding site in the variable region of immunoglobulins" PNAS, 93(12):6019-24, 1993.
Roben et al. "VH3 family antibodies bind domain D of staphylococcal protein A" J. Immunology 154(12):6437-45, 1995).
Saunders et al. "An in vivo platform for identifying inhibitors of protein aggregation" Nat. Chem. Biol. 12:94-101; 1988.
Sblattero et al. "Exploiting recombination in single bacteria to make large phage antibody libraries" Nat. Biotechnol. 18, 75-80 (2000).
Shusta et al. "Yeast polypeptide fusion surface display levels predict thermal stability and soluble secretion efficiency" J. Mol. Biol. 292(5):949-56, 1999.
Smith, "Filamentous fusion phage: novel expression vectors that display cloned antigens on the virion surface" (1985) Science 228:1315-1317.

Traxlmayr et al. "Directed evolution of Her2/neu-binding IgG1-Fc for improved stability and resistance to aggregation by using yeast surface display" Protein Eng. Des. Sel. 26(4):255-65, 2013.
Traxlmayr et al. "Directed evolution of proteins for increased stability and expression using yeast display" Arch. Biochem. Biophys. 526(2):174-80, 2012.
Traxlmayr et al. "Directed evolution of stabilized IgG1-Fc scaffolds by application of strong heat shock to libraries displayed on yeast" Biochim. Biophys. Acta. 1824(4):542-9, 2012.
Van den Beucken et al. "Affinity maturation of Fab antibody fragments by fuorescent-activated cell sorting of yeast-displayed libraries" FEBS Lett. 546(2-3):288-294, 2003.
Velappan et al. Selection and characterization of scFv antibodies against the Sin Nombre hantavirus nucleocapsid protein Journal of immunological methods, 321(1-2):60-9, 2007.
Vincke et al. "Introduction to Heavy Chain Antibodies and Derived Nanobodies" Methods Mol. Biol. 911:15-26 (2012).
Waldo et al. "Rapid protein-folding assay using green fluorescent protein" Nat. Biotechnol. 17:691-5; 1999.
Wang et al. "Increasing stability of antibody via antibody engineering: Stability engineering on an anti-hVEGF" Proteins, 82(10):2620-30, 2014.
Wu et al, "Discovery of highly soluble antibodies prior to purification using affinity-capture self-interaction nanoparticle spectroscopy" Protein Eng. Des. Sel. 28(10):403-14, 2015.
Xu et al. "Addressing polyspecificity of antibodies selected from an in vitro yeast presentation system: a FACS-based, high-throughput selection and analytical tool" Protein Eng. Des. Sel. 26(10):663-70, 2013.
Xu, L. et al. "Rapid optimization and prototyping for therapeutic antibody-like molecules" MAbs 5(2): 237-254 (2013).
Van Blarcom et al. Productive common light chain libraries yield diverse panels of high affinity bispecific antibodies. MAbs. Feb./Mar. 2018;10(2):256-268. Epub Dec. 14, 2017.
Yang et al. "Developability studies before initiation of process development" MAbs 5(5):787-94, 2013.
Yang et al. "Rapid assessment of oxidation via middle-down LCMS correlates with methionine side-chain solvent-accessible surface area for 121 clinical stage monoclonal antibodies" MAbs 9(4):646-53, 2017.
International Search Report PCT/US19/40843 dated Oct. 11, 2019, 4 pages.
Soderlind, E. et al. "Recombining germline-derived CDR sequences for creating diverse single-framework antibody libraries" Nature 18(8):852-856, 2000.
Bai, X. et al. "A Novel Human scFv Library with Non-Combinatorial Synthetic CDR Diversity" PLoS One. vol. 10, No. 10, pp. 1-18, Oct. 20, 2015.
Waterhouse, Peter et al. "Combinatorial infection and in vivo recombination: a strategy for making large phage antibody repertoires" Nucleic Acids Research. vol. 21, No. 9, pp. 2265-2266, May 11, 1993.
Palazzolo, Michael J. et al. "Phage lambda cDNA cloning vectors for subtractive hybridization, fusion-protein synthesis and Cre-loxP automatic plasmid subcloning" Gene vol. 88, No. 1, pp. 25-36, Mar. 30, 1990.
D'Angelo, Sara et al. "Many Routes To An Antibody Heavy-Chain CDR3: Necessary, Yet Insufficient, For Specific Binding" Frontiers in Immunology. vol. 9, pp. 1-13, Mar. 8, 2018.
Barbas et al. "Assembly of combinatorial antibody libraries on phage surfaces: the gene III site" PNAS vol. 88, No. 18, pp. 7978-7982, Sep. 15, 1991.
Boldicke, Antibody Engineering "2.3.2 Case study of synthetic antibody libraries: n-CoDeR". Feb. 1, 2018. 3 pages.
Frenzel et al. Phage display-derived human antibodies in clinical development and therapy. MAbs. Oct. 2016; 8(7):1177-1194.
Ponsel et al. High affinity, developability and functional size: the holy grail of combinatorial antibody library generation. Molecules. May 3, 2011;16(5):3675-700.
Urlinger, Ylanthia—A New Antibody Library Concept. Dec. 1, 2011. 33 pages.
U.S. Appl. No. 16/505,358, Patented, Jul. 8, 2019.
U.S. Appl. No. 17/163,170, Patented, Jan. 29, 2021.

(56) References Cited

OTHER PUBLICATIONS

U.S. Appl. No. 17/208,877, Patented, Mar. 22, 2021.
U.S. Appl. No. 18/430,601, Pending, Feb. 1, 2024.
U.S. Appl. No. 18/592,473, Published, Feb. 29, 2024.
U.S. Appl. No. 18/592,484, Pending, Feb. 29, 2024.
U.S. Appl. No. 18/592,499, Pending, Feb. 29, 2024.
U.S. Appl. No. 17/860,041, Published, Jul. 7, 2022.
U.S. Appl. No. 18/577,398, Pending, Jan. 8, 2024.
U.S. Appl. No. 18/171,063, Published, Feb. 17, 2023.
U.S. Appl. No. 18/807,409, Pending, Aug. 16, 2024.
U.S. Appl. No. 18/839,070, Pending, Aug. 16, 2024.

* cited by examiner

Figure 3

Two BsaI sites in opposite orientations
- Scarless cloning
- Removes the exact portion of the CDR as well as the BsaI site

```
GTGTTACCATCACCTGTCGTGCTTCTagagaccatggccagtaxxxxxxctctCTGGCTTGGTACAGCAGAAA
CACAATGGTAGTGGACAGCACGAAGAxxxxxxtaxxxxxxxxxxxxxaGACCGAACCATGGTCGTCTTT
```

18 19 20 21 22 23 24 25 26 1 2 3 4 5 6 7 8 9 1 2 3 4 5 6 7
X V T I T C X A S X X H G Q * G X S X L A W X Q Q X

Internal SfiI site
- Minimize uncut vector background
- Serves as spacer between BsaI sites

Ochre stop codon and frame-shift
- Prevent expression of background sequences

Figure 5

| Deamidation | Isomerization | Glycosylation | Unpaired cysteine |
|---|---|---|---|
| EW.GWISGY..NY | EW.GVIYPG.DTRY | EW.G.WIRP..GTSY | EW.GIINPNSG.TNY |
| EW.GWISTY..NY | EW.GLIYPG.DTRY | EW.G.WINL..GITY | EW.GWINPNV.GTNY |
| EW.GWISVY..BY | EW.GIIFPG.DTRY | EW.G.RIPP..DTNY | EW.GMIYPGN.DTSY |
| EW.GWISAY..KY | EW.GIIYPG.DIRY | EW.G...PGDPDTRY | EW.GIIYPGS.ETKY |
| EW.GRISAY..NY | EW.GIIYPG.ETRY | EW.G.KI..GGSTSY | EW.GGIPIF.TEYY |
| EW.GWISAY.DTNY | EW.GIIYPG.DTSY | EW.G.II..GGTTSY | EW.GII.PGDAATRY |
| EW.GWISAY.KTBY | EW.GIIYPG.DTKY | EW.G.II..SRFTSY | EW.G.ISAYYGNPNY |
| EW.GWISPY..BY | EW.GIIYPG.DTTY | EWIG.II..SGSTSY | EWVGVISHDGGNE.Y |
| EW.GWINP.GDTNY | EW.GIIYPS.DTRY | EW.G.IS..GGSTSY | EW.G.NAADGNTKY |
| EW.GWINP.GATRY | EW.GIIYPA.DTRY | EWLG.II..GGSTRY | EW.G.FEPKDGETIY |
| EW.GWINI.GGTDY | EW.GIIYPD.DTRY | EWVG.II..GGATRY | EWLAHI.SNDG.KRY |
| EW.GWINP.GGTSY | EWLALIY.W.GDKRY | EWVS.SI..GGSTYY | EWIGLINQ.GSTNY. |
| EW.GWINP.GGTKY | EWLALVY.W..KRY | EWVS.TI..GGKTHY | EWIGYIYY.GSPNY. |
| EW.GWINP.GGABY | EWLALIY.WND.KRY | EWVA...GGGGAIYY | EWLSYSS.SGTPIYY |
| EW.GRIN.GGTBY | EWLALIY.W..RRY | EWVA.YI..GSTIYY | EWVSYI.GSSSTIYY |
| EW.GWISP.GGTNY | EWLARID.W..KYY | EWVD.VIWYAGR..Y | EWVSSISS.GSSTYY |
| EW.GWISP.GGTNY | EWLALIY.W..KYY | EWVA.VISHDRS..Y | EWVSYISS.GSTINY |
| EWIGEIN.HS..BY | EWLAVIY.W..KRY | EW.S.WI..SGGTNY | EWVSIIYR.G.TTYY |
| EWLAHIF.S.DE.Y | EWLAFIY.W..KRY | EW.GR..ILG.IANY | EW.GYIY..SSSANY |
| EWLAHIF.S..EKSY | EWLAIIY.W..KRY | EW.GG..IFG.KANY | EW.GRIYP.DSYINY |

Figure 7

- Cysteines comprise up to 4% of HCDR3 amino acids
  - Depends upon HCDR3 length and position
- 85% of cysteines in HCDR3 pair within the HCDR3
- 10% pair with an additional cysteine elsewhere
- Cysteine-cysteine placement highly structured
  - Generally separated by 2 or 4
  - There are exceptions AGPSITESHYLDCAAKDYYYGLDV
AKDARDCLLCADWHFDL
AKFSGKDCSGTSCRDY
ARAPDCADADCHKGAFGY
ARDGGHGFCSSASCFGPDY ARRGSCDYCGDFPWQY
ARSPSCICCGGTCVFDH ARVGYCSSTSCNRGAFDI
VRGHCDGCTCSRCY
VRKGPCCPHCCDFHWQH
VRSVCPRYCGGFCYGEFDY
VRTADCCRDCCKGWVFPH VTLPDLCPGDNCTYPDAS
VRGRSCCGCRRHCCGADCFNWDFQH
AKDLRCDECECWSDYDFGKQLPCRKSRGVAGIFD
G http://dunbrack2.fccc.edu/PyIgClassify/default.aspx 2 aa   4 aa   5 + 11 aa   15 aa Cysteines in CDRs should be paired and structurally placed

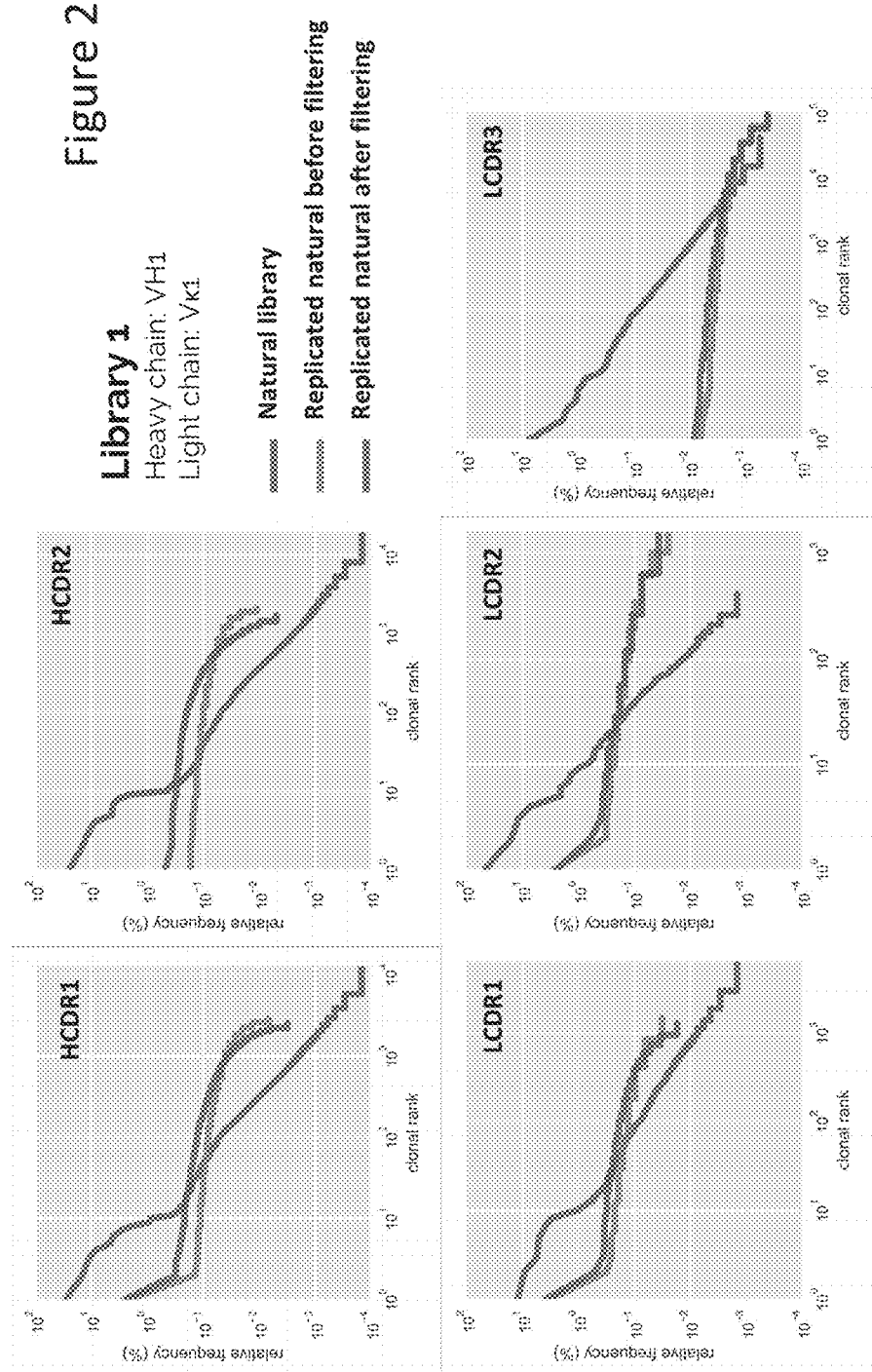

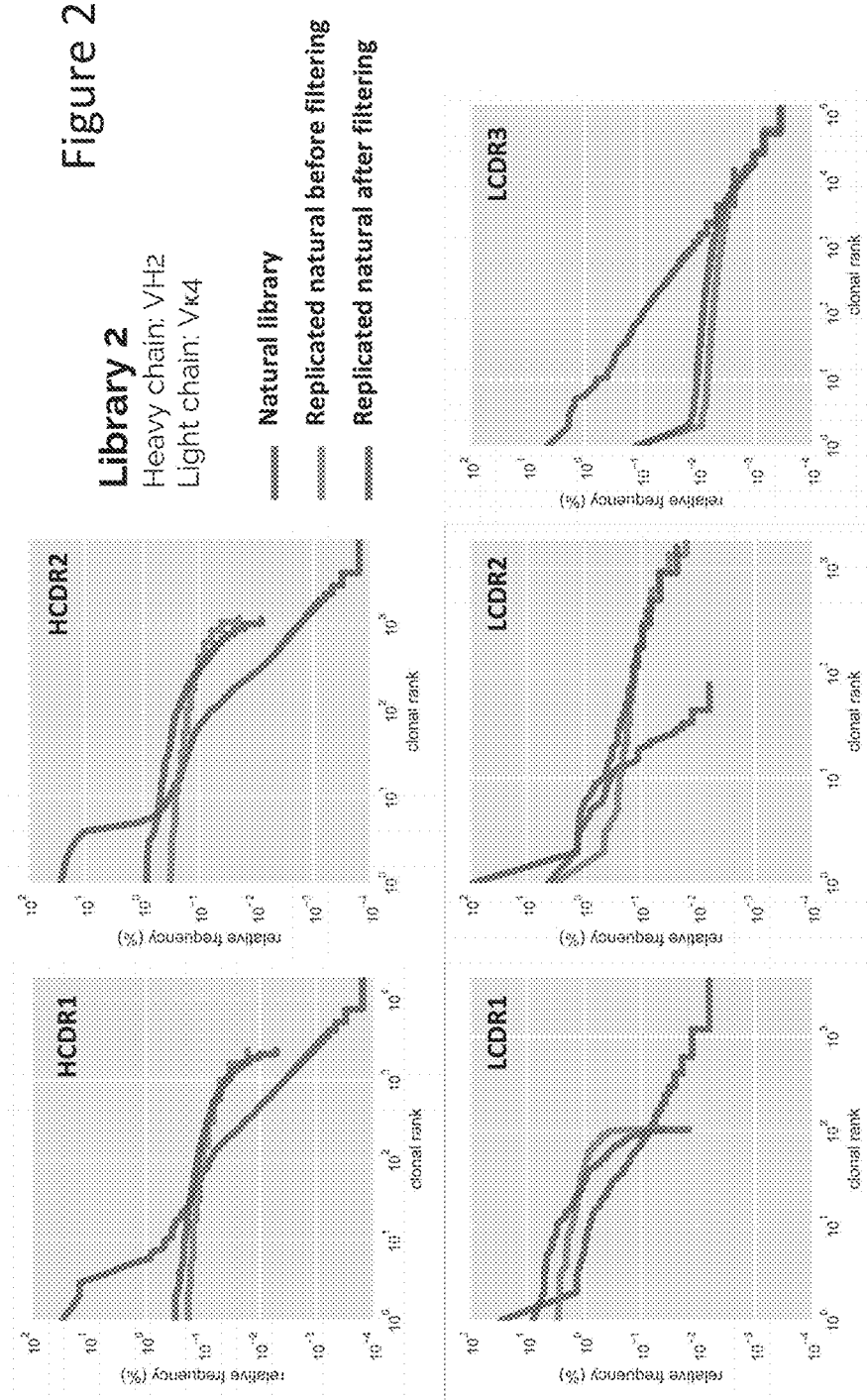

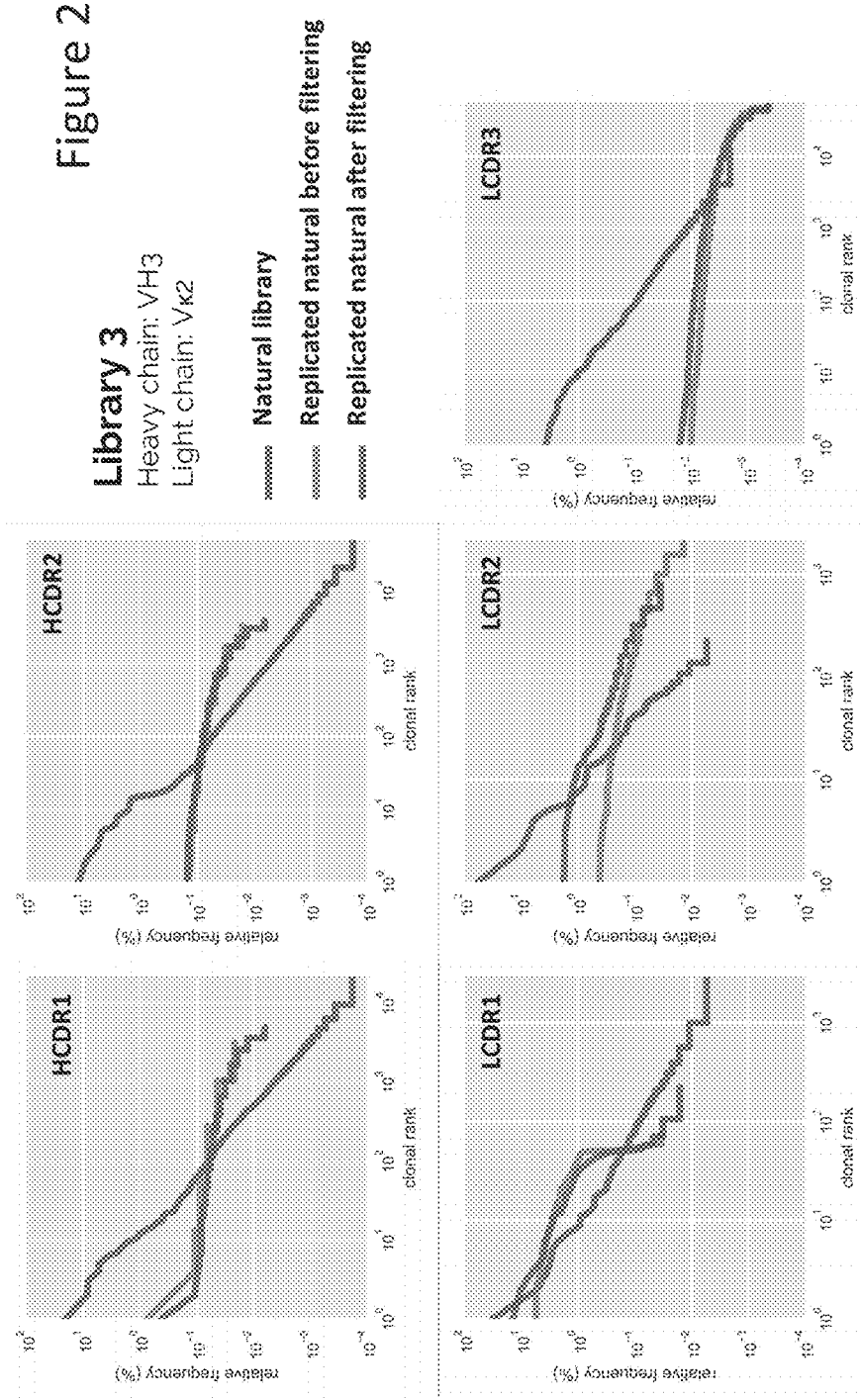

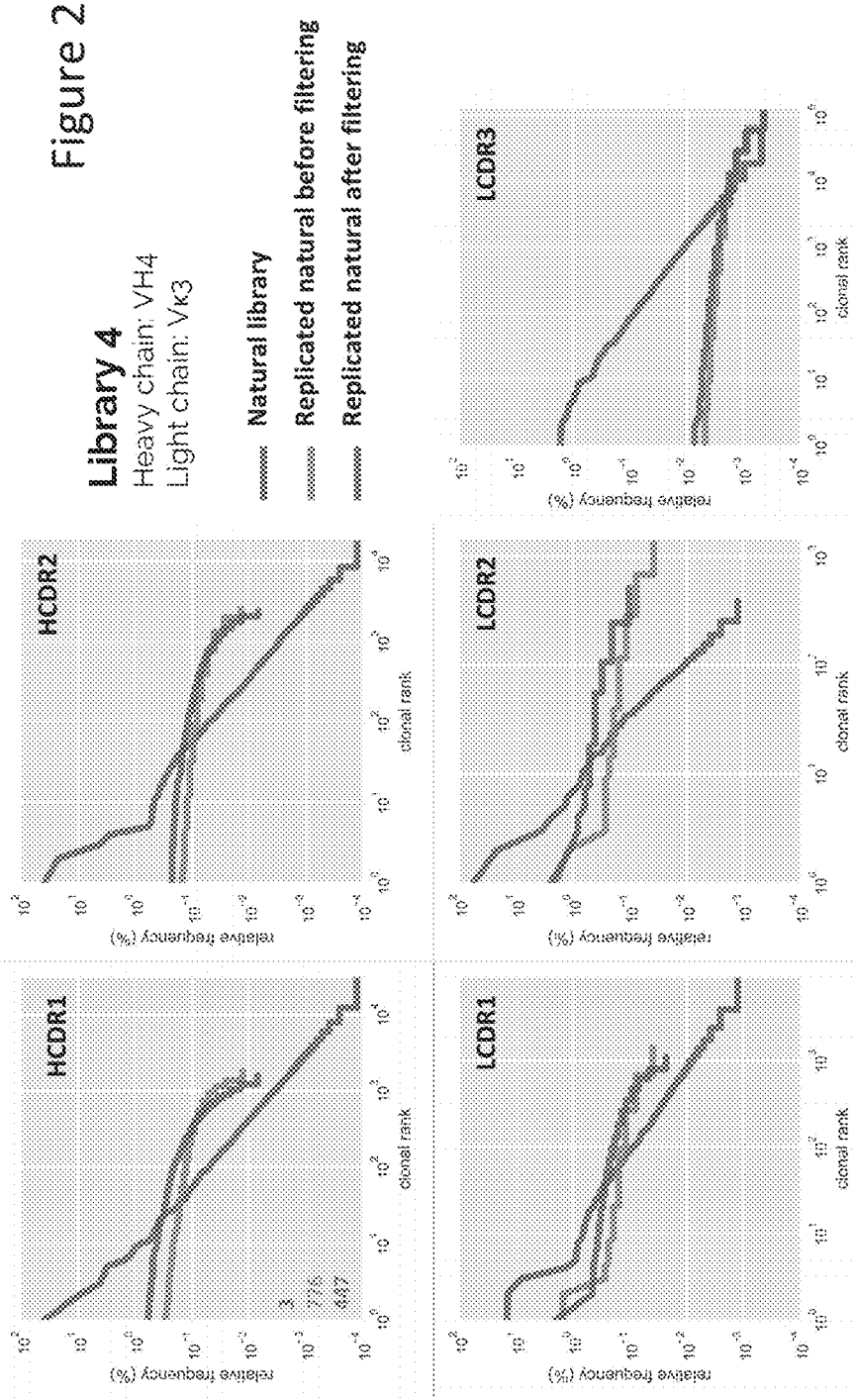

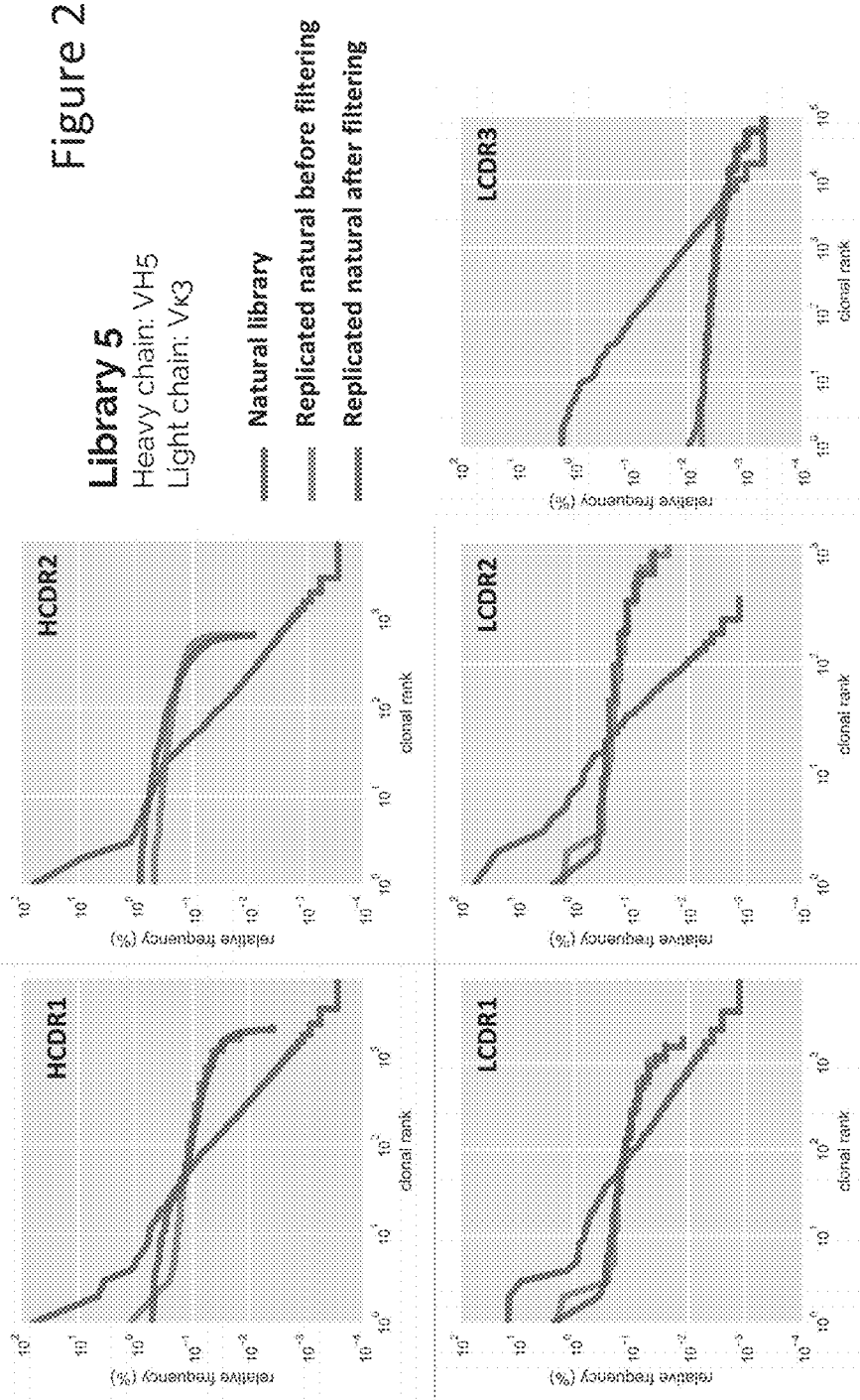

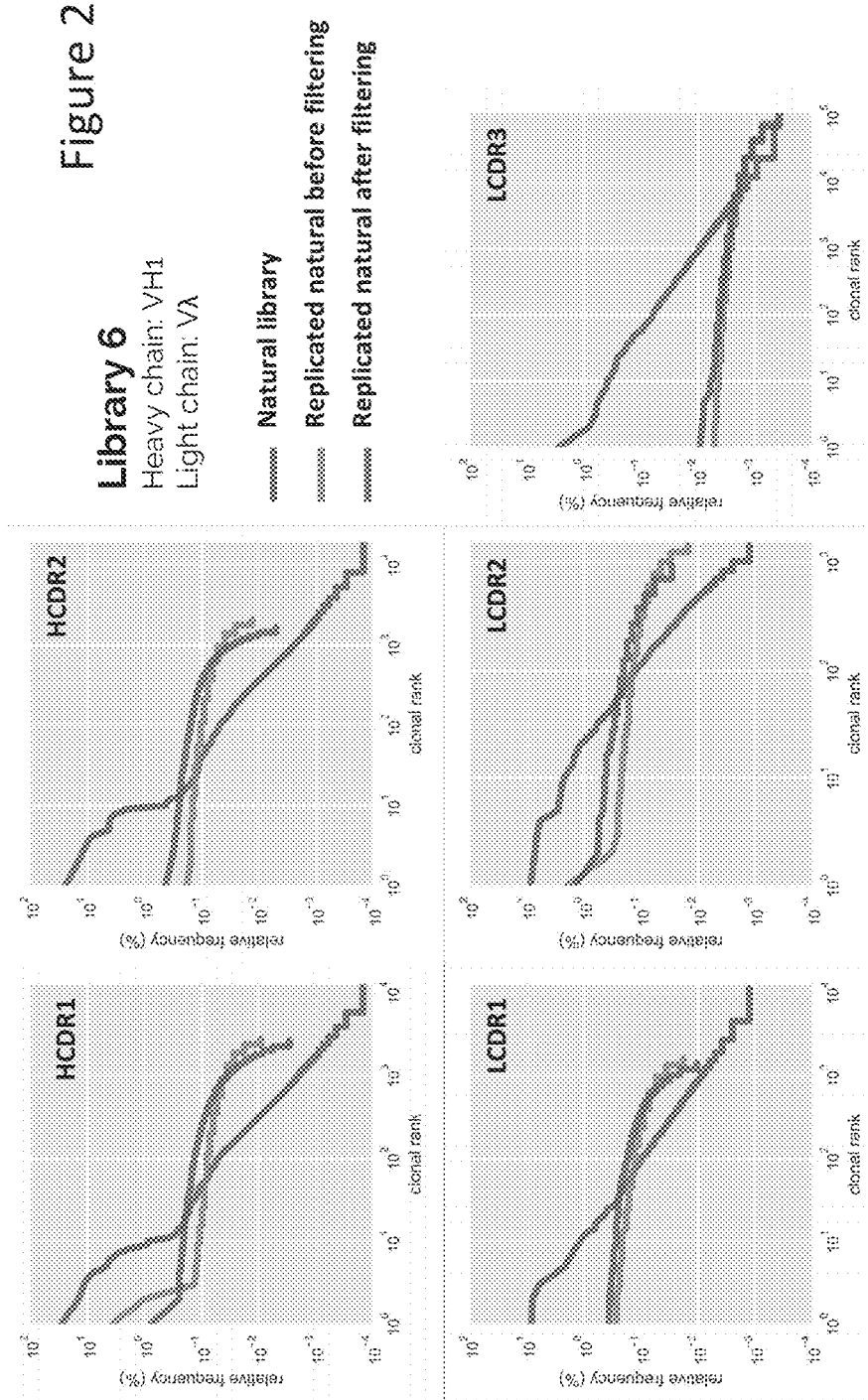

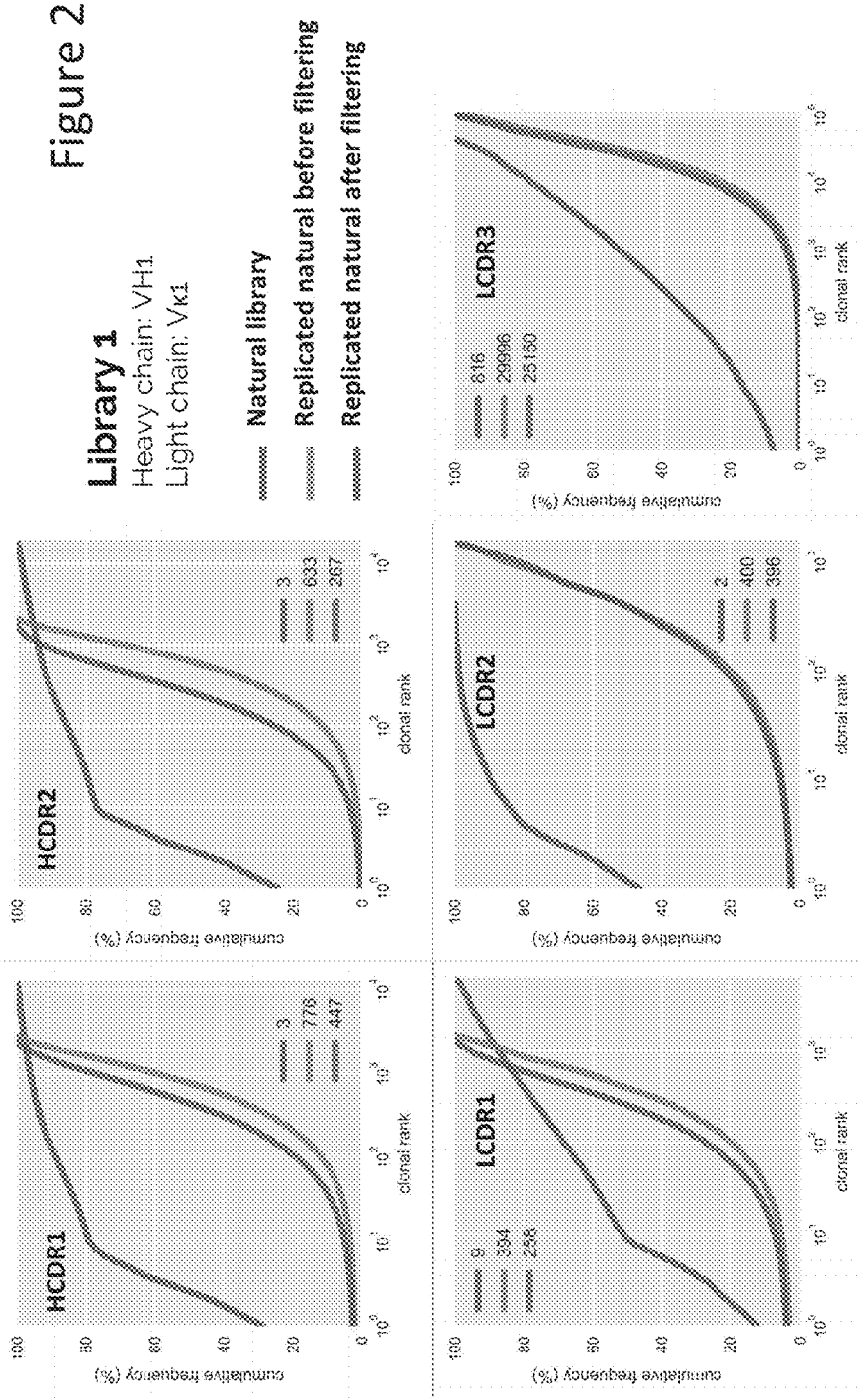

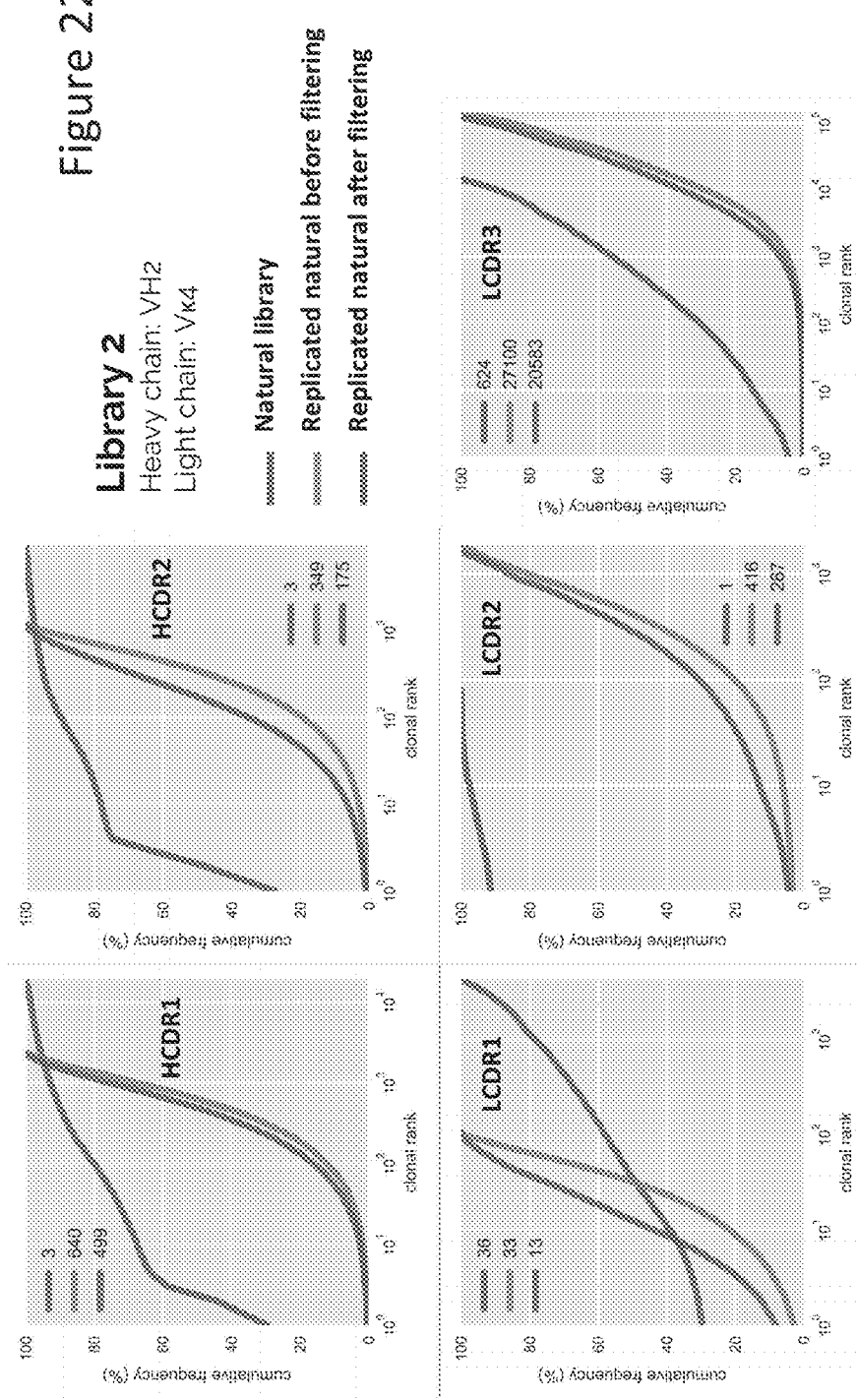

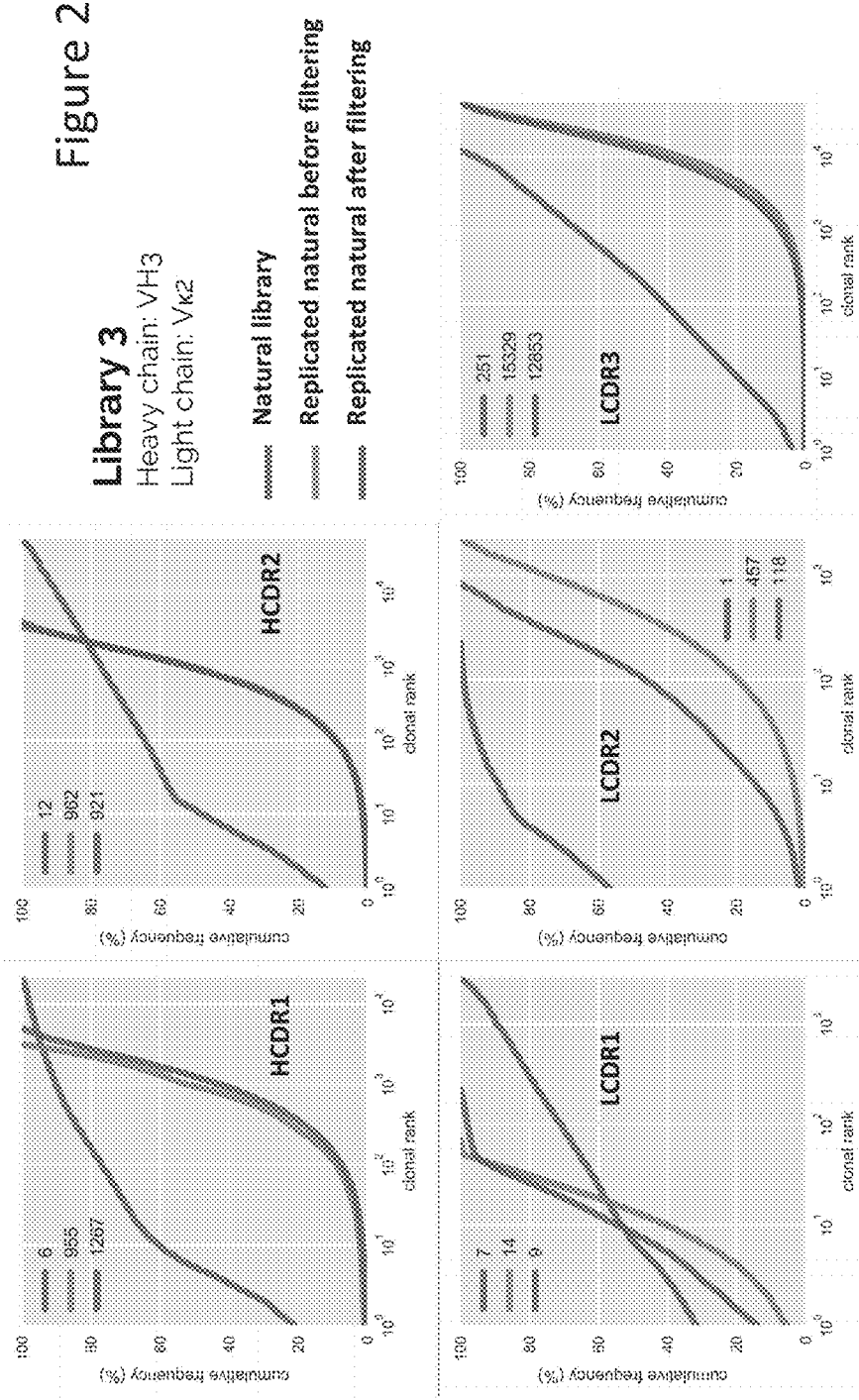

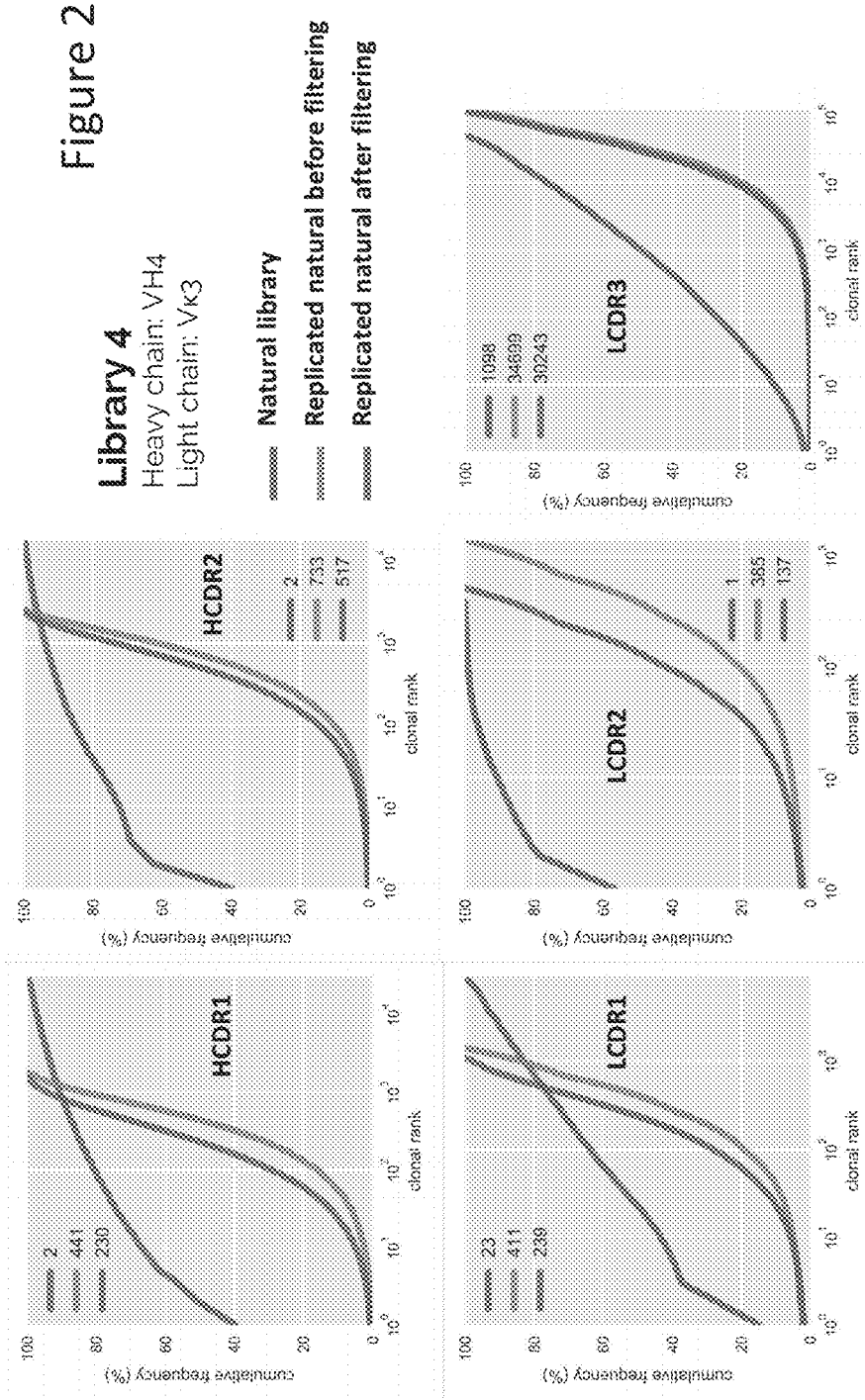

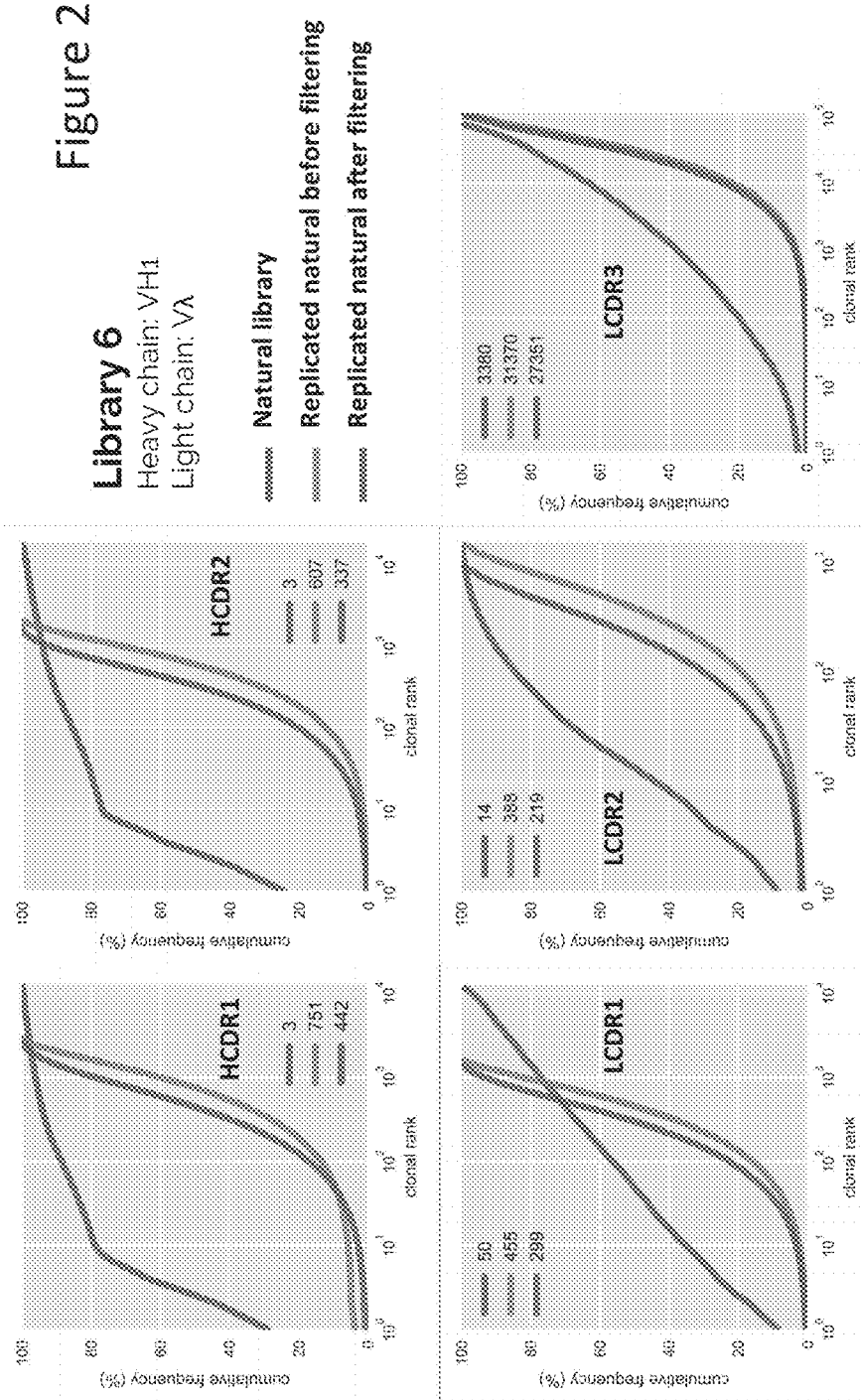

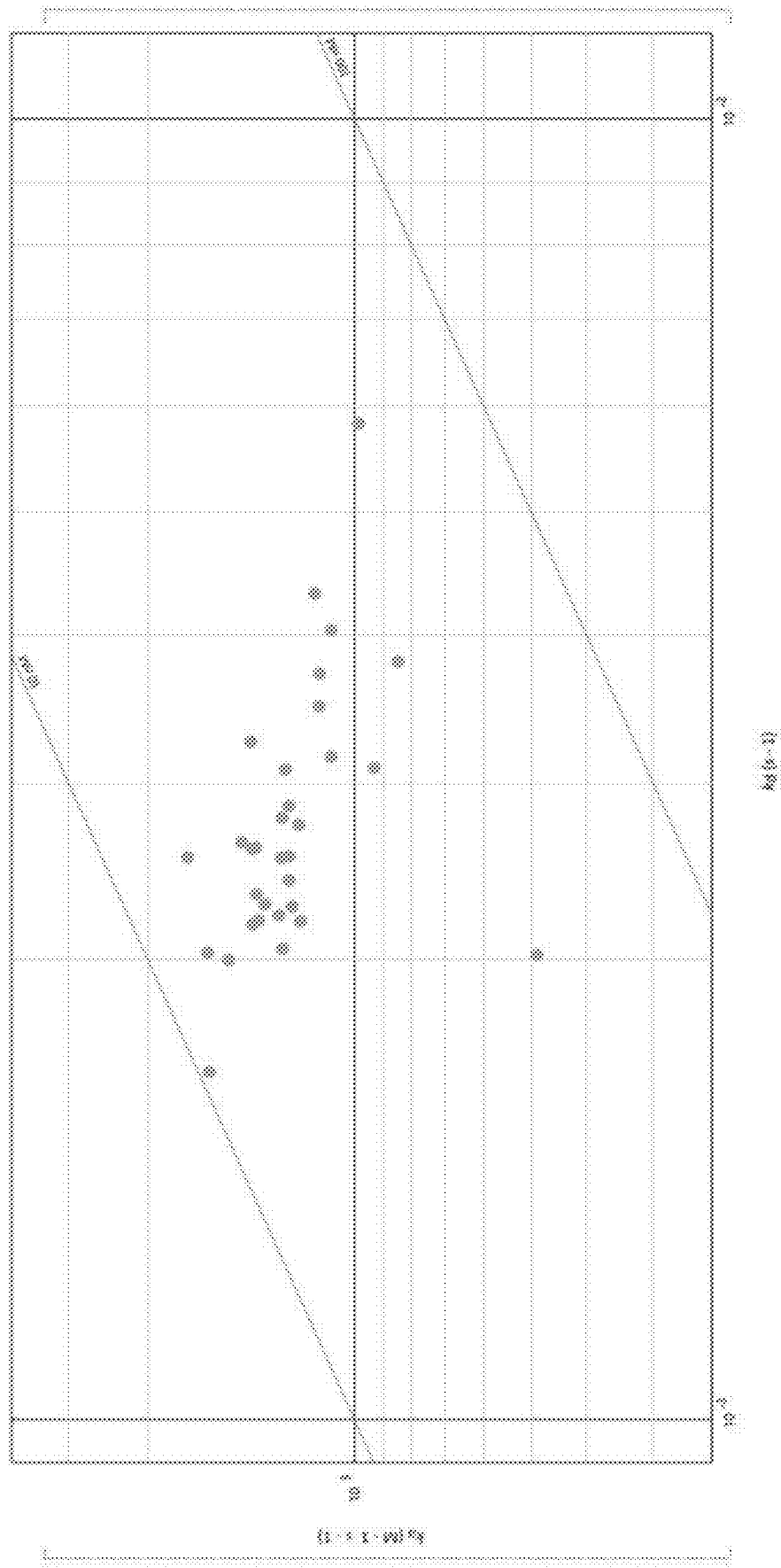

SEQUENCE LISTING

```
Sequence total quantity: 298
SEQ ID NO: 1            moltype = DNA  length = 76
FEATURE                 Location/Qualifiers
misc_feature            1..76
                        note = Cloning Vector
source                  1..76
                        mol_type = other DNA
                        organism = synthetic construct
SEQUENCE: 1
gtgttaccat cacctgtcgt gcttctagag accatggcca gtaaggccgg tctctctggc   60
ttggtaccag cagaaa                                                   76

SEQ ID NO: 2            moltype = DNA  length = 76
FEATURE                 Location/Qualifiers
misc_feature            1..76
                        note = Cloning Vector
source                  1..76
                        mol_type = other DNA
                        organism = synthetic construct
SEQUENCE: 2
cacaatggta gtggacagca cgaagatctc tggtaccggt cattccggcc agagagaccg   60
aaccatggtc gtcttt                                                   76

SEQ ID NO: 3            moltype = AA   length = 24
FEATURE                 Location/Qualifiers
REGION                  1..24
```

```
                            note = Cloning Vector
source                      1..24
                            mol_type = protein
                            organism = synthetic construct
SEQUENCE: 3
RVTITCRASR DHGQGRSLAW YQQK                                              24

SEQ ID NO: 4                moltype = AA  length = 15
FEATURE                     Location/Qualifiers
SITE                        3
                            note = MISC_FEATURE - Xaa at position 3 is Met, Ile, or Leu
SITE                        4
                            note = MISC_FEATURE - Xaa at position 4 is Gly or Ala
SITE                        5
                            note = MISC_FEATURE - Xaa at position 5 is Trp, Arg, Glu,
                             or His
SITE                        7
                            note = MISC_FEATURE - Xaa at position 7 is Ser, Asn, or Phe
SITE                        8
                            note = MISC_FEATURE - Xaa at position 8 is optional or is
                             Gly, Thr, Val, Ala, or Pro
SITE                        9
                            note = MISC_FEATURE - Xaa at position 9 is Tyr, Asn, His,
                             or Ser
SITE                        10
                            note = MISC_FEATURE - Xaa at position 10 is Asn, Ser, or Thr
SITE                        11
                            note = MISC_FEATURE - Xaa at position 11 is Gly or Asp
SITE                        12
                            note = MISC_FEATURE - Xaa at position 12 is Asn, Asp, Lys,
                             Ala, Gly, or Glu
SITE                        13
                            note = MISC_FEATURE - Xaa at position 13 is Thr, Ala, Asn,
                             or Lys
SITE                        14
                            note = MISC_FEATURE - Xaa at position 14 is Asn, Lys, Asp,
                             or Ser
source                      1..15
                            mol_type = protein
                            organism = Homo sapiens
SEQUENCE: 4
EWXXXIXXXX XXXXY                                                        15

SEQ ID NO: 5                moltype = AA  length = 15
FEATURE                     Location/Qualifiers
source                      1..15
                            mol_type = protein
                            organism = Homo sapiens
SEQUENCE: 5
EWMGWISGYN GNTNY                                                        15

SEQ ID NO: 6                moltype = AA  length = 15
FEATURE                     Location/Qualifiers
source                      1..15
                            mol_type = protein
                            organism = Homo sapiens
SEQUENCE: 6
EWMGWISTYN GNTNY                                                        15

SEQ ID NO: 7                moltype = AA  length = 15
FEATURE                     Location/Qualifiers
source                      1..15
                            mol_type = protein
                            organism = Homo sapiens
SEQUENCE: 7
EWMGWISVYN GNTNY                                                        15

SEQ ID NO: 8                moltype = AA  length = 15
FEATURE                     Location/Qualifiers
source                      1..15
                            mol_type = protein
                            organism = Homo sapiens
SEQUENCE: 8
EWMGWISAYN GNTKY                                                        15

SEQ ID NO: 9                moltype = AA  length = 15
FEATURE                     Location/Qualifiers
source                      1..15
                            mol_type = protein
```

```
                        organism = Homo sapiens
SEQUENCE: 9
EWMGRISAYN GNTNY                                                    15

SEQ ID NO: 10           moltype = AA   length = 15
FEATURE                 Location/Qualifiers
source                  1..15
                        mol_type = protein
                        organism = Homo sapiens
SEQUENCE: 10
EWMGWISAYN GDTNY                                                    15

SEQ ID NO: 11           moltype = AA   length = 15
FEATURE                 Location/Qualifiers
source                  1..15
                        mol_type = protein
                        organism = Homo sapiens
SEQUENCE: 11
EWMGWISAYN GKTNY                                                    15

SEQ ID NO: 12           moltype = AA   length = 15
FEATURE                 Location/Qualifiers
source                  1..15
                        mol_type = protein
                        organism = Homo sapiens
SEQUENCE: 12
EWMGWISPYN GNTNY                                                    15

SEQ ID NO: 13           moltype = AA   length = 15
FEATURE                 Location/Qualifiers
source                  1..15
                        mol_type = protein
                        organism = Homo sapiens
SEQUENCE: 13
EWMGWINPNS GDTNY                                                    15

SEQ ID NO: 14           moltype = AA   length = 15
FEATURE                 Location/Qualifiers
source                  1..15
                        mol_type = protein
                        organism = Homo sapiens
SEQUENCE: 14
EWMGWINPNS GATNY                                                    15

SEQ ID NO: 15           moltype = AA   length = 15
FEATURE                 Location/Qualifiers
source                  1..15
                        mol_type = protein
                        organism = Homo sapiens
SEQUENCE: 15
EWMGWINPNS GGTDY                                                    15

SEQ ID NO: 16           moltype = AA   length = 15
FEATURE                 Location/Qualifiers
source                  1..15
                        mol_type = protein
                        organism = Homo sapiens
SEQUENCE: 16
EWMGWINPNS GGTSY                                                    15

SEQ ID NO: 17           moltype = AA   length = 15
FEATURE                 Location/Qualifiers
source                  1..15
                        mol_type = protein
                        organism = Homo sapiens
SEQUENCE: 17
EWMGWINPNS GGTKY                                                    15

SEQ ID NO: 18           moltype = AA   length = 15
FEATURE                 Location/Qualifiers
source                  1..15
                        mol_type = protein
                        organism = Homo sapiens
SEQUENCE: 18
EWMGWINPNS GGANY                                                    15

SEQ ID NO: 19           moltype = AA   length = 15
FEATURE                 Location/Qualifiers
source                  1..15
```

```
                        mol_type = protein
                        organism = Homo sapiens
SEQUENCE: 19
EWMGRINPNS GGTNY                                                        15

SEQ ID NO: 20           moltype = AA  length = 15
FEATURE                 Location/Qualifiers
source                  1..15
                        mol_type = protein
                        organism = Homo sapiens
SEQUENCE: 20
EWMGWINPNN GGTNY                                                        15

SEQ ID NO: 21           moltype = AA  length = 15
FEATURE                 Location/Qualifiers
source                  1..15
                        mol_type = protein
                        organism = Homo sapiens
SEQUENCE: 21
EWMGWINPNT GGTNY                                                        15

SEQ ID NO: 22           moltype = AA  length = 14
FEATURE                 Location/Qualifiers
source                  1..14
                        mol_type = protein
                        organism = Homo sapiens
SEQUENCE: 22
EWIGEINHSG NTNY                                                         14

SEQ ID NO: 23           moltype = AA  length = 14
FEATURE                 Location/Qualifiers
source                  1..14
                        mol_type = protein
                        organism = Homo sapiens
SEQUENCE: 23
EWLAHIFSND ENSY                                                         14

SEQ ID NO: 24           moltype = AA  length = 14
FEATURE                 Location/Qualifiers
source                  1..14
                        mol_type = protein
                        organism = Homo sapiens
SEQUENCE: 24
EWLAHIFSNG EKSY                                                         14

SEQ ID NO: 25           moltype =    length =
SEQUENCE: 25
000

SEQ ID NO: 26           moltype = AA  length = 15
FEATURE                 Location/Qualifiers
source                  1..15
                        mol_type = protein
                        organism = Homo sapiens
SEQUENCE: 26
EWMGVIYPGD SDTRY                                                        15

SEQ ID NO: 27           moltype = AA  length = 15
FEATURE                 Location/Qualifiers
source                  1..15
                        mol_type = protein
                        organism = Homo sapiens
SEQUENCE: 27
EWMGLIYPGD SDTRY                                                        15

SEQ ID NO: 28           moltype = AA  length = 15
FEATURE                 Location/Qualifiers
source                  1..15
                        mol_type = protein
                        organism = Homo sapiens
SEQUENCE: 28
EWMGIIFPGD SDTRY                                                        15

SEQ ID NO: 29           moltype = AA  length = 15
FEATURE                 Location/Qualifiers
source                  1..15
                        mol_type = protein
                        organism = Homo sapiens
SEQUENCE: 29
```

```
EWMGIIYPGD SDIRY                                                           15

SEQ ID NO: 30          moltype = AA  length = 15
FEATURE                Location/Qualifiers
source                 1..15
                       mol_type = protein
                       organism = Homo sapiens SEQUENCE: 30
EWMGIIYPGD SETRY                                                           15

SEQ ID NO: 31          moltype = AA  length = 15
FEATURE                Location/Qualifiers
source                 1..15
                       mol_type = protein
                       organism = Homo sapiens SEQUENCE: 31
EWMGIIYPGD SDTSY                                                           15

SEQ ID NO: 32          moltype = AA  length = 15
FEATURE                Location/Qualifiers
source                 1..15
                       mol_type = protein
                       organism = Homo sapiens SEQUENCE: 32
EWMGIIYPGD SDTKY                                                           15

SEQ ID NO: 33          moltype = AA  length = 15
FEATURE                Location/Qualifiers
source                 1..15
                       mol_type = protein
                       organism = Homo sapiens SEQUENCE: 33
EWMGIIYPGD SDTTY                                                           15

SEQ ID NO: 34          moltype = AA  length = 15
FEATURE                Location/Qualifiers
source                 1..15
                       mol_type = protein
                       organism = Homo sapiens SEQUENCE: 34
EWMGIIYPSD SDTRY                                                           15

SEQ ID NO: 35          moltype = AA  length = 15
FEATURE                Location/Qualifiers
source                 1..15
                       mol_type = protein
                       organism = Homo sapiens SEQUENCE: 35
EWMGIIYPAD SDTRY                                                           15

SEQ ID NO: 36          moltype = AA  length = 15
FEATURE                Location/Qualifiers
source                 1..15
                       mol_type = protein
                       organism = Homo sapiens SEQUENCE: 36
EWMGIIYPDD SDTRY                                                           15

SEQ ID NO: 37          moltype = AA  length = 14
FEATURE                Location/Qualifiers
source                 1..14
                       mol_type = protein
                       organism = Homo sapiens SEQUENCE: 37
EWLALIYWDG DKRY                                                            14

SEQ ID NO: 38          moltype = AA  length = 14
FEATURE                Location/Qualifiers
source                 1..14
                       mol_type = protein
                       organism = Homo sapiens SEQUENCE: 38
EWLALVYWDD DKRY                                                            14

SEQ ID NO: 39          moltype = AA  length = 14
FEATURE                Location/Qualifiers
source                 1..14
                       mol_type = protein
                       organism = Homo sapiens
```

```
SEQUENCE: 39
EWLALIYWND DKRY                                                              14

SEQ ID NO: 40           moltype = AA  length = 14
FEATURE                 Location/Qualifiers
source                  1..14
                        mol_type = protein
                        organism = Homo sapiens
SEQUENCE: 40
EWLALIYWDD DRRY                                                              14

SEQ ID NO: 41           moltype = AA  length = 14
FEATURE                 Location/Qualifiers
source                  1..14
                        mol_type = protein
                        organism = Homo sapiens
SEQUENCE: 41
EWLARIDWDD DKYY                                                              14

SEQ ID NO: 42           moltype = AA  length = 14
FEATURE                 Location/Qualifiers
source                  1..14
                        mol_type = protein
                        organism = Homo sapiens
SEQUENCE: 42
EWLALIYWDD DKYY                                                              14

SEQ ID NO: 43           moltype = AA  length = 14
FEATURE                 Location/Qualifiers
source                  1..14
                        mol_type = protein
                        organism = Homo sapiens
SEQUENCE: 43
EWLAVIYWDD DKRY                                                              14

SEQ ID NO: 44           moltype = AA  length = 14
FEATURE                 Location/Qualifiers
source                  1..14
                        mol_type = protein
                        organism = Homo sapiens
SEQUENCE: 44
EWLAFIYWDD DKRY                                                              14

SEQ ID NO: 45           moltype = AA  length = 14
FEATURE                 Location/Qualifiers
source                  1..14
                        mol_type = protein
                        organism = Homo sapiens
SEQUENCE: 45
EWLAIIYWDD DKRY                                                              14

SEQ ID NO: 46           moltype =     length =
SEQUENCE: 46
000

SEQ ID NO: 47           moltype = AA  length = 15
FEATURE                 Location/Qualifiers
source                  1..15
                        mol_type = protein
                        organism = Homo sapiens
SEQUENCE: 47
EWMGWINPNR SGTSY                                                             15

SEQ ID NO: 48           moltype = AA  length = 15
FEATURE                 Location/Qualifiers
source                  1..15
                        mol_type = protein
                        organism = Homo sapiens
SEQUENCE: 48
EWMGWINLNR SGTTY                                                             15

SEQ ID NO: 49           moltype = AA  length = 15
FEATURE                 Location/Qualifiers
source                  1..15
                        mol_type = protein
                        organism = Homo sapiens
SEQUENCE: 49
EWMGRINPNR SDTNY                                                             15
```

| | | |
|---|---|---|
| SEQ ID NO: 50<br>FEATURE<br>source | moltype = AA   length = 15<br>Location/Qualifiers<br>1..15<br>mol_type = protein<br>organism = Homo sapiens | |
| SEQUENCE: 50<br>EWMGNISPGD PDTRY | | 15 |
| SEQ ID NO: 51<br>FEATURE<br>source | moltype = AA   length = 15<br>Location/Qualifiers<br>1..15<br>mol_type = protein<br>organism = Homo sapiens | |
| SEQUENCE: 51<br>EWMGKINRSG GSTSY | | 15 |
| SEQ ID NO: 52<br>FEATURE<br>source | moltype = AA   length = 15<br>Location/Qualifiers<br>1..15<br>mol_type = protein<br>organism = Homo sapiens | |
| SEQUENCE: 52<br>EWMGIINHSG GTTSY | | 15 |
| SEQ ID NO: 53<br>FEATURE<br>source | moltype = AA   length = 15<br>Location/Qualifiers<br>1..15<br>mol_type = protein<br>organism = Homo sapiens | |
| SEQUENCE: 53<br>EWMGIINLSS RFTSY | | 15 |
| SEQ ID NO: 54<br>FEATURE<br>source | moltype = AA   length = 15<br>Location/Qualifiers<br>1..15<br>mol_type = protein<br>organism = Homo sapiens | |
| SEQUENCE: 54<br>EWIGIINLSS GSTSY | | 15 |
| SEQ ID NO: 55<br>FEATURE<br>source | moltype = AA   length = 15<br>Location/Qualifiers<br>1..15<br>mol_type = protein<br>organism = Homo sapiens | |
| SEQUENCE: 55<br>EWMGISNLSG GSTSY | | 15 |
| SEQ ID NO: 56<br>FEATURE<br>source | moltype = AA   length = 15<br>Location/Qualifiers<br>1..15<br>mol_type = protein<br>organism = Homo sapiens | |
| SEQUENCE: 56<br>EWLGIINASG GSTRY | | 15 |
| SEQ ID NO: 57<br>FEATURE<br>source | moltype = AA   length = 15<br>Location/Qualifiers<br>1..15<br>mol_type = protein<br>organism = Homo sapiens | |
| SEQUENCE: 57<br>EWVGIINLTG GATRY | | 15 |
| SEQ ID NO: 58<br>FEATURE<br>source | moltype = AA   length = 15<br>Location/Qualifiers<br>1..15<br>mol_type = protein<br>organism = Homo sapiens | |
| SEQUENCE: 58<br>EWVSSINWSG GSTYY | | 15 |
| SEQ ID NO: 59<br>FEATURE<br>source | moltype = AA   length = 15<br>Location/Qualifiers<br>1..15<br>mol_type = protein<br>organism = Homo sapiens | |
| SEQUENCE: 59<br>EWVSTINESG GKTHY | | 15 |

```
SEQ ID NO: 60           moltype = AA  length = 15
FEATURE                 Location/Qualifiers
source                  1..15
                        mol_type = protein
                        organism = Homo sapiens
SEQUENCE: 60
EWVANISGGG GAIYY                                                          15

SEQ ID NO: 61           moltype = AA  length = 15
FEATURE                 Location/Qualifiers
source                  1..15
                        mol_type = protein
                        organism = Homo sapiens
SEQUENCE: 61
EWVAYINRSG STIYY                                                          15

SEQ ID NO: 62           moltype = AA  length = 15
FEATURE                 Location/Qualifiers
source                  1..15
                        mol_type = protein
                        organism = Homo sapiens
SEQUENCE: 62
EWVDVIWYAG RNKSY                                                          15

SEQ ID NO: 63           moltype = AA  length = 15
FEATURE                 Location/Qualifiers
source                  1..15
                        mol_type = protein
                        organism = Homo sapiens
SEQUENCE: 63
EWVAVISHDR SNKSY                                                          15

SEQ ID NO: 64           moltype = AA  length = 15
FEATURE                 Location/Qualifiers
source                  1..15
                        mol_type = protein
                        organism = Homo sapiens
SEQUENCE: 64
EWMSWINASS GGTNY                                                          15

SEQ ID NO: 65           moltype = AA  length = 15
FEATURE                 Location/Qualifiers
source                  1..15
                        mol_type = protein
                        organism = Homo sapiens
SEQUENCE: 65
EWMGRNITIL GIANY                                                          15

SEQ ID NO: 66           moltype = AA  length = 15
FEATURE                 Location/Qualifiers
source                  1..15
                        mol_type = protein
                        organism = Homo sapiens
SEQUENCE: 66
EWMGGNITIF GKANY                                                          15

SEQ ID NO: 67           moltype =     length =
SEQUENCE: 67
000

SEQ ID NO: 68           moltype = AA  length = 15
FEATURE                 Location/Qualifiers
source                  1..15
                        mol_type = protein
                        organism = Homo sapiens
SEQUENCE: 68
EWMGIINPNS GCTNY                                                          15

SEQ ID NO: 69           moltype = AA  length = 15
FEATURE                 Location/Qualifiers
source                  1..15
                        mol_type = protein
                        organism = Homo sapiens
SEQUENCE: 69
EWMGWINPNV CGTNY                                                          15

SEQ ID NO: 70           moltype = AA  length = 15
FEATURE                 Location/Qualifiers
```

```
                                -continued
source                  1..15
                        mol_type = protein
                        organism = Homo sapiens
SEQUENCE: 70
EWMGMIYPGN CDTSY                                                        15

SEQ ID NO: 71           moltype = AA  length = 15
FEATURE                 Location/Qualifiers
source                  1..15
                        mol_type = protein
                        organism = Homo sapiens
SEQUENCE: 71
EWMGIIYPGS CETKY                                                        15

SEQ ID NO: 72           moltype = AA  length = 15
FEATURE                 Location/Qualifiers
source                  1..15
                        mol_type = protein
                        organism = Homo sapiens
SEQUENCE: 72
EWMGGIIPIF CTEYY                                                        15

SEQ ID NO: 73           moltype = AA  length = 15
FEATURE                 Location/Qualifiers
source                  1..15
                        mol_type = protein
                        organism = Homo sapiens
SEQUENCE: 73
EWMGIICPGD AATRY                                                        15

SEQ ID NO: 74           moltype = AA  length = 15
FEATURE                 Location/Qualifiers
source                  1..15
                        mol_type = protein
                        organism = Homo sapiens
SEQUENCE: 74
EWMGCISAYY GNPNY                                                        15

SEQ ID NO: 75           moltype = AA  length = 15
FEATURE                 Location/Qualifiers
source                  1..15
                        mol_type = protein
                        organism = Homo sapiens
SEQUENCE: 75
EWVGVISHDG GNECY                                                        15

SEQ ID NO: 76           moltype = AA  length = 15
FEATURE                 Location/Qualifiers
source                  1..15
                        mol_type = protein
                        organism = Homo sapiens
SEQUENCE: 76
EWMGCINAAD GNTKY                                                        15

SEQ ID NO: 77           moltype = AA  length = 15
FEATURE                 Location/Qualifiers
source                  1..15
                        mol_type = protein
                        organism = Homo sapiens
SEQUENCE: 77
EWMGCFEPKD GETIY                                                        15

SEQ ID NO: 78           moltype = AA  length = 14
FEATURE                 Location/Qualifiers
source                  1..14
                        mol_type = protein
                        organism = Homo sapiens
SEQUENCE: 78
EWLAHICSND GKRY                                                         14

SEQ ID NO: 79           moltype = AA  length = 14
FEATURE                 Location/Qualifiers
source                  1..14
                        mol_type = protein
                        organism = Homo sapiens
SEQUENCE: 79
EWIGLINQCG STNY                                                         14

SEQ ID NO: 80           moltype = AA  length = 14
```

| FEATURE | Location/Qualifiers |
|---|---|
| source | 1..14<br>mol_type = protein<br>organism = Homo sapiens |

SEQUENCE: 80
EWIGYIYYCG SPNY                                                              14

| SEQ ID NO: 81 | moltype = AA length = 15 |
|---|---|
| FEATURE | Location/Qualifiers |
| source | 1..15<br>mol_type = protein<br>organism = Homo sapiens |

SEQUENCE: 81
EWLSYSSCSG TPIYY                                                             15

| SEQ ID NO: 82 | moltype = AA length = 15 |
|---|---|
| FEATURE | Location/Qualifiers |
| source | 1..15<br>mol_type = protein<br>organism = Homo sapiens |

SEQUENCE: 82
EWVSYICGSS STIYY                                                             15

| SEQ ID NO: 83 | moltype = AA length = 15 |
|---|---|
| FEATURE | Location/Qualifiers |
| source | 1..15<br>mol_type = protein<br>organism = Homo sapiens |

SEQUENCE: 83
EWVSSISSCG SSTYY                                                             15

| SEQ ID NO: 84 | moltype = AA length = 15 |
|---|---|
| FEATURE | Location/Qualifiers |
| source | 1..15<br>mol_type = protein<br>organism = Homo sapiens |

SEQUENCE: 84
EWVSYISSCG STINY                                                             15

| SEQ ID NO: 85 | moltype = AA length = 14 |
|---|---|
| FEATURE | Location/Qualifiers |
| source | 1..14<br>mol_type = protein<br>organism = Homo sapiens |

SEQUENCE: 85
EWVSIIYRCG TTYY                                                              14

| SEQ ID NO: 86 | moltype = AA length = 14 |
|---|---|
| FEATURE | Location/Qualifiers |
| source | 1..14<br>mol_type = protein<br>organism = Homo sapiens |

SEQUENCE: 86
EWMGYIYCSS SANY                                                              14

| SEQ ID NO: 87 | moltype = AA length = 15 |
|---|---|
| FEATURE | Location/Qualifiers |
| source | 1..15<br>mol_type = protein<br>organism = Homo sapiens |

SEQUENCE: 87
EWMGRIYPCD SYINY                                                             15

| SEQ ID NO: 88 | moltype = AA length = 25 |
|---|---|
| FEATURE | Location/Qualifiers |
| source | 1..25<br>mol_type = protein<br>organism = Homo sapiens |

SEQUENCE: 88
AGPSITESHY CLDCAAKDYY YGLDV                                                  25

| SEQ ID NO: 89 | moltype = AA length = 17 |
|---|---|
| FEATURE | Location/Qualifiers |
| source | 1..17<br>mol_type = protein<br>organism = Homo sapiens |

SEQUENCE: 89
AKDARDCLLC ADWHFDL                                                           17

```
SEQ ID NO: 90           moltype = AA  length = 16
FEATURE                 Location/Qualifiers
source                  1..16
                        mol_type = protein
                        organism = Homo sapiens
SEQUENCE: 90
AKFSGKDCSG TSCRDY                                                         16

SEQ ID NO: 91           moltype = AA  length = 18
FEATURE                 Location/Qualifiers
source                  1..18
                        mol_type = protein
                        organism = Homo sapiens
SEQUENCE: 91
ARAPDCADAD CHKGAFGY                                                       18

SEQ ID NO: 92           moltype = AA  length = 19
FEATURE                 Location/Qualifiers
source                  1..19
                        mol_type = protein
                        organism = Homo sapiens
SEQUENCE: 92
ARDGGHGFCS SASCFGPDY                                                      19

SEQ ID NO: 93           moltype = AA  length = 16
FEATURE                 Location/Qualifiers
source                  1..16
                        mol_type = protein
                        organism = Homo sapiens
SEQUENCE: 93
ARRGSCDYCG DFPWQY                                                         16

SEQ ID NO: 94           moltype = AA  length = 17
FEATURE                 Location/Qualifiers
source                  1..17
                        mol_type = protein
                        organism = Homo sapiens
SEQUENCE: 94
ARSPSYICSG GTCVFDH                                                        17

SEQ ID NO: 95           moltype = AA  length = 18
FEATURE                 Location/Qualifiers
source                  1..18
                        mol_type = protein
                        organism = Homo sapiens
SEQUENCE: 95
ARVGYCSSTS CNRGAFDI                                                       18

SEQ ID NO: 96           moltype = AA  length = 14
FEATURE                 Location/Qualifiers
source                  1..14
                        mol_type = protein
                        organism = Homo sapiens
SEQUENCE: 96
VRGHCDGTTC SRAY                                                           14

SEQ ID NO: 97           moltype = AA  length = 17
FEATURE                 Location/Qualifiers
source                  1..17
                        mol_type = protein
                        organism = Homo sapiens
SEQUENCE: 97
VRKGPSCPHC GDFHWQH                                                        17

SEQ ID NO: 98           moltype = AA  length = 20
FEATURE                 Location/Qualifiers
source                  1..20
                        mol_type = protein
                        organism = Homo sapiens
SEQUENCE: 98
VRSVTPRYCG GGFCYGEFDY                                                     20

SEQ ID NO: 99           moltype = AA  length = 18
FEATURE                 Location/Qualifiers
source                  1..18
                        mol_type = protein
                        organism = Homo sapiens
SEQUENCE: 99
VRTADCERDP CKGWVFPH                                                       18
```

```
SEQ ID NO: 100         moltype = AA  length = 18
FEATURE                Location/Qualifiers
source                 1..18
                       mol_type = protein
                       organism = Homo sapiens
SEQUENCE: 100
VTLPDLCPGD NCTYPDAS                                                       18

SEQ ID NO: 101         moltype = AA  length = 25
FEATURE                Location/Qualifiers
source                 1..25
                       mol_type = protein
                       organism = Homo sapiens
SEQUENCE: 101
VRGRSCCGGR RHCNGADCFN WDFQH                                               25

SEQ ID NO: 102         moltype = AA  length = 37
FEATURE                Location/Qualifiers
source                 1..37
                       mol_type = protein
                       organism = Homo sapiens
SEQUENCE: 102
AKDLREDECE EWWSDYYDFG KQLPCRKSRG VAGIFDG                                  37

SEQ ID NO: 103         moltype = DNA  length = 96
FEATURE                Location/Qualifiers
misc_feature           1..96
                       note = Yeast Display Vector
source                 1..96
                       mol_type = other DNA
                       organism = synthetic construct
SEQUENCE: 103
ggtgatcgtg ttactattac ctgtcgtgct tctagagacc atggccagta aggccggtct         60
ctctggcttg gtaccagcag aaaccaggta aagctc                                   96

SEQ ID NO: 104         moltype = DNA  length = 96
FEATURE                Location/Qualifiers
misc_feature           1..96
                       note = Yeast Display Vector
source                 1..96
                       mol_type = other DNA
                       organism = synthetic construct
SEQUENCE: 104
ccactagcac aatgataatg gacagcacga agatctctgg taccggtcat tccggccaga         60
gagaccgaac catggtcgtc tttggtccat ttcgag                                   96

SEQ ID NO: 105         moltype = DNA  length = 29
FEATURE                Location/Qualifiers
misc_feature           1..29
                       note = Yeast Display Vector
source                 1..29
                       mol_type = other DNA
                       organism = synthetic construct
SEQUENCE: 105
ggtgatcgtg ttactattac ctgtcgtgc                                           29

SEQ ID NO: 106         moltype = DNA  length = 34
FEATURE                Location/Qualifiers
misc_feature           1..34
                       note = Yeast Display Vector
source                 1..34
                       mol_type = other DNA
                       organism = synthetic construct
SEQUENCE: 106
ctggcttggt accagcagaa accaggtaaa gctc                                     34

SEQ ID NO: 107         moltype = DNA  length = 33
FEATURE                Location/Qualifiers
misc_feature           1..33
                       note = Yeast Display Vector
source                 1..33
                       mol_type = other DNA
                       organism = synthetic construct
SEQUENCE: 107
ccactagcac aatgataatg gacagcacga aga                                      33

SEQ ID NO: 108         moltype = DNA  length = 30
FEATURE                Location/Qualifiers
```

```
misc_feature          1..30
                      note = Yeast Display Vector
source                1..30
                      mol_type = other DNA
                      organism = synthetic construct
SEQUENCE: 108
gaaccatggt cgtctttggt ccatttcgag                                          30

SEQ ID NO: 109        moltype = DNA  length = 33
FEATURE               Location/Qualifiers
misc_feature          1..33
                      note = Amplified LCDR1 Oligo
source                1..33
                      mol_type = other DNA
                      organism = synthetic construct
SEQUENCE: 109
ggtgatcgtg ttactattac ctgtcgtgct tct                                      33

SEQ ID NO: 110        moltype = DNA  length = 34
FEATURE               Location/Qualifiers
misc_feature          1..34
                      note = Amplified LCDR1 Oligo
source                1..34
                      mol_type = other DNA
                      organism = synthetic construct
SEQUENCE: 110
ctggcttggt accagcagaa accaggtaaa gctc                                     34

SEQ ID NO: 111        moltype = DNA  length = 33
FEATURE               Location/Qualifiers
misc_feature          1..33
                      note = Amplified LCDR1 Oligo
source                1..33
                      mol_type = other DNA
                      organism = synthetic construct
SEQUENCE: 111
ccactagcac aatgataatg gacagcacga aga                                      33

SEQ ID NO: 112        moltype = DNA  length = 34
FEATURE               Location/Qualifiers
misc_feature          1..34
                      note = Amplified LCDR1 Oligo
source                1..34
                      mol_type = other DNA
                      organism = synthetic construct
SEQUENCE: 112
gaccgaacca tggtcgtctt tggtccattt cgag                                     34

SEQ ID NO: 113        moltype = DNA  length = 33
FEATURE               Location/Qualifiers
misc_feature          1..33
                      note = Cloned Construct
source                1..33
                      mol_type = other DNA
                      organism = synthetic construct
SEQUENCE: 113
ggtgatcgtg ttactattac ctgtcgtgct tct                                      33

SEQ ID NO: 114        moltype = DNA  length = 34
FEATURE               Location/Qualifiers
misc_feature          1..34
                      note = Cloned Construct
source                1..34
                      mol_type = other DNA
                      organism = synthetic construct
SEQUENCE: 114
ctggcttggt accagcagaa accaggtaaa gctc                                     34

SEQ ID NO: 115        moltype = DNA  length = 33
FEATURE               Location/Qualifiers
misc_feature          1..33
                      note = Cloned Construct
source                1..33
                      mol_type = other DNA
                      organism = synthetic construct
SEQUENCE: 115
ccactagcac aatgataatg gacagcacga aga                                      33

SEQ ID NO: 116        moltype = DNA  length = 34
```

```
FEATURE              Location/Qualifiers
misc_feature         1..34
                     note = Cloned Construct
source               1..34
                     mol_type = other DNA
                     organism = synthetic construct
SEQUENCE: 116
gaccgaacca tggtcgtctt tggtccattt cgag                             34

SEQ ID NO: 117       moltype = AA  length = 4
FEATURE              Location/Qualifiers
REGION               1..4
                     note = Streptavidin Binding Motif
source               1..4
                     mol_type = protein
                     organism = synthetic construct
SEQUENCE: 117
EPDW                                                              4

SEQ ID NO: 118       moltype = AA  length = 5
FEATURE              Location/Qualifiers
REGION               1..5
                     note = Streptavidin Binding Motif
SITE                 3
                     note = MISC_FEATURE - Xaa is any amino acid
source               1..5
                     mol_type = protein
                     organism = synthetic construct
SEQUENCE: 118
PWXWL                                                             5

SEQ ID NO: 119       moltype = AA  length = 6
FEATURE              Location/Qualifiers
REGION               1..6
                     note = Streptavidin Binding Motif
source               1..6
                     mol_type = protein
                     organism = synthetic construct
SEQUENCE: 119
GDWVFI                                                            6

SEQ ID NO: 120       moltype = AA  length = 6
FEATURE              Location/Qualifiers
REGION               1..6
                     note = Streptavidin Binding Motif
source               1..6
                     mol_type = protein
                     organism = synthetic construct
SEQUENCE: 120
PWPWLG                                                            6

SEQ ID NO: 121       moltype = AA  length = 107
FEATURE              Location/Qualifiers
source               1..107
                     mol_type = protein
                     organism = Homo sapiens
SEQUENCE: 121
DIQMTQSPSS VSASVGDRVT ITCRASQGIS SWLAWYQQKP GKAPKLLIYG ASNLESGVPS  60
RFSGSGSGTD FTLTISSLQP EDFANYYCQQ ANSFPWTFGG GTKVEIK              107

SEQ ID NO: 122       moltype = AA  length = 21
FEATURE              Location/Qualifiers
REGION               1..21
                     note = Linker Sequence
source               1..21
                     mol_type = protein
                     organism = synthetic construct
SEQUENCE: 122
SGGSTITSYN VYYTKLSSSG T                                           21

SEQ ID NO: 123       moltype = AA  length = 118
FEATURE              Location/Qualifiers
source               1..118
                     mol_type = protein
                     organism = Homo sapiens
SEQUENCE: 123
QVQLVQSGAE VKKPGASVKV SCKVSGYTLS DLSIHWVRQA PGKGLEWMGG FDPQDGETIY  60
AQKFQGRVTM TEDTSTDTAY MELSSLKSED TAVYYCATGS SSWFDPWGQ GTLVTVSS   118
```

```
SEQ ID NO: 124           moltype = AA   length = 113
FEATURE                  Location/Qualifiers
source                   1..113
                         mol_type = protein
                         organism = Homo sapiens
SEQUENCE: 124
DIVMTQSPDS LAVSLGERAT INCKSSQSLL NSGNQKNYLA WYQQKPGQPP KLLIYGASTR    60
ESGVPDRFSG SGSGTDFTLT ISSLQAEDVA VYYCQNVHSF PFTFGGGTKV EIK          113

SEQ ID NO: 125           moltype = AA   length = 21
FEATURE                  Location/Qualifiers
REGION                   1..21
                         note = Linker Sequence
source                   1..21
                         mol_type = protein
                         organism = synthetic construct
SEQUENCE: 125
SGGSTITSYN VYYTKLSSSG T                                              21

SEQ ID NO: 126           moltype = AA   length = 118
FEATURE                  Location/Qualifiers
source                   1..118
                         mol_type = protein
                         organism = Homo sapiens
SEQUENCE: 126
QVTLRESGPA LVKPTQTLTL TCTVSGFSLS AYSVNWIRQP PGKALEWLAM IWGDGKIVYN    60
SALKSRLTIS KDTSKNQVVL TMTNMDPVDT ATYYCAGDGY YPYAMDNWGQ GTLVTVSS     118

SEQ ID NO: 127           moltype = AA   length = 112
FEATURE                  Location/Qualifiers
source                   1..112
                         mol_type = protein
                         organism = Homo sapiens
SEQUENCE: 127
DIVMTQSPLS LPVTPGEPAS ISCRSSQSLV YSNGDTYLHW YLQKPGQSPQ LLIYKVSNRF    60
SGVPDRFSGS GSGTDFTLKI SRVEAEDVGV YYCSQSTHVP WTFGGGTKVE IK           112

SEQ ID NO: 128           moltype = AA   length = 21
FEATURE                  Location/Qualifiers
REGION                   1..21
                         note = Linker Sequence
source                   1..21
                         mol_type = protein
                         organism = synthetic construct
SEQUENCE: 128
SGGSTITSYN VYYTKLSSSG T                                              21

SEQ ID NO: 129           moltype = AA   length = 112
FEATURE                  Location/Qualifiers
source                   1..112
                         mol_type = protein
                         organism = Homo sapiens
SEQUENCE: 129
EVQLVESGGG LVQPGGSLRL SCAASGFTFS SYGMSWVRQA PGKGLELVAS INSNGGSTYY    60
PDSVKGRFTI SRDNAKNSLY LQMNSLRAED TAVYYCASGD YWGQGTTVTV SS           112

SEQ ID NO: 130           moltype = AA   length = 107
FEATURE                  Location/Qualifiers
source                   1..107
                         mol_type = protein
                         organism = Homo sapiens
SEQUENCE: 130
EIVMTQSPAT LSLSPGERAT LSCRASQSVS SYLAWYQQKP GQAPRLLIYD ASNRATGIPA    60
RFSGSGSGTD FTLTISSLEP EDFAVYYCHQ YGSTPLTFGG GTKVEIK                 107

SEQ ID NO: 131           moltype = AA   length = 21
FEATURE                  Location/Qualifiers
REGION                   1..21
                         note = Linker Sequence
source                   1..21
                         mol_type = protein
                         organism = synthetic construct
SEQUENCE: 131
SGGSTITSYN VYYTKLSSSG T                                              21

SEQ ID NO: 132           moltype = AA   length = 121
FEATURE                  Location/Qualifiers
source                   1..121
                         mol_type = protein
```

```
                        organism = Homo sapiens
SEQUENCE: 132
QVQLQESGPG LVKPSQTLSL TCTVSGGSIS SGDYYWSWIR QPPGKGLEWI GYIYYSGSTD      60
YNPSLKSRVT MSVDTSKNQF SLKVNSVTAA DTAVYYCARV SIFGVGTFDY WGQGTLVTVS     120
S                                                                    121

SEQ ID NO: 133          moltype = AA   length = 108
FEATURE                 Location/Qualifiers
source                  1..108
                        mol_type = protein
                        organism = Homo sapiens
SEQUENCE: 133
EIVLTQSPGT LSLSPGERAT LSCRASQSVS SSFLAWYQQK PGQAPRLLIY GASSRATGIP      60
DRLSGSGSGT DFTLTITRLE PEDFAVYYCQ QYDSSAITFG GGTKVEIK                  108

SEQ ID NO: 134          moltype = AA   length = 21
FEATURE                 Location/Qualifiers
REGION                  1..21
                        note = Linker Sequence
source                  1..21
                        mol_type = protein
                        organism = synthetic construct
SEQUENCE: 134
SGGSTITSYN VYYTKLSSSG T                                                21

SEQ ID NO: 135          moltype = AA   length = 117
FEATURE                 Location/Qualifiers
source                  1..117
                        mol_type = protein
                        organism = Homo sapiens
SEQUENCE: 135
EVQLVQSGAE VKKPGESLKI SCKGSGYIFT NYWIAWVRQV PGKGLESMGI IYPGDSDIRY      60
SPSFQGQVTI SADKSITTAY LQWSSLKASD TAIYYCARHD IEGFDYWGRG TLVTVSS       117

SEQ ID NO: 136          moltype = AA   length = 109
FEATURE                 Location/Qualifiers
source                  1..109
                        mol_type = protein
                        organism = Homo sapiens
SEQUENCE: 136
ESALTQPASV SGSPGQSITI SCTGTSSDVG GYNSVSWYQQ HPGKAPKLMI YEVSNRPSGV      60
SNRFSGSKSG NTASLTISGL QAEDEADYYC NSYTSTSMVF GGGTKLTVL                 109

SEQ ID NO: 137          moltype = AA   length = 21
FEATURE                 Location/Qualifiers
REGION                  1..21
                        note = Linker Sequence
source                  1..21
                        mol_type = protein
                        organism = synthetic construct
SEQUENCE: 137
SGGSTITSYN VYYTKLSSSG T                                                21

SEQ ID NO: 138          moltype = AA   length = 114
FEATURE                 Location/Qualifiers
source                  1..114
                        mol_type = protein
                        organism = Homo sapiens
SEQUENCE: 138
VQLVQSGAEV KKPGASVKVS CKASGYTLTS YGISWVRQAP GQGLEWMGWV SFYNGNTNYA      60
QKLQGRGTMT TDPSTSTAYM ELRSLRSDDT AVYYCARGYG MDVWGQGTTV TVSS           114

SEQ ID NO: 139          moltype = DNA  length = 816
FEATURE                 Location/Qualifiers
misc_feature            1..816
                        note = Oligonucleotide
source                  1..816
                        mol_type = other DNA
                        organism = synthetic construct
SEQUENCE: 139
cagttagata aaagaggcgc ggcagcaagc ggcgcgcatg ccgatatcca gatgacccag      60
tctccatctt ctgtttctgc ttctgttggt gatcgtgtta ctattacctg tcgtgcttct     120
cagggtatct cttcttggct ggcttggtac cagcagaaac aggtaaagc tccaaaactg     180
ctgatctacg gtgcttctaa cctggaatct ggtgttccat ctcgtttctc tggttctggt    240
tctggtaccg atttcaccct gaccatctct tctctgcagc cagaagattt cgctaactac    300
tactgtcagc aggctaactc ttttcccatgg accttcggtg tggtaccaa agttgaaatc    360
aaatccggag gtcgaccat aacttcgtat aatgtatact atacgaagtt atcctcgagc    420
ggtacccagg ttcagctggt tcagtctggt gctgaagtta aaaaaccagg tgcttctgtt    480
aaagtttctt gtaaagtttc tggttacacc tgtctgatc tgtctatcca ctgggttcgt    540
```

```
caggctccag gtaaaggtct ggaatggatg ggtggtttcg atccacagga tggtgaaacc    600
atctacgctc agaaattcca gggtcgtgtt accatgaccg aagatacctc taccgatacc    660
gcttacatgg aactgtcttc tctgaaatct gaggacacgg ccgtgtatta ctgtgctacc    720
ggttcttctt cttcttggtt cgatccatgg ggtcagggaa ccctggtcac cgtctcctca    780
gctagcggca aaccaatccc aaacccactg ctgggc                              816

SEQ ID NO: 140           moltype = DNA  length = 827
FEATURE                  Location/Qualifiers
misc_feature             1..827
                         note = Oligonucleotide
source                   1..827
                         mol_type = other DNA
                         organism = synthetic construct
SEQUENCE: 140
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
agagaccatg gccagtaagg ccggtctctc tggcttggta ccagcagaaa ccaggtaaag    180
ctccaaaact gctgatctac ggtgcttcta acctggaatc tggtgttcca tctcgtttct    240
ctggttctgg ttctggtacc gatttcaccc tgaccatctc ttctctgcag ccagaagatt    300
tcgctaacta ctactgtcag caggctaact ctttcccatg gaccttcggt ggtggtacca    360
aagttgaaat caaatccgga gggtcgacca taacttcgta taatgtatac tatacgaagt    420
tatcctcgag cggtacccag gttcagctgg ttcagtctgg tgaagtt aaaaaaccag       480
gtgcttctgt taaagtttct tgtaaagttt ctggttacac cctgtctgat ctgtctatcc    540
actgggttcg tcaggctcca ggtaaaggtc tggaatggat gggtggtttc gatccacagg    600
atggtgaaac catctacgct cagaaattcc agggtcgtgt taccatgacc gaagatacct    660
ctaccgatac cgcttacatg gaactgtctt ctctgaaatc tgaggacacg gccgtgtatt    720
actgtgctac cggttcttct tcttcttggt tcgatccatg gggtcaggga accctggtca    780
ccgtctcctc agctagcggc aaaccaatcc caaacccact gctgggc                  827

SEQ ID NO: 141           moltype = DNA  length = 824
FEATURE                  Location/Qualifiers
misc_feature             1..824
                         note = Oligonucleotide
source                   1..824
                         mol_type = other DNA
                         organism = synthetic construct
SEQUENCE: 141
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctaca gagaccatgg ccagtaaggc cggtctctgg tgttccatct cgtttctctg    240
gttctggttc tggtaccgat tcacccctga ccatctcttc tctgcagcca gaagatttcg    300
ctaactacta ctgtcagcag gctaactctt tcccatgggac cttcggtggt ggtaccaaag    360
ttgaaatcaa atccggaggg tcgaccataa cttcgtataa tgtatactat acgaagttat    420
cctcgagcgg tacccaggtt cagctggttc agtctggtgc tgaagttaaa aaaccaggtg    480
cttctgttaa agtttcttgt aaagtttctg gttacaccct gtctgatctg tctatccact    540
gggttcgtca ggctccaggt aaaggtctgg aatggatggg tggtttcgat ccacaggatg    600
gtgaaaccat ctacgctcag aaattccagg gtcgtgttac catgaccgaa gatacctcta    660
ccgataccgc ttacatggaa ctgtcttctc tgaaatctga ggacacggcc gtgtattact    720
gtgctaccgg ttcttcttct tcttggttcg atccatgggg tcagggaacc ctggtcaccg    780
tctcctcagc tagcggcaaa ccaatcccaa acccactgct gggc                     824

SEQ ID NO: 142           moltype = DNA  length = 818
FEATURE                  Location/Qualifiers
misc_feature             1..818
                         note = Oligonucleotide
source                   1..818
                         mol_type = other DNA
                         organism = synthetic construct
SEQUENCE: 142
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctacg gtgcttctaa cctggaatct ggtgttccat ctcgtttctc tggttctggt    240
tctggtaccg atttcaccct gaccatctct tctctgcagc cagaagattt cgctaactac    300
tactgtagag accatggcca gtaaggccgg tctctttcgg tggtggtacc aaagttgaaa    360
tcaaatccgg agggtcgacc ataacttcgt ataatgtata ctatacgaag ttatcctcga    420
gcggtaccca ggttcagctg gttcagtctg gtgctgaagt taaaaaaccag gtgcttctg    480
ttaaagtttc ttgtaaagtt tctggttaca ccctgtctga tctgtctatc cactgggttc    540
gtcaggctcc aggtaaaggt ctggaatgga tgggtggttt cgatccacag gatggtgaaa    600
ccatctacgc tcagaaattc cagggtcgtg ttaccatgac cgaagatacc tctaccgata    660
ccgcttacat ggaactgtct tctctgaaat ctgaggacac ggccgtgtat tactgtgcta    720
ccggttcttc ttcttcttgg ttcgatccat ggggtcaggg aaccctggtc accgtctcct    780
cagctagcgg caaaccaatc ccaaacccac tgctgggc                            818

SEQ ID NO: 143           moltype = DNA  length = 821
FEATURE                  Location/Qualifiers
misc_feature             1..821
                         note = Oligonucleotide
```

|            |                                 |     |
|------------|---------------------------------|-----|
| source     | 1..821                          |     |
|            | mol_type = other DNA            |     |
|            | organism = synthetic construct  |     |

SEQUENCE: 143
```
cagttagata aaagaggcgc ggcagcaagc ggcgcgcatg ccgatatcca gatgacccag   60
tctccatctt ctgtttctgc ttctgttggt gatcgtgtta ctattacctg tcgtgcttct  120
cagggtatct cttcttggct ggcttggtac cagcagaaac caggtaaagc tccaaaactg  180
ctgatctacg gtgcttctaa cctggaatct ggtgttccat ctcgtttctc tggttctggt  240
tctggtaccg atttcaccct gaccatctct tctctgcagc cagaagattt cgctaactac  300
tactgtcagc aggctaactc tttcccatgg accttcggtg gtggtaccaa agttgaaatc  360
aaatccggag ggtcgaccat aacttcgtat aatgtatact atacgaagtt atcctcgagc  420
ggtacccagg ttcagctggt tcagtctggt gctgaagtta aaaaccagg tgcttctgtt  480
aaagtttctt gtaaagtttc tagagaccat ggccagtaag gccggtctct atccactggg  540
ttcgtcaggc tccaggtaaa ggtctggaat ggatgggttt cgatcca caggatggtg  600
aaaccatcta cgctcagaaa ttccagggtc gtgttaccat gaccgaagat acctctaccg  660
ataccgctta catggaactg tcttctctga aatctgagga cacggccgtg tattactgtg  720
ctaccggttc ttcttcttct tggttcgatc catgggtca gggaaccctg gtcaccgtct  780
cctcagctag cggcaaacca atcccaaacc cactgctggg c                     821
```

|            |                                 |     |
|------------|---------------------------------|-----|
| SEQ ID NO: 144 | moltype = DNA  length = 821 |     |
| FEATURE    | Location/Qualifiers             |     |
| misc_feature | 1..821                        |     |
|            | note = Oligonucleotide          |     |
| source     | 1..821                          |     |
|            | mol_type = other DNA            |     |
|            | organism = synthetic construct  |     |

SEQUENCE: 144
```
cagttagata aaagaggcgc ggcagcaagc ggcgcgcatg ccgatatcca gatgacccag   60
tctccatctt ctgtttctgc ttctgttggt gatcgtgtta ctattacctg tcgtgcttct  120
cagggtatct cttcttggct ggcttggtac cagcagaaac caggtaaagc tccaaaactg  180
ctgatctacg gtgcttctaa cctggaatct ggtgttccat ctcgtttctc tggttctggt  240
tctggtaccg atttcaccct gaccatctct tctctgcagc cagaagattt cgctaactac  300
tactgtcagc aggctaactc tttcccatgg accttcggtg gtggtaccaa agttgaaatc  360
aaatccggag ggtcgaccat aacttcgtat aatgtatact atacgaagtt atcctcgagc  420
ggtacccagg ttcagctggt tcagtctggt gctgaagtta aaaaccagg tgcttctgtt  480
aaagtttctt gtaaagtttc tggttacacc ctgtctgatc tgtctatcca ctgggttcgt  540
caggctccag gtaaaggtct ggaatggatg gtggtagag accatggcca gtaaggccgg  600
tctctatcta cgctcagaaa ttccagggtc gtgttaccat gaccgaagat acctctaccg  660
ataccgctta catggaactg tcttctctga aatctgagga cacggccgtg tattactgtg  720
ctaccggttc ttcttcttct tggttcgatc catgggtca gggaaccctg gtcaccgtct  780
cctcagctag cggcaaacca atcccaaacc cactgctggg c                     821
```

|            |                                 |     |
|------------|---------------------------------|-----|
| SEQ ID NO: 145 | moltype = DNA  length = 803 |     |
| FEATURE    | Location/Qualifiers             |     |
| misc_feature | 1..803                        |     |
|            | note = Oligonucleotide          |     |
| source     | 1..803                          |     |
|            | mol_type = other DNA            |     |
|            | organism = synthetic construct  |     |

SEQUENCE: 145
```
cagttagata aaagaggcgc ggcagcaagc ggcgcgcatg ccgatatcca gatgacccag   60
tctccatctt ctgtttctgc ttctgttggt gatcgtgtta ctattacctg tcgtgcttct  120
cagggtatct cttcttggct ggcttggtac cagcagaaac caggtaaagc tccaaaactg  180
ctgatctacg gtgcttctaa cctggaatct ggtgttccat ctcgtttctc tggttctggt  240
tctggtaccg atttcaccct gaccatctct tctctgcagc cagaagattt cgctaactac  300
tactgtcagc aggctaactc tttcccatgg accttcggtg gtggtaccaa agttgaaatc  360
aaatccggag ggtcgaccat aacttcgtat aatgtatact atacgaagtt atcctcgagc  420
ggtacccagg ttcagctggt tcagtctggt gctgaagtta aaaaccagg tgcttctgtt  480
aaagtttctt gtaaagtttc tggttacacc ctgtctgatc tgtctatcca ctgggttcgt  540
caggctccag gtaaaggtct ggaatggatg gtggtttcg atccacagga tggtgaaacc  600
atctacgctc agaaattcca gggtcgtgtt accatgaccg aagatacctc taccgatacc  660
gcttacatgg aactgtcttc tctgaaatct gaggacacgg ccgtgtatta ctgtagagac  720
catggccagt aaggccggtc tctggaaccc tggtcaccgt ctcctcagct agcggcaaac  780
caatcccaaa cccactgctg ggc                                          803
```

|            |                                 |     |
|------------|---------------------------------|-----|
| SEQ ID NO: 146 | moltype = DNA  length = 834 |     |
| FEATURE    | Location/Qualifiers             |     |
| misc_feature | 1..834                        |     |
|            | note = Oligonucleotide          |     |
| source     | 1..834                          |     |
|            | mol_type = other DNA            |     |
|            | organism = synthetic construct  |     |

SEQUENCE: 146
```
cagttagata aaagaggcgc ggcagcaagc ggcgcgcatg ccgatatcgt tatgacccag   60
tctccagatt ctctggctgt ttctctgggt gaacgtgcta ccatcaactg caaatcttct  120
cagtctctgc tgaactctgg taaccagaaa aactacctgg cttggtacca gcagaaacca  180
ggtcagccac caaaactgct gatctacggt gcttctaccc gtgaatctgg tgttccagat  240
cgtttctctg gttctggttc tggtaccgat ttcaccctga ccatctcttc tctgcaggct  300
gaagatgttg ctgtttacta ctgtcagaac gttcactctt tcccattcac cttcggtggt  360
```

```
ggtaccaaag ttgaaatcaa atccggaggg tcgaccataa cttcgtataa tgtatactat    420
acgaagttat cctcgagcgg tacccaggtt accctgcgtg aatctggtcc agctctggtt    480
aaaccaaccc agaccctgac cctgacctgt accgtttctg gtttctctct gtctgcttac    540
tctgttaact ggatccgtca gccaccaggt aaagctctgg aatggctggc tatgatctgg    600
ggtgatggta aaatcgttta caactctgct ctgaaatctg gtctgaccat ctctaaagat    660
acctctaaaa accaggttgt tctgaccatg accaacatgg atcctgtgga cacagccaca    720
tattactgtg ctggtgatgg ttactaccca tacgctatgg ataactgggg tcagggaacc    780
ctggtcaccg tctcctcagc tagcggcaaa ccaatcccaa acccactgct gggc           834

SEQ ID NO: 147          moltype = DNA   length = 827
FEATURE                 Location/Qualifiers
misc_feature            1..827
                        note = Oligonucleotide
source                  1..827
                        mol_type = other DNA
                        organism = synthetic construct
SEQUENCE: 147
cagttagata aaagaggcgc ggcagcaagc ggcgcgcatg ccgatatcgt tatgacccag     60
tctccagatt ctctggctgt ttctctgggt gaacgtgcta ccatcaactg caaatcttct    120
agagaccatg gccagtaagg ccggtctctc tggcttggta ccagcagaaa ccaggtcagc    180
caccaaaact gctgatctac ggtgcttcta cccgtgaatc tggtgttcca gatcgtttct    240
ctggttctgg ttctggtacc gatttcaccc tgaccatctc ttctctgcag gctgaagatg    300
ttgctgttta ctactgtcag aacgttcact ctttcccatt caccttcggt ggtggtacca    360
aagttgaaat caaatccgga gggtcgacca taacttcgta taatgtatac tatacgaagt    420
tatcctcgag cggtacccag gttaccctgc gtgaatctgg tccagctctg gttaaaccaa    480
cccagaccct gaccctgacc tgtaccgttt ctggtttctc tctgtctgct tactctgtta    540
actggatccg tcagccacca ggtaaagctc tggaatggct ggctatgatc tggggtgatg    600
gtaaaatcgt ttacaactct gctctgaaat ctggtctgac catctctaaa gatacctcta    660
aaaaccaggt tgttctgacc atgaccaaca tggatcctgt ggacacagcc acatattact    720
gtgctggtga tggttactac ccatacgcta tggataactg gggtcaggga accctggtca    780
ccgtctcctc agctagcggc aaaccaatcc caaacccact gctgggc                   827

SEQ ID NO: 148          moltype = DNA   length = 842
FEATURE                 Location/Qualifiers
misc_feature            1..842
                        note = Oligonucleotide
source                  1..842
                        mol_type = other DNA
                        organism = synthetic construct
SEQUENCE: 148
cagttagata aaagaggcgc ggcagcaagc ggcgcgcatg ccgatatcgt tatgacccag     60
tctccagatt ctctggctgt ttctctgggt gaacgtgcta ccatcaactg caaatcttct    120
cagtctctgc tgaactctgg taaccagaaa aactacctgg cttggtacca gcagaaacca    180
ggtcagccac caaaactgct gatctacaga gaccatggcc agtaaggccg gtctctggtg    240
ttccagatcg tttctctggt tctggttctg gtaccgattt caccctgacc atctcttctc    300
tgcaggctga agatgttgct gtttactact gtcagaacgt tcactctttc ccattcacct    360
tcggtggtgg taccaaagtt gaaatcaaat ccggagggtc gaccataact tcgtataatg    420
tatactatac gaagttatcc tcgagcggta cccaggttac cctgcgtgaa tctggtccag    480
ctctggttaa accaacccag accctgaccc tgacctgtac cgtttctggt ttctctctgt    540
ctgcttactc tgttaactgg atccgtcagc caccaggtaa agctctggaa tggctggcta    600
tgatctgggg tgatggtaaa atcgtttaca actctgctct gaaatctggt ctgaccatct    660
ctaaagatac ctctaaaaac caggttgttc tgaccatgac caacatggat cctgtggaca    720
cagccacata ttactgtgct ggtgatggtt actacccata cgctatggat aactggggtc    780
agggaaccct ggtcaccgtc tcctcagcta gcggcaaacc aatcccaaac ccactgctgg    840
gc                                                                    842

SEQ ID NO: 149          moltype = DNA   length = 836
FEATURE                 Location/Qualifiers
misc_feature            1..836
                        note = Oligonucleotide
source                  1..836
                        mol_type = other DNA
                        organism = synthetic construct
SEQUENCE: 149
cagttagata aaagaggcgc ggcagcaagc ggcgcgcatg ccgatatcgt tatgacccag     60
tctccagatt ctctggctgt ttctctgggt gaacgtgcta ccatcaactg caaatcttct    120
cagtctctgc tgaactctgg taaccagaaa aactacctgg cttggtacca gcagaaacca    180
ggtcagccac caaaactgct gatctacggt gcttctaccc gtgaatctgg tgttccagat    240
cgtttctctg gttctggttc tggtaccgat ttcaccctga ccatctcttc tctgcaggct    300
gaagatgttg ctgtttacta ctgtagagac catggccagt aaggccggtc tctttcggtg    360
gtggtaccaa agttgaaatc aaatccggag ggtcgaccat aacttcgtat aatgtatact    420
atacgaagtt atcctcgagc ggtacccagg ttaccctgcg tgaatctggt ccagctctgg    480
ttaaaccaac ccagaccctg accctgacct gtaccgtttc tggtttctct ctgtctgctt    540
actctgttaa ctggatccgt cagccaccag gtaaagctct ggaatggctg gctatgatct    600
ggggtgatgg taaaatcgtt tacaactctg ctctgaaatc tggtctgacc atctctaaag    660
atacctctaa aaaccaggtt gttctgacca tgaccaacat ggatcctgtg gacacagcca    720
catattactg tgctggtgat ggttactacc catacgctat ggataactgg ggtcagggaa    780
ccctggtcac cgtctcctca gctagcggca aaccaatccc aaacccactg ctgggc         836
```

```
SEQ ID NO: 150              moltype = DNA   length = 837
FEATURE                     Location/Qualifiers
misc_feature                1..837
                            note = Oligonucleotide
source                      1..837
                            mol_type = other DNA
                            organism = synthetic construct
SEQUENCE: 150
cagttagata aaagaggcgc ggcagcaagc ggcgcgcatg ccgatatcgt tatgacccag    60
tctccagatt ctctggctgt ttctctgggt gaacgtgcta ccatcaactg caaatcttct   120
cagtctctgc tgaactctgg taaccagaaa aactacctgg cttggtacca gcagaaacca   180
ggtcagccac caaaactgct gatctacggt ttctacccgt gaatctggtg ttccagatcg   240
tttctctggt tctggttctg gtaccgattt caccctgacc atctcttctc tgcaggctga   300
agatgttgct gtttactact gtcagaacgt tcactctttc ccattcacct tcggtggtga   360
taccaaagtt gaaatcaaat ccggagggtc gaccataact tcgtataatg tatactatac   420
gaagttatcc tcgagcggta cccaggttac cctgcgtgaa tctggtccag ctctggttaa   480
accaaccccag accctgaccc tgacctgtac cgtttctaga gaccatggcc agtaaggccg   540
gtctctgtta actggatccg tcagccacca ggtaaagctc tggaatggct ggctatgatc   600
tggggtgatg gtaaaatcgt ttacaactct gctctgaaat ctcgtctgac catctctaaa   660
gatacctcta aaaccaggt tgttctgacc atgaccaaca tggatcctgt ggacacagcc   720
acatattact gtgctggtga tggttactac ccatacgcta tggataactg gggtcaggga   780
accctggtca ccgtctcctc agctagcggc aaaccaatcc caaacccact gctgggc     837

SEQ ID NO: 151              moltype = DNA   length = 845
FEATURE                     Location/Qualifiers
misc_feature                1..845
                            note = Oligonucleotide
source                      1..845
                            mol_type = other DNA
                            organism = synthetic construct
SEQUENCE: 151
cagttagata aaagaggcgc ggcagcaagc ggcgcgcatg ccgatatcgt tatgacccag    60
tctccagatt ctctggctgt ttctctgggt gaacgtgcta ccatcaactg caaatcttct   120
cagtctctgc tgaactctgg taaccagaaa aactacctgg cttggtacca gcagaaacca   180
ggtcagccac caaaactgct gatctacggt gcttctaccc gtgaatctgg tgttccagat   240
cgtttctctg gttctggttc tggtaccgat ttcaccctga ccatctcttc tctgcaggct   300
gaagatgttg ctgtttacta ctgtcagaac gttcactctt tcccattcac cttcggtggt   360
ggtaccaaag ttgaaatcaa atccggaggg tcgaccataa cttcgtataa tgtatactat   420
acgaagttat cctcgagcgg tacccaggtt accctgcgtg aatctggtcc agctctggtt   480
aaaccaaccc agaccctgac cctgacctgt accgtttctg gtttctctct gtctgcttac   540
tctgttaact ggatccgtca gccaccaggt aaagctctgg aatggctggc tatgagagac   600
catggccagt aaggccggtc tctatcgttt acaactctgc tctgaaatct cgtctgacca   660
tctctaaaga tacctctaaa aaccaggttg ttctgaccat gaccaacatg gatcctgtt   720
acacagccac atattactgt gctggtgatg gttactaccc atacgctatg gataactggg   780
gtcagggaac cctggtcacc gtctcctcag ctagcggcaa accaatccca aacccactgc   840
tgggc                                                               845

SEQ ID NO: 152              moltype = DNA   length = 818
FEATURE                     Location/Qualifiers
misc_feature                1..818
                            note = Oligonucleotide
source                      1..818
                            mol_type = other DNA
                            organism = synthetic construct
SEQUENCE: 152
cagttagata aaagaggcgc ggcagcaagc ggcgcgcatg ccgatatcgt tatgacccag    60
tctccagatt ctctggctgt ttctctgggt gaacgtgcta ccatcaactg caaatcttct   120
cagtctctgc tgaactctgg taaccagaaa aactacctgg cttggtacca gcagaaacca   180
ggtcagccac caaaactgct gatctacggt gcttctaccc gtgaatctgg tgttccagat   240
cgtttctctg gttctggttc tggtaccgat ttcaccctga ccatctcttc tctgcaggct   300
gaagatgttg ctgtttacta ctgtcagaac gttcactctt tcccattcac cttcggtggt   360
ggtaccaaag ttgaaatcaa atccggaggg tcgaccataa cttcgtataa tgtatactat   420
acgaagttat cctcgagcgg tacccaggtt accctgcgtg aatctggtcc agctctggtt   480
aaaccaaccc agaccctgac cctgacctgt accgtttctg gtttctctct gtctgcttac   540
tctgttaact ggatccgtca gccaccaggt aaagctctgg aatggctggc tatgatcgg   600
ggtgatggta aaatcgttta caactctgct ctgaaatctc gtctgaccat ctctaaagat   660
acctctaaaa accaggttgt tctgaccatg accaacatgg atcctgtgga cacagccaca   720
tattactgta gagaccatgg ccagtaaggc cggtctctgg aaccctggtc accgtctcct   780
cagctagcgg caaaccaatc ccaaacccac tgctgggc                           818

SEQ ID NO: 153              moltype = DNA   length = 813
FEATURE                     Location/Qualifiers
misc_feature                1..813
                            note = Oligonucleotide
source                      1..813
                            mol_type = other DNA
                            organism = synthetic construct
SEQUENCE: 153
cagttagata aaagaggcgc ggcagcaagc ggcgcgcatg ccgatatcgt tatgacccag    60
```

```
tctccactgt ctctgccagt taccccaggt gaaccagctt ctatttcttg tcgttcttct    120
cagtctctgg tttactctaa cggtgatacc tacctgcact ggtacctgca gaaaccaggt    180
cagtctccac agctgctgat ctacaaagtt tctaaccgtt tctctggtgt tccagatcgt    240
ttctctggtt ctggttctgg taccgatttc accctgaaaa tctctcgtgt tgaagctgaa    300
gatgttggtg tttactactg ttctcagtct acccacgttc catggacctt cggtggtggt    360
accaaagttg aaatcaaatc cggagggtcg accataactt cgtataatgt atactatacg    420
aagttatcct cgagcggtac cgaagttcag ctggttgaat ctggtggtgg tctggttcag    480
ccaggtggtt ctctgcgtct gtcttgtgct gcttctggtt tcaccttctc ttcttacggt    540
atgtcttggg ttcgtcaggc tccaggtaaa ggtctggaac tggttgcttc tatcaactct    600
aacggtggtt ctacctacta cccagattct gttaaaggtc gtttcaccat ctctcgtgat    660
aacgctaaaa actctctgta cctgcagatg aactctctgc gtgccgagga cacggctgtg    720
tattactgtg cttctggtga ttactggggt caggggacca cggtcaccgt ctcctcagct    780
agcggcaaac caatcccaaa cccactgctg ggc                                 813

SEQ ID NO: 154           moltype = DNA   length = 809
FEATURE                  Location/Qualifiers
misc_feature             1..809
                         note = Oligonucleotide
source                   1..809
                         mol_type = other DNA
                         organism = synthetic construct
SEQUENCE: 154
cagttagata aaagaggcgc ggcagcaagc ggcgcgcatg ccgatatcgt tatgacccag     60
tctccactgt ctctgccagt taccccaggt gaaccagctt ctatttcttg tcgttcttct    120
agagaccatg gccagtaagg ccggtctctc tgcactggta cctgcagaaa ccaggtcagt    180
ctccacagct gctgatctac aaagtttcta accgtttctc tggtgttcca gatcgtttct    240
ctggttctgg ttctggtacc gatttcaccc tgaaaatctc tcgtgttgaa gctgaagatg    300
ttggtgttta ctactgttct cagtctaccc acgttccatg gaccttcggt ggtggtacca    360
aagttgaaat caaatccgga gggtcgacca taacttcgta taatgtatac tatacgaagt    420
tatcctcgag cggtaccgaa gttcagctgg ttgaatctgg tggtggtctg gttcagccag    480
gtggttctct gcgtctgtct tgtgctgctt ctggtttcac cttctcttct tacggtatgt    540
cttgggttcg tcaggctcca ggtaaaggtc tggaactggt tgcttctatc aactctaacg    600
gtggttctac ctactaccca gattctgtta aaggtcgttt caccatctct cgtgataacg    660
ctaaaaactc tctgtacctg cagatgaact ctctgcgtgc cgaggacacg gctgtgtatt    720
actgtgcttc tggtgattac tggggtcagg ggaccacggt caccgtctcc tcagctagcg    780
gcaaaccaat cccaaaccca ctgctgggc                                      809

SEQ ID NO: 155           moltype = DNA   length = 821
FEATURE                  Location/Qualifiers
misc_feature             1..821
                         note = Oligonucleotide
source                   1..821
                         mol_type = other DNA
                         organism = synthetic construct
SEQUENCE: 155
cagttagata aaagaggcgc ggcagcaagc ggcgcgcatg ccgatatcgt tatgacccag     60
tctccactgt ctctgccagt taccccaggt gaaccagctt ctatttcttg tcgttcttct    120
cagtctctgg tttactctaa cggtgatacc tacctgcact ggtacctgca gaaaccaggt    180
cagtctccac agctgctgat ctacagagac catggccagt aaggccggtc tctggtgttc    240
cagatcgttt ctctggttct ggttctggta ccgatttcac cctgaaaatc tctcgtgttg    300
aagctgaaga tgttggtgtt tactactgtt ctcagtctac ccacgttcca tggaccttcg    360
gtggtggtac caaagttgaa atcaaatccg gagggtcgac cataacttcg tataatgtat    420
actatacgaa gttatcctcg agcggtaccg aagttcagct ggttgaatct ggtggtggtc    480
tggttcagcc aggtggttct ctgcgtctgt cttgtgctgc ttctggtttc accttctctt    540
cttacggtat gtcttgggtt cgtcaggctc caggtaaagg tctggaactg gttgcttcta    600
tcaactctaa cggtggttct acctactacc cagattctgt taaaggtcgt ttcaccatct    660
ctcgtgataa cgctaaaaac tctctgtacc tgcagatgaa ctctctgcgt gccgaggaca    720
cggctgtgta ttactgtgct tctggtgatt actggggtca ggggaccacg gtcaccgtct    780
cctcagctag cggcaaacca atcccaaacc cactgctggg c                        821

SEQ ID NO: 156           moltype = DNA   length = 815
FEATURE                  Location/Qualifiers
misc_feature             1..815
                         note = Oligonucleotide
source                   1..815
                         mol_type = other DNA
                         organism = synthetic construct
SEQUENCE: 156
cagttagata aaagaggcgc ggcagcaagc ggcgcgcatg ccgatatcgt tatgacccag     60
tctccactgt ctctgccagt taccccaggt gaaccagctt ctatttcttg tcgttcttct    120
cagtctctgg tttactctaa cggtgatacc tacctgcact ggtacctgca gaaaccaggt    180
cagtctccac agctgctgat ctacaaagtt tctaaccgtt tctctggtgt tccagatcgt    240
ttctctggtt ctggttctgg taccgatttc accctgaaaa tctctcgtgt tgaagctgaa    300
gatgttggtg tttactactg tagagaccat ggccagtaag gccggtctct tgcggtggtg    360
gtaccaaagt tgaaatcaaa tccgagggtc gaccataac ttcgtataat gtatactata    420
cgaagttatc tcgagcggt accgaagttc agctggttga atctggtggt ggtctggttc    480
agccaggtgg ttctctgcgt ctgtcttgtg ctgcttctgg tttcaccttc tcttcttacg    540
gtatgtcttg ggttcgtcag gctccaggta aaggtctgga actggttgct tctatcaact    600
ctaacggtgg ttctacctac tacccagatt ctgttaaagg tcgtttcacc atctctcgtg    660
```

```
ataacgctaa aaactctctg tacctgcaga tgaactctct gcgtgccgag gacacggctg   720
tgtattactg tgcttctggt gattactggg gtcaggggac cacggtcacc gtctcctcag   780
ctagcggcaa accaatccca aacccactgc tgggc                              815
```

```
SEQ ID NO: 157          moltype = DNA   length = 818
FEATURE                 Location/Qualifiers
misc_feature            1..818
                        note = Oligonucleotide
source                  1..818
                        mol_type = other DNA
                        organism = synthetic construct
SEQUENCE: 157
cagttagata aaagaggcgc ggcagcaagc ggcgcgcatg ccgatatcgt tatgacccag    60
tctccactgt ctctgccagt taccccaggt gaaccagctt ctatttcttg tcgttcttct   120
cagtctctgg tttactctaa cggtgatacc tacctgcact ggtacctgca gaaaccaggt   180
cagtctccac agctgctgat ctacaaagtt tctaaccgtt tctctggtgt tccagatcgt   240
ttctctggtt ctggttctgg taccgatttc accctgaaaa tctctcgtgt tgaagctgaa   300
gatgttggtg tttactactg ttctcagtct acccacgttc catggacctt cggtggtggt   360
accaaagttg aaatcaaatc cggagggtcg accataactt cgtataatgt atactatacg   420
aagttatcct cgagcggtac cgaagttcag ctggttgaat ctggtggtgg tctggttcag   480
ccaggtggtt ctctgcgtct gtcttgtgct gcttctagag accatggcca gtaaggccgg   540
tctctatgtc ttgggttcgt caggctccag gtaaaggtct ggaactggtt gcttctatca   600
actctaacgg tggttctacc tactacccag attctgttaa aggtcgtttc accatctctc   660
gtgataacgc taaaaactct ctgtacctgc agatgaactc tctgcgtgcc gaggacacgg   720
ctgtgtatta ctgtgcttct ggtgattact ggggtcaggg gaccacggtc accgtctcct   780
cagctagcgg caaaccaatc ccaaacccac tgctgggc                           818
```

```
SEQ ID NO: 158          moltype = DNA   length = 818
FEATURE                 Location/Qualifiers
misc_feature            1..818
                        note = Oligonucleotide
source                  1..818
                        mol_type = other DNA
                        organism = synthetic construct
SEQUENCE: 158
cagttagata aaagaggcgc ggcagcaagc ggcgcgcatg ccgatatcgt tatgacccag    60
tctccactgt ctctgccagt taccccaggt gaaccagctt ctatttcttg tcgttcttct   120
cagtctctgg tttactctaa cggtgatacc tacctgcact ggtacctgca gaaaccaggt   180
cagtctccac agctgctgat ctacaaagtt tctaaccgtt tctctggtgt tccagatcgt   240
ttctctggtt ctggttctgg taccgatttc accctgaaaa tctctcgtgt tgaagctgaa   300
gatgttggtg tttactactg ttctcagtct acccacgttc catggacctt cggtggtggt   360
accaaagttg aaatcaaatc cggagggtcg accataactt cgtataatgt atactatacg   420
aagttatcct cgagcggtac cgaagttcag ctggttgaat ctggtggtgg tctggttcag   480
ccaggtggtt ctctgcgtct gtcttgtgct gcttctggtt tcaccttctc ttcttacggt   540
atgtcttggg ttcgtcaggc tccaggtaaa ggtctggaac tggttgcttc tagagaccat   600
ggccagtaag gccggtctct tactacccag attctgttaa aggtcgtttc accatctctc   660
gtgataacgc taaaaactct ctgtacctgc agatgaactc tctgcgtgcc gaggacacgg   720
ctgtgtatta ctgtgcttct ggtgattact ggggtcaggg gaccacggtc accgtctcct   780
cagctagcgg caaaccaatc ccaaacccac tgctgggc                           818
```

```
SEQ ID NO: 159          moltype = DNA   length = 818
FEATURE                 Location/Qualifiers
misc_feature            1..818
                        note = Oligonucleotide
source                  1..818
                        mol_type = other DNA
                        organism = synthetic construct
SEQUENCE: 159
cagttagata aaagaggcgc ggcagcaagc ggcgcgcatg ccgatatcgt tatgacccag    60
tctccactgt ctctgccagt taccccaggt gaaccagctt ctatttcttg tcgttcttct   120
cagtctctgg tttactctaa cggtgatacc tacctgcact ggtacctgca gaaaccaggt   180
cagtctccac agctgctgat ctacaaagtt tctaaccgtt tctctggtgt tccagatcgt   240
ttctctggtt ctggttctgg taccgatttc accctgaaaa tctctcgtgt tgaagctgaa   300
gatgttggtg tttactactg ttctcagtct acccacgttc catggacctt cggtggtggt   360
accaaagttg aaatcaaatc cggagggtcg accataactt cgtataatgt atactatacg   420
aagttatcct cgagcggtac cgaagttcag ctggttgaat ctggtggtgg tctggttcag   480
ccaggtggtt ctctgcgtct gtcttgtgct gcttctggtt tcaccttctc ttcttacggt   540
atgtcttggg ttcgtcaggc tccaggtaaa ggtctggaac tggttgcttc tatcaactct   600
aacggttgct tacctacta cccagattct gttaaaggtc gtttccaccat ctctcgtgat   660
aacgctaaaa actctctgta cctgcagatg aactctctgc gtgccgagga cacggctgtg   720
tattactgta gagaccatgg ccagtaaggc cggtctctgg gaccacggtc accgtctcct   780
cagctagcgg caaaccaatc ccaaacccac tgctgggc                           818
```

```
SEQ ID NO: 160          moltype = DNA   length = 825
FEATURE                 Location/Qualifiers
misc_feature            1..825
                        note = Oligonucleotide
source                  1..825
                        mol_type = other DNA
```

-continued

```
                        organism = synthetic construct
SEQUENCE: 160
cagttagata aaagaggcgc ggcagcaagc ggcgcgcatg ccgaaatcgt tatgacccag   60
tctccagcta ccctgtctct gtctccaggt gaacgtgcca ctctgtcttg tcgtgcttc   120
cagtctgttt cttcttacct ggcttggtac cagcagaaac caggtcaggc tccacgtctg  180
ctgatctacg atgcttctaa ccgtgctacc ggtatcccag ctcgtttctc tggttctggt  240
tctggtaccg atttcaccct gaccatctct tctctggaac cagaagattt cgctgtttac  300
tactgtcacc agtacggttc taccccactg accttcggtg gtggtaccaa agttgaaatc  360
aaatccggag ggtcgaccat aacttcgtat aatgtatact atacgaagtt atcctcgagc  420
ggtacccagg ttcagctgca ggaatctggt ccaggtctgg ttaaaccatc tcagacccctg 480
tctctgacct gtaccgtttc tggtggttct atctcttctg gtgattacta ctggtcttgg  540
atccgtcagc caccaggtaa aggtctggaa tggatcggtt acatctacta ctctggttct  600
accgattaca acccatctct gaaatctcgt gttaccatgt ctgttgatac ctctaaaaac  660
cagttctctc tgaaagttaa ctctgttacc gccgcgaca cggctgtgta ttactgtgcc  720
cgtgtttcta tcttcggtgt tggtaccttc gattactggg gtcagggaac cctggtcacc  780
gtctcctcag ctagcggcaa accaatccca aacccactgc tgggc             825

SEQ ID NO: 161        moltype = DNA    length = 836
FEATURE               Location/Qualifiers
misc_feature          1..836
                      note = Oligonucleotide
source                1..836
                      mol_type = other DNA
                      organism = synthetic construct
SEQUENCE: 161
cagttagata aaagaggcgc ggcagcaagc ggcgcgcatg ccgaaatcgt tatgacccag   60
tctccagcta ccctgtctct gtctccaggt gaacgtgcca ctctgtcttg tcgtgcttct  120
agagaccatg gccagtaagg ccggtctctc tggcttggta ccagcagaaa ccaggtcagg  180
ctccacgtct gctgatctac gatgcttcta accgtgctac cggtatccca gctcgtttct  240
ctggttctgg ttctggtacc gatttcaccc tgaccatctc ttctctggaa ccagaagatt  300
tcgctgttta ctactgtcac cagtacggtt ctaccccact gaccttcggt ggtggtacca  360
aagttgaaat caaatccgga gggtcgacca taacttcgta taatgtatac tatacgaagt  420
tatcctcgag cggtacccag gttcagctgc aggaatctgg tccaggtctg gttaaaccat  480
ctcagaccct gtctctgacc tgtaccgttt ctggtggttc tatctcttct ggtgattact  540
actggtcttg gatccgtcag ccaccaggta aaggtctgga atggatcggt tacatctact  600
actctggttc taccgattac aacccatctc tgaaatctcg tgttaccatg tctgttgata  660
cctctaaaaa ccagttctct ctgaaagtta actctgttac cgccgcgac acggctgtgt   720
attactgtgc tcgtgtttct atcttcggtg ttggtacctt cgattactgg ggtcagggaa  780
ccctggtcac cgtctcctca gctagcggca aaccaatccc aaacccactg ctgggc      836

SEQ ID NO: 162        moltype = DNA    length = 833
FEATURE               Location/Qualifiers
misc_feature          1..833
                      note = Oligonucleotide
source                1..833
                      mol_type = other DNA
                      organism = synthetic construct
SEQUENCE: 162
cagttagata aaagaggcgc ggcagcaagc ggcgcgcatg ccgaaatcgt tatgacccag   60
tctccagcta ccctgtctct gtctccaggt gaacgtgcca ctctgtcttg tcgtgcttct  120
cagtctgttt cttcttacct ggcttggtac cagcagaaac caggtcaggc tccacgtctg  180
ctgatctaca gagaccatgg ccagtaaggc cggtctctgg tatccagct cgtttctctg  240
gttctggttc tggtaccgat ttcaccctga ccatctcttc tctggaacca gaagatttcg  300
ctgtttacta ctgtcaccag tacggttcta ccccactgac cttcggtggt ggtaccaaag  360
ttgaaatcaa atccggaggg tcgaccataa cttcgtata tgtatactat acgaagttat  420
cctcgagcgg tacccaggtt cagctgcagg aatctggtcc aggtctggtt aaaccatctc  480
agaccctgtc tctgacctgt accgtttctg gtggttctat ctcttctggt gattactact  540
ggtcttggat ccgtcagcca ccaggtaaag gtctggaatg gatcggttac atctactact  600
ctggttctac cgattacaac ccatctctga aatctcgtgt taccatgtct gttgatacct  660
ctaaaaacca gttctctctg aaagttaact ctgttaccgc cgcgacacg gctgtgtatt   720
actgtgctcg tgtttctatc ttcggtgttg gtaccttcga ttactggggt cagggaaccc  780
tggtcaccgt ctcctcagct agcggcaaac caatcccaaa cccactgctg ggc          833

SEQ ID NO: 163        moltype = DNA    length = 827
FEATURE               Location/Qualifiers
misc_feature          1..827
                      note = Oligonucleotide
source                1..827
                      mol_type = other DNA
                      organism = synthetic construct
SEQUENCE: 163
cagttagata aaagaggcgc ggcagcaagc ggcgcgcatg ccgaaatcgt tatgacccag   60
tctccagcta ccctgtctct gtctccaggt gaacgtgcca ctctgtcttg tcgtgcttct  120
cagtctgttt cttcttacct ggcttggtac cagcagaaac caggtcaggc tccacgtctg  180
ctgatctacg atgcttctaa ccgtgctacc ggtatcccag ctcgtttctc tggttctggt  240
tctggtaccg atttcaccct gaccatctct tctctggaac cagaagattt cgctgtttac  300
tactgtagag accatggcca gtaaggccgg tctctttcgg tggtggtacc aaagttgaaa  360
tcaaatccgg agggtcgacc ataacttcgt ataatgtata ctatacgaag ttatcctcga  420
gcggtaccca ggttcagctg caggaatctg gtccaggtct ggttaaacca tctcagaccc  480
```

```
tgtctctgac ctgtaccgtt tctggtggtt ctatctcttc tggtgattac tactggtctt    540
ggatccgtca gccaccaggt aaaggtctgg aatggatcgg ttacatctac tactctggtt    600
ctaccgatta caacccatct ctgaaatctc gtgttaccat gtctgttgat acctctaaaa    660
accagttctc tctgaaagtt aactctgtta ccgccgcgga cacggctgtg tattactgtg    720
ctcgtgtttc tatcttcggt gttggtacct tcgattactg ggtcaggga accctggtca    780
ccgtctcctc agctagcggc aaaccaatcc caaacccact gctgggc                  827

SEQ ID NO: 164              moltype = DNA  length = 824
FEATURE                     Location/Qualifiers
misc_feature                1..824
                            note = Oligonucleotide
source                      1..824
                            mol_type = other DNA
                            organism = synthetic construct
SEQUENCE: 164
cagttagata aaagaggcgc ggcagcaagc ggcgcgcatg ccgaaatcgt tatgacccag     60
tctccagcta ccctgtctct gtctccaggt gaacgtgcca ctctgtcttg tcgtgcttct    120
cagtctgttt cttcttacct ggcttggtac cagcagaaac caggtcaggc tccacgtctg    180
ctgatctacg atgcttctaa ccgtgctacc ggtatcccag ctcgtttctc tggttctggt    240
tctggtaccg atttcaccct gaccatctct tctctggaac cagaagattt cgctgtttac    300
tactgtcacc agtacggttc taccccactg accttcggtg tggtaccaa agttgaaatc    360
aaatccggag ggtcgaccat aacttcgtat aatgtatact atacgaagtt atcctcgagc    420
ggtacccagg ttcagctgca ggaatctggt ccaggtctgg ttaaaccatc tcagaccctg    480
tctctgacct gtaccgtttc tagagaccat ggccagtaag gccggtctct tggtcttgga    540
tccgtcagcc accaggtaaa ggtctggaat ggatcggtta catctactac tctggttcta    600
ccgattacaa cccatctctg aaatctcgtg ttaccatgtc tgttgatacc tctaaaaacc    660
agttctctct gaaagttaac tctgttaccg ccgcggacac ggctgtgtat tactgtctc    720
gtgtttctat cttcggtgtt ggtaccttcg attactgggg tcaggaacc ctggtcaccg    780
tctcctcagc tagcggcaaa ccaatcccaa acccactgct gggc                     824

SEQ ID NO: 165              moltype = DNA  length = 833
FEATURE                     Location/Qualifiers
misc_feature                1..833
                            note = Oligonucleotide
source                      1..833
                            mol_type = other DNA
                            organism = synthetic construct
SEQUENCE: 165
cagttagata aaagaggcgc ggcagcaagc ggcgcgcatg ccgaaatcgt tatgacccag     60
tctccagcta ccctgtctct gtctccaggt gaacgtgcca ctctgtcttg tcgtgcttct    120
cagtctgttt cttcttacct ggcttggtac cagcagaaac caggtcaggc tccacgtctg    180
ctgatctacg atgcttctaa ccgtgctacc ggtatcccag ctcgtttctc tggttctggt    240
tctggtaccg atttcaccct gaccatctct tctctggaac cagaagattt cgctgtttac    300
tactgtcacc agtacggttc taccccactg accttcggtg tggtaccaa agttgaaatc    360
aaatccggag ggtcgaccat aacttcgtat aatgtatact atacgaagtt atcctcgagc    420
ggtacccagg ttcagctgca ggaatctggt ccaggtctgg ttaaaccatc tcagaccctg    480
tctctgacct gtaccgtttc tggtggttct atctcttcg gattacta ctggtcttgg     540
atccgtcagc caccaggtaa aggtctggaa tggatcggtt acagagacca tggccagtaa    600
ggccggtctc tgattacaac ccatctctga aatctcgtgt taccatgtct gttgatacct    660
ctaaaaacca gttctctctg aaagttaact ctgttaccgc cgcggacacg gctgtgtatt    720
actgtgctcg tgtttctatc ttcggtgttg gtaccttcga ttactgggt cagggaaccc    780
tggtcaccgt ctcctcagct agcggcaaac caatcccaaa cccactgctg ggc           833

SEQ ID NO: 166              moltype = DNA  length = 806
FEATURE                     Location/Qualifiers
misc_feature                1..806
                            note = Oligonucleotide
source                      1..806
                            mol_type = other DNA
                            organism = synthetic construct
SEQUENCE: 166
cagttagata aaagaggcgc ggcagcaagc ggcgcgcatg ccgaaatcgt tatgacccag     60
tctccagcta ccctgtctct gtctccaggt gaacgtgcca ctctgtcttg tcgtgcttct    120
cagtctgttt cttcttacct ggcttggtac cagcagaaac caggtcaggc tccacgtctg    180
ctgatctacg atgcttctaa ccgtgctacc ggtatcccag ctcgtttctc tggttctggt    240
tctggtaccg atttcaccct gaccatctct tctctggaac cagaagattt cgctgtttac    300
tactgtcacc agtacggttc taccccactg accttcggtg tggtaccaa agttgaaatc    360
aaatccggag ggtcgaccat aacttcgtat aatgtatact atacgaagtt atcctcgagc    420
ggtacccagg ttcagctgca ggaatctggt ccaggtctgg ttaaaccatc tcagaccctg    480
tctctgacct gtaccgtttc tggtggttct atctcttctg gtgattacta ctggtcttgg    540
atccgtcagc caccaggtaa aggtctggaa tggatcggtt acatctacta ctctggttct    600
accgattaca acccatctct gaaatctcgt gttaccatgt ctgttgatac ctctaaaaac    660
cagttctctc tgaaagttaa ctctgttacc gccgcggaca cggctgtgta ttactgtaga    720
gaccatggcc agtaaggccg gtctctggaa ccctggtcac gtctcctca gctagcgca    780
aaccaatccc aaacccactg ctgggc                                         806

SEQ ID NO: 167              moltype = DNA  length = 816
FEATURE                     Location/Qualifiers
misc_feature                1..816
```

```
                        note = Oligonucleotide
source                  1..816
                        mol_type = other DNA
                        organism = synthetic construct
SEQUENCE: 167
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct   120
cagtctgttt cttcttcttt cctggcttgg taccagcaga aaccaggtca ggctccacgt   180
ctgctgatct acggtgcttc ttctcgtgct accggtatcc cagatcgtct gtctggttct   240
ggttctggta ccgatttcac cctgaccatc accgtctctgg aaccagaaga tttcgctgtt   300
tactactgtc agcagtacga ttcttctgct atcaccttcg gtggtggtac caaagttgaa   360
atcaaatccg gagggtcgac cataacttcg tataatgtat actatacgaa gttatcctcg   420
agcggtaccg aagttcagct ggttcagtct ggtgctgaag ttaaaaaacc aggtgaatct   480
ctgaaaatct cttgtaaagg ttctggttac atcttcacca actactggat cgcttgggtt   540
cgtcaggttc caggtaaagg tctggaatct atgggtatca tctacccagg tgattctgat   600
atccgttact ctccatcttt ccagggtcag gttaccatct ctgctgataa atctatcacc   660
accgcttacc tgcagtggtc ttctctgaaa gcctcggaca ccgccattta ttactgtgct   720
cgtcacgata tcgaaggttt cgattactgg ggtcgtggaa ccctggtcac cgtctcctca   780
gctagcggca aaccccaatccc aaacccactg ctgggc                           816

SEQ ID NO: 168          moltype = DNA  length = 824
FEATURE                 Location/Qualifiers
misc_feature            1..824
                        note = Oligonucleotide
source                  1..824
                        mol_type = other DNA
                        organism = synthetic construct
SEQUENCE: 168
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct   120
agagaccatg gccagtaagg ccggtctctc tggcttggta ccagcagaaa ccaggtcagg   180
ctccacgtct gctgatctac ggtgcttctt ctcgtgctac cggtatccca gatcgtctgt   240
ctggttctgg ttctggtacc gatttcaccc tgaccatcac ccgtctggaa ccagaagatt   300
tcgctgttta ctactgtcag cagtacgatt cttctgctat caccttcggt ggtggtacca   360
aagttgaaat caaatccgga gggtcgacca taacttcgta taatgtatac tatacgaagt   420
tatcctcgag cggtaccgaa gttcagctgg ttcagtctgg tgctgaagtt aaaaaaccag   480
gtgaatctct gaaaatctct tgtaaaggtt ctggttacat cttccaccaac tactggatcg   540
cttgggttcg tcaggttcca ggtaaaggtc tggaatctat gggtatcatc tacccaggtg   600
attctgatat ccgttactct ccatctttcc agggtcaggt taccatctct gctgataaat   660
ctatcaccac cgcttacctg cagtggtctt ctctgaaagc ctcggacacc gccatttatt   720
actgtgctcg tcacgatatc gaaggtttcg attactgggg tcgtggaacc ctggtcaccg   780
tctcctcagc tagcggcaaa ccaatcccaa acccactgct gggc                    824

SEQ ID NO: 169          moltype = DNA  length = 824
FEATURE                 Location/Qualifiers
misc_feature            1..824
                        note = Oligonucleotide
source                  1..824
                        mol_type = other DNA
                        organism = synthetic construct
SEQUENCE: 169
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct   120
cagtctgttt cttcttcttt cctggcttgg taccagcaga aaccaggtca ggctccacgt   180
ctgctgatct acagagacca tggccagtaa ggccggtctc tggtatccca gatcgtctgt   240
ctggttctgg ttctggtacc gatttcaccc tgaccatcac ccgtctggaa ccagaagatt   300
tcgctgttta ctactgtcag cagtacgatt tttctgctat caccttcggt ggtggtacca   360
aagttgaaat caaatccgga gggtcgacca taacttcgta taatgtatac tatacgaagt   420
tatcctcgag cggtaccgaa gttcagctgg ttcagtctgg tgctgaagtt aaaaaaccag   480
gtgaatctct gaaaatctct tgtaaaggtt ctggttacat cttcaccaac tactggatcg   540
cttgggttcg tcaggttcca ggtaaaggtc tggaatctat gggtatcatc tacccaggtg   600
attctgatat ccgttactct ccatctttcc agggtcaggt taccatctct gctgataaat   660
ctatcaccac cgcttacctg cagtggtctt ctctgaaagc ctcggacacc gccatttatt   720
actgtgctcg tcacgatatc gaaggtttcg attactgggg tcgtggaacc ctggtcaccg   780
tctcctcagc tagcggcaaa ccaatcccaa acccactgct gggc                    824

SEQ ID NO: 170          moltype = DNA  length = 818
FEATURE                 Location/Qualifiers
misc_feature            1..818
                        note = Oligonucleotide
source                  1..818
                        mol_type = other DNA
                        organism = synthetic construct
SEQUENCE: 170
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct   120
cagtctgttt cttcttcttt cctggcttgg taccagcaga aaccaggtca ggctccacgt   180
ctgctgatct acggtgcttc ttctcgtgct accggtatcc cagatcgtct gtctggttct   240
ggttctggta ccgatttcac cctgaccatc accgtctctgg aaccagaaga tttcgctgtt   300
```

```
tactactgta gagaccatgg ccagtaaggc cggtctcttt cggtggtggt accaaagttg    360
aaatcaaatc cggagggtcg accataactt cgtataatgt atactatacg aagttatcct    420
cgagcggtac cgaagttcag ctggttcagt ctggtgctga agttaaaaaa ccaggtgaat    480
ctctgaaaat ctcttgtaaa ggttctggtt acatcttcac caactactgg atcgcttggg    540
ttcgtcaggt tccaggtaaa ggttctggaa tctatgggtat catctaccca ggtgattctg    600
atatccgtta ctctccatct ttccagggtc aggttaccat ctctgctgat aaatctatca    660
ccaccgctta cctgcagtgg tcttctctga agcctcgga caccgccatt tattactgtg    720
ctcgtcacga tatcgaaggt ttcgattact ggggtcgtgg aaccctggtc accgtctcct    780
cagctagcgg caaaccaatc ccaaacccac tgctgggc                            818
```

```
SEQ ID NO: 171           moltype = DNA   length = 821
FEATURE                  Location/Qualifiers
misc_feature             1..821
                         note = Oligonucleotide
source                   1..821
                         mol_type = other DNA
                         organism = synthetic construct
SEQUENCE: 171
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct    120
cagtctgttt cttcttcttt cctggcttgg taccagcaga aaccaggtca ggctccacgt    180
ctgctgatct acggtgcttc ttctcgtgct accggtatcc cagatcgtct gtctggttct    240
ggttctggta ccgatttcac cctgaccatc acccgtctgg aaccagaaga tttcgctgtt    300
tactactgtc agcagtacga ttcttctgct atccccttcg gtggtggtac caaagttgaa    360
atcaaatccg gagggtcgac cataacttcg tataatgtat actatacgaa gttatcctcg    420
agcggtaccg aagttcagct ggttcagtct ggtgctgaag ttaaaaaacc aggtgaatct    480
ctgaaaatct cttgtaaagg ttctagagac catggccagt aaggccggtc tctatcgctt    540
gggttcgtca ggttccaggt aaaggtctgg aatctatggg tatcatctac ccaggtgatt    600
ctgatatccg ttactctcca tctttccagg gtcaggttac catctctgct gataaatcta    660
tcaccaccgc ttacctgcag tggtcttctc tgaaagcctc ggaaccgcc atttattact    720
gtgctcgtca cgatatcgaa ggtttcgatt actggggtcg tggaaccctg gtcaccgtct    780
cctcagctag cggcaaacca atcccaaacc cactgctggg c                       821
```

```
SEQ ID NO: 172           moltype = DNA   length = 820
FEATURE                  Location/Qualifiers
misc_feature             1..820
                         note = Oligonucleotide
source                   1..820
                         mol_type = other DNA
                         organism = synthetic construct
SEQUENCE: 172
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct    120
cagtctgttt cttcttcttt cctggcttgg taccagcaga aaccaggtca ggctccacgt    180
ctgctgatct acggtgcttc ttctcgtgct accggtatcc cagatcgtct gtctggttct    240
ggttctggta ccgatttcac cctgaccatc acccgtctgg aaccagaaga tttcgctgtt    300
tactactgtc agcagtacga ttcttctgct atccccttcg gtggtggtac caaagttgaa    360
atcaaatccg gagggtcgac cataacttcg tataatgtat actatacgaa gttatcctcg    420
agcggtaccg aagttcagct ggttcagtct ggtgctgaag ttaaaaaacc aggtgaatct    480
ctgaaaatct cttgtaaagg ttctggttac atcttcacca ctactggat cgcttggggtt    540
cgtcaggttc caggtaaagg tctggaatct atgggtatca gagaccatgg ccagtaaggc    600
cggtctctcg ttactctcca tctttccagg gtcaggttac catctctgct gataaatcta    660
tcaccaccgc ttacctgcag tggtcttctc tgaaagcctc gacaccgcca tttattactg    720
tgctcgtcac gatatcgaag gtttcgatta ctggggtcgt ggaaccctgg tcaccgtctc    780
ctcagctagc ggcaaaccaa tcccaaaccc actgctgggc                          820
```

```
SEQ ID NO: 173           moltype = DNA   length = 806
FEATURE                  Location/Qualifiers
misc_feature             1..806
                         note = Oligonucleotide
source                   1..806
                         mol_type = other DNA
                         organism = synthetic construct
SEQUENCE: 173
cagttagata aaagaggcgc ggcagcaagc ggcgcgcatg ccgaaatcgt tctgacccag    60
tctccaggta ccctgtctct gtctccaggt gaacgtgcca ctctgtcttg tcgtgcttct    120
cagtctgttt cttcttcttt cctggcttgg taccagcaga aaccaggtca ggctccacgt    180
ctgctgatct acggtgcttc ttctcgtgct accggtatcc cagatcgtct gtctggttct    240
ggttctggta ccgatttcac cctgaccatc acccgtctgg aaccagaaga tttcgctgtt    300
tactactgtc agcagtacga ttcttctgct atccccttcg gtggtggtac caaagttgaa    360
atcaaatccg gagggtcgac cataacttcg tataatgtat actatacgaa gttatcctcg    420
agcggtaccg aagttcagct ggttcagtct ggtgctgaag ttaaaaaacc aggtgaatct    480
ctgaaaatct cttgtaaagg ttctggttac atcttcacca ctactggat cgcttggggtt    540
cgtcaggttc caggtaaagg tctggaatct atgggtatca tcacccagg tgattctgat    600
atccgttact ctccatcttt ccagggtcag gttaccatct ctgctgataa atctatcacc    660
accgcttacc tgcagtggtc ttctctgaaa gcctcggaca ccgccattta ttactgtaga    720
gaccatggca gtaaggccg gtctctgaa ccctggtcac gtctcctca gctagcggca      780
aaccaatccc aaacccactg ctgggc                                          806
```

SEQ ID NO: 174          moltype = DNA   length = 813
FEATURE                 Location/Qualifiers
misc_feature            1..813
                        note = Oligonucleotide
source                  1..813
                        mol_type = other DNA
                        organism = synthetic construct
SEQUENCE: 174
cagttagata aaagaggcgc ggcagcaagc ggcgcgcatg ccgaatctgc tctgacccag    60
ccagcttctg tttctggttc tccaggtcag tctatcacca tctcttgtac cggtacctct   120
tctgatgttg gtggttacaa ctctgtttct tggtaccagc agcacccagg taaagctcca   180
aaactgatga tctacgaagt ttctaaccgt ccatctggtg tttctaaccg tttctctggt   240
tctaaatctg gtaacaccgc ttctctgacc atctctggtc tgcaggctga agatgaagct   300
gattactact gtaactctta cacctctacc tctatggttt ctggtggtgg taccaaactg   360
accgttctgt ccggagggtc gaccataact tcgtataatg tatactatac gaagttatcc   420
tcgagcggta ccgaagttca gctggttcag tctggtgctg aagttaaaaa accaggtgct   480
tctgttaaag tttcttgtaa agcttctggt tacaccctga cctcttacgg tatctcttgg   540
gttcgtcagg ctccaggtca gggtctggaa tggatgggtt gggtttcttt ctacaacggt   600
aacaccaact acgctcagaa actgcagggt cgtggtacca tgaccaccga tccatctacc   660
tctaccgctt acatggaact gcgttctctg cgttctgacg acacgccgt gtattactgt   720
gctcgtggtt acggtatgga tgtttggggt caggggacca cggtcaccgt ctcctcagct   780
agcggcaaac caatcccaaa cccactgctg ggc                                 813

SEQ ID NO: 175          moltype = DNA   length = 815
FEATURE                 Location/Qualifiers
misc_feature            1..815
                        note = Oligonucleotide
source                  1..815
                        mol_type = other DNA
                        organism = synthetic construct
SEQUENCE: 175
cagttagata aaagaggcgc ggcagcaagc ggcgcgcatg ccgaatctgc tctgacccag    60
ccagcttctg tttctggttc tccaggtcag tctatcacca tctcttgtac cggtaccaga   120
gaccatggcc agtaaggccg gtctctgttt cttggtacca gcagcaccca ggtaaagctc   180
caaaactgat gatctacgaa gtttctaacc gtccatctgg tgtttctaac cgtttctctg   240
gttctaaatc tggtaacacc gcttctctga ccatctctgg tctgcaggct gaagatgaag   300
ctgattacta ctgtaactct tacacctcta cctctatggt tttcggtggt ggtaccaaac   360
tgaccgttct gtccggaggg tcgaccataa cttcgtataa tgtatactat acgaagttat   420
cctcgagcgg taccgaagtt cagctggttc agtctggtgc tgaagttaaa aaaccaggtg   480
cttctgttaa agtttcttgt aaagcttctg gttacaccct gacctcttac ggtatctctt   540
gggttcgtca ggctccaggt cagggtctgg aatggatggg ttgggtttct tctacaacg   600
gtaacaccaa ctacgctcag aaactgcagg gtcgtggtac catgaccacc gatccatcta   660
cctctaccgc ttacatggaa ctgcgttctc tgcgttctga cgacacggcc gtgtattact   720
gtgctcgtgg ttacggtatg gatgtttggg gtcaggggac cacggtcacc gtctcctcag   780
ctagcggcaa accaatccca aacccactgc tgggc                              815

SEQ ID NO: 176          moltype = DNA   length = 821
FEATURE                 Location/Qualifiers
misc_feature            1..821
                        note = Oligonucleotide
source                  1..821
                        mol_type = other DNA
                        organism = synthetic construct
SEQUENCE: 176
cagttagata aaagaggcgc ggcagcaagc ggcgcgcatg ccgaatctgc tctgacccag    60
ccagcttctg tttctggttc tccaggtcag tctatcacca tctcttgtac cggtacctct   120
tctgatgttg gtggttacaa ctctgtttct tggtaccagc agcacccagg taaagctcca   180
aaactgatga tctacagaga ccatggccag taaggccggt ctctggtgtt tctaaccgtt   240
tctctggttc taaatctggt aacaccgctt ctctgaccat ctctggtctg caggctgaag   300
atgaagctga ttactactgt aactcttaca cctctacctc tatggttttc ggtggtggta   360
ccaaactgac cgttctgtcc ggagggtcga ccataacttc gtataatgta tactatacga   420
agttatcctc gagcggtacc gaagttcagc tggttcagtc tggtgctgaa gttaaaaaac   480
caggtgcttc tgttaaagtt tcttgtaaag cttctggtta caccctgacc tcttacggta   540
tctcttgggt tcgtcaggct ccaggtcagg gtctggaatg gatgggttgg gtttctttct   600
acaacggtaa caccaactac gctcagaaac tgcagggtcg tggtaccatg accaccgatc   660
catctacctc taccgcttac atggaactgc gttctctgcg ttctgacgac acggccgtgt   720
attactgtgc tcgtggttac ggtatggatg tttggggtca ggggaccacg gtcaccgtct   780
cctcagctag cggcaaacca atcccaaacc cactgctggg c                        821

SEQ ID NO: 177          moltype = DNA   length = 815
FEATURE                 Location/Qualifiers
misc_feature            1..815
                        note = Oligonucleotide
source                  1..815
                        mol_type = other DNA
                        organism = synthetic construct
SEQUENCE: 177
cagttagata aaagaggcgc ggcagcaagc ggcgcgcatg ccgaatctgc tctgacccag    60
ccagcttctg tttctggttc tccaggtcag tctatcacca tctcttgtac cggtacctct   120

```
tctgatgttg gtggttacaa ctctgtttct tggtaccagc agcacccagg taaagctcca    180
aaactgatga tctacgaagt ttctaaccgt ccatctggtg tttctaaccg tttctctggt    240
tctaaatctg gtaacaccgc ttctctgacc atctctggtc tgcaggctga agatgaagct    300
gattactact gtagagacca tggccagtaa ggccggtctc tttcggtggt ggtaccaaac    360
tgaccgttct gtccggaggg tcgaccataa cttcgtataa tgtatactat acgaagttat    420
cctcgagcgg taccgaagtt cagctggttc agtctggtgc tgaagttaaa aaaccaggtg    480
cttctgttaa agtttcttgt aaagcttctg gttacccct gacctcttac ggtatctctt     540
gggttcgtca ggtccaggt cagggtctgg aatggatggg ttgggtttct ttctacaacg      600
gtaacaccaa ctacgctcag aaaactgcag gtcgtgtac catgaccacc gatccatca       660
cctctaccgc ttacatggaa ctgcgttctc tgcgttctga cgacacggcc gtgtattact     720
gtgctcgtgg ttacggtatg gatgtttggg gtcaggggac cacggtcacc gtctcctcag    780
ctagcggcaa accaatccca aacccactgc tgggc                                815

SEQ ID NO: 178         moltype = DNA   length = 818
FEATURE                Location/Qualifiers
misc_feature           1..818
                       note = Oligonucleotide
source                 1..818
                       mol_type = other DNA
                       organism = synthetic construct
SEQUENCE: 178
cagttagata aaagaggcgc ggcagcaagc ggcgcgcatg ccgaatctgc tctgacccag     60
ccagcttctg tttctggttc tccaggtcag tctatcacca tctcttgtac cggtacctct    120
tctgatgttg gtggttacaa ctctgtttct tggtaccagc agcacccagg taaagctcca    180
aaactgatga tctacgaagt ttctaaccgt ccatctggtg tttctaaccg tttctctggt    240
tctaaatctg gtaacaccgc ttctctgacc atctctggtc tgcaggctga agatgaagct    300
gattactact gtaactctta cacctctacc tctatggttt tcggtggtgg taccaaactg    360
accgttctgt ccggagggtc gaccataact tcgtataatg tatactatac gaagttatcc    420
tcgagcggta ccgaagttca gctggttcag tctggtgctg aagttaaaaa accaggtgct    480
tctgttaaag tttcttgtaa agcttctaga gaccatggcc agtaaggccg gtctctatct    540
cttgggttcg tcaggctcca ggtcagggtc tggaatggat gggttgggtt tctttctaca    600
acggtaacac caactacgct cagaaactgc agggtcgtgg taccatgacc accgatccat    660
ctacctctac cgcttacatg gaactgcgtt ctctgcgttc tgacgacacg gccgtgtatt    720
actgtgctcg tggttacggt atggatgttt ggggtcaggg gaccacggtc accgtctcct    780
cagctagcgg caaaccaatc ccaaacccac tgctgggc                            818

SEQ ID NO: 179         moltype = DNA   length = 818
FEATURE                Location/Qualifiers
misc_feature           1..818
                       note = Oligonucleotide
source                 1..818
                       mol_type = other DNA
                       organism = synthetic construct
SEQUENCE: 179
cagttagata aaagaggcgc ggcagcaagc ggcgcgcatg ccgaatctgc tctgacccag     60
ccagcttctg tttctggttc tccaggtcag tctatcacca tctcttgtac cggtacctct    120
tctgatgttg gtggttacaa ctctgtttct tggtaccagc agcacccagg taaagctcca    180
aaactgatga tctacgaagt ttctaaccgt ccatctggtg tttctaaccg tttctctggt    240
tctaaatctg gtaacaccgc ttctctgacc atctctggtc tgcaggctga agatgaagct    300
gattactact gtaactctta cacctctacc tctatggttt tcggtggtgg taccaaactg    360
accgttctgt ccggagggtc gaccataact tcgtataatg tatactatac gaagttatcc    420
tcgagcggta ccgaagttca gctggttcag tctggtgctg aagttaaaaa accaggtgct    480
tctgttaaag tttcttgtaa agcttctggt tacaccctga cctcttacgg tatctcttgg    540
gttcgtcagg ctccaggtca gggtctggaa tggatgggtt ggagagacca tggccagtaa    600
ggccggtctc taactacgct cagaaactgc agggtcgtgg taccatgacc accgatccat    660
ctacctctac cgcttacatg gaactgcgtt ctctgcgttc tgacgacacg gccgtgtatt    720
actgtgctcg tggttacggt atggatgttt ggggtcaggg gaccacggtc accgtctcct    780
cagctagcgg caaaccaatc ccaaacccac tgctgggc                            818

SEQ ID NO: 180         moltype = DNA   length = 809
FEATURE                Location/Qualifiers
misc_feature           1..809
                       note = Oligonucleotide
source                 1..809
                       mol_type = other DNA
                       organism = synthetic construct
SEQUENCE: 180
cagttagata aaagaggcgc ggcagcaagc ggcgcgcatg ccgaatctgc tctgacccag     60
ccagcttctg tttctggttc tccaggtcag tctatcacca tctcttgtac cggtacctct    120
tctgatgttg gtggttacaa ctctgtttct tggtaccagc agcacccagg taaagctcca    180
aaactgatga tctacgaagt ttctaaccgt ccatctggtg tttctaaccg tttctctggt    240
tctaaatctg gtaacaccgc ttctctgacc atctctggtc tgcaggctga agatgaagct    300
gattactact gtaactctta cacctctacc tctatggttt tcggtggtgg taccaaactg    360
accgttctgt ccggagggtc gaccataact tcgtataatg tatactatac gaagttatcc    420
tcgagcggta ccgaagttca gctggttcag tctggtgctg aagttaaaaa accaggtgct    480
tctgttaaag tttcttgtaa agcttctggt tacaccctga cctcttacgg tatctcttgg    540
gttcgtcagg ctccaggtca gggtctggaa tggatgggtt gggtttcttt ctacaacggt    600
aacaccaact acgctcagaa actgcagggt cgtggtacca tgaccaccga tccatctacc    660
tctaccgctt acatggaact gcgttctctg cgttctgacg acacggccgt gtattactgt    720
```

```
agagaccatg gccagtaagg ccggtctctg ggaccacggt caccgtctcc tcagctagcg    780
gcaaaccaat cccaaaccca ctgctgggc                                      809
```

SEQ ID NO: 181                moltype = DNA   length = 42
FEATURE                        Location/Qualifiers
misc_feature               1..42
                               note = Primer
source                         1..42
                               mol_type = other DNA
                               organism = synthetic construct
SEQUENCE: 181
```
gcttctgttg gtgatcgtgt tactattacc tgtcgtgctt ct                        42
```

SEQ ID NO: 182                moltype = DNA   length = 42
FEATURE                        Location/Qualifiers
misc_feature               1..42
                               note = Primer
source                         1..42
                               mol_type = other DNA
                               organism = synthetic construct
SEQUENCE: 182
```
gtttctctgg gtgaacgtgc taccatcaac tgcaaatctt ct                        42
```

SEQ ID NO: 183                moltype = DNA   length = 42
FEATURE                        Location/Qualifiers
misc_feature               1..42
                               note = Primer
source                         1..42
                               mol_type = other DNA
                               organism = synthetic construct
SEQUENCE: 183
```
gttaccccag gtgaaccagc ttctatttct tgtcgttctt ct                        42
```

SEQ ID NO: 184                moltype = DNA   length = 42
FEATURE                        Location/Qualifiers
misc_feature               1..42
                               note = Primer
source                         1..42
                               mol_type = other DNA
                               organism = synthetic construct
SEQUENCE: 184
```
ctgtctccag gtgaacgtgc cactctgtct tgtcgtgctt ct                        42
```

SEQ ID NO: 185                moltype = DNA   length = 42
FEATURE                        Location/Qualifiers
misc_feature               1..42
                               note = Primer
source                         1..42
                               mol_type = other DNA
                               organism = synthetic construct
SEQUENCE: 185
```
ctgtctccag gtgaacgtgc cactctgtct tgtcgtgctt ct                        42
```

SEQ ID NO: 186                moltype = DNA   length = 42
FEATURE                        Location/Qualifiers
misc_feature               1..42
                               note = Primer
source                         1..42
                               mol_type = other DNA
                               organism = synthetic construct
SEQUENCE: 186
```
ggttctccag gtcagtctat caccatctct tgtaccggta cc                        42
```

SEQ ID NO: 187                moltype = DNA   length = 42
FEATURE                        Location/Qualifiers
misc_feature               1..42
                               note = Primer
source                         1..42
                               mol_type = other DNA
                               organism = synthetic construct
SEQUENCE: 187
```
cagttttgga gctttacctg gtttctgctg gtaccaagcc ag                        42
```

SEQ ID NO: 188                moltype = DNA   length = 42
FEATURE                        Location/Qualifiers
misc_feature               1..42
                               note = Primer
source                         1..42
                               mol_type = other DNA

```
                        organism = synthetic construct
SEQUENCE: 188
cagttttggt ggctgacctg gtttctgctg gtaccaagcc ag                              42

SEQ ID NO: 189          moltype = DNA   length = 42
FEATURE                 Location/Qualifiers
misc_feature            1..42
                        note = Primer
source                  1..42
                        mol_type = other DNA
                        organism = synthetic construct
SEQUENCE: 189
cagctgtgga gactgacctg gtttctgcag gtaccagtgc ag                              42

SEQ ID NO: 190          moltype = DNA   length = 42
FEATURE                 Location/Qualifiers
misc_feature            1..42
                        note = Primer
source                  1..42
                        mol_type = other DNA
                        organism = synthetic construct
SEQUENCE: 190
cagacgtgga gcctgacctg gtttctgctg gtaccaagcc ag                              42

SEQ ID NO: 191          moltype = DNA   length = 42
FEATURE                 Location/Qualifiers
misc_feature            1..42
                        note = Primer
source                  1..42
                        mol_type = other DNA
                        organism = synthetic construct
SEQUENCE: 191
cagacgtgga gcctgacctg gtttctgctg gtaccaagcc ag                              42

SEQ ID NO: 192          moltype = DNA   length = 42
FEATURE                 Location/Qualifiers
misc_feature            1..42
                        note = Primer
source                  1..42
                        mol_type = other DNA
                        organism = synthetic construct
SEQUENCE: 192
cagttttgga gctttacctg ggtgctgctg gtaccaagaa ac                              42

SEQ ID NO: 193          moltype = DNA   length = 42
FEATURE                 Location/Qualifiers
misc_feature            1..42
                        note = Primer
source                  1..42
                        mol_type = other DNA
                        organism = synthetic construct
SEQUENCE: 193
taccagcaga aaccaggtaa agctccaaaa ctgctgatct ac                              42

SEQ ID NO: 194          moltype = DNA   length = 42
FEATURE                 Location/Qualifiers
misc_feature            1..42
                        note = Primer
source                  1..42
                        mol_type = other DNA
                        organism = synthetic construct
SEQUENCE: 194
taccagcaga aaccaggtca gccaccaaaa ctgctgatct ac                              42

SEQ ID NO: 195          moltype = DNA   length = 42
FEATURE                 Location/Qualifiers
misc_feature            1..42
                        note = Primer
source                  1..42
                        mol_type = other DNA
                        organism = synthetic construct
SEQUENCE: 195
tacctgcaga aaccaggtca gtctccacag ctgctgatct ac                              42

SEQ ID NO: 196          moltype = DNA   length = 42
FEATURE                 Location/Qualifiers
misc_feature            1..42
                        note = Primer
source                  1..42
```

```
                        mol_type = other DNA
                        organism = synthetic construct
SEQUENCE: 196
taccagcaga aaccaggtca ggctccacgt ctgctgatct ac                              42

SEQ ID NO: 197          moltype = DNA   length = 42
FEATURE                 Location/Qualifiers
misc_feature            1..42
                        note = Primer
source                  1..42
                        mol_type = other DNA
                        organism = synthetic construct
SEQUENCE: 197
taccagcaga aaccaggtca ggctccacgt ctgctgatct ac                              42

SEQ ID NO: 198          moltype = DNA   length = 42
FEATURE                 Location/Qualifiers
misc_feature            1..42
                        note = Primer
source                  1..42
                        mol_type = other DNA
                        organism = synthetic construct
SEQUENCE: 198
taccagcagc acccaggtaa agctccaaaa ctgatgatct ac                              42

SEQ ID NO: 199          moltype = DNA   length = 42
FEATURE                 Location/Qualifiers
misc_feature            1..42
                        note = Primer
source                  1..42
                        mol_type = other DNA
                        organism = synthetic construct
SEQUENCE: 199
atcggtacca gaaccagaac cagagaaacg agatggaaca cc                              42

SEQ ID NO: 200          moltype = DNA   length = 42
FEATURE                 Location/Qualifiers
misc_feature            1..42
                        note = Primer
source                  1..42
                        mol_type = other DNA
                        organism = synthetic construct
SEQUENCE: 200
atcggtacca gaaccagaac cagagaaacg atctggaaca cc                              42

SEQ ID NO: 201          moltype = DNA   length = 42
FEATURE                 Location/Qualifiers
misc_feature            1..42
                        note = Primer
source                  1..42
                        mol_type = other DNA
                        organism = synthetic construct
SEQUENCE: 201
atcggtacca gaaccagaac cagagaaacg atctggaaca cc                              42

SEQ ID NO: 202          moltype = DNA   length = 42
FEATURE                 Location/Qualifiers
misc_feature            1..42
                        note = Primer
source                  1..42
                        mol_type = other DNA
                        organism = synthetic construct
SEQUENCE: 202
atcggtacca gaaccagaac cagagaaacg agctgggata cc                              42

SEQ ID NO: 203          moltype = DNA   length = 42
FEATURE                 Location/Qualifiers
misc_feature            1..42
                        note = Primer
source                  1..42
                        mol_type = other DNA
                        organism = synthetic construct
SEQUENCE: 203
atcggtacca gaaccagaac cagacagacg atctgggata cc                              42

SEQ ID NO: 204          moltype = DNA   length = 42
FEATURE                 Location/Qualifiers
misc_feature            1..42
                        note = Primer
```

```
source                    1..42
                          mol_type = other DNA
                          organism = synthetic construct
SEQUENCE: 204
ggtgttacca gatttagaac cagagaaacg gttagaaaca cc              42

SEQ ID NO: 205            moltype = DNA  length = 42
FEATURE                   Location/Qualifiers
misc_feature              1..42
                          note = Primer
source                    1..42
                          mol_type = other DNA
                          organism = synthetic construct
SEQUENCE: 205
atctcttctc tgcagccaga agatttcgct aactactact gt              42

SEQ ID NO: 206            moltype = DNA  length = 42
FEATURE                   Location/Qualifiers
misc_feature              1..42
                          note = Primer
source                    1..42
                          mol_type = other DNA
                          organism = synthetic construct
SEQUENCE: 206
atctcttctc tgcaggctga agatgttgct gtttactact gt              42

SEQ ID NO: 207            moltype = DNA  length = 42
FEATURE                   Location/Qualifiers
misc_feature              1..42
                          note = Primer
source                    1..42
                          mol_type = other DNA
                          organism = synthetic construct
SEQUENCE: 207
atctctcgtg ttgaagctga agatgttggt gtttactact gt              42

SEQ ID NO: 208            moltype = DNA  length = 42
FEATURE                   Location/Qualifiers
misc_feature              1..42
                          note = Primer
source                    1..42
                          mol_type = other DNA
                          organism = synthetic construct
SEQUENCE: 208
atctcttctc tggaaccaga agatttcgct gtttactact gt              42

SEQ ID NO: 209            moltype = DNA  length = 42
FEATURE                   Location/Qualifiers
misc_feature              1..42
                          note = Primer
source                    1..42
                          mol_type = other DNA
                          organism = synthetic construct
SEQUENCE: 209
atcacccgtc tggaaccaga agatttcgct gtttactact gt              42

SEQ ID NO: 210            moltype = DNA  length = 42
FEATURE                   Location/Qualifiers
misc_feature              1..42
                          note = Primer
source                    1..42
                          mol_type = other DNA
                          organism = synthetic construct
SEQUENCE: 210
atctctggtc tgcaggctga agatgaagct gattactact gt              42

SEQ ID NO: 211            moltype = DNA  length = 42
FEATURE                   Location/Qualifiers
misc_feature              1..42
                          note = Primer
source                    1..42
                          mol_type = other DNA
                          organism = synthetic construct
SEQUENCE: 211
cgaccctccg gatttgattt caactttggt accaccaccg aa              42

SEQ ID NO: 212            moltype = DNA  length = 42
FEATURE                   Location/Qualifiers
misc_feature              1..42
```

```
                            note = Primer
source                      1..42
                            mol_type = other DNA
                            organism = synthetic construct
SEQUENCE: 212
cgaccctccg gacagaacgg tcagtttggt accaccaccg aa                       42

SEQ ID NO: 213              moltype = DNA   length = 42
FEATURE                     Location/Qualifiers
misc_feature                1..42
                            note = Primer
source                      1..42
                            mol_type = other DNA
                            organism = synthetic construct
SEQUENCE: 213
aaaaaaccag gtgcttctgt taaagtttct tgtaaagttt ct                       42

SEQ ID NO: 214              moltype = DNA   length = 42
FEATURE                     Location/Qualifiers
misc_feature                1..42
                            note = Primer
source                      1..42
                            mol_type = other DNA
                            organism = synthetic construct
SEQUENCE: 214
gttaaaccaa cccagaccct gaccctgacc tgtaccgttt ct                       42

SEQ ID NO: 215              moltype = DNA   length = 42
FEATURE                     Location/Qualifiers
misc_feature                1..42
                            note = Primer
source                      1..42
                            mol_type = other DNA
                            organism = synthetic construct
SEQUENCE: 215
gttcagccag gtggttctct gcgtctgtct tgtgctgctt ct                       42

SEQ ID NO: 216              moltype = DNA   length = 42
FEATURE                     Location/Qualifiers
misc_feature                1..42
                            note = Primer
source                      1..42
                            mol_type = other DNA
                            organism = synthetic construct
SEQUENCE: 216
gttaaaccat ctcagaccct gtctctgacc tgtaccgttt ct                       42

SEQ ID NO: 217              moltype = DNA   length = 42
FEATURE                     Location/Qualifiers
misc_feature                1..42
                            note = Primer
source                      1..42
                            mol_type = other DNA
                            organism = synthetic construct
SEQUENCE: 217
aaaaaaccag gtgaatctct gaaaatctct tgtaaaggtt ct                       42

SEQ ID NO: 218              moltype = DNA   length = 42
FEATURE                     Location/Qualifiers
misc_feature                1..42
                            note = Primer
source                      1..42
                            mol_type = other DNA
                            organism = synthetic construct
SEQUENCE: 218
aaaaaaccag gtgcttctgt taaagtttct tgtaaagctt ct                       42

SEQ ID NO: 219              moltype = DNA   length = 42
FEATURE                     Location/Qualifiers
misc_feature                1..42
                            note = Primer
source                      1..42
                            mol_type = other DNA
                            organism = synthetic construct
SEQUENCE: 219
ccattccaga cctttacctg gagcctgacg aacccagtgg at                       42

SEQ ID NO: 220              moltype = DNA   length = 42
FEATURE                     Location/Qualifiers
```

```
misc_feature              1..42
                          note = Primer
source                    1..42
                          mol_type = other DNA
                          organism = synthetic construct
SEQUENCE: 220
ccattccaga gctttacctg gtggctgacg gatccagtta ac                    42

SEQ ID NO: 221            moltype = DNA  length = 42
FEATURE                   Location/Qualifiers
misc_feature              1..42
                          note = Primer
source                    1..42
                          mol_type = other DNA
                          organism = synthetic construct
SEQUENCE: 221
cagttccaga cctttacctg gagcctgacg aacccaagac at                    42

SEQ ID NO: 222            moltype = DNA  length = 42
FEATURE                   Location/Qualifiers
misc_feature              1..42
                          note = Primer
source                    1..42
                          mol_type = other DNA
                          organism = synthetic construct
SEQUENCE: 222
ccattccaga cctttacctg gtggctgacg gatccaagac ca                    42

SEQ ID NO: 223            moltype = DNA  length = 42
FEATURE                   Location/Qualifiers
misc_feature              1..42
                          note = Primer
source                    1..42
                          mol_type = other DNA
                          organism = synthetic construct
SEQUENCE: 223
agattccaga cctttacctg gaacctgacg aacccaagcg at                    42

SEQ ID NO: 224            moltype = DNA  length = 42
FEATURE                   Location/Qualifiers
misc_feature              1..42
                          note = Primer
source                    1..42
                          mol_type = other DNA
                          organism = synthetic construct
SEQUENCE: 224
ccattccaga ccctgacctg gagcctgacg aacccaagag at                    42

SEQ ID NO: 225            moltype = DNA  length = 42
FEATURE                   Location/Qualifiers
misc_feature              1..42
                          note = Primer
source                    1..42
                          mol_type = other DNA
                          organism = synthetic construct
SEQUENCE: 225
gttcgtcagg ctccaggtaa aggtctggaa tggatgggtg gt                    42

SEQ ID NO: 226            moltype = DNA  length = 42
FEATURE                   Location/Qualifiers
misc_feature              1..42
                          note = Primer
source                    1..42
                          mol_type = other DNA
                          organism = synthetic construct
SEQUENCE: 226
atccgtcagc caccaggtaa agctctggaa tggctggcta tg                    42

SEQ ID NO: 227            moltype = DNA  length = 42
FEATURE                   Location/Qualifiers
misc_feature              1..42
                          note = Primer
source                    1..42
                          mol_type = other DNA
                          organism = synthetic construct
SEQUENCE: 227
gttcgtcagg ctccaggtaa aggtctggaa ctggttgctt ct                    42

SEQ ID NO: 228            moltype = DNA  length = 42
```

```
FEATURE              Location/Qualifiers
misc_feature         1..42
                     note = Primer
source               1..42
                     mol_type = other DNA
                     organism = synthetic construct
SEQUENCE: 228
atccgtcagc caccaggtaa aggtctggaa tggatcggtt ac                          42

SEQ ID NO: 229       moltype = DNA  length = 42
FEATURE              Location/Qualifiers
misc_feature         1..42
                     note = Primer
source               1..42
                     mol_type = other DNA
                     organism = synthetic construct
SEQUENCE: 229
gttcgtcagg ttccaggtaa aggtctggaa tctatgggta tc                          42

SEQ ID NO: 230       moltype = DNA  length = 42
FEATURE              Location/Qualifiers
misc_feature         1..42
                     note = Primer
source               1..42
                     mol_type = other DNA
                     organism = synthetic construct
SEQUENCE: 230
gttcgtcagg ctccaggtca gggtctggaa tggatgggtt gg                          42

SEQ ID NO: 231       moltype = DNA  length = 42
FEATURE              Location/Qualifiers
misc_feature         1..42
                     note = Primer
source               1..42
                     mol_type = other DNA
                     organism = synthetic construct
SEQUENCE: 231
ttcggtcatg gtaacacgac cctggaattt ctgagcgtag at                          42

SEQ ID NO: 232       moltype = DNA  length = 42
FEATURE              Location/Qualifiers
misc_feature         1..42
                     note = Primer
source               1..42
                     mol_type = other DNA
                     organism = synthetic construct
SEQUENCE: 232
agagatggtc agacgagatt tcagagcaga gttgtaaacg at                          42

SEQ ID NO: 233       moltype = DNA  length = 42
FEATURE              Location/Qualifiers
misc_feature         1..42
                     note = Primer
source               1..42
                     mol_type = other DNA
                     organism = synthetic construct
SEQUENCE: 233
acgagagatg gtgaaacgac ctttaacaga atctgggtag ta                          42

SEQ ID NO: 234       moltype = DNA  length = 42
FEATURE              Location/Qualifiers
misc_feature         1..42
                     note = Primer
source               1..42
                     mol_type = other DNA
                     organism = synthetic construct
SEQUENCE: 234
aacagacatg gtaacacgag atttcagaga tgggttgtaa tc                          42

SEQ ID NO: 235       moltype = DNA  length = 42
FEATURE              Location/Qualifiers
misc_feature         1..42
                     note = Primer
source               1..42
                     mol_type = other DNA
                     organism = synthetic construct
SEQUENCE: 235
agcagagatg gtaacctgac cctggaaaga tggagagtaa cg                          42
```

```
SEQ ID NO: 236            moltype = DNA  length = 42
FEATURE                   Location/Qualifiers
misc_feature              1..42
                          note = Primer
source                    1..42
                          mol_type = other DNA
                          organism = synthetic construct
SEQUENCE: 236
ggtggtcatg gtaccacgac cctgcagttt ctgagcgtag tt                      42

SEQ ID NO: 237            moltype = DNA  length = 42
FEATURE                   Location/Qualifiers
misc_feature              1..42
                          note = Primer
source                    1..42
                          mol_type = other DNA
                          organism = synthetic construct
SEQUENCE: 237
ctgtcttctc tgaaatctga ggacacggcc gtgtattact gt                      42

SEQ ID NO: 238            moltype = DNA  length = 42
FEATURE                   Location/Qualifiers
misc_feature              1..42
                          note = Primer
source                    1..42
                          mol_type = other DNA
                          organism = synthetic construct
SEQUENCE: 238
atgaccaaca tggatcctgt ggacacagcc acatattact gt                      42

SEQ ID NO: 239            moltype = DNA  length = 42
FEATURE                   Location/Qualifiers
misc_feature              1..42
                          note = Primer
source                    1..42
                          mol_type = other DNA
                          organism = synthetic construct
SEQUENCE: 239
atgaactctc tgcgtgccga ggacacggct gtgtattact gt                      42

SEQ ID NO: 240            moltype = DNA  length = 42
FEATURE                   Location/Qualifiers
misc_feature              1..42
                          note = Primer
source                    1..42
                          mol_type = other DNA
                          organism = synthetic construct
SEQUENCE: 240
gttaactctg ttaccgccgc ggacacggct gtgtattact gt                      42

SEQ ID NO: 241            moltype = DNA  length = 42
FEATURE                   Location/Qualifiers
misc_feature              1..42
                          note = Primer
source                    1..42
                          mol_type = other DNA
                          organism = synthetic construct
SEQUENCE: 241
tggtcttctc tgaaagcctc ggacaccgcc atttattact gt                      42

SEQ ID NO: 242            moltype = DNA  length = 42
FEATURE                   Location/Qualifiers
misc_feature              1..42
                          note = Primer
source                    1..42
                          mol_type = other DNA
                          organism = synthetic construct
SEQUENCE: 242
ctgcgttctc tgcgttctga cgacacggcc gtgtattact gt                      42

SEQ ID NO: 243            moltype = DNA  length = 42
FEATURE                   Location/Qualifiers
misc_feature              1..42
                          note = Primer
source                    1..42
                          mol_type = other DNA
                          organism = synthetic construct
SEQUENCE: 243
gattggtttg ccgctagctg aggagacggt gaccagggtt cc                      42
```

```
SEQ ID NO: 244              moltype = DNA  length = 42
FEATURE                     Location/Qualifiers
misc_feature                1..42
                            note = Primer
source                      1..42
                            mol_type = other DNA
                            organism = synthetic construct
SEQUENCE: 244
gattggtttg ccgctagctg aggagacggt gaccgtggtc cc                           42

SEQ ID NO: 245              moltype = DNA  length = 24
FEATURE                     Location/Qualifiers
misc_feature                1..24
                            note = Primer
source                      1..24
                            mol_type = other DNA
                            organism = synthetic construct
SEQUENCE: 245
gtagatcagc agttttggag cttt                                               24

SEQ ID NO: 246              moltype = DNA  length = 21
FEATURE                     Location/Qualifiers
misc_feature                1..21
                            note = Primer
source                      1..21
                            mol_type = other DNA
                            organism = synthetic construct
SEQUENCE: 246
gtagatcagc agttttggtg g                                                  21

SEQ ID NO: 247              moltype = DNA  length = 21
FEATURE                     Location/Qualifiers
misc_feature                1..21
                            note = Primer
source                      1..21
                            mol_type = other DNA
                            organism = synthetic construct
SEQUENCE: 247
gtagatcagc agctgtggag a                                                  21

SEQ ID NO: 248              moltype = DNA  length = 20
FEATURE                     Location/Qualifiers
misc_feature                1..20
                            note = Primer
source                      1..20
                            mol_type = other DNA
                            organism = synthetic construct
SEQUENCE: 248
gtagatcagc agacgtggag                                                    20

SEQ ID NO: 249              moltype = DNA  length = 20
FEATURE                     Location/Qualifiers
misc_feature                1..20
                            note = Primer
source                      1..20
                            mol_type = other DNA
                            organism = synthetic construct
SEQUENCE: 249
gtagatcagc agacgtggag                                                    20

SEQ ID NO: 250              moltype = DNA  length = 25
FEATURE                     Location/Qualifiers
misc_feature                1..25
                            note = Primer
source                      1..25
                            mol_type = other DNA
                            organism = synthetic construct
SEQUENCE: 250
gtagatcatc agttttggag cttta                                              25

SEQ ID NO: 251              moltype = DNA  length = 21
FEATURE                     Location/Qualifiers
misc_feature                1..21
                            note = Primer
source                      1..21
                            mol_type = other DNA
                            organism = synthetic construct
SEQUENCE: 251
```

```
ctggcttggt accagcagaa a                                                        21

SEQ ID NO: 252          moltype = DNA  length = 21
FEATURE                 Location/Qualifiers
misc_feature            1..21
                        note = Primer
source                  1..21
                        mol_type = other DNA
                        organism = synthetic construct
SEQUENCE: 252
ctggcttggt accagcagaa a                                                        21

SEQ ID NO: 253          moltype = DNA  length = 21
FEATURE                 Location/Qualifiers
misc_feature            1..21
                        note = Primer
source                  1..21
                        mol_type = other DNA
                        organism = synthetic construct
SEQUENCE: 253
ctgcactggt acctgcagaa a                                                        21

SEQ ID NO: 254          moltype = DNA  length = 21
FEATURE                 Location/Qualifiers
misc_feature            1..21
                        note = Primer
source                  1..21
                        mol_type = other DNA
                        organism = synthetic construct
SEQUENCE: 254
ctggcttggt accagcagaa a                                                        21

SEQ ID NO: 255          moltype = DNA  length = 21
FEATURE                 Location/Qualifiers
misc_feature            1..21
                        note = Primer
source                  1..21
                        mol_type = other DNA
                        organism = synthetic construct
SEQUENCE: 255
ctggcttggt accagcagaa a                                                        21

SEQ ID NO: 256          moltype = DNA  length = 21
FEATURE                 Location/Qualifiers
misc_feature            1..21
                        note = Primer
source                  1..21
                        mol_type = other DNA
                        organism = synthetic construct
SEQUENCE: 256
gtttcttggt accagcagca c                                                        21

SEQ ID NO: 257          moltype = DNA  length = 25
FEATURE                 Location/Qualifiers
misc_feature            1..25
                        note = Primer
source                  1..25
                        mol_type = other DNA
                        organism = synthetic construct
SEQUENCE: 257
acagtagtag ttagcgaaat cttct                                                    25

SEQ ID NO: 258          moltype = DNA  length = 25
FEATURE                 Location/Qualifiers
misc_feature            1..25
                        note = Primer
source                  1..25
                        mol_type = other DNA
                        organism = synthetic construct
SEQUENCE: 258
acagtagtaa acagcaacat cttca                                                    25

SEQ ID NO: 259          moltype = DNA  length = 25
FEATURE                 Location/Qualifiers
misc_feature            1..25
                        note = Primer
source                  1..25
                        mol_type = other DNA
                        organism = synthetic construct
```

```
SEQUENCE: 259
acagtagtaa acaccaacat cttca                                              25

SEQ ID NO: 260          moltype = DNA   length = 25
FEATURE                 Location/Qualifiers
misc_feature            1..25
                        note = Primer
source                  1..25
                        mol_type = other DNA
                        organism = synthetic construct
SEQUENCE: 260
acagtagtaa acagcgaaat cttct                                              25

SEQ ID NO: 261          moltype = DNA   length = 25
FEATURE                 Location/Qualifiers
misc_feature            1..25
                        note = Primer
source                  1..25
                        mol_type = other DNA
                        organism = synthetic construct
SEQUENCE: 261
acagtagtaa acagcgaaat cttct                                              25

SEQ ID NO: 262          moltype = DNA   length = 25
FEATURE                 Location/Qualifiers
misc_feature            1..25
                        note = Primer
source                  1..25
                        mol_type = other DNA
                        organism = synthetic construct
SEQUENCE: 262
acagtagtaa tcagcttcat cttca                                              25

SEQ ID NO: 263          moltype = DNA   length = 21
FEATURE                 Location/Qualifiers
misc_feature            1..21
                        note = Primer
source                  1..21
                        mol_type = other DNA
                        organism = synthetic construct
SEQUENCE: 263
ggtgttccat ctcgtttctc t                                                  21

SEQ ID NO: 264          moltype = DNA   length = 21
FEATURE                 Location/Qualifiers
misc_feature            1..21
                        note = Primer
source                  1..21
                        mol_type = other DNA
                        organism = synthetic construct
SEQUENCE: 264
ggtgttccag atcgtttctc t                                                  21

SEQ ID NO: 265          moltype = DNA   length = 21
FEATURE                 Location/Qualifiers
misc_feature            1..21
                        note = Primer
source                  1..21
                        mol_type = other DNA
                        organism = synthetic construct
SEQUENCE: 265
ggtgttccag atcgtttctc t                                                  21

SEQ ID NO: 266          moltype = DNA   length = 21
FEATURE                 Location/Qualifiers
misc_feature            1..21
                        note = Primer
source                  1..21
                        mol_type = other DNA
                        organism = synthetic construct
SEQUENCE: 266
ggtatcccag ctcgtttctc t                                                  21

SEQ ID NO: 267          moltype = DNA   length = 21
FEATURE                 Location/Qualifiers
misc_feature            1..21
                        note = Primer
source                  1..21
                        mol_type = other DNA
```

```
                              organism = synthetic construct
SEQUENCE: 267
ggtatcccag atcgtctgtc t                                            21

SEQ ID NO: 268       moltype = DNA   length = 22
FEATURE              Location/Qualifiers
misc_feature         1..22
                     note = Primer
source               1..22
                     mol_type = other DNA
                     organism = synthetic construct
SEQUENCE: 268
ggtgtttcta accgtttctc tg                                           22

SEQ ID NO: 269       moltype = DNA   length = 20
FEATURE              Location/Qualifiers
misc_feature         1..20
                     note = Primer
source               1..20
                     mol_type = other DNA
                     organism = synthetic construct
SEQUENCE: 269
accacccatc cattccagac                                              20

SEQ ID NO: 270       moltype = DNA   length = 20
FEATURE              Location/Qualifiers
misc_feature         1..20
                     note = Primer
source               1..20
                     mol_type = other DNA
                     organism = synthetic construct
SEQUENCE: 270
catagccagc cattccagag                                              20

SEQ ID NO: 271       moltype = DNA   length = 21
FEATURE              Location/Qualifiers
misc_feature         1..21
                     note = Primer
source               1..21
                     mol_type = other DNA
                     organism = synthetic construct
SEQUENCE: 271
agaagcaacc agttccagac c                                            21

SEQ ID NO: 272       moltype = DNA   length = 21
FEATURE              Location/Qualifiers
misc_feature         1..21
                     note = Primer
source               1..21
                     mol_type = other DNA
                     organism = synthetic construct
SEQUENCE: 272
gtaaccgatc cattccagac c                                            21

SEQ ID NO: 273       moltype = DNA   length = 24
FEATURE              Location/Qualifiers
misc_feature         1..24
                     note = Primer
source               1..24
                     mol_type = other DNA
                     organism = synthetic construct
SEQUENCE: 273
gatacccata gattccagac cttt                                         24

SEQ ID NO: 274       moltype = DNA   length = 20
FEATURE              Location/Qualifiers
misc_feature         1..20
                     note = Primer
source               1..20
                     mol_type = other DNA
                     organism = synthetic construct
SEQUENCE: 274
ccaacccatc cattccagac                                              20

SEQ ID NO: 275       moltype = DNA   length = 19
FEATURE              Location/Qualifiers
misc_feature         1..19
                     note = Primer
source               1..19
```

```
                            mol_type = other DNA
                            organism = synthetic construct
SEQUENCE: 275
atccactggg ttcgtcagg                                                        19

SEQ ID NO: 276          moltype = DNA   length = 21
FEATURE                 Location/Qualifiers
misc_feature            1..21
                        note = Primer
source                  1..21
                        mol_type = other DNA
                        organism = synthetic construct
SEQUENCE: 276
gttaactgga tccgtcagcc a                                                     21

SEQ ID NO: 277          moltype = DNA   length = 21
FEATURE                 Location/Qualifiers
misc_feature            1..21
                        note = Primer
source                  1..21
                        mol_type = other DNA
                        organism = synthetic construct
SEQUENCE: 277
atgtcttggg ttcgtcaggc t                                                     21

SEQ ID NO: 278          moltype = DNA   length = 19
FEATURE                 Location/Qualifiers
misc_feature            1..19
                        note = Primer
source                  1..19
                        mol_type = other DNA
                        organism = synthetic construct
SEQUENCE: 278
tggtcttgga tccgtcagc                                                        19

SEQ ID NO: 279          moltype = DNA   length = 21
FEATURE                 Location/Qualifiers
misc_feature            1..21
                        note = Primer
source                  1..21
                        mol_type = other DNA
                        organism = synthetic construct
SEQUENCE: 279
atcgcttggg ttcgtcaggt t                                                     21

SEQ ID NO: 280          moltype = DNA   length = 21
FEATURE                 Location/Qualifiers
misc_feature            1..21
                        note = Primer
source                  1..21
                        mol_type = other DNA
                        organism = synthetic construct
SEQUENCE: 280
atctcttggg ttcgtcaggc t                                                     21

SEQ ID NO: 281          moltype = DNA   length = 21
FEATURE                 Location/Qualifiers
misc_feature            1..21
                        note = Primer
source                  1..21
                        mol_type = other DNA
                        organism = synthetic construct
SEQUENCE: 281
acagtaatac acggccgtgt c                                                     21

SEQ ID NO: 282          moltype = DNA   length = 23
FEATURE                 Location/Qualifiers
misc_feature            1..23
                        note = Primer
source                  1..23
                        mol_type = other DNA
                        organism = synthetic construct
SEQUENCE: 282
acagtaatat gtggctgtgt cca                                                   23

SEQ ID NO: 283          moltype = DNA   length = 21
FEATURE                 Location/Qualifiers
misc_feature            1..21
                        note = Primer
```

```
source                  1..21
                        mol_type = other DNA
                        organism = synthetic construct
SEQUENCE: 283
acagtaatac acagccgtgt c                                             21

SEQ ID NO: 284          moltype = DNA   length = 21
FEATURE                 Location/Qualifiers
misc_feature            1..21
                        note = Primer
source                  1..21
                        mol_type = other DNA
                        organism = synthetic construct
SEQUENCE: 284
acagtaatac acagccgtgt c                                             21

SEQ ID NO: 285          moltype = DNA   length = 22
FEATURE                 Location/Qualifiers
misc_feature            1..22
                        note = Primer
source                  1..22
                        mol_type = other DNA
                        organism = synthetic construct
SEQUENCE: 285
acagtaataa atggcggtgt cc                                            22

SEQ ID NO: 286          moltype = DNA   length = 21
FEATURE                 Location/Qualifiers
misc_feature            1..21
                        note = Primer
source                  1..21
                        mol_type = other DNA
                        organism = synthetic construct
SEQUENCE: 286
acagtaatac acggccgtgt c                                             21

SEQ ID NO: 287          moltype = DNA   length = 22
FEATURE                 Location/Qualifiers
misc_feature            1..22
                        note = Primer
source                  1..22
                        mol_type = other DNA
                        organism = synthetic construct
SEQUENCE: 287
atctacgctc agaaattcca gg                                            22

SEQ ID NO: 288          moltype = DNA   length = 24
FEATURE                 Location/Qualifiers
misc_feature            1..24
                        note = Primer
source                  1..24
                        mol_type = other DNA
                        organism = synthetic construct
SEQUENCE: 288
gtttacaact ctgctctgaa atct                                          24

SEQ ID NO: 289          moltype = DNA   length = 24
FEATURE                 Location/Qualifiers
misc_feature            1..24
                        note = Primer
source                  1..24
                        mol_type = other DNA
                        organism = synthetic construct
SEQUENCE: 289
tactacccag attctgttaa aggt                                          24

SEQ ID NO: 290          moltype = DNA   length = 24
FEATURE                 Location/Qualifiers
misc_feature            1..24
                        note = Primer
source                  1..24
                        mol_type = other DNA
                        organism = synthetic construct
SEQUENCE: 290
gattacaacc catctctgaa atct                                          24

SEQ ID NO: 291          moltype = DNA   length = 21
FEATURE                 Location/Qualifiers
misc_feature            1..21
```

```
                              note = Primer
source                        1..21
                              mol_type = other DNA
                              organism = synthetic construct
SEQUENCE: 291
cgttactctc catctttcca g                                              21

SEQ ID NO: 292                moltype = DNA  length = 21
FEATURE                       Location/Qualifiers
misc_feature                  1..21
                              note = Primer
source                        1..21
                              mol_type = other DNA
                              organism = synthetic construct
SEQUENCE: 292
aactacgctc agaaactgca g                                              21

SEQ ID NO: 293                moltype = DNA  length = 23
FEATURE                       Location/Qualifiers
misc_feature                  1..23
                              note = Primer
source                        1..23
                              mol_type = other DNA
                              organism = synthetic construct
SEQUENCE: 293
cggattgtct tcaaccaaca caa                                            23

SEQ ID NO: 294                moltype = DNA  length = 20
FEATURE                       Location/Qualifiers
misc_feature                  1..20
                              note = Primer
source                        1..20
                              mol_type = other DNA
                              organism = synthetic construct
SEQUENCE: 294
ctcctcctgt tgaatccagg                                                20

SEQ ID NO: 295                moltype = DNA  length = 21
FEATURE                       Location/Qualifiers
misc_feature                  1..21
                              note = Primer
source                        1..21
                              mol_type = other DNA
                              organism = synthetic construct
SEQUENCE: 295
cagttagata aaagaggcgc g                                              21

SEQ ID NO: 296                moltype = DNA  length = 18
FEATURE                       Location/Qualifiers
misc_feature                  1..18
                              note = Primer
source                        1..18
                              mol_type = other DNA
                              organism = synthetic construct
SEQUENCE: 296
gcccagcagt gggtttgg                                                  18

SEQ ID NO: 297                moltype = DNA  length = 19
FEATURE                       Location/Qualifiers
misc_feature                  1..19
                              note = Primer
source                        1..19
                              mol_type = other DNA
                              organism = synthetic construct
SEQUENCE: 297
tccggagggt cgaccataa                                                 19

SEQ ID NO: 298                moltype = DNA  length = 21
FEATURE                       Location/Qualifiers
misc_feature                  1..21
                              note = Primer
source                        1..21
                              mol_type = other DNA
                              organism = synthetic construct
SEQUENCE: 298
ggtaccgctc gaggataact t                                              21
```

ANTIBODY LIBRARIES WITH MAXIMIZED ANTIBODY DEVELOPABILITY CHARACTERISTICS

CROSS REFERENCE TO RELATED APPLICATIONS

The present application is a continuation of, and claims the benefit of and priority to, U.S. patent application Ser. No. 17/163,170, filed Jan. 29, 2021, which issued on Mar. 5, 2025 as U.S. Pat. No. 11,920,258, which is a continuation of, and claims the benefit of and priority to, U.S. patent application Ser. No. 16/505,358, filed on Jul. 8, 2019, which issued on Mar. 23, 2021 as U.S. Pat. No. 10,954,508, which claims the benefit of, and priority to, U.S. Provisional Application No. 62/822,671, filed on Mar. 22, 2019, and U.S. Provisional Application No. 62/695,065, filed on Jul. 8, 2018, the entire contents of each of which are incorporated by reference herein.

SEQUENCE LISTING

The instant application contains a Sequence Listing which has been filed electronically in XML format and is hereby incorporated by reference in its entirety. Said XML copy, created on Feb. 29, 2024, is named 112310-0125-7000US05_SEQ.XML and is 371,564 bytes in size.

BACKGROUND OF THE INVENTION

There are currently three recombinant antibody platforms used to generate human antibodies for human therapeutic use: (1) the "humanization" of murine monoclonal antibodies; (2) the immunization of transgenic mice containing human antibody genes; and (3) in vitro selection from vast human antibody libraries. Immunization approaches depend upon the occurrence of appropriate in vivo immune responses, and may not yield antibodies with desired characteristics. In contrast, in vitro selection has the advantage that antibodies with specific properties can be directly selected, and once selected, can be easily improved in terms of affinity or specificity.

In general, there are two types of antibody libraries: synthetic and natural antibody libraries. Synthetic antibody libraries can be constructed by introducing randomized complementarity determining region (CDR) sequences into antibody frameworks. Such antibody libraries can have vast potential genetic diversity and improved expression via selection of well-behaved frameworks. However, synthetic antibody libraries also include many non-functional antibody members and exclude much natural diversity due to the formulaic manner used to generate diversity within a restricted set of framework scaffolds. Antibody libraries created from natural sources, known as natural antibody libraries, have the advantage that the rearranged V genes undergo quality control in the B cell, and consequently a far higher proportion of the V genes are biologically functional, even if the potential diversity is lower. Disadvantages include the challenges of obtaining large numbers of B-cells to increase diversity, and the poor expression and biophysical properties of some antibodies expressed recombinantly in *E. coli*, yeast or mammalian cells.

SUMMARY OF THE INVENTION

Provided herein are antibody libraries that comprise diversified heavy chain variable domains (VH) and/or light chain variable domains (VL), which comprise complementary determining regions (CDRs) obtained from naturally-occurring antibodies (e.g., naturally-occurring human antibodies or naturally-occurring camelid antibodies). Optionally, any of the VH CDRs and/or VL CDRs excludes at least members carrying one or more liabilities that affect one or more features of an antibody carrying such. Such antibody libraries, comprising CDRs from natural antibodies such as human antibodies, would have a high number of functional members and reflect natural diversity of human antibodies. Excluding members carrying one or more liabilities as described herein would enhance the percentage of members having desired properties, for example, high yield when produced by recombinant technology, high stability, reduced aggregation capacity, reduced liabilities as described below etc. Thus, the antibody libraries described herein would maximize antibody developability characteristics.

Accordingly, one aspect of the present disclosure features an antibody heavy chain library, comprising a plurality of nucleic acids or a plurality of genetic packages comprising the nucleic acids. The plurality of nucleic acids encode a population of antibody heavy chain variable domains, which collectively (in combination) comprise a population of heavy chain CDR1s, a population of heavy chain CDR2s, and/or a population of heavy chain CDR3s located at the CDR1 region, the CDR2 region, and the CDR3 region of a common antibody heavy chain variable domain gene. The heavy chain CDR1s, CDR2s, and/or CDR3s may be derived from naturally-occurring antibodies of a mammalian species, for example, human or camelid. In some embodiments, the plurality of nucleic acids encode a population of antibody heavy chain variable domains (e.g., human antibody heavy chain variable domains), which collectively (in combination) comprise a population of heavy chain CDR1s, a population of heavy chain CDR2s, and a population of heavy chain CDR3s.

In some embodiments, the common antibody heavy chain variable domain gene may be a human antibody heavy chain variable domain gene. Examples include VH1-24, VH2-70, VH3-7, VH4-30-4, VH5-51, VH1-18, VH1-69, VH3-23, VH5-10-1, VH3-9, or VH3-11. In some instances, the human antibody heavy chain variable region gene may be derived from a therapeutic antibody, for example, abrilumab, mepolizumab, crenezumab, necitumumab, anifrolumab, evoculumab, abituzumab, adalimumab, alemtuzumab, alirocumab, bapineuzumab, benralizumab, brodalumab, canakinumab, certolizumab, clazakizumab, dacetuzumab, daclizumab, daratumumab, eculizumab, efalizumab, elotuzumab, epratuzumab, farletuzumab, fasinumab, ficlatuzumab, fletikumab, fresolimumab, fulranumab, gevokizumab, ibalizumab, lintuzumab, matuzumab, mavrilimumab, mogamulizumab, motavizumab, natalizumab, nivolumab, obinutuzumab, ofatumumab, olokizumab, omalizumab, onartuzumab, otelixizumab, otlertuzumab, palivizumab, panitumumab, panobacumab, pertuzumab, pinatuzumab, polatuzumab, radretumab, ramucirumab, reslizumab, romosozumab, sarilumab, secukinumab, sifalimumab, tabalumab, tigatuzumab, tildrakizumab, tocilizumab, tovetumab, trastuzumab, vedolizumab, veltuzumab, zalutumumab, or zanolimumab.

In some embodiments, the population of heavy chain CDR1s, the population of heavy chain CDR2s, and/or the population of heavy chain CDR3s can be free (e.g., substantially free) of members comprising one or more of the following liabilities:

(i) a glycosylation site (e.g., comprising the motif NXS, NXT, or NXC, in which X represents any naturally-occurring amino acid residue except for proline),
(ii) a deamidation site (e.g., comprising the motif of NG, NS, NT, NN, NA, NH, ND, GNF, GNY, GNT, or GNG),
(iii) an isomerization site (e.g., comprising the motif of DT, DH, DS, DG, or DD),
(iv) an unpaired cysteine,
(v) net charge greater than 1 (e.g., in LCDR1-2 and/or HCDR1-2),
(vi) a tripeptide motif containing at least two aromatic residues (e.g., HYF or HWH), which may affect viscosity;
(vii) a motif that promotes aggregation (e.g., comprising the motif of FHW);
(viii) a polyspecificity site (e.g., GG, GGG, RR, VG, W, WV, WW, WWW, YY, or WXW, X referring to any amino acid residue),
(ix) a protease sensitive site (e.g., comprising the motif DX, in which X can be P, G, S, V, Y, F, Q, K, L, or D),
(x) an integrin binding site (e.g., comprising the motif RGD, LDV, or KGD),
(xi) a lysine glycation site such as a lysine glycation site (e.g., KE, EK, or ED),
(xii) a metal catalyzed fragmentation site (e.g., comprises the motif of HS, SH, KT, HXS, or SXH, in which X represents any amino acid residue),
(xiii) a polyspecificity aggregation site (e.g., the motif of of $X_1X_2X_3$, wherein each of $X_1$, $X_2$, and $X_3$ independently is F, I, L, V, W, or Y), and/or
(xiv) a streptavidin binding motif of (e.g., comprises the motif HPQ, EPDW (SEQ ID NO: 117), PWXWL (SEQ ID NO: 118), in which X represents any amino acid residue, GDWVFI (SEQ ID NO: 119), or PWPWLG (SEQ ID NO: 120)).

Alternatively, or in addition, the population of heavy chain CDR1s, the population of heavy chain CDR2s, and/or the population of heavy chain CDR3s in the antibody library described herein is free of non-functional members.

In some embodiments, the population of antibody heavy chain CDR1 fragments, the population of antibody heavy chain CDR2 fragments, and/or the population of antibody heavy chain CDR3 fragments is free of members comprising at least two of (i)-(xiv). In some examples, at least the population of antibody heavy chain CDR1 fragments, the population of antibody heavy chain CDR2 fragments, and/or the population of antibody heavy chain CDR3 fragments is free of members comprising (i)-(ix), and optionally free of members comprising one or more of (x)-(xiv).

In some embodiments, the antibody library described herein comprise a population of heavy chain CDR1s and/or a population of heavy chain CDR2s that is free of members comprising one or more of (i)-(xiv), and a population of heavy chain CDR3s is derived from naturally-occurring human antibodies (without removal of one or more the liability (i)-(xiv) disclosed herein), for example, derived from human B lymphocytes or precursor cells thereof.

In some instances, members of the antibody library described herein comprise heavy chain CDR1, heavy chain CDR2, and/or heavy chain CDR3 that are not from the same naturally-occurring antibody. For examples, at least 50% of the members in the antibody library do not comprise heavy chain CDR1, heavy chain CDR2, and/or heavy chain CDR3 that are from the same naturally-occurring antibody.

In another aspect, the instant disclosure provides an antibody light chain library, comprising a plurality of nucleic acids or a plurality of genetic packages comprising the nucleic acids. The plurality of nucleic acids encode a population of antibody light chain variable domains (e.g., human antibody light chain variable domains), which collectively (in combination) comprise a population of light chain CDR1s, a population of light chain CDR2s, and/or a population of light chain CDR3s located at the CDR1 region, the CDR2 region, and the CDR3 region of a common antibody light chain variable domain gene (e.g., a human antibody light chain variable domain gene). The light chain CDR1s, CDR2s, and CDR3s, and optionally the common light chain variable domain gene may be derived from naturally-occurring antibodies of the same mammal species, for example, human. In some embodiments, the population of human antibody light chain variable domains collectively comprises a population of light chain CDR1s, a population of light chain CDR2s, and a population of light chain CDR3s. In some embodiments, the population of light chain CDR1s, the population of light chain CDR2s, and/or the population of light chain CDR3s is free of members comprising one or more of the liabilities described herein (e.g., (i)-(xiv) described herein).

In some embodiments, the antibody light chain library described herein may comprise members having light chain CDR1, light chain CDR2, and/or light chain CDR3 that are not from the same naturally-occurring antibody. For example, at least 50% of the members in the antibody light chain library do not comprise light chain CDR1, light chain CDR2, and/or light chain CDR3 that are from the same naturally-occurring antibody.

In some embodiments, the common antibody light chain variable domain gene used in the antibody light chain library may be a human antibody light chain variable domain gene. Examples include K1-12, K4-1, K2D-29, K3-11, K3-20, or L2-14. In some instances, the human antibody heavy chain variable region gene is derived from a therapeutic antibody such as those described herein.

Also provided herein is an antibody library that comprises (i) a first plurality of nucleic acids encoding the population of antibody heavy chain variable domains of the antibody heavy chain library described herein, and (ii) a second plurality of nucleic acids encoding the population of antibody light chain variable domains of the antibody light chain library described herein. Alternatively, the antibody library provided herein may comprise (i) a first plurality of nucleic acids encoding the population of antibody heavy chain variable domains of the antibody heavy chain library described herein, and (ii) a common light chain variable domain, which may be VK3-20.

Any of the antibody libraries disclosed herein may be of a suitable format, for example, a library of full-length antibodies, a library of antigen-binding fragments such as Fab fragments, a library of single-chain antibodies, or a library of single-domain antibodies (e.g., VHH antibodies). In some examples, the antibody library disclosed herein may be a human antibody library. In other examples, the antibody library disclosed herein may be a camelid VHH antibody library.

In another aspect, the present disclosure features a method for producing an antibody library, comprising:
providing (a) a first plurality of nucleic acids encoding a population of naturally-occurring antibody heavy chain complementary determining region 1 (CDR1) fragments, and/or (b) a second plurality of nucleic acids encoding a population of naturally-occurring antibody heavy chain complementary determining region 2 (CDR2) fragments; and inserting the first plurality of nucleic acids and/or the second plurality of nucleic acids into the CDR1 region and/or the CDR2 region, respectively, of an antibody heavy chain variable domain gene (e.g., those described herein), thereby producing an antibody library.

The method may further comprise:
providing a third plurality of nucleic acids encoding a population of naturally-occurring heavy chain complementary determining region 3 (CDR3) fragments, and inserting the third plurality of nucleic acids into the CDR3 region of the heavy chain variable region gene.

The heavy chain CDR1 fragments, the heavy chain CDR2 fragments, and the heavy chain CDR3 fragments may be derived from naturally-occurring antibodies of a mammalian species as disclosed herein. In some embodiments, the heavy chain CDR1, CDR2, and CDR3 fragments can be derived from the same mammalian species. Optionally, the common heavy chain variable region gene may also be derived from the same mammalian species.

In some embodiments, the antibody library comprises members in each of which the heavy chain CDR1, the heavy chain CDR2, and/or the heavy chain CDR3 are not from the same naturally-occurring antibody. For example, at least 50% of the members in the antibody library do not contain heavy chain CDR1, the heavy chain CDR2, and/or the heavy chain CDR3 from the same naturally-occurring antibody.

In some embodiments, the population of antibody heavy chain CDR1 fragments, the population of antibody heavy chain CDR2 fragments, and/or the population of antibody heavy chain CDR3 fragments is free of members comprising one or more of the liabilities described herein, e.g., (i)-(xiv) disclosed herein For example, the population of antibody heavy chain CDR1 fragments, the population of antibody heavy chain CDR2 fragments, and/or the population of antibody heavy chain CDR3 fragments may be free of members comprising at least two of (i)-(xiv). In some instances, the population of antibody heavy chain CDR1 fragments, the population of antibody heavy chain CDR2 fragments, and/or the population of antibody heavy chain CDR3 fragments is free of members comprising any of (i)-(ix), optionally further free of one or more of (x)-(xiv).

In other embodiments, the population of antibody heavy chain CDR1 fragments and/or the population of antibody heavy chain CDR2 fragments is free of members comprising one or more of the liabilities described herein (e.g., at least two of (i) to (xiv) or all of (i) to (xiv)) and the population of human antibody heavy chain CDR3 fragments are from naturally-occurring human antibodies (e.g., derived from B cells), which may not have the one or more liabilities excluded.

In some embodiments, the first plurality of nucleic acids, the second plurality of nucleic acids, and/or the third plurality of nucleic acids is produced by a process comprising:
(a) obtaining amino acid sequences of the heavy chain CDR1 regions, the heavy chain CDR2 regions, and/or the heavy chain CDR3 regions of a population of naturally-occurring antibodies (e.g., naturally-occurring human antibodies);
  (b) excluding from (a) the heavy chain CDR1 amino acid sequences, the heavy chain CDR2 amino acid sequences, and/or the heavy chain CDR3 amino acid sequences that comprise one or more of liabilities (i) to (xiv) to obtain liability-free heavy chain CDR1 sequences, heavy chain CDR2 sequences, and/or heavy chain CDR3 sequences; and
  (c) synthesizing the first plurality of nucleic acids that encode the liability-free heavy chain CDR1 regions, the second plurality of nucleic acids that encode the liability-free heavy chain CDR2 regions, and/or the third plurality of nucleic acids that encode the liability-free heavy chain CDR3 regions.

In some instances, the process described above may further comprise (d) isolating functional members from the liability-free heavy chain CDR1, CDR2, and/or CDR3 regions. For example, the functional members of the liability-free heavy chain CDR1, CDR2, and/or CDR3 can be isolated by expressing antibodies comprising the liability-free heavy chain CDR1, CDR2, and/or CDR3 regions in host cells in a manner that the antibodies are displayed on surface of the host cells, isolating the antibodies that display on the host cells, show improved folding, and/or show reduced binding to polyspecificity reagents and identifying the CDR1, CDR2, and/or CDR3 regions in the displayed antibodies, which are functional members of the liability-free heavy chain CDR1, CDR2, and/or CDR3 regions.

The method for producing an antibody library as described herein may further comprise:
  (i) providing a fourth plurality of nucleic acids encoding a population of naturally-occurring antibody light chain complementary determining region 1 (CDR1) fragments, a fifth plurality of nucleic acids encoding a population of naturally-occurring antibody light chain complementary determining region 2 (CDR2) fragments, and/or a sixth plurality of nucleic acids encoding a population of naturally-occurring human antibody light chain complementary determining region 3 (CDR3) fragments, and
  (ii) inserting the fourth plurality of nucleic acids, the fifth plurality of nucleic acids, and/or the sixth plurality of nucleic acids into the CDR1 region, the CDR2 region, and the CDR3 region, respectively, of an antibody light chain variable domain gene (e.g., those described herein).

The light chain CDR1 fragments, the light chain CDR2 fragments, and the light chain CDR3 fragments may be derived from naturally-occurring antibodies of a mammalian species as disclosed herein. In some embodiments, the light chain CDR1, CDR2, and CDR3 fragments can be derived from the same mammalian species. Optionally, the common light chain variable region gene may also be derived from the same mammalian species.

The population of naturally-occurring antibody light chain CDR1 fragments, the population of antibody light chain CDR2 fragments, and/or the population of antibody light chain CDR3 fragments may be free of members comprising one or more of the liabilities described herein (e.g., at least two or all of (i) to (xiv) described herein). The antibody library may comprise members, each of which comprises a light chain CDR1, a light chain CDR2, and/or a light chain CDR3 that are not found in the same naturally-occurring antibody. For example, at least 50% of the members in the antibody library comprise light chain CDR1, light chain CDR2, and/or light chain CDR3 that are not found in the same naturally-occurring antibody.

In some embodiments, the fourth plurality of nucleic acids, the fifth plurality of nucleic acids, and/or the sixth plurality of nucleic acids is produced by a process comprising:
  (a) obtaining amino acid sequences of the light chain CDR1, CDR2, and/or CDR3 regions of a population of naturally-occurring antibodies (e.g., naturally-occurring human antibodies),
  (b) excluding from (a) the light chain CDR1, CDR2, and/or CDR3 amino acid sequences that comprise one or more of (i) to (x) to obtain liability-free light chain CDR1, CDR2, and/or CDR3 sequences, and (c) synthesizing the fourth plurality of nucleic acids, the fifth plurality of the nucleic acids, and/or the sixth plurality of nucleic acids that encode the liability-free light chain CDR1, CDR2, and/or CDR3 regions.

The above process may further comprise (d) isolating functional members from the liability-free light chain CDR1, CDR2, and/or CDR3 regions. For example, the functional members of the liability-free light chain CDR1, CDR2, and/or CDR3 are isolated by expressing antibodies comprising the liability-free light chain CDR1, CDR2, and/or CDR3 regions in host cells in a manner that the antibodies are displayed on surface of the host cells, isolating the antibodies that display on the host cells, show improved folding, and/or show reduced binding to polyspecificity reagents and identifying the CDR1, CDR2, and/or CDR3 regions in the displayed antibodies, which are functional members of the liability-free light chain CDR1, CDR2, and/or CDR3 regions.

Further, the present disclosure features a method for making an antibody light chain library, the method comprising:

(i) providing a first plurality of nucleic acids encoding a population of naturally-occurring antibody light chain complementary determining region 1 (CDR1) fragments, a second plurality of nucleic acids encoding a population of naturally-occurring antibody light chain complementary determining region 2 (CDR2) fragments, and/or a third plurality of nucleic acids encoding a population of naturally-occurring antibody light chain complementary determining region 3 (CDR3) fragments, and (ii) inserting the first plurality of nucleic acids, the second plurality of nucleic acids, and/or the third plurality of nucleic acids into the CDR1 region, the CDR2 region, and the CDR3 region, respectively, of an antibody light chain variable domain gene (e.g., those described herein).

The light chain CDR1 fragments, the light chain CDR2 fragments, and the light chain CDR3 fragments may be derived from naturally-occurring antibodies of a mammalian species as disclosed herein. In some embodiments, the light chain CDR1, CDR2, and CDR3 fragments can be derived from the same mammalian species. Optionally, the common light chain variable region gene may also be derived from the same mammalian species.

Also within the scope of the present disclosure are antibody libraries (e.g., antibody heavy chain libraries, antibody light chain libraries, or a combination thereof) produced by any of the methods described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 3 is a schematic illustrating an exemplary design of cloning LCDR1 (as an example) into a selected light chain scaffold. Exemplary vector nucleic acids and corresponding amino acids are shown. The nucleic acid sequences correspond to SEQ ID NO: 1 (top) and SEQ ID NO: 2 (bottom). The amino acid sequence corresponds to SEQ ID NO: 3.

FIG. 5 illustrates exemplary HCDR2 sequences comprising liabilities, such as deamidation sites, isomerization sites, glycosylation sites, or unpaired cysteine (highlighted). The first sequence of each column shows a graphical representation of a consensus sequence, which is followed by exemplary variant sequences. The depicted sequences in the "Deamidation column" correspond to SEQ ID NOs: 4-24 (top to bottom). The depicted sequences in the "Isomerization column" correspond to SEQ ID NOs: 25-45 (top to bottom). The depicted sequences in the "Glycosylation column" correspond to SEQ ID NOs: 46-66 (top to bottom). The depicted sequences in the "Unpaired Cysteine column" correspond to SEQ ID NOs: 67-87 (top to bottom).

FIG. 7 shows presence of cysteine residues in heavy chain CDR3. Sequences correspond to SEQ ID NOs: 88-102 (from top to bottom).

FIGS. 22A-22F includes graphs showing natural distribution (blue) and replicated natural designed distributions before (red) and after (green) filtering for well folded sequences. Data is shows for 6 different scaffolds/germlines at each of LCDR1-3 and HCDR1-2. The results are based on sequencing the libraries illustrated in FIG. 25B-G.

FIGS. 22G-22L includes cumulative plots for the diversity at each CDR position assessed for a natural distribution (natural library—blue), and replicated natural designed distributions before (red) and after (green) filtering for well folded sequences. The results are based on sequencing the libraries illustrated in FIG. 25B-25G.

FIGS. 38A-38C include diagrams showing isolation of high affinity antibodies (having binding affinity at the sub-nanomolar level) from the libraries disclosed herein.

DETAILED DESCRIPTION OF THE INVENTION

Figure 1:
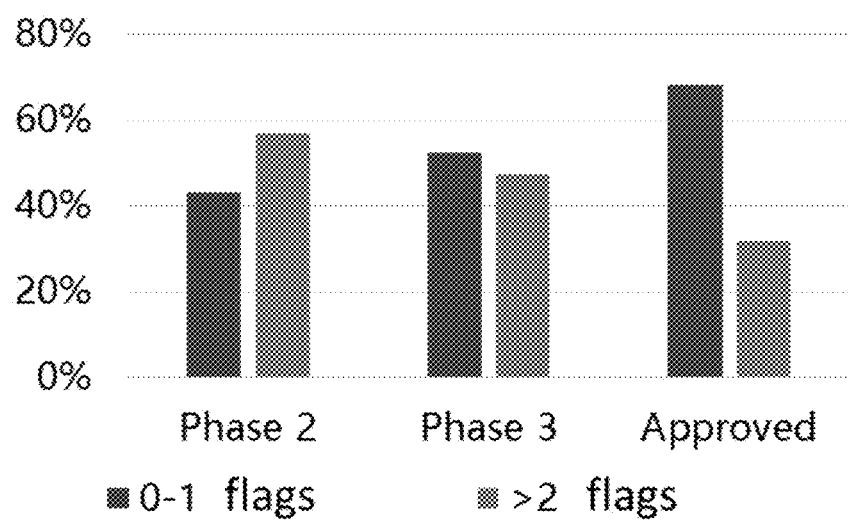
FIG. 1 is a chart showing the percentages of therapeutic antibodies in Phase 2 or Phase 3 clinical trials or approved therapeutic antibodies that are suitable or non-suitable for use as scaffold for antibody library construction. Suitable scaffolds for each of Phase 2, Phase 3, and Approved: 0-1 flags (left bar). Non-suitable scaffolds for each of Phase 2, Phase 3, and Approved: >2 flags (right bar).

It is generally accepted that the larger or more diverse an antibody library, measured in terms of the number of different antibodies, the better the antibodies that can be selected from it. Griffiths et al., *EMBO J* 13(14):3245-3260, 1994 and Perelson et al., *J Theor Biol.*, 81(4):645-70, 1979. The diversity of most antibody libraries has been estimated by counting the number of transformants, assuming that each colony represents a different antibody.

It was generally assumed that the VH gene diversity was the same as the number of colonies obtained, e.g., ~$10^8$ for the library described in Sblattero et al., *Nat Biotechnol.*, 18(1):75-80, 2000. However, next-generation sequencing (NGS) showed that the VH clonal diversity (unique HCDR3 amino acid sequences) was actually ~30 fold lower ($3\times10^6$). D'Angelo et al., *MAbs.*, 6(1):160-72, 2014. Notwithstanding this apparent low diversity, many antibodies have been selected from this library. See, e.g., Sblattero et al., *Nat Biotechnol.*, 18(1):75-80, 2000; Glanville et al., *Curr Opin Struct Biol.*, 33:146-60, 2015; Lou et al., *Journal of immunological methods;* 253(1-2):233-42, 2001; Kehoe et al., *Mol Cell Proteomics*, 5(12):2350-63, 2006; Ayriss et al., *J Proteome Res.* 6(3):1072-82, 2007; Velappan et al., *Journal of immunological methods*, 321(1-2):60-9, 2007; Lillo et al., *PLoS One,* 6(12):e27756, 2011; Ferrara et al., *PLoS One,* 7(11):e49535, 2012; Close et al., *BMC Microbiol.* 13:270, 2013; and Ferrara et al., *MAbs,* 7(1):32-41, 2015.

NGS sequencing of another natural antibody library showed an even lower measured VH diversity ($2 \times 10^5$), even though the number of donors used (654) was extremely high, and the estimated number of colonies was $3 \times 10^{10}$. Glanville et al., *Proceedings of the National Academy of Sciences of the United States of America,* 106(48):20216-21, 2009. Further, Fantini et al. *PLoS One.* 12(5):e0177574, 2017 described three libraries with maximal diversities (numbers of colonies) $6\text{-}16 \times 10^6$, and estimated NGS diversities of $3\text{-}9 \times 10^6$.

While genetic diversity is essential, effective functional diversity is even more important: a high genetic diversity is of no utility if the encoded antibodies are non-functional and unable to fold properly. Indeed, a single amino acid change in an antibody can result in dramatic changes in expression levels and stability. Some publications have shown the superiority of natural antibody libraries over synthetic ones. Hugo et al., *Protein Eng.*, 16(5):381-6, 2003; Wang et al., *Proteins,* 82(10):2620-30, 2014; and Chan et al., *Journal of immunological methods,* 373(1-2):79-88, 2011. Natural diversity has the advantage that it has been prescreened for functionality by the immune system. However, it has the disadvantage that some antibodies are poorly expressed and folded in in vitro display systems, and that diversity can be dominated by a small number of clones.

The present disclosure aims, at least in part, at constructing antibody libraries comprising natural diversity such that the members of the libraries would be prescreened by the immune system for functionality, while excluding members that contain potential liabilities, would be poorly expressed, aggregating and/or poorly folded in a common screening system (e.g., yeast display, phage display, or a folding reporter such as ß-lactamase; see, e.g., Saunders et al., *Nat. Che Biol.*, 12:94-101; 1988; and D'Angelo et al., *BMC genomics* 12, suppl. 1, S1-S5; 2011; or green fluorescent protein; see e.g. Waldo, et al., *Nat. Biotechnol.,* 17: 691-5; 1999; Cabantous, et al., *PLoS ONE.,* 3:e2387; 2008; and Cabantous, et al., *J Struct Funct Genomics,* 6:113-9; 2005). The present disclosure thus features, in some embodiments, a method to create extremely diverse, highly functional antibody libraries by combining naturally occurring CDRs, including naturally occurring CDRs containing somatic mutations generated in vivo, within antibody scaffolds such that members of the antibody libraries are expected to be well expressed and/or folded, and lacking liabilities.

As used herein, the term "liability" refers to a motif in an antibody (e.g., located in a heavy chain or light chain CDR region) that would negatively affect one or more desired features of the antibody (e.g., stability, good expression in an expression or display system, proper folding, no or reduced aggregation, solubility, no or reduced integrin binding, no or reduced glycosylation, no or reduced deamidation, no or reduced isomerization, no unpaired cysteine, or no or reduced protease sensitivity, etc.). By virtue of being comprised of highly functional members, such an antibody library would be expected to be functionally much larger than libraries of similar genetic size, in which antibodies are present that contain any of these liabilities. In other words, the antibody libraries disclosed herein would have a much larger effective diversity.

I. Antibody Libraries and Methods of Construction

Provided herein are antibody libraries comprising the heavy chain and/or light chain CDR populations as described herein, wherein the heavy chain CDRs and/or light chain CDRs are inserted into a pre-selected heavy chain variable domain gene and/or a pre-selected light chain variable domain gene as also described herein, as well as methods of producing such antibody libraries. The heavy chain CDR1s, CDR2s, and/or CDR3s, and the pre-selected heavy chain variable domain may be of a mammalian species, for example, human, mouse, rat, rabbit, dog, pig, or camelid such as camel or llama. In some instances, the heavy chain CDR1s, CDR2s, and CDR3s may be derived from antibodies of the same mammalian species (e.g., human or camelid). Optionally, the pre-selected heavy chain variable domain gene may be from the same mammalian species. Alternatively, the heavy chain CDR1s, CDR2s, and/or CDR3s, and optionally the pre-selected heavy chain variable domain gene may be derived from naturally-occurring antibodies of different mammalian species.

Similarly, the light chain CDR1s, CDR2s, and CDR3s, as well as the pre-selected light chain variable domain gene may be of a mammalian species such as those described herein. In some instances, the light chain CDR1s, CDR2s, and CDR3s may be derived from antibodies of the same mammalian species (e.g., human or camelid). Optionally, the pre-selected light chain variable domain gene may be from the same mammalian species. Alternatively, the light chain CDR1s, CDR2s, and/or CDR3s, and optionally the pre-selected light chain variable domain gene may be derived from naturally-occurring antibodies of different mammalian species.

In some embodiments, the heavy chain CDRs and the pre-selected variable domain gene, and the light chain CDRs and the pre-selected variable domain gene are all of the same mammal species, for example, human.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody encompasses not only intact (e.g., full-length) antibodies, but also antigen-binding fragments thereof (such as Fab, Fab', F(ab')2, Fv), single-chain antibody (scFv), fusion proteins comprising an antibody portion, diabodies, nanobodies, single domain antibodies (also known as nanobodies, e.g., a Vii only antibody such as the VhH antibodies found in camelids), or multispecific antibodies (e.g., bispecific antibodies).

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, A1-lazikani et al (1997) J. Molec. Biol. 273:927-948; and Almagro, J. Mol. Recognit. 17:132-143 (2004). See also hgmp.mrc.ac.uk and bioinf.org.uk/abs).

Single-domain antibodies, also known as nanobodies, are also within the scope of the present disclosure. In some embodiments, a single-domain antibody contains only a heavy chain (VHH). Heavy chain only antibodies (HcAb) are naturally produced by camelids and sharks. The antigen binding portion of the HcAb is comprised of the VHH fragment. Vincke et al., *Methods Mol Biol.* 911:15-26 (2012).

The antibody libraries disclosed herein may contain a population of antibodies of any suitable format. In some embodiments, the antibody library discloses herein comprise a population of full-length antibodies, which may be of any suitable family (e.g., IgG, or IgA). In other embodiments, the antibody library disclosed herein comprise a population of antigen-binding fragments, for example Fab fragments. In yet other embodiments, the antibody library disclosed herein comprise a population of single-chain antibodies. Alternatively, the antibody library disclosed herein may comprise a population of single-domain antibodies such as VHH fragments.

Exemplary steps for constructing the antibody libraries described herein may include:

(1) Identifying suitable VH/VL pairs for use as variable gene scaffolds;
(2) Generating vectors based on the scaffolds containing a single insertion site for each CDR, the remaining CDRs may remain unchanged;
(3) Identifying naturally occurring CDRs by analysis of a database of naturally occurring antibody sequences (which may be obtained from sequencing members of a natural antibody library);
(4) Eliminating from the database of naturally occurring CDR sequences those sequences likely to encode liabilities;
(5) Synthesize the remaining set of CDRs as oligonucleotides;
(6) Inserting the CDRs at their appropriate sites within the previously modified scaffolds, each scaffold containing CDRs at only one site (e.g., the identified collection of HCDR1s is inserted at the HCDR1 site of the modified scaffold).

In some embodiments, the CDRs (e.g., CDR1, CDR2, CDR3, or a combination thereof) identified as described herein may be experimentally screened or selected for good folding and/or expression and screened or selected against liabilities such as poor folding, poor expression, polyreactivity or aggregation. The selected CDRs may be inserted into complete V domains within the context of the scaffolds. The resultant complete V domains could be further screened and selected for good folding and/or expression, and/or screened and selected against liabilities such as poor folding or expression, polyreactivity or aggregation. The selected VH/VL complete scaffold pairs can be assembled and cloned into an appropriate display vector (e.g., phage or yeast) for screening of antibodies having desired binding specificity.

A. Selection of Heavy Chain and Light Chain Variable Domain Framework Scaffolds

In some embodiments, the heavy chain and/or light chain framework scaffolds used in constructing the antibody libraries described here may be derived from commercially available therapeutic antibodies (e.g., those whose marketing authorization has been approved by the US Food and Drug Administration or/and the European Medicines Agency) or therapeutic antibodies that are currently in clinical trials, for example, in phase II or phase III trials. As used herein, a therapeutic antibody refers to the antibody molecule of an approved drug product (e.g., in the US, in EP, or in other jurisdictions such as CA or JP), or an antibody molecule that has been or is currently in a clinical trial in a suitable jurisdiction, for example, in the US or in Europe.

The germline heavy chain variable domain and light chain variable domain genes used in such therapeutic antibodies can be examined for features such as aggregation, hydrophobic interaction, polyspecificity, monomericity, level of expression in mammalian host cells (e.g., in HEK cells or CHO cells), Tm of its Fab form, and purification characteristics. See Table 1. Those having desired features, for example, high expression levels in mammalian cells (e.g., ≥50 mg/L in HEK cells), high Fab Tm (e.g., >64° C.), low slope for accelerated stability (e.g., <0.09), etc. can be selected as framework scaffolds for library constructions. Additional features and selection criterion are provided in Table 1, which shows as exemplary examples those therapeutic antibodies with the best properties, as well as three additional antibodies with poor therapeutic properties. This data is derived from Jain, T. et al. Biophysical properties of the clinical-stage antibody landscape. *Proceedings of the National Academy of Sciences of the United States of America* 114, 944-949, doi:10.1073/pnas.1616408114 (2017).

For each characteristic being evaluated, the worst 10% of the evaluated therapeutic antibodies can be assigned with a flag. See FIG. 1. In some instances, those therapeutic antibodies having less than 2 flags (e.g., having 1 flag or none) may be selected for use as the heavy chain and/or light chain framework scaffold.

In some embodiments, the heavy chain variable domain gene for use as the heavy chain framework scaffold can be VH1-24, VH2-70, VH3-7, VH4-30-4, VH5-51, VH1-18, VH1-69, VH3-23, VH5-10-1, VH3-9, or VH3-11. Alternatively, or in addition, the light chain variable domain gene for use as the light chain framework scaffold can be K1-12, K4-1, K2D-29, K3-11, K3-20, or L2-14. Such heavy chain and/or light chain framework scaffolds may be germline VH and/or VL genes. Alternatively, the heavy chain and/or light chain framework scaffolds may contain one or more mutations in one or more framework regions (e.g., FR1, FR2, FR3, or FR4) as compared with the germline gene counterpart. Such mutations may be present within the therapeutic antibody, or may be introduced to avoid specific liabilities, e.g., methionine oxidation, aggregation, integrin binding, glycosylation, deamidation, isomerization, unpaired cysteine, or protease sensitivity. In specific examples, the antibody library described herein uses the following VH and VL framework scaffold pairs: VH1-24/VK1-12, VH2-70/VK4-1, VH3-7/VK2D-29, VH4-30-4/VK3-11, VH5-51/VK3-20, or VH1-18/VL2-14.

In some specific examples, the VH and/or VL framework scaffolds used in the antibody library described herein are derived from abrilumab, mepolizumab, crenezumab, necitumumab, anifrolumab, or evoculumab, the characteristics of each of which are provided in Table 2. As used herein, "derived from" refers to the use of the VH and/or VL genes of any of these therapeutic antibodies, either with no modification, or with one or more mutations introduced into one or more of the framework regions, for example, up to 5 amino acid substitutions (e.g., up to 4, 3, 2, or 1 amino acid substitutions) in the VH gene (e.g., in one or more of the framework regions) and/or in the VL gene (e.g., in one or more of the framework regions).

In some instances, the mutations introduced into a germ-line VH and/or VL gene or introduced into the VH and/or VL gene of a reference therapeutic antibody (e.g., those listed in Table 2) may be conservative substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The amino acid sequences of exemplary VH and VL framework scaffolds are provided below (with CDRs that are modified indicated in boldface and mutations relative to parent therapeutic antibodies listed in Table 2 underlined):
Scaffold Derived from Abrilumab:
  CDRs are bold and underlined
  Mutations from the original antibody are italicized (all Jκ have been replaced for Jκ4).

VL:
(SEQ ID NO: 121)
DIQMTQSPSSVSASVGDRVTITCRASQGISSWLAWYQQKPGKAPKLLIYGASNLESGVPSRFSGSGSGTDFTLTISSLQPEDFANYYCQQANSEPWTFGGGTKVEIK

Linker:
(SEQ ID NO: 122)
SGGSTITSYNVYYTKLSSSGT

VH:
(SEQ ID NO: 123)
QVQLVQSGAEVKKPGASVKVSCKVSGYTLSDLSIHWVRQAPGKGLEWMGGFDPQDGETIYAQKFQGRVTMTEDTSTDTAYMELSSLKSEDTAVYYCAT GSSSSWEDPWGQGTLVTVSS

Scaffold derived from mepolizumab:
VL:
(SEQ ID NO: 124)
DIVMTQSPDSLAVSLGERATINCKSSQSLLNSGNQKNYLAWYQQKPGQPPKLLIYGASTRESGVPDRFSGSGSGTDFTLTISSLQAEDVAVYYCQNVHSFPF TFGGGTKVEIK Linker:
(SEQ ID NO: 125)
SGGSTITSYNVYYTKLSSSGT VH:
(SEQ ID NO: 126)
QVTLRESGPALVKPTQTLTLTCTVSGFSLSAYSVNWIRQPPGKALEWLAMI WGDGKIVYNSALKSRLTISKDTSKNQVVLTMTNMDPVDTATYYCAGDGYYP YAMDNWGQGTLVTVSS Scaffold derived from crenezumab:
VL:
(SEQ ID NO: 127)
DIVMTQSPLSLPVTPGEPASISCRSSQSLVYSNGDTYLHWYLQKPGQSPQL LIYKVSNRFSGVPDRFSGSGSGTDFTLKISRVEAEDVGVYYCSQSTHVPWT FGGGTKVEIK Linker:
(SEQ ID NO: 128)
SGGSTITSYNVYYTKLSSSGT VH:
(SEQ ID NO: 129)
EVQLVESGGGLVQPGGSLRLSCAASGFTFSSYGMSWVRQAPGKGLELVASI NSNGGSTYYPDSVKGRFTISRDNAKNSLYLQMNSLRAEDTAVYYCASGDYW GQGTTVTVSS Scaffold derived from necitumumab:
VL:
(SEQ ID NO: 130)
EIVMTQSPATLSLSPGERATLSCRASQSVSSYLAWYQQKPGQAPRLLIYDA SNRATGIPARFSGSGSGTDFTLTISSLEPEDFAVYYCHQYGSTPLTFGGGT KVEIK Linker:
(SEQ ID NO: 131)
SGGSTITSYNVYYTKLSSSGT VH:
(SEQ ID NO: 132)
QVQLQESGPGLVKPSQTLSLTCTVSGGSISSGDYYWSWIRQPPGKGLEWIG YIYYSGSTDYNPSLKSRVTMSVDTSKNQFSLKVNSVTAADTAVYYCARVSI FGVGTFDYWGQGTLVTVSS Scaffold derived from anifrolumab:
VL:
(SEQ ID NO: 133)
EIVLTQSPGTLSLSPGERATLSCRASQSVSSSFLAWYQQKPGQAPRLLIYG ASSRATGIPDRLSGSGSGTDFTLTITRLEPEDFAVYYCQQYDSSAITFGGG TKVEIK Linker:
(SEQ ID NO: 134)
SGGSTITSYNVYYTKLSSSGT VH:
(SEQ ID NO: 135)
EVQLVQSGAEVKKPGESLKISCKGSGYIFTNYWIAWVRQVPGKGLESMGII YPGDSDIRYSPSFQGQVTISADKSITTAYLQWSSLKASDTAIYYCARHDIE GFDYWGRGTLVTVSS Scaffold derived from evolocumab:
VL:
(SEQ ID NO: 136)
ESALTQPASVSGSPGQSITISCTGTSSDVGGYNSVSWYQQHPGKAPKLM IYEVSNRPSGVSNRFSGSKSGNTASLTISGLQAEDEADYYCNSYTSTSM VFGGGTKLTVL Linker:
(SEQ ID NO: 137)
SGGSTITSYNVYYTKLSSSGT VH:
(SEQ ID NO: 138)
EVQLVQSGAEVKKPGASVKVSCKASGYTLTSYGISWVRQAPGQGLEWMG WVSFYNGNTNYAQKLQGRGTMTTDPSTSTAYMELRSLRSDDTAVYYCAR GYGMDVWGQGTTVTVSS Any of the VH and/or VL framework scaffolds described herein can be used to construct a cassette that allows for cloning of one or more of pluralities of nucleic acids each encoding a diverse population of a heavy chain CDR or a light chain CDR into the corresponding framework scaffold at the corresponding CDR position.

In some instances, restriction sites can be introduced into a heavy chain scaffold flanking the CDR1 region, the CDR2 region, or the CDR3 region for cloning a plurality of nucleic acids encoding a diverse population of heavy chain CDR1s, heavy chain CDR2s, or heavy chain CDR3s, respectively. In some instances, restriction sites can be introduced into a heavy chain framework scaffold flanking at least two or the CDR11, CDR2, and CDR3 (e.g., CDR1+CDR2, CDR1+CDR3, or CDR2+CDR3) for cloning a combination of the corresponding CDR regions into the framework scaffold. In one example, restriction sites can be introduced into a heavy chain framework scaffold flanking all of the CDR1, CDR2, and CDR3 regions for cloning diverse heavy chain CDR1s, CDR2s, and CDR3s at the corresponding locations.

In some instances, restriction sites can be introduced into a light chain scaffold flanking the CDR1 region, the CDR2 region, or the CDR3 region for cloning a plurality of nucleic acids encoding a diverse population of light chain CDR1s, heavy chain CDR2s, or heavy chain CDR3s, respectively. In some instances, restriction sites can be introduced into a light chain framework scaffold flanking at least two or the CDR1, CDR2, and CDR3 (e.g., CDR1+CDR2, CDR1+CDR3, or CDR2+CDR3) for cloning a combination of the corresponding CDR regions into the framework scaffold. In one example, restriction sites can be introduced into a light chain framework scaffold flanking all of the CDR1, CDR2, and CDR3 regions for cloning diverse light chain CDR1s, CDR2s, and CDR3s at the corresponding locations.

Figure 2:
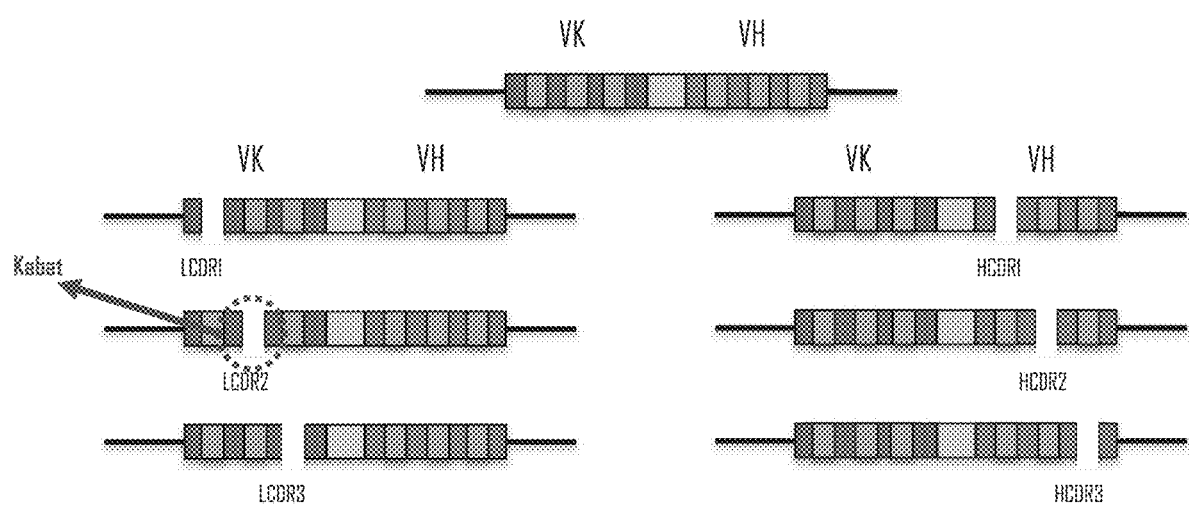
FIG. 2 is a schematic showing the seven scaffolds developed from the VH and/or VL gene of a selected therapeutic antibody. Except for LCDR2, all CDRs are as described by IMGT. LCDR2 uses the Kabat description.

FIGS. 2 and 3 illustrate an exemplary scheme for construction of cassettes for introducing heavy chain CDR1, CDR2, or CDR3 diversities into a heavy chain scaffold and/or cassette for introducing light chain CDR1, CDR2, or CDR3 diversities into a light chain scaffold.

The resultant cassettes can be located in a suitable expression vector for producing the encoded antibodies in a suitable expression, display or folding reporter system.

B. Heavy Chain and Light Chain CDR Populations

The heavy chain and/or light chain CDR1, CDR2, and/or CDR3 populations in the antibody libraries can be derived from naturally-occurring human antibodies. Such CDR sequences can be obtained by sequencing naturally-occurring antibodies (e.g., human antibodies) in existing natural antibody libraries and analyzing the heavy chain and light chain sequences thus obtained by conventional methods to identify heavy chain and/or light chain CDR sequences. Alternatively, or in addition, naturally-occurring antibody CDR sequences can be obtained by analyzing sequences of such antibodies in publicly available databases of naturally-occurring antibody sequences (e.g., human antibody sequences or camelid VHH antibody sequences), e.g., the NCBI database, the IMGT database, sequences from Jackson et al., J. Immunol. Methods, 324:26, 2007, and/or the sequences from Lee et al., Immunogenetics, 57:917, 2006, The Observed Antibody Space (antibodymap.org) described in Kovaltsuk, A. et al. Observed Antibody Space: A Resource for Data Mining Next-Generation Sequencing of Antibody Repertoires. *Journal of Immunology*, doi:10.4049/jimmunol.1800708 (2018), and/or the iReceptor database (ireceptor.irmacs.sfu.ca) described in Corrie, B. D. et al. iReceptor: A platform for querying and analyzing antibody/B-cell and T-cell receptor repertoire data across federated repositories. *Immunol Rev* 284, 24-41, doi:10.1111/imr.12666 (2018), and/or the sequence database described in Briney, B. et al., Commonality despite exceptional diversity in the baseline human antibody repertoire. *Nature*, doi: 10.1038/s41586-019-0879-y (2019).

The extent of the framework region and CDRs can be precisely identified using methodology known in the art, for example, by the Kabat definition, the IMGT definition, the Chothia definition, the AbM definition, and/or the contact definition, all of which are well known in the art. See, e.g. Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; Lefranc, M. P. et al. IMGT unique numbering for immunoglobulin and T cell receptor variable domains and Ig superfamily V-like domains. *Dev Comp Immunol* 27, 55-77 (2003) and Almagro, J. Mol. Recognit. 17:132-143 (2004). See also hgmp.mrc.ac.uk, IMGT.org and bioinf.org.uk/abs.

The heavy chain and/or light chain CDR1, CDR2, and/or CDR3 sequences thus obtained may be further analyzed to remove those that comprise a liability, e.g., those listed in Table 4. In some instances, heavy chain and/or light chain CDR1, CDR2, and/or CDR3 sequences comprising one of the liabilities listed in Table 4 (e.g., a glycosylation site, a deamidation site, an isomerization site, an unpaired cysteine, a net charge greater than 1 (e.g., in LCDR1-2 and/or HC CDR1-2), a tripeptide motif containing at least two aromatic residues (which may affect viscosity), a motif that promotes aggregation, (viii) a polyspecificity site such as those containing a motif of GG, GGG, RR, VG, W, WV, WW, WWW, YY, or, WXW, in which X represents any amino acid residue; a protease sensitive site (fragmentation sensitive site), or an integrin binding site) and/or FIG. 5 (using HC CDR2 as an example) can be removed such that the resultant antibody library is free (substantially free or completely free) of members comprising the excluded liability.

Alternatively or in addition, potential glycation sites such as lysine glycation sites may be removed. A glycation site refers to a site in a protein molecule that can be linked to a sugar molecule via a nonenzymatic process. Exemplary glycation sites include, but are not limited to, KE, EK, and ED. Additional liabilities include metal catalyzed fragmentation site (e.g., HS, SH, KT, HXS, or SXH, in which X represents any amino acid residue), polyspecificity aggregation site (e.g., having a motif of $X_1X_2X_3$, in which each of $X_1$, $X_2$, and $X_3$ is independently F, I, L, V, W, or Y), and streptavidin binding motif (e.g., HPQ, EPDW (SEQ ID NO: 117), PWXWL (SEQ ID NO: 118), in which X represents any amino acid residue, GDWVFI (SEQ ID NO: 119), and PWPWLG (SEQ ID NO: 120)).

Substantially free means that the number of a heavy or light chain CDR comprising the liability is less than 20% in the library, e.g., less than 15% or less than 10%.

In some examples, heavy chain and/or light chain CDR1, CDR2, and/or CDR3 sequences comprising two or more (e.g., 3, 4, 5, 6, 7, or more) of the liabilities noted above can be removed such that the resultant library is free of (substantially free of or completely free of) members comprising the excluded liabilities. In one example, heavy chain and/or light chain CDR1, CDR2, and/or CDR3 sequences comprising all of the liabilities listed in Table 4 can be removed such that the resultant library is free of (substantially free of or completely free of) members comprising any of the liabilities. Alternatively or in addition, heavy chain and/or light chain CDR1, CDR2, and/or CDR3 sequences comprising all of the liabilities listed in FIG. 5 can be removed such that the resultant library is free of (substantially free of or completely free of) members comprising any of the liabilities. In one specific example, heavy chain and/or light chain CDR1, CDR2, and/or CDR3 sequences comprising all of the liabilities disclosed herein can be removed such that the resultant library is free of (substantially free of or completely free of) members comprising any of the liabilities.

In some examples, heavy chain CDR1 and CDR2 sequences comprising one or more of liabilities, e.g., those listed in Table 4 and/or FIG. 5, can be removed, while heavy chain CDR3 sequences can be derived from naturally-occurring human antibodies without removal of members having the liabilities. Alternatively, heavy chain CDR3 sequences comprising one or more liabilities can also be removed. Alternatively, or in addition, light chain CDR1, CDR2, and CDR3 sequences comprising one or more of liabilities, e.g., those listed in Table 4 and illustrated by way of example in FIG. 5, can be removed.

In some examples, heavy and/or light chain CDR1, CDR2, and/or CDR3 sequences having anomalous lengths can also be excluded. For example, light chain CDR1 and/or CDR2 having a length that is beyond the scope of germline length±2-aa could be excluded. See FIGS. 16-21.

In some examples, heavy chain CDR1 and CDR2 members containing deamidation sites (e.g., NG, NS, NT, NN, GNF, GNY, GNT, GNG), isomerization sites (e.g., DG, DS, DD), aggregation site (FHW); motifs affecting viscosity (e.g., HYF and HWH), motifs indicating poor developability (e.g., net charge ≥+1 in LCDR1-2 and/or HCDR1-2), unpaired cysterine, polyspecificity site (e.g., GGG, RR, VG, VV, VVV, WW, WWW, YY, WXW, X referring to any amino acid residue, and GG), and glycosylation sites (e.g., NXS or NXT, in which X is any amino acid residue except for proline) can be excluded. In some examples, one or more of the following liabilities in heavy chain CDR1 and heavy chain CDR2 members can also be excluded: additional glycosylation sites (e.g., NXC, X being any amino acid residue except for proline), additional deamination sites (e.g., NA, NH, and/or ND), additional isomerization sites (e.g., DT and/or DH), lysine glycation sites (e.g., KE, EK, and ED), integrin binding sites (e.g., RGD, RYD, LDV, and KGD), protease sensitive sites (fragmentation site) (e.g., DP, DG, DS, DV, DY, DF, DQ, DK, DL, and DD), metal catalyzed fragmentation sites (e.g., HS, SH, KT, HXS, and SXH, in which X represents any amino acid residue), polyspecificity aggregatin sites (e.g., having a motif of $X_1X_2X_3$, in which each of $X_1$, $X_2$, and $X_3$ independently is F, I, L, V, W, or Y), and/or streptavidin binding sites (e.g., HPQ, EPDW (SEQ ID NO: 117), PWXWL (SEQ ID NO: 118), in which X represents any amino acid residue, GDWVFI (SEQ ID NO: 119), and PWPWLG (SEQ ID NO: 120)).

In some examples, the heavy chain CDR3 members having the one or more liabilities described herein can also be excluded. Alternatively, the heavy chain CDR3 members may include those derived from naturally-occurring antibodies directly without removal of the one or more liabilities described herein.

Alternatively or in addition, light chain CDR1, CDR2, and/or CDR3 members containing deamidation sites (e.g., NG, NS, NT, NN, GNF, GNY, GNT, GNG), isomerization sites (e.g., DG, DS, DD), aggregation site (FHW); motifs affecting viscosity (e.g., HYF and HWH), motifs indicating poor developability (e.g., net charge≥+1 in LCDR1-2, HCDR1-2), unpaired cysterine, polyspecificity site (e.g., GGG, RR, VG, VV, VVV, WW, WWW, YY, WXW, X referring to any amino acid residue, and GG), and glycosylation sites (e.g., NXS or NXT, in which X is any amino acid residue except for proline) can be excluded. In some examples, one or more of the following liabilities in light chain CDR1, CDR2, and/or CDR3 members can also be excluded: additional glycosylation sites (e.g., NXC, X being any amino acid residue except for proline), additional deamidation sites (e.g., NA, NH, and/or ND), additional isomerization sites (e.g., DT and/or DH), lysine glycation sites (e.g., KE, EK, and ED), integrin binding sites (e.g., RGD, RYD, LDV, and KGD), protease sensitive sites (fragmentation site) (e.g., DP, DG, DS, DV, DY, DF, DQ, DK, DL, and DD), metal catalyzed fragmentation sites (e.g., HS, SH, KT, HXS, and SXH, in which X represents any amino acid residue), polyspecificity aggregatin sites (e.g., having a motif of $X_1X_2X_3$, wherein each of $X_1$, $X_2$, and $X_3$ independently is F, I, L, V, W, or Y), and/or streptavidin binding sites (e.g., HPQ, EPDW (SEQ ID NO: 117), PWXWL (SEQ ID NO: 118), in which X represents any amino acid residue, GDWVFI (SEQ ID NO: 19), and PWPWLG (SEQ ID NO: 120)).

In some examples, the one or more liabilities described herein may be excluded from all of the light chain CDR1, CDR2, and CDR3 members.

The resultant heavy chain and/or light chain CDR1, CDR2, and/or CDR3 sequences obtained from naturally-occurring antibodies, either excluding sequences comprising one or more liabilities or maintaining all sequences, can be used as templates to synthesis nucleic acids encoding, and replicating, the CDR sequences. Such nucleic acids can be inserted into the corresponding CDR position in the VH and/or VL scaffolds disclosed herein, and are termed "replicated natural CDRs".

When desired, expression vectors carrying the VH and/or VL scaffolds with one or more heavy chain and or light chain CDRs inserted can be introduced into a suitable expression/display system for isolating functional members. Functional members include those having one or more superior features, for example, good expression and display in a suitable display system, improved folding, reduced aggregation or polyreactivity, and/or greater Tm. Such functional members can be identified by collecting host cells displaying antibodies produced from the expression vectors, and sequencing the corresponding heavy and/or light chain CDR sequences encoded by the expression vectors in the collected host cells.

For example, an initial antibody library may also be sorted for yeast displaying antibodies that have been stained with conformational probes that detect correct antibody folding. Traxlmayr et al., Arch Biochem Biophys. 526(2):174-80, 2012. Examples of such conformational probes include protein A (Hillson et al., The Journal of experimental medicine. 178(1):331-6, 1993; Akerstrom et al., 1994; J. Imm Methods, 177(1-2):151-63, 1994; and Roben et al., J. Immunology 154(12):6437-45, 1995) or protein L (Charbit et al., Gene, 70(1):181-9, 1988; Graille et al., Structure, 9(8):679-87, 2001; and Enever et al., Journal of molecular biology, 347(1):107-20, 2005), that are able to bind to VH3 and VK domains respectively, and derivatives of indole 3-butyric acid (Alves et al., Langmuir, 28(25):9640-8, 2012; Alves et al., Anal Chem., 84(18):7721-8, 2012; Alves et al., Bioconjug Chem., 25(7):1198-202, 2014; and Mustafaoglu et al., Biotechnol Bioeng., 112(7):1327-34, 2015) that binds to the "nucleotide binding site" found in all antibodies (Rajagopalan et al., Proceedings of the National Academy of Sciences of the United States of America, 93(12):6019-24, 1993).

The previous use of conformational probes has been shown to predict high expression and thermostability (Traximayr et al., 2012; Shusta et al., J Mol Biol. 292(5):949-56, 1999; Traxlmayr et al., Biochim Biophys Acta., 1824(4):542-9, 2012; Traxlmayr et al., Protein Eng Des Sel., 26(4):255-65, 2013; and Hasenhindl et al., Protein Eng Des Sel., 26(10):675-82, 2013) in yeast display. This approach selects for antibody fragments that are well expressed and well folded. Rather than positive selection for good display, each individual CDR library can be depleted of CDRs that contain liabilities. For example, adapting screens used for antibody screening (Yang et al., MAbs., 5(5):787-94, 2013; Kelly et al., MAbs, 7(4):770-7, 2015; Kohli et al., MAbs. 7(4):752-8, 2015; Obrezanova et al., MAbs., 7(2):352-63, 2015; Wu et al, Protein Eng Des Sel., 28(10):403-14, 2015; Yang et al., MAbs., 9(4):646-53, 2017; Xu et al., Protein Eng Des Sel., 26(10):663-70, 2013; and Kelly et al., MAbs., 9(7):1036-40, 2017) to yeast display sorting, and isolating those yeast displaying antibodies that correspond to the more "developable" phenotype selects for suitable CDRs that can then be combined to create highly functional libraries.

Examples of such selections include polyspecificity reagents, heparin or chaperones and only retaining those antibodies that do not bind such substances. Further stability increases can be generated by applying a heat shock step (Traxlmayr et al., 2012; Shusta et al., J Mol Biol. 292(5): 949-56, 1999; Traxlmayr et al., Biochim Biophys Acta., 1824(4):542-9, 2012; Traxlmayr et al., Protein Eng Des Sel., 26(4):255-65, 2013; and Hasenhindl et al., Protein Eng Des Sel., 26(10):675-82, 2013). See also FIG. 23.

The sequences encoding functional members of the heavy and/or light CDR1, CDR2, and/or CDR3 can be used as templates for synthesizing nucleic acids coding for such functional members, or used directly. The resultant nucleic acids can then be inserted into the VH and/or VL scaffold as described herein to produce antibody libraries as also described herein. In some embodiments, the antibody library disclosed herein is substantially free of non-functional members, e.g., having less than 10% (e.g., less than 8%, less than 5%, less than 3%, less than 1%, or lower) non-functional members.

C. Antibody Libraries

The antibody libraries described herein may comprise a plurality of nucleic acids encoding a plurality of antibody heavy chain and/or antibody light chain variable domains, which collectively comprise a common VH and/or VL framework scaffold (e.g., those described herein) with a diverse population of heavy or light chain CDR1s, a diverse population of heavy or light chain CDR2s, and/or a diverse population of heavy or light chain CDRs inserted at the corresponding CDR positions.

In some embodiments, the antibody library described herein is a heavy chain library comprising a plurality of nucleic acids encoding a plurality of antibody heavy chain variable domains. In some examples, the heavy chain library may comprise at least $10^2$ diversity of heavy chain CDR1s (having at least $10^2$ unique heavy chain CDR1 sequences), for example, at least $10^3$, $10^4$, $10^5$ diversity or at least $10^6$ diversity. Alternatively, or in addition, the heavy chain library may comprise at least $10^2$ diversity of heavy chain CDR2s (having at least $10^2$ unique heavy chain CDR2 sequences), for example, at least $10^3$, $10^4$, $10^5$ diversity or at least $10^6$ diversity. In other examples, the heavy chain library may comprise at least $10^2$ diversity of heavy chain CDR3s (having at least $10^2$ unique heavy chain CDR3 sequences), for example, at least $10^3$, $10^4$, $10^5$ diversity, at least $10^6$ diversity, at least $10^7$ diversity, or at least $10^8$ diversity.

In some examples, the heavy chain library may comprise diversity only in the heavy chain CDR1s, the heavy chain CDR2s, or the heavy chain CDR3s. In other examples, the heavy chain library may comprise diversity in at least two of the heavy chain CDR1, CDR2, and CDR3 regions (e.g., CDR1+CDR2, CDR1+CDR3, or CDR2+CDR3). In one specific example, the heavy chain library comprises diversity in all of the heavy chain CDR1, CDR2, and CDR3 regions.

In some embodiments, the heavy chain library is a secondary library generated for affinity maturation of a pre-selected antibody (the parent antibody) with binding activity to a target antigen. Such a secondary library may comprise diversity in one or two of the heavy chain CDR regions, while keeping the other CDR sequence(s) of the parent antibody. For example, the secondary library may comprise the same heavy CDR1 and CDR2 sequences as the parent antibody, and a diverse population of heavy chain CDR3 sequences. Alternatively, the secondary library may comprise the same heavy CDR3 sequence as the parent antibody and a diverse population of heavy chain CDR1 and/or CDR2 sequences.

Any of the heavy chain libraries disclosed herein may be paired with a common light chain variable region. Alternatively, it may be paired with any of the light chain antibody libraries as also described herein.

Also provided herein are antibody light chain libraries that comprise a plurality of nucleic acids encoding a plurality of antibody light chain variable domains. In some examples, the light chain library may comprise at least $10^2$ diversity of light chain CDR1s (having at least $10^2$ unique light chain CDR1 sequences), for example, at least $10^3$, $10^4$, $10^5$ diversity or at least $10^6$ diversity. Alternatively, or in addition, the light chain library may comprise at least $10^2$ diversity of light chain CDR2s (having at least $10^2$ unique light chain CDR2 sequences), for example, at least $10^3$, $10^4$, $10^5$ diversity or at least $10^6$ diversity. In other examples, the light chain library may comprise at least $10^2$ diversity of light chain CDR3s (having at least $10^2$ unique light chain CDR3 sequences), for example, at least $10^3$, $10^4$, $10^5$ diversity, at least $10^6$ diversity, at least $10^7$ diversity, or at least $10^8$ diversity.

In some examples, the light chain library may comprise diversity only in the light chain CDR1s, the light chain CDR2s, or the light chain CDR3s. In other examples, the light chain library may comprise diversity in at least two of the light chain CDR1, CDR2, and CDR3 regions (e.g., CDR1+CDR2, CDR1+CDR3, or CDR2+CDR3). In one specific example, the light chain library comprises diversity in all of the light chain CDR1, CDR2, and CDR3 regions.

In some embodiments, the light chain library is a secondary library generated for affinity maturation of a pre-selected antibody (the parent antibody) with binding activity to a target antigen. Such a secondary library may comprise diversity in one or two of the light chain CDR regions, while keeping the other CDR sequence(s) of the parent antibody. For example, the secondary library may comprise the same light CDR1 and CDR2 sequences as the parent antibody, and a diverse population of light chain CDR3 sequences. Alternatively, the secondary library may comprise the same light CDR3 sequence as the parent antibody and a diverse population of light chain CDR1 and/or CDR2 sequences.

Figure 35:
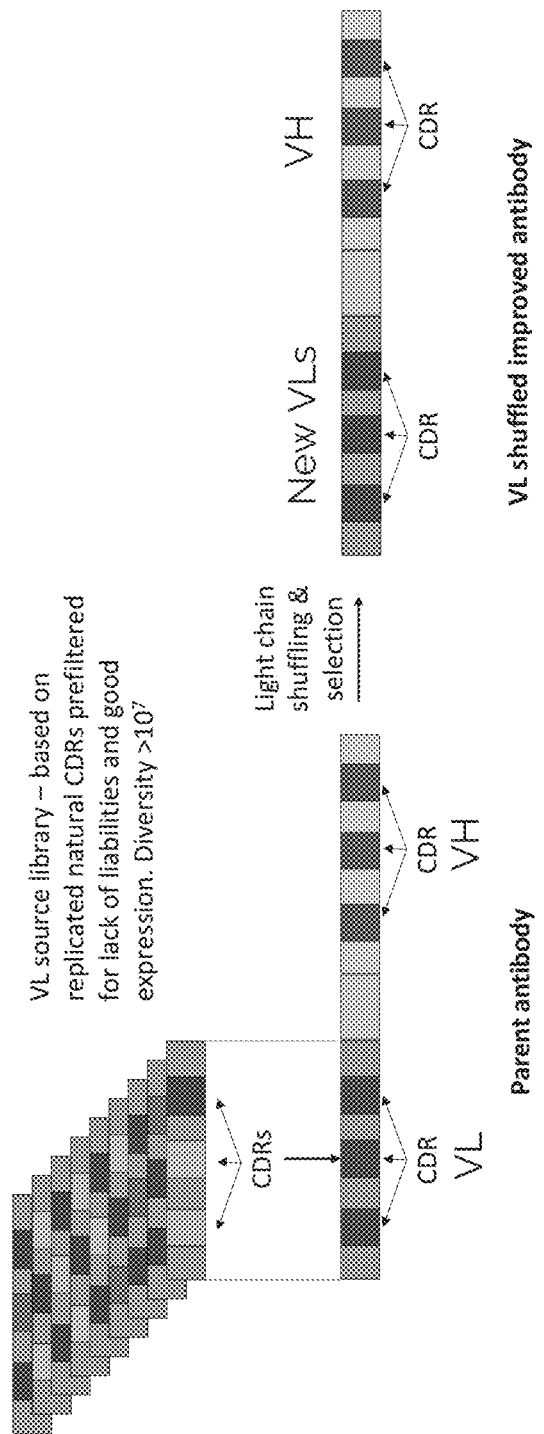
FIG. 35 is a diagram illustrating an exemplary affinity maturation approach via VL shuffling.
Figure 36:
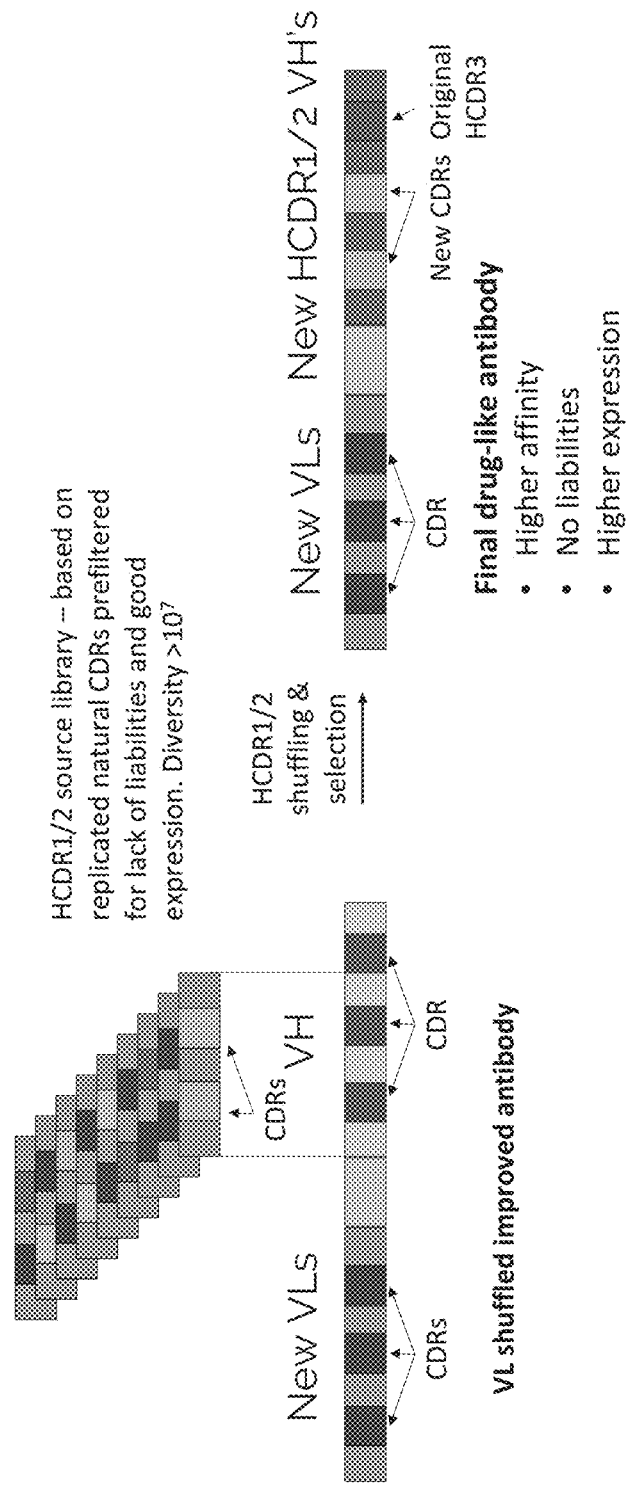
FIG. 36 is a diagram illustrating further HC CDR1 and HC CDR2 shuffling, following the VL shuffling depicted in FIG. 32.

As illustrated in FIG. 35 and FIG. 36, a secondary library may be generated via VL shuffling and/or VH CDR1 and/or CDR2 shuffling.

Any of the light chain libraries disclosed herein may be paired with a common heavy chain variable region. See, e.g., FIG. 26. Alternatively, it may be paired with any of the heavy chain antibody libraries as also described herein. See, e.g., FIG. 27.

II. Antibody Library Screening

Any of the antibody libraries described herein may be used to screen for antibodies having binding specificity to an antigen of interest. Antibodies encoded by the nucleic acids in the library can be expressed and displayed using a suitable expressing/display system, for example, a cell-free display system (e.g., ribosome display), a phage display system, a prokaryotic cell-based display system (e.g., bacterial display), or a eukaryotic cell-based display system (e.g., yeast display or mammalian cell display). In certain embodiments, the antibody libraries are expressed and displayed on yeast cells. In other embodiments, the antibody libraries are expressed and displayed on phage particles (phage display). In other embodiments two or more display systems are used, e.g. phage display followed by yeast display.

The library of antibodies may be expressed/displayed in a suitable system, e.g., those described herein, in any format. Examples include intact antibodies (full-length antibodies), antigen-binding fragments thereof (e.g., Fab), or single chain antibodies (scFv).

Phage display is a protein display format using bacteriophages (e.g., phage f1, fd, and M13). In this system, at least one antibody chain (e.g., the heavy chain and/or the light chain) is typically covalently linked to a bacteriophage coat protein, for example, a gene III protein, a gene VIII protein, or a major coat protein (see, e.g., WO 00/71694). Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; and Hoogenboom et al. (1991) *Nuc Acid Res* 19:4133-4137.

Bacteriophage displaying the protein component can be grown and harvested using standard phage preparatory methods, e.g., PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

In other embodiments, a eukaryotic expression/display system, e.g., yeast cells or mammalian cells, can be used for expressing and displaying the library of antibodies as described herein. Yeast display is a protein display format, in which a protein component (e.g., an antibody component) is linked to a yeast cell wall protein (e.g., Aga1p or Aga2p) directly or indirectly. In some instances, one chain of an antibody can be covalently fused to the yeast cell wall protein for direct display. In other instances, the association between an antibody component and a yeast cell wall component can be mediated by an intermediate agent. Yeast display is described in, e.g., Cho et al., J. Immunol. Methods, 220(1-2):179-188, 1998; Boder et al., Methods Enzymol. 192(2):243-248, 2000; van den Beucken et al., FEBS Lett 546(2-3):288-294, 2003; and Boder et al., Arch Biochem Biophys 526(2):99-106, 2012.

To screen an antibody library as described herein for isolating antibodies capable of binding to a target antigen, the library of antibodies can be in contact with the target antigen under suitable conditions allowing for antibody-antigen binding. Phage particles or host cells displaying antibodies binding to the target antigen can be isolated, for example, by retention or a support member on which the target antigen is immobilized, amplified if needed, and the nucleic acids coding for the displayed antibodies can be determined. The screening process can be repeated multiple time, and display systems can be used in combination. When needed different antigens can be used for selecting antibody members having desired binding specificity or for negative selection to exclude antibody members having binding activity to a non-target antigen.

The screening of the antibodies derived from the libraries described herein can be carried out by any appropriate means. For example, binding activity can be evaluated by standard immunoassay and/or affinity chromatography. Determining the ability of candidate antibodies to bind therapeutic targets can be assayed in vitro using, e.g., a BIACORE™ instrument, which measures binding rates of an antibody to a given target antigen based on surface plasmon resonance. In vivo assays can be conducted using any of a number of animal models and then subsequently tested, as appropriate, in humans. Cell-based biological assays are also contemplated.

A lead antibody identified from antibody library screening may be subject to affinity maturation as described herein. A secondary library resulting from affinity maturation may be screened for binders having desired features, e.g., high binding affinity and/or binding specificity, following routine practice and/or disclosures provided herein.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985; *Transcription and Translation* (B. D. Hames & S. J. Higgins, eds. (1984; *Animal Cell Culture* (R. I. Freshney, ed. (0986»); Immobilized Cells and Enzymes (IRL Press, (1986; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Identifying Suitable VH VL Pairs for Use as Scaffolds

Suitable VH/VL pairs as scaffold for CDR insertions are crucial for creating highly diverse, highly functional antibody libraries. The usual rational for selecting scaffolds are: (i) the scaffolds are commonly used in nature (e.g., VH1-69, VH3-23); (ii) the scaffolds are chosen from known antibodies; (iii) the scaffolds are widely used by others; (iv) the scaffolds contains consensus germline sequences; and (v) the VH and VL pairs in the scaffold are considered to be stable, well expressed and non-aggregating.

Provided herein is an alternative approach for identifying suitable VH/VL pairs for use as a scaffold for antibody library construction. A recent publication describing certain approved antibodies and antibodies that are currently approved, or in Phase 2 or Phase 3 clinical trials (Jain, T. et al. Biophysical properties of the clinical-stage antibody landscape. *Proceedings of the National Academy of Sciences of the United States of America* 114, 944-949, doi:10.1073/pnas.1616408114 (2017)) was analyzed. The VH and VL germline genes of these antibodies were determined. Based on the developability data (e.g., aggregation, hydrophobic interaction, polyspecificity, monomericity, expression level in HEK cells, and Fab Tm) provided for each clinical antibody in the paper, the frequency and developability of these germline genes in clinical antibodies was assessed. The antibodies displaying the value in the worst 10% for each of the standard tested was flagged (highlighted in bold and italics in Table 1) and only antibodies with si flag were considered developable. In Table 1 all the clinical antibodies containing 51 flag are indicated in rows 2-69. In rows 70-72 examples of antibodies with >2 flags are indicated (Table 1). The antibodies chosen as exemplary examples are highlighted in bold. The correlation between the clinical development stage of the antibodies and the percentage of flags in these antibodies is shown in FIG. 1.

Six therapeutic antibodies (abrilumab, mepolizumab, crenezumab, necitumumab, anifrolumab, and evoculumab) are selected as our final scaffold choices (Highlighted in bold and italics in Table 1, and further described in Table 2). They are well expressed, showing no or minimal liabilities, containing few framework mutations and having low immunogenicity indicating the presence of suitable antibody scaffolds in these antibodies.

For each of the therapeutic antibodies listed in Table 2, seven vectors were designed and synthesized, as described in Example 2. The diagrammatic representation of vectors encoding the original scaffold, the heavy chain CDR1, heavy chain CDR2, heavy CDR3, light chain CDR1, light chain CDR2, and light chain CDR3 scaffolds derived from the six original scaffolds listed in Table 2 is shown in FIG. 2. The scaffolds represent five VH gene families (VH1-5) and five VL families (VK1-4; Vλ2). Table 2. Naturally occurring replicated CDRs can be inserted into these selected exemplary antibody scaffolds, which were identified as being well expressed, folded and lacking liabilities, for further testing.

TABLE 1

Analysis of Therapeutic Antibodies.

| Row | Name | HEK Titer (mg/L) <50 | Fab Tm by DSF (° C.) ≤64 | SGAC-SINS AS100 $(NH_4)_2SO_4$ mM) ≤300 | HIC Retention Time (Min) ≥11.8 | SMAC Retention Time (Min) ≥13.0 | Slope for Accelerated Stability ≥0.09 | Poly-Specificity Reagent (PSR) SMP (0-1) ≥0.27 | Affinity-Capture Self-Interaction Nanoparticle Spectroscopy (AC-SINS) Δλmax (nm) Average ≥13.1 | CIC Retention Time (Min) >10 | CSI-BLI Delta Response (nm) ≥0.02 | ELISA >2.0 | BVP ELISA ≥4.35 |
|---|---|---|---|---|---|---|---|---|---|---|---|---|---|
| 2 | abituzumab | 89.6 | 75.5 | 900.0 | 9.2 | 8.7 | 0.06 | 0.17 | 1.5 | 8.6 | 0.00 | 1.14 | 2.72 |
| 3 | abrilumab | 100.2 | 71.0 | 900.0 | 9.4 | 8.7 | 0.03 | 0.00 | −0.9 | 8.4 | −0.02 | 1.12 | 1.82 |
| 4 | adalimumab | 134.9 | 71.0 | 900.0 | 8.8 | 8.7 | 0.05 | 0.00 | 1.1 | 8.9 | −0.01 | 1.08 | 1.49 |
| 5 | alemtuzumab | 144.7 | 74.5 | 1000.0 | 8.8 | 8.7 | 0.06 | 0.00 | −0.8 | 8.5 | −0.02 | 1.16 | 1.46 |
| 6 | alirocumab | 69.2 | 71.5 | 900.0 | 9.0 | 8.7 | 0.03 | 0.00 | 1.2 | 8.8 | −0.01 | 1.20 | 2.18 |
| 7 | anifrolumab | 82.0 | 62.5 | 700.0 | 8.8 | 8.6 | 0.07 | 0.00 | −0.6 | 8.5 | −0.02 | 1.16 | 1.62 |
| 8 | bapineuzumab | 151.1 | 73.0 | 1000.0 | 8.9 | 8.7 | 0.07 | 0.00 | −0.7 | 8.6 | 0.06 | 1.21 | 3.55 |
| 9 | benralizumab | 146.7 | 76.0 | 800.0 | 9.5 | 9.1 | 0.02 | 0.35 | 6.0 | 9.6 | −0.01 | 1.23 | 1.42 |
| 10 | brodalumab | 150.9 | 74.5 | 900.0 | 9.1 | 8.7 | 0.02 | 0.27 | 11.2 | 9.0 | −0.01 | 1.48 | 2.93 |
| 11 | canakinumab | 45.7 | 72.0 | 800.0 | 9.3 | 8.7 | 0.04 | 0.00 | 0.7 | 8.6 | 0.00 | 1.20 | 2.55 |
| 12 | certolizumab | 186.7 | 81.5 | 500.0 | 11.5 | 10.8 | 0.04 | 0.00 | 0.2 | 9.3 | −0.01 | 1.14 | 1.65 |
| 13 | clazakizumab | 113.5 | 69.5 | 800.0 | 9.6 | 8.9 | 0.05 | 0.00 | 0.9 | 8.7 | −0.03 | 1.28 | 4.12 |
| 14 | crenezumab | 149.3 | 72.0 | 700.0 | 10.0 | 8.7 | 0.05 | 0.10 | 6.4 | 8.9 | 0.00 | 1.13 | 2.78 |
| 15 | dacetuzumab | 128.5 | 68.0 | 1000.0 | 8.5 | 8.6 | 0.00 | 0.00 | 0.0 | 8.5 | −0.04 | 1.08 | 1.34 |

TABLE 1-continued

Analysis of Therapeutic Antibodies.

| Row | Name | HEK Titer (mg/L) <50 | Fab Tm by DSF (° C.) ≤64 | SGAC-SINS AS100 (NH$_4$)$_2$SO$_4$ mM) ≤300 | HIC Retention Time (Min) ≥11.8 | SMAC Retention Time (Min) ≥13.0 | Slope for Accelerated Stability ≥0.09 | Poly-Specificity Reagent (PSR) SMP (0-1) ≥0.27 | Affinity-Capture Self-Interaction Nanoparticle Spectroscopy (AC-SINS) Δλmax (nm) Average ≥13.1 | CIC Retention Time (Min) >10 | CSI-BLI Delta Response (nm) ≥0.02 | ELISA >2.0 | BVP ELISA ≥4.35 |
|---|---|---|---|---|---|---|---|---|---|---|---|---|---|
| 16 | daclizumab | 245.1 | 74.0 | 900.0 | 9.3 | 8.8 | 0.03 | 0.00 | -0.1 | 8.5 | -0.02 | 1.18 | 1.41 |
| 17 | daratumumab | 233.3 | 71.0 | 800.0 | 9.5 | 8.6 | 0.06 | 0.00 | 1.8 | 8.9 | 0.00 | 1.21 | 3.15 |
| 18 | eculizumab | 226.5 | 66.0 | 700.0 | 10.4 | 9.3 | 0.01 | 0.00 | 0.0 | 8.5 | -0.04 | 0.96 | 3.00 |
| 19 | efalizumab | 167.0 | 72.5 | 900.0 | 8.7 | 8.6 | 0.00 | 0.00 | 0.7 | 8.5 | -0.02 | 0.98 | 1.24 |
| 20 | elotuzumab | 213.2 | 83.5 | 700.0 | 10.3 | 9.3 | 0.00 | 0.00 | -0.2 | 8.5 | -0.03 | 0.98 | 1.26 |
| 21 | epratuzumab | 78.2 | 65.0 | 900.0 | 9.2 | 8.6 | 0.03 | 0.13 | 3.0 | 8.7 | -0.01 | 1.47 | 2.34 |
| 22 | evolocumab | 260.7 | 65.0 | 700.0 | 10.4 | 9.1 | 0.03 | 0.20 | 2.2 | 9.3 | -0.01 | 1.75 | 1.75 |
| 23 | farletuzumab | 220.8 | 75.5 | 800.0 | 9.5 | 9.1 | 0.01 | 0.00 | -0.5 | 8.7 | -0.01 | 1.07 | 1.32 |
| 24 | fasinumab | 110.4 | 71.0 | 900.0 | 10.0 | 8.7 | 0.07 | 0.00 | -0.7 | 8.4 | -0.02 | 1.16 | 2.53 |
| 25 | ficlatuzumab | 249.0 | 75.0 | 900.0 | 9.4 | 8.9 | 0.05 | 0.00 | -0.9 | 8.5 | -0.02 | 1.13 | 1.23 |
| 26 | fletikumab | 220.4 | 71.5 | 700.0 | 11.0 | 9.1 | 0.02 | 0.00 | -0.1 | 8.5 | -0.02 | 1.02 | 1.41 |
| 27 | fresolimumab | 166.0 | 74.0 | 700.0 | 10.9 | 9.1 | 0.06 | 0.00 | -0.5 | 8.5 | -0.02 | 1.30 | 3.51 |
| 28 | fulranumab | 142.0 | 68.5 | 900.0 | 9.3 | 9.3 | 0.07 | 0.19 | 11.6 | 9.3 | 0.00 | 1.85 | 6.92 |
| 29 | gevokizumab | 136.4 | 71.5 | 1000.0 | 8.8 | 8.6 | 0.07 | 0.00 | -0.5 | 8.6 | -0.03 | 1.18 | 1.93 |
| 30 | ibalizumab | 133.3 | 72.0 | 800.0 | 10.2 | 9.8 | 0.04 | 0.00 | -0.3 | 8.7 | -0.03 | 0.99 | 1.13 |
| 31 | lintuzumab | 230.0 | 75.5 | 700.0 | 10.9 | 9.4 | 0.05 | 0.00 | 0.9 | 8.9 | -0.02 | 1.05 | 1.25 |
| 32 | matuzumab | 224.3 | 72.0 | 900.0 | 9.8 | 8.8 | 0.02 | 0.00 | -0.9 | 8.6 | -0.03 | 1.06 | 1.03 |
| 33 | mavrilimumab | 150.5 | 68.5 | 700.0 | 10.3 | 8.7 | 0.05 | 0.00 | -0.8 | 8.5 | -0.01 | 1.21 | 2.16 |
| 34 | mepolizumab | 221.5 | 78.5 | 900.0 | 9.2 | 8.8 | 0.04 | 0.00 | -1.0 | 8.4 | -0.04 | 1.13 | 1.05 |
| 35 | mogamulizumab | 89.8 | 68.5 | 800.0 | 9.6 | 8.8 | 0.04 | 0.00 | -0.5 | 8.6 | -0.02 | 1.12 | 2.17 |
| 36 | motavizumab | 133.6 | 86.0 | 800.0 | 9.7 | 8.8 | 0.04 | 0.00 | 2.5 | 8.7 | -0.01 | 1.23 | 5.36 |
| 37 | natalizumab | 251.7 | 79.5 | 900.0 | 9.7 | 8.8 | 0.02 | 0.00 | 0.8 | 8.8 | -0.01 | 1.06 | 1.52 |
| 38 | necitumumab | 198.6 | 76.5 | 600.0 | 10.8 | 9.9 | 0.02 | 0.00 | 1.3 | 8.8 | -0.02 | 1.05 | 1.31 |
| 39 | nivolumab | 178.8 | 66.0 | 900.0 | 9.0 | 8.7 | 0.03 | 0.14 | 2.4 | 8.9 | -0.01 | 1.15 | 1.32 |
| 40 | obinutuzumab | 176.4 | 73.0 | 600.0 | 10.6 | 9.0 | 0.01 | 0.11 | 1.8 | 8.8 | -0.01 | 0.95 | 1.63 |
| 41 | ofatumumab | 249.8 | 68.0 | 800.0 | 9.7 | 9.5 | 0.03 | 0.00 | 1.2 | 9.2 | -0.02 | 1.12 | 1.18 |
| 42 | olokizumab | 115.3 | 69.0 | 700.0 | 9.9 | 9.0 | 0.04 | 0.00 | -0.5 | 8.7 | -0.03 | 1.11 | 1.23 |
| 43 | omalizumab | 150.4 | 77.5 | 800.0 | 9.5 | 8.7 | 0.05 | 0.00 | -0.4 | 8.5 | -0.02 | 1.12 | 1.17 |
| 44 | onartuzumab | 147.9 | 80.0 | 800.0 | 9.9 | 8.9 | 0.04 | 0.00 | 0.0 | 8.9 | -0.02 | 1.12 | 1.19 |
| 45 | otelixizumab | 152.1 | 75.5 | 1000.0 | 9.1 | 8.7 | 0.09 | 0.00 | 4.4 | 8.7 | -0.02 | 1.13 | 1.40 |
| 46 | otlertuzumab | 149.6 | 68.5 | 600.0 | 11.0 | 10.3 | 0.07 | 0.00 | 2.3 | 9.5 | -0.03 | 1.17 | 1.78 |
| 47 | palivizumab | 243.1 | 79.5 | 900.0 | 9.3 | 8.7 | 0.04 | 0.00 | -0.9 | 8.5 | -0.03 | 1.12 | 2.88 |
| 48 | panitumumab | 179.6 | 78.5 | 900.0 | 9.5 | 8.8 | 0.04 | 0.00 | -1.1 | 8.4 | -0.03 | 1.06 | 1.18 |
| 49 | panobacumab | 107.6 | 69.0 | 900.0 | 9.8 | 8.9 | 0.02 | 0.00 | -0.4 | 9.0 | -0.01 | 1.21 | 1.90 |
| 50 | pertuzumab | 31.4 | 78.5 | 700.0 | 10.1 | 8.9 | 0.04 | 0.00 | -0.2 | 8.6 | -0.04 | 1.21 | 1.69 |
| 51 | pinatuzumab | 130.6 | 79.0 | 800.0 | 9.2 | 8.8 | 0.07 | 0.01 | 0.6 | 8.8 | -0.02 | 1.27 | 2.49 |
| 52 | polatuzumab | 225.1 | 74.0 | 1000.0 | 8.8 | 8.7 | 0.06 | 0.00 | -1.0 | 8.3 | -0.05 | 1.36 | 3.62 |
| 53 | radretumab | 151.2 | 77.0 | 900.0 | 9.5 | 8.7 | 0.00 | 0.13 | 3.4 | 8.9 | 0.00 | 1.26 | 3.29 |
| 54 | ramucirumab | 90.7 | 66.0 | 900.0 | 9.4 | 8.7 | 0.02 | 0.00 | 0.0 | 8.6 | -0.02 | 1.05 | 1.25 |
| 55 | reslizumab | 191.6 | 75.5 | 700.0 | 9.8 | 8.9 | 0.06 | 0.23 | 1.7 | 8.9 | 0.00 | 1.25 | 2.02 |
| 56 | romosozumab | 227.7 | 76.0 | 1000.0 | 9.2 | 8.6 | 0.03 | 0.00 | -1.0 | 8.4 | -0.03 | 1.01 | 1.47 |
| 57 | sarilumab | 181.8 | 64.0 | 900.0 | 9.0 | 8.7 | 0.05 | 0.00 | 1.1 | 8.7 | -0.01 | 1.09 | 2.17 |
| 58 | secukinumab | 149.0 | 72.0 | 800.0 | 11.4 | 8.9 | 0.05 | 0.00 | -0.6 | 8.4 | -0.04 | 1.09 | 1.69 |
| 59 | sifalimumab | 158.6 | 67.0 | 800.0 | 9.7 | 8.8 | 0.01 | 0.06 | 2.1 | 9.0 | -0.02 | 2.60 | 2.50 |
| 60 | tabalumab | 121.6 | 64.0 | 700.0 | 10.8 | 9.9 | 0.06 | 0.00 | 2.0 | 9.1 | -0.01 | 1.26 | 3.68 |
| 61 | tigatuzumab | 179.0 | 64.5 | 700.0 | 10.0 | 8.7 | 0.00 | 0.13 | 5.5 | 8.7 | -0.01 | 1.17 | 1.70 |
| 62 | tildrakizumab | 181.9 | 77.5 | 600.0 | 11.1 | 9.9 | -0.01 | 0.00 | 0.8 | 8.7 | -0.01 | 1.19 | 1.77 |
| 63 | tocilizumab | 139.6 | 91.5 | 900.0 | 9.1 | 8.8 | 0.05 | 0.00 | 1.3 | 8.9 | 0.00 | 1.14 | 2.81 |
| 64 | tovetumab | 277.2 | 63.5 | 900.0 | 8.7 | 8.6 | 0.01 | 0.00 | 2.2 | 8.8 | -0.01 | 1.35 | 2.95 |
| 65 | trastuzumab | 159.5 | 78.5 | 800.0 | 9.7 | 8.8 | 0.04 | 0.00 | 2.0 | 8.8 | -0.02 | 1.06 | 1.34 |
| 66 | vedolizumab | 221.8 | 80.5 | 600.0 | 10.9 | 12.3 | 0.07 | 0.00 | 0.4 | 9.0 | -0.02 | 1.15 | 1.58 |
| 67 | veltuzumab | 225.0 | 70.0 | 700.0 | 11.1 | 9.7 | 0.04 | 0.00 | 4.8 | 8.8 | -0.02 | 0.89 | 1.21 |
| 68 | zalutumumab | 200.5 | 72.5 | 900.0 | 9.3 | 8.7 | 0.05 | 0.00 | -0.8 | 8.4 | -0.02 | 1.28 | 2.90 |
| 69 | zanolimumab | 116.4 | 80.5 | 700.0 | 9.6 | 8.8 | 0.03 | 0.13 | 1.5 | 8.6 | -0.01 | 1.10 | 1.46 |
| 70 | atezolizumab | 164.1 | 73.5 | 300.0 | 13.4 | 19.3 | 0.06 | 0.07 | 15.0 | 10.8 | 0.06 | 1.29 | 6.20 |
| 71 | belimumab | 10.5 | 60.0 | 800.0 | 10.5 | 9.3 | 0.13 | 0.00 | 0.8 | 8.6 | -0.03 | 3.61 | 12.23 |
| 72 | bevacizumab | 50.0 | 63.5 | 700.0 | 11.8 | 11.1 | 0.22 | 0.00 | 0.8 | 9.8 | -0.02 | 1.29 | 2.78 |

TABLE 2

Summary of Final Scaffold Choices.

| Therapeutic | Target | Phase | Type | VH gene | VK gene | Framework VH mutations | Framework VL mutations | % Immuno-genicity* | Fab Tm °C. | Phage display used |
|---|---|---|---|---|---|---|---|---|---|---|
| Abrilumab | a4-β7 integrin | Phase 2 | Human | 1-24 | 1-12 | 1 | 1 | 0 | 71.0 | Other H1-24 & K1-12 |
| Mepolizumab | IL-5 | Approved | Humanized | 2-70 | 4-1 | 4 | 0 | 6 | 78.5 | Other H2-70 & K4-1 |
| Crenezumab | Aβ | Phase 3 | Humanized | 3-7 | 2D-29 | 2 | 3 | ND | 72.0 | None |
| Necitumumab | EGFR | Approved | Human | 4-30-4 | 3-11 | 3 | 1 | 4.1 | 76.5 | For Necitumumab |
| Anifrolumab | Interferon receptor | Phase 3 | Human | 5-51 | 3-20 | 1^ | 2 | 3.3 | 62.5 | Other H5-51 & K3-20 |
| Evoculumab | PCSK9 | Approved | Human | 1-18 | 12-14 | 2 | 1 | 0.3 | 65 | Other H1-18 |

*These identified CDRs are identical, but synthesized with different flanking regions corresponding to different VH1 genes (VH1-18 and VH1-24).
^These identified CDRs are identical, but synthesized with different flanking regions corresponding to different VK3 genes (VK3-20 and VK3-11).

Example 2: Creating Vectors for Experimental CDR Screening

For each of the six libraries created using the six scaffolds shown in Table 2, seven polynucleotides encoding single-chain variable fragment (scFv) corresponding to each of the scaffolds were synthesized. One of the seven synthesized polynucleotides encodes for the non-modified scFv, and the other six polynucleotides were modified to have one of the original CDRs replaced by a combination of restriction sites including two inverted BsaI sites (a type IIs enzyme that cuts outside of its recognition sequence), an additional SfiI site to ensure cleavage of the vector and serve as a spacer between the BsaI sites, a frameshift and an ochre stop codon to prevent expression of background sequence (FIGS. 2-3). Each of these modified polynucleotides encoding the scaffolds was cloned into a yeast display vector, and the presence of the stop codon in this sequence prevented the expression of the scaffold on the yeast surface until the modified CDR1s replaced with a functional CDR.

Figure 4:
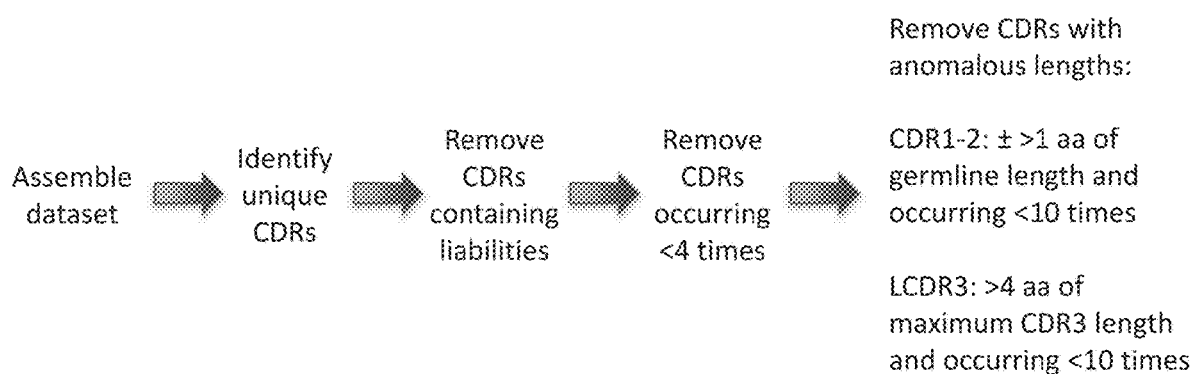
FIG. 4 is a flow chart describing an exemplary process of identifying unique CDRs and informatically removing CDRs based on liabilities, occurrence rate, and/or anomalous length.

Example 3: Generating a Database of CDR Sequences and Informatic Elimination of CDRs Demonstrating Potential Liabilities The process taken to identify suitable CDRs for use in the libraries exemplified herein is illustrated in FIG. 4. To generate a database of naturally occurring CDRs (CDRs found in naturally-occurring antibodies such as human antibodies), next generation sequencing (NGS) of the variable genes derived from a total of 40 donors was carried out, comprising a total of >140 million reads. NovaSeq analysis was applied to LCDR3 sequencing data and MiSeq analysis was applied to heavy chain and light chain CDR1 and CDR2 sequencing data. Analysis of the variable gene sequences allowed identification of the numbers of CDRs shown in Table 3.

Altogether, unique CDRs corresponding to the following heavy chain and light chain CDRs were identified showing both unique CDRs and CDRs including potential flanking scaffold oligos (in parentheses). The number of oligos is greater than the number of CDRs because of the need to synthesize some CDRs with different flanking sequences corresponding to different scaffolds:

~52,675 (66,020) LCDR1s;

~19,550 (23,854) LCDR2s;

~2,180,922 (2,617,051) LCDR3s;

~147,741 (167,376) HCDR1s;

~170,758 (202,170) HCDR2s; and

~13,588,754 HCDR3s

Figure 6:
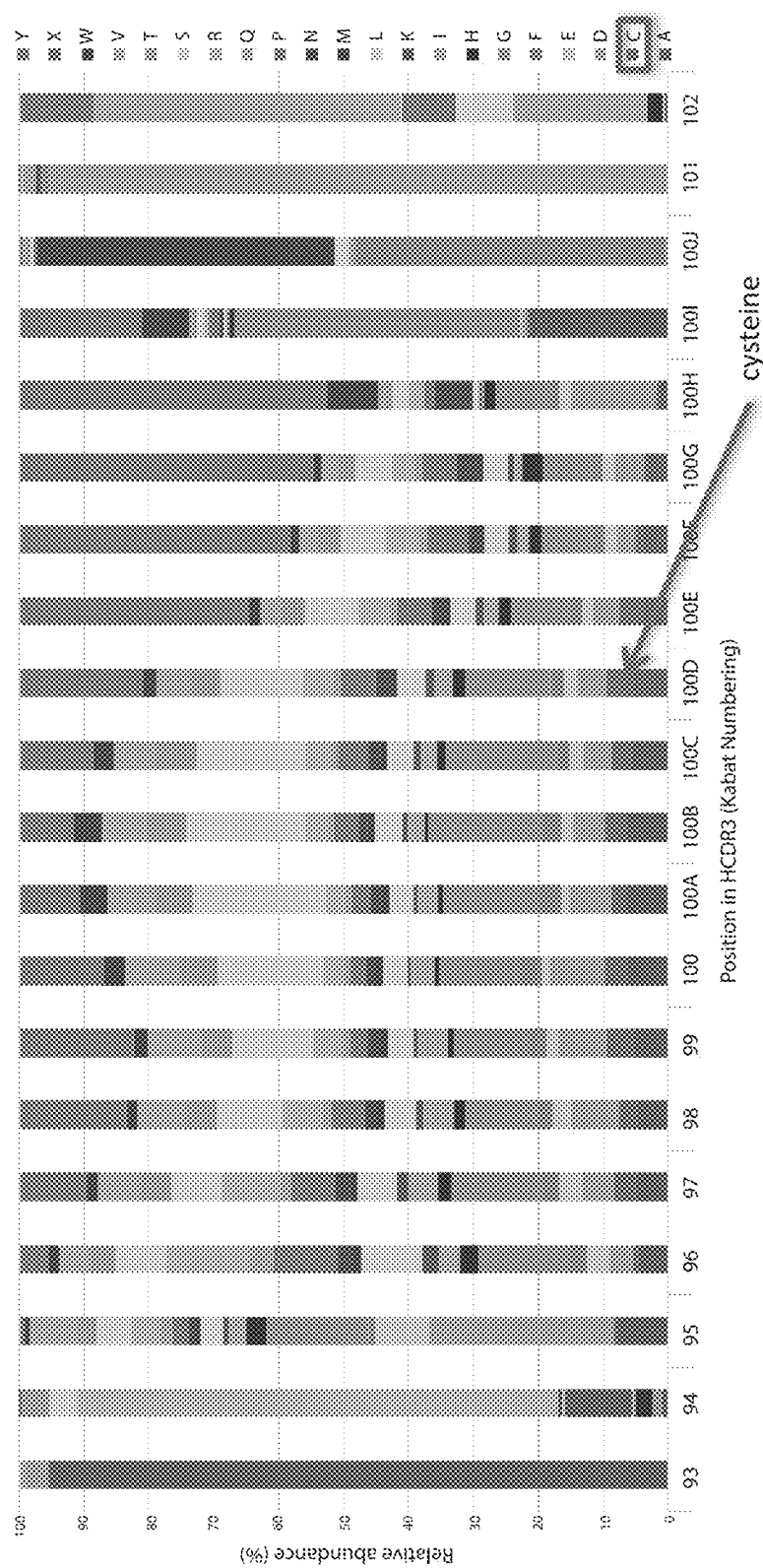
FIG. 6 is a diagram showing presence of cysteine residues in heavy chain CDR3.
Figure 8:
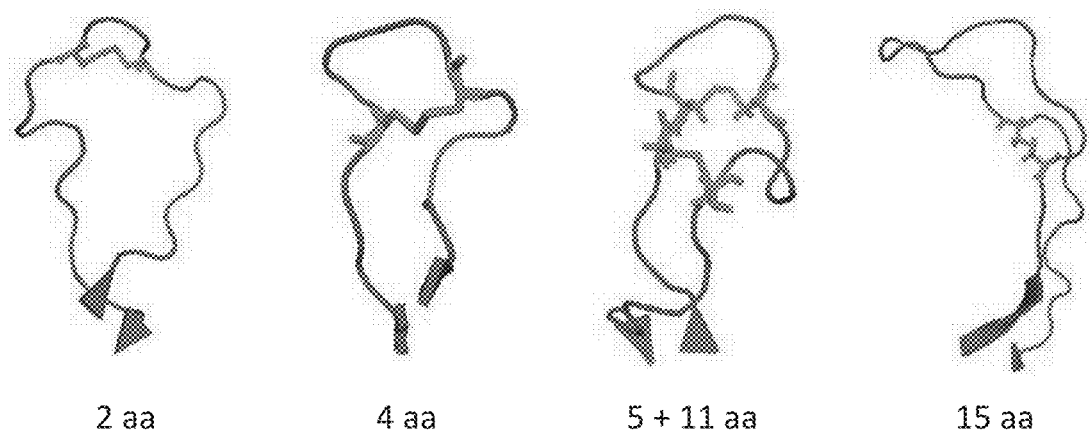
FIG. 8 is a diagram illustrating paired cysteine residues in CDRs.
Figure 9:
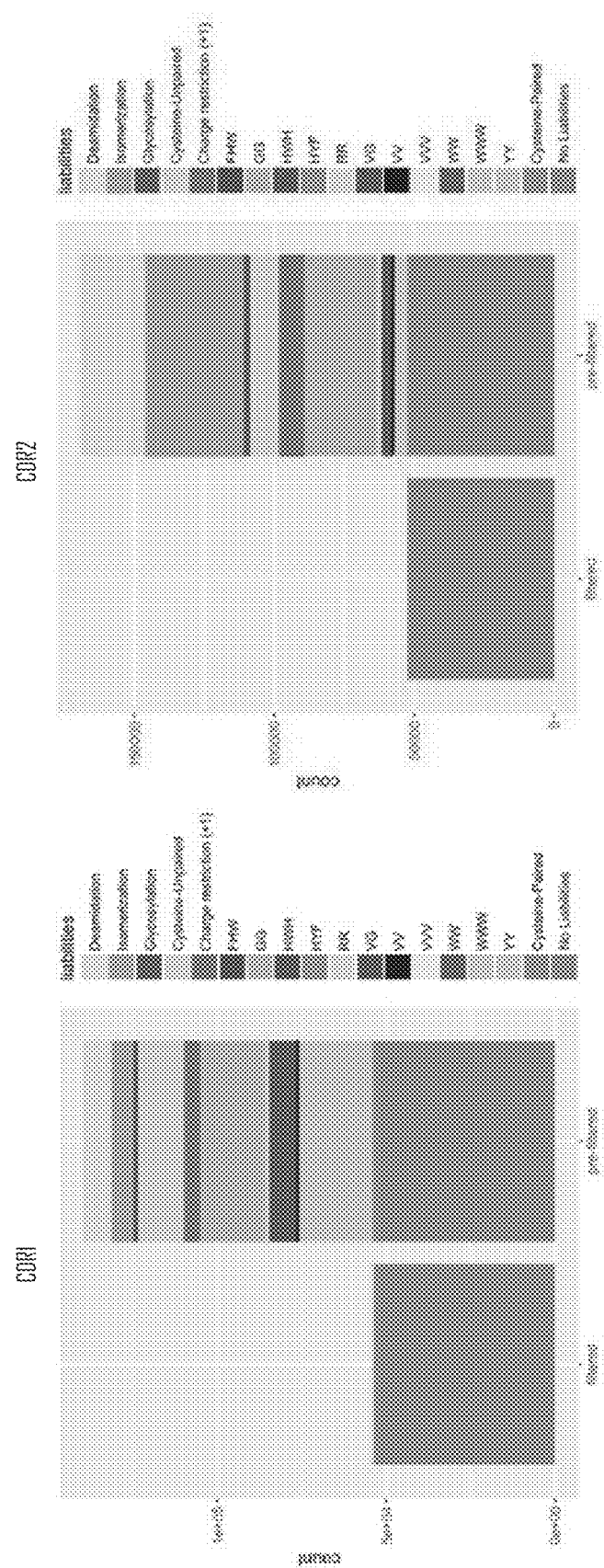
FIG. 9 includes graphs showing the presence of liabilities in heavy chain CDR1 (left panel) and CDR2 (right panel) regions before and after bioinformatic filtration.
Figure 10:
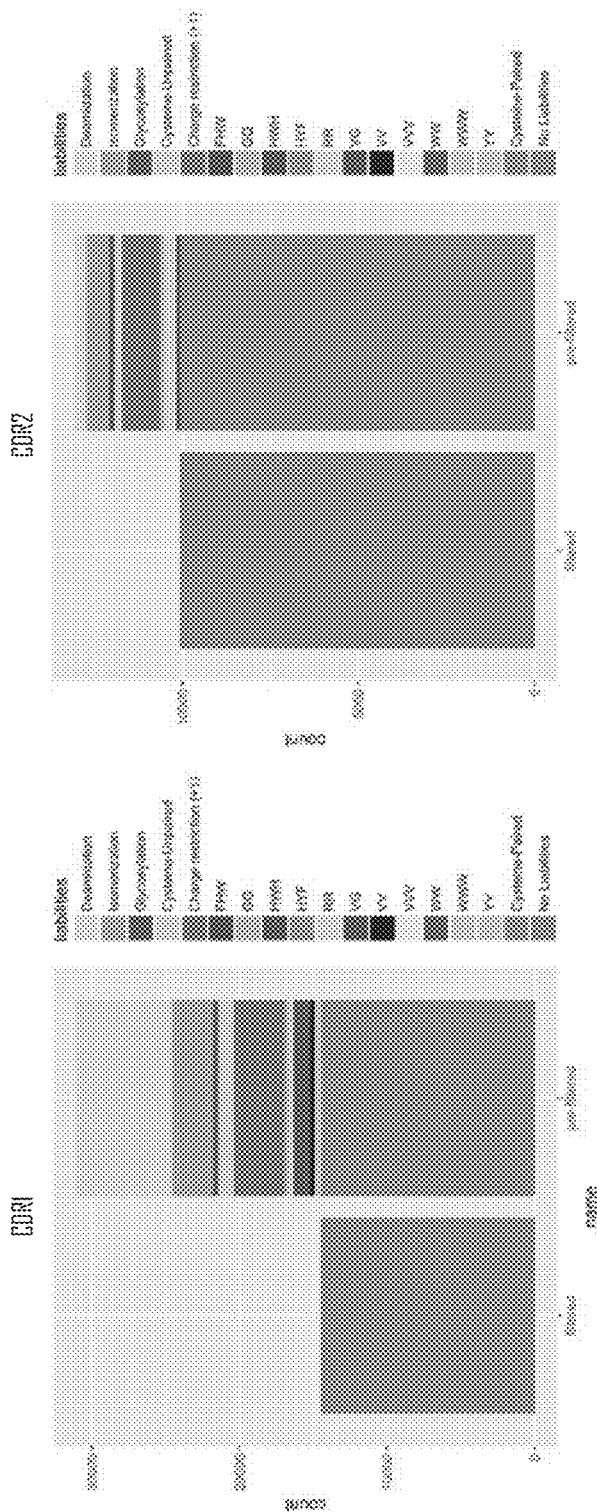
FIG. 10 includes graphs showing the presence of liabilities in VK CDR1 (left panel) and CDR2 (right panel) regions before and after bioinformatic filtration.
Figure 11:
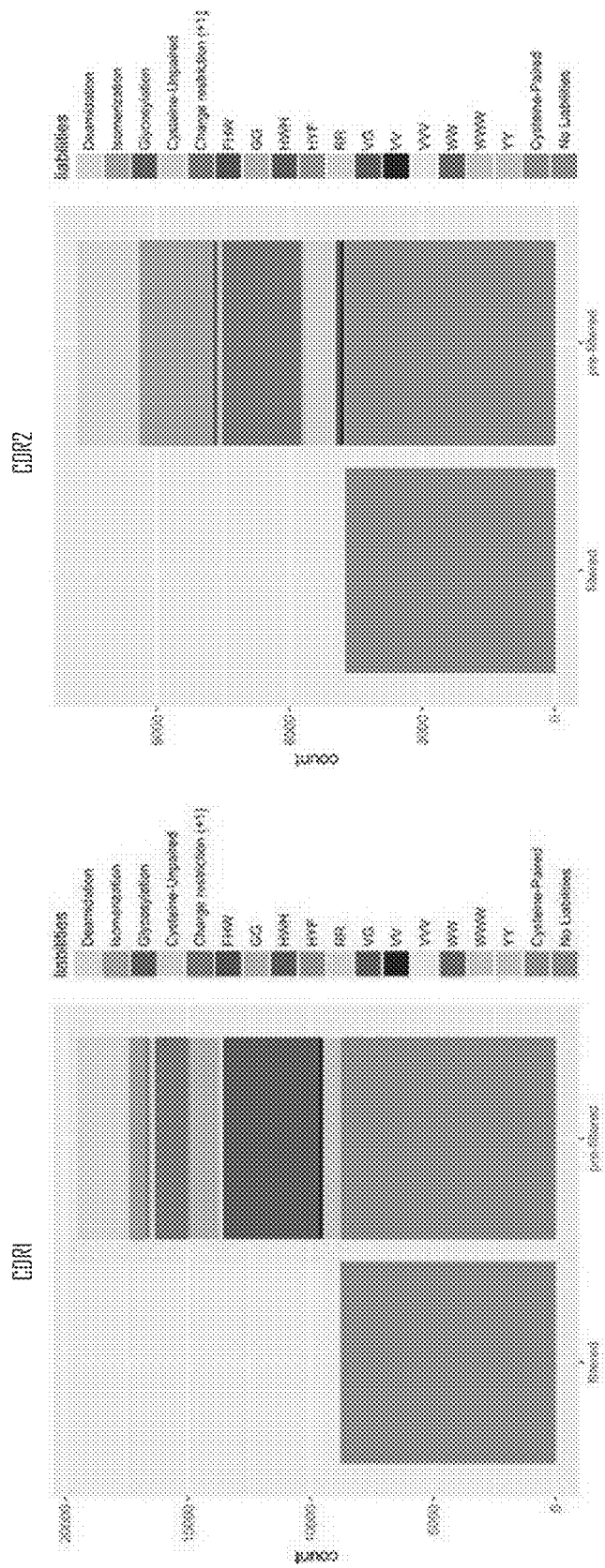
FIG. 11 includes graphs showing the presence of liabilities in Vλ CDR1 (left panel) and CDR2 (right panel) before and after bioinformatic filtration.
Figure 12:
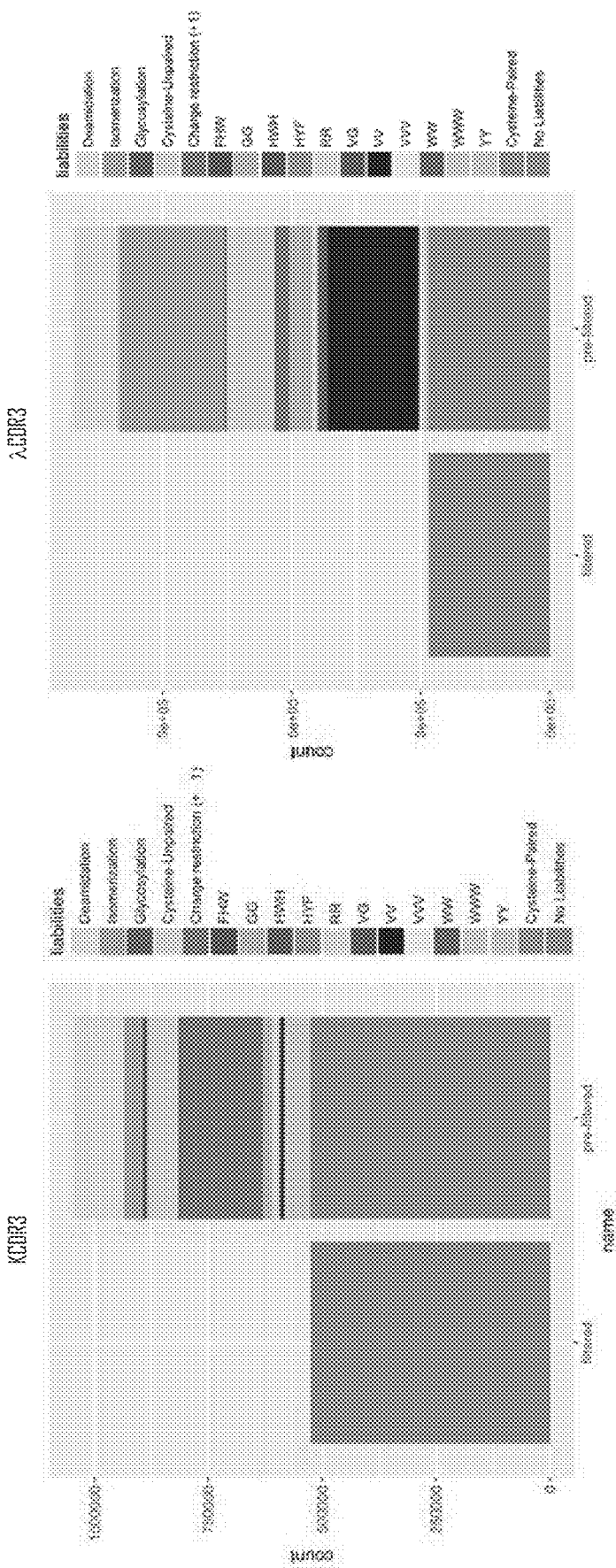
FIG. 12 includes graphs showing the presence of liabilities in VK CDR3 (left panel) ad Vλ CDR3 (right panel) before and after bioinformatic filtration.
Figure 13:
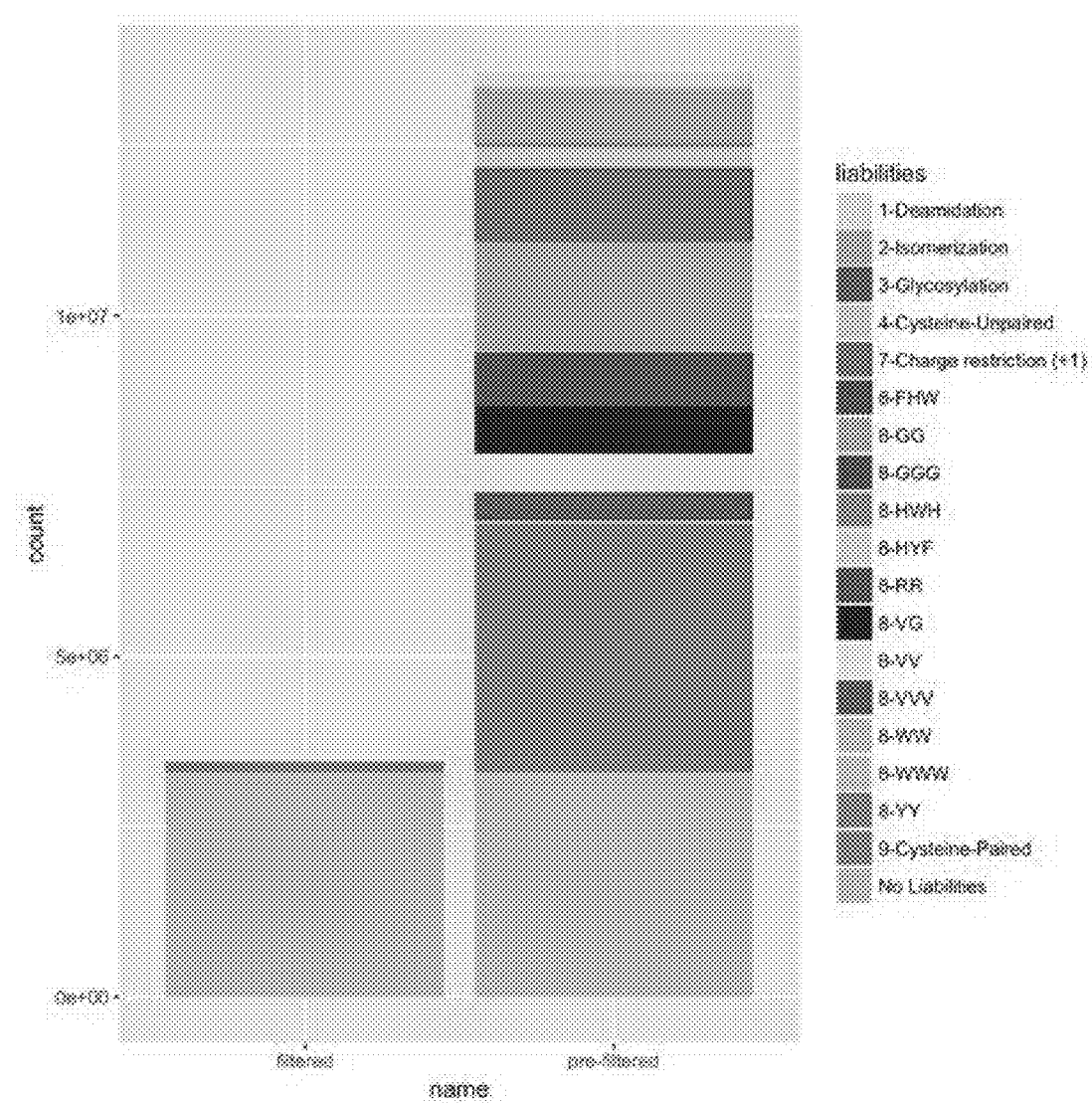
FIG. 13 includes a graph showing presence of liabilities in HC CDR3 before and after bioinformatic filtration.

Liabilities that were reduced to short sequences were used to identify CDRs containing them. For example, HCDR2 sequences containing liabilities such as deamidation, isomerization, glycosylation or unpaired cysteines are highlighted in pink (in FIG. 5). To underscore the importance of identifying liabilities and eliminating CDRs containing liabilities from the libraries, unpaired cysteines in HCDR3 were illustrated in FIGS. 6-8 as an example. Cysteines comprise up to 4% of HCDR3 amino acid and they need to be paired and structurally positioned, otherwise the presence of unpaired cysteines or poorly positioned cysteines would introduce undesirable structure or chemical reactivity into the CDR thus rendering the CDR non-functional or non-developable. The list of exemplary liabilities identified is described in Table 4, and it is clear that additional sequence-based liabilities can be similarly screened. The list of unique CDRs previously identified in Table 3 was examined for occurrence of the listed liabilities, and all CDRs containing a liability were computationally eliminated from the list of unique CDRs. FIGS. 9-13 reflects the extent of elimination of liabilities from the different CDR populations.

TABLE 3

Unique CDRs Identified and the Remaining Unique CDRs after Elimination of liabilities.

| Library | VH | VL | unique LCDR1 total | unique LCDR1 final | unique LCDR2 total | unique LCDR2 final | unique LCDR3 total | unique LCDR3 final |
|---|---|---|---|---|---|---|---|---|
| 1 Abrilumab | VH1-24 | VK1-12 | 8,838 | 1,717 | 6,483 | 1,406 | 385,836 | 74,091 |

TABLE 3-continued

Unique CDRs Identified and the Remaining Unique CDRs after Elimination of liabilities.

| | | | | | | | | |
|---|---|---|---|---|---|---|---|---|
| 2 Mepolizumab | VH2-70 | VK4-1 | 6,039 | 103 | 685 | 140 | 130628 | 17,917 |
| 3 Crenezumab | VH3-7 | VK2D-29 | 4,668 | 50 | 1591 | 229 | 122745 | 32,092 |
| 4 Necitumumab | VH4-30-4 | VK3-11 | 13,345 | 1,910 | 685 | 972 | 436129 | 79,038^ |
| 5 Anifrolumab | VH5-51 | VK3-20 | 13,345 | 1,910 | 685 | 972 | 436129 | 79,038^ |
| 6 Evolocumab | VH1-18 | V12-14 | 19,785 | 1,696 | 10,792 | 1,197 | 1,105,584 | 94,371 |
| | | Total | 66,020 | 5,476 | 20,921 | 3,944 | 2,617,051 | 297,509 |

| | unique HCDR1 | | unique HCDR2 | | Unique HCDR3 | | Theoretical diversity | |
|---|---|---|---|---|---|---|---|---|
| Library | total | final | total | final | total | final | No HCDR3 | with 1e8 HCDR3's |
| 1 Abrilumab | 19,635* | 2,860 | 31,412 | 2,171 | 13,588,754 | 1,791,801 | 1.11E+18 | 1.11E+26 |
| 2 Mepolizumab | 31,486 | 2,296 | 15,550 | 1,253 | | | 7.43E+14 | 7.43E+22 |
| 3 Crenezumab | 34,575 | 5,920 | 82,817 | 4,565 | | | 9.93E+15 | 9.93E+23 |
| 4 Necitumumab | 50,335 | 1,285 | 28,267 | 2,739 | | | 5.16E+17 | 5.16E+25 |
| 5 Anifrolumab | 11,710 | 1,979 | 12,712 | 669 | | | 1.94E+17 | 1.94E+25 |
| 6 Evolocumab | 19,635* | 2,860 | 31,412 | 2,171 | | | 1.19E+18 | 1.19E+26 |
| | 167,376 | 17,200 | 202,170 | 13,568 | 13,588,754 | 1,791,801 | 3.00E+18 | 3.00E+26 |

Sum of final CDRs (LCDR1-3 HCDR1-2): 337, 697.
*These identified CDRs are identical, but synthesized with different flanking regions corresponding to different VH1 genes (VH1-18 and VH1-24).
^These identified CDRs are identical, but synthesized with different flanking regions corresponding to different VK3 genes (VK3-20 and VK3-11).

TABLE 4

Liabilities to be Removed.

| Type of Liabilities | Exemplary Motif |
|---|---|
| Glycosylation - impacts stability, solubility, half-life, heterogeneity, and effector function. | NXS, → X = Any Amino Acid but Proline<br>NXT, → X = Any Amino Acid but Proline<br>NXC → X = Any Amino Acid but Proline |
| Deamidation - Therapeutic antibodies may undergo deamidation during manufacture and storage leading to protein structural changes, aggregation, change in pharmacokinetics, loss of activity and immunogenicity. | NG, NS, NT, NN, NA, NH, ND, GNF, GNY, GNT, or GNG |
| Isomerization - Asp residues can undergo isomerization and reported in CDRs. Known to increase charge heterogeneity | DT, DH, DG, DS, DD |
| Based on creation of synthetic library, selection against polyspecificity (PSR) and sequencing | GG, GGG, RR, VG, VV, VVV, WW, WWW, YY, WXW (X represents any amino acid residue) |
| Single cluster in IL-13 human mAb HCDR3 which highly aggregating, alanine mutations increase solubility (aggregation) | FHW |
| Two aromatic tripeptides in HCDR3 mutated improve viscosity. Compatible with idea that 3 consecutive aromatics is bad news and should be eliminated | HYF, HWH |
| Positive charge associated with poor developability properties. | Net Charge (+1) in LCDR1-3, HCDR1-2 |

TABLE 4-continued

Liabilities to be Removed.

| Type of Liabilities | Exemplary Motif |
|---|---|
| Unpaired cysteine can impact protein folding, function and stability. These reactive centers lead to formation of covalent aggregates and reduce protein stability | Unpaired Cysteine |
| Protease sensitivity (fragmentation) | DP, DG, DS, DV, DY, DF, DQ, DK, DL, DD |
| Integrin binding site | RGD, RYD, LDV, KGD |
| Lysine glycation site | KE, EK, or ED |
| Metal catalyzed fragmentation | HS, SH, KT, HXS, SXH (X represents any amino acid residue) |
| Polyspecificity, aggregation | $X_1X_2X_3$, in which each of $X_1$, $X_2$, and $X_3$ independent is F, I, L, V, W, or Y |
| Streptavidin binding motifs | HPQ, EPDW (SEQ ID NO: 117), PWXWL (SEQ ID NO: 118), GDWVFI (SEQ ID NO: 119), PWPWLG (SEQ ID NO: 120) (X represents any amino acid residue) |

Example 4: Elimination of CDRs Arising from Sequencing Errors

Following the removal of CDRs containing potential liabilities disclosed in Example 3 above, CDRs that may have arisen as a result of sequencing errors were also computationally eliminated. Sequencing errors are more likely when the CDRs sequenced are oversampled. In general, the more copies of a particular CDR, the more likely that it is real, and not the result of a sequencing error.

Figure 14:
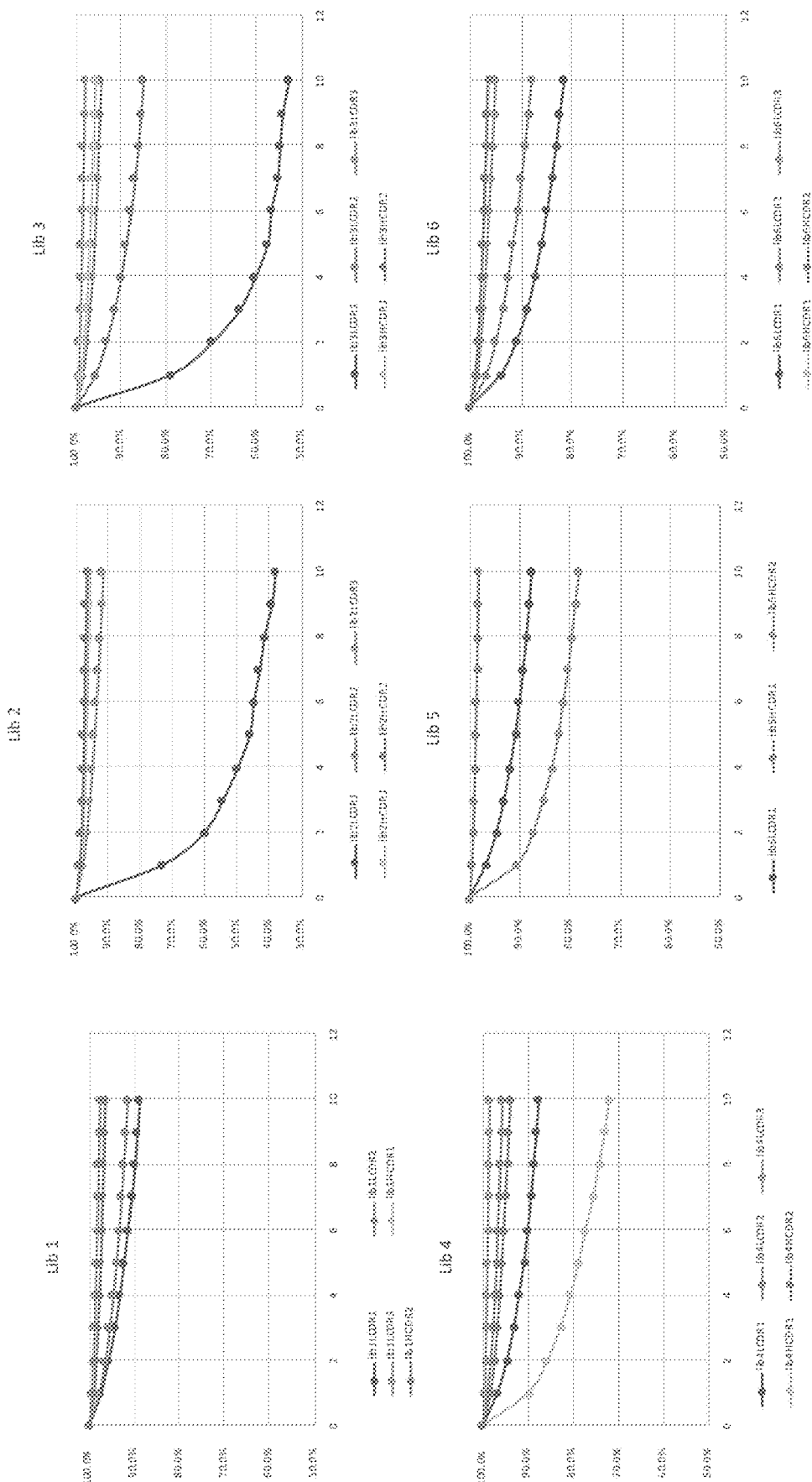
FIG. 14 includes charts showing the percentage of CDRs in each library that are excluded at different abundance threshold. Single thread of 4 reads is used across different libraries to exclude CDRs that arise by sequencing error.

The abundance of each unique CDR in the dataset was assessed after those containing liabilities had been removed. For each of the different libraries and individual CDRs, the percentage of sequences retained at different abundances (number of reads) was assessed. The more information retained, the more likely that rare CDRs are the result of sequencing errors, and not naturally occurring CDRs. The percentage of sequences eliminated for different CDRs except for HCDR3 at the application of different threshold numbers in each library is represented in FIG. 14. A threshold of 4 or more reads was evaluated for each unique CDR to represent the best balance between the number of unique CDRs and the retained sequence information. It is clear that different threshold numbers can be chosen depending upon the number of total reads, and the number of total unique CDRs identified. While different thresholds for each individual CDR for each library could be used, the single threshold of 4 reads was chosen to be consistent. CDRs with less than 4 reads were removed from the library.

Figure 15:
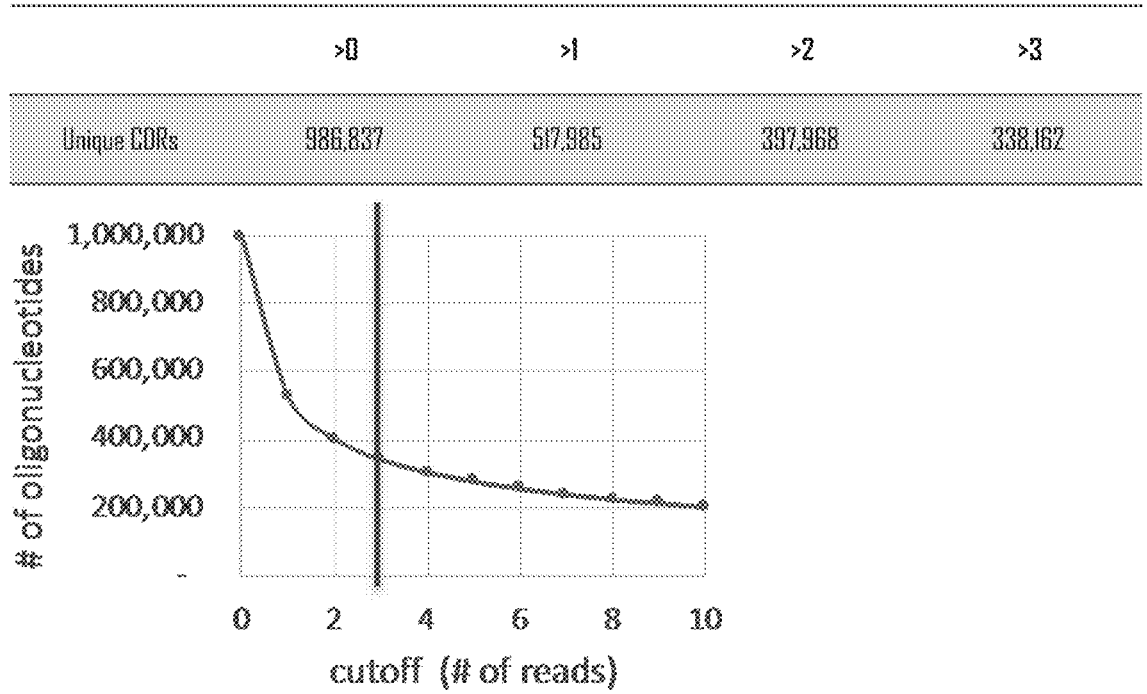
FIG. 15 includes a chart showing the number of CDRs remaining for all pooled CDRs except heavy chain CDR3 after exclusion at different threshold reads.
Figure 16:
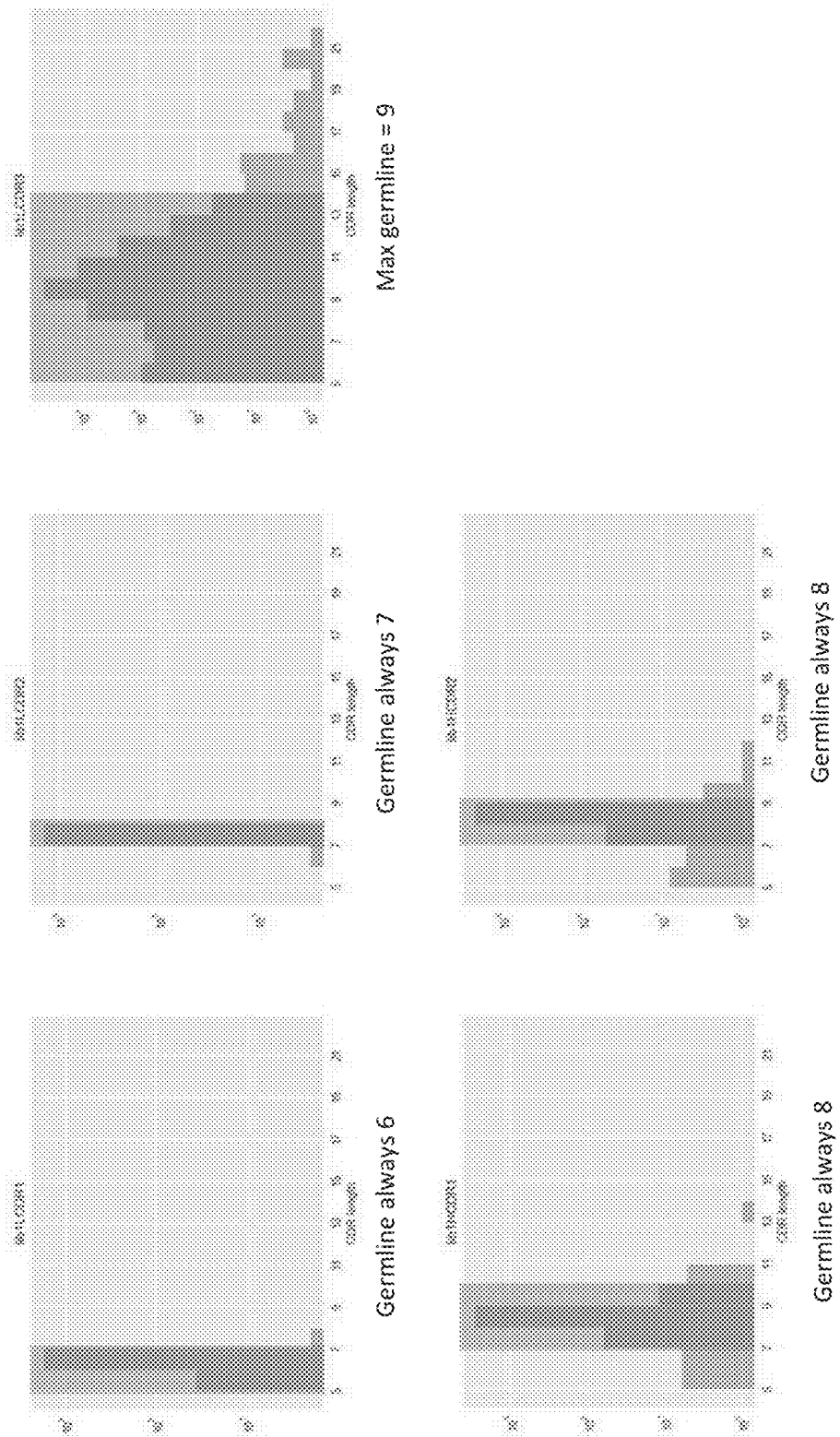
FIG. 16 includes graphs showing the length distribution of CDRs in Library 1 (using scaffold derived from abrilumab). The germline length for each CDR is indicated under each graph and the CDRs outside of the highlighted region are eliminated for anomalous length.
Figure 17:
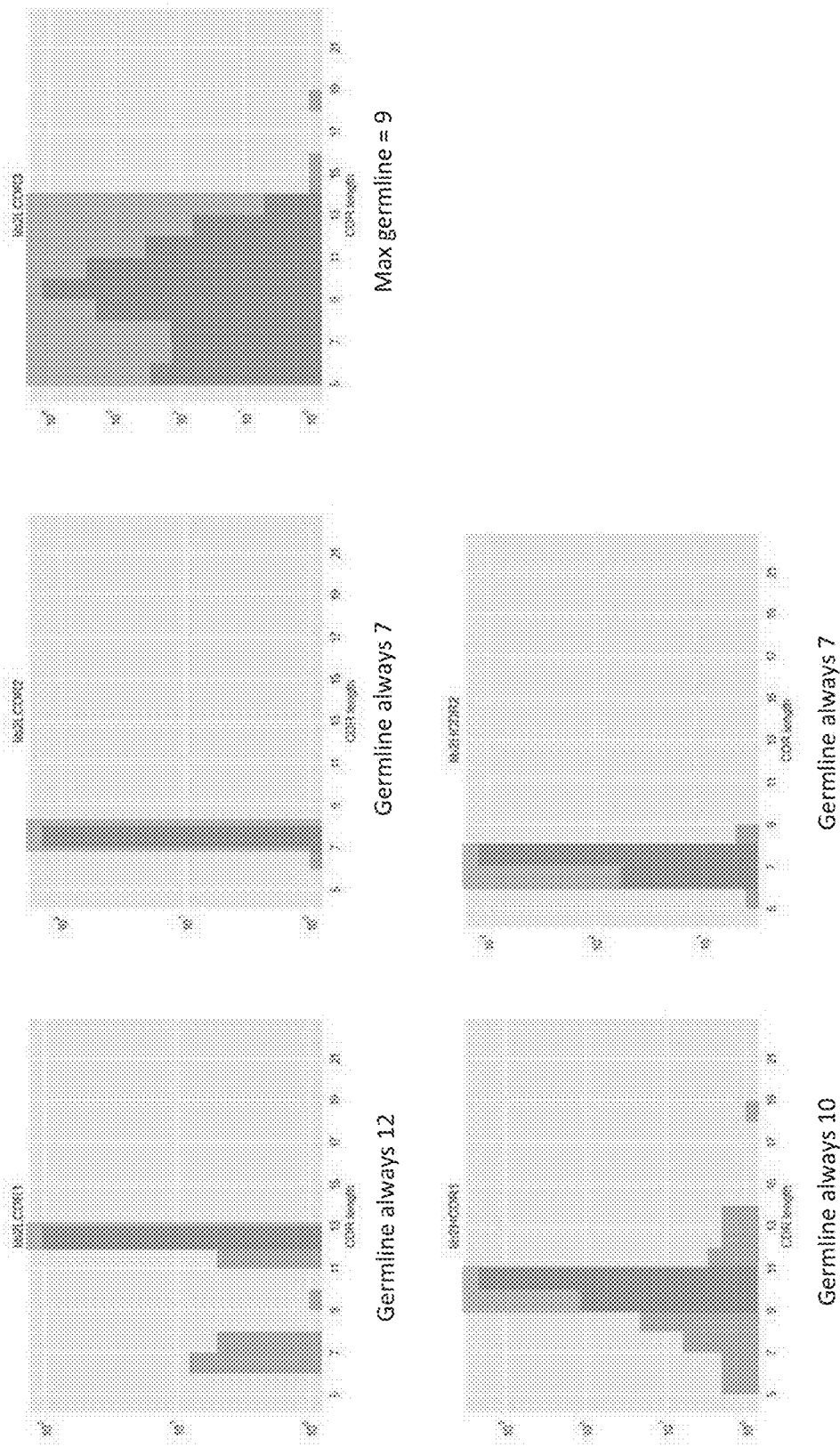
FIG. 17 includes graphs showing the length distribution of CDRs in Library 2 (using scaffold derived from mepolizumab). The germline length for each CDR is indicated under each graph and the CDRs outside of the highlighted region are eliminated for anomalous length.
Figure 18:
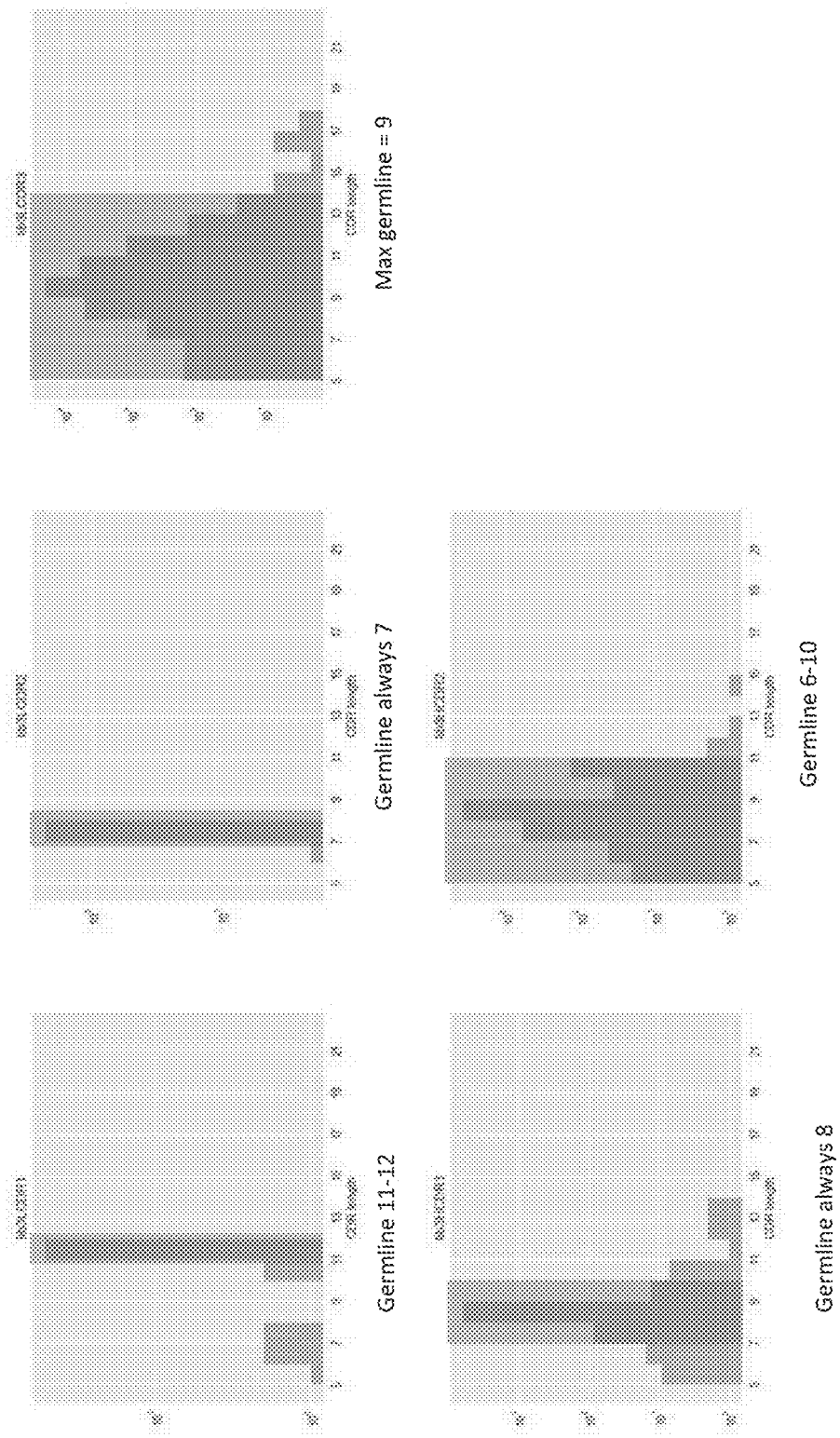
FIG. 18 includes graphs showing the length distribution of CDRs in Library 3 (using scaffold derived from crenezumab). The germline length for each CDR is indicated under each graph and the CDRs outside of the highlighted region are eliminated for anomalous length.
Figure 19:
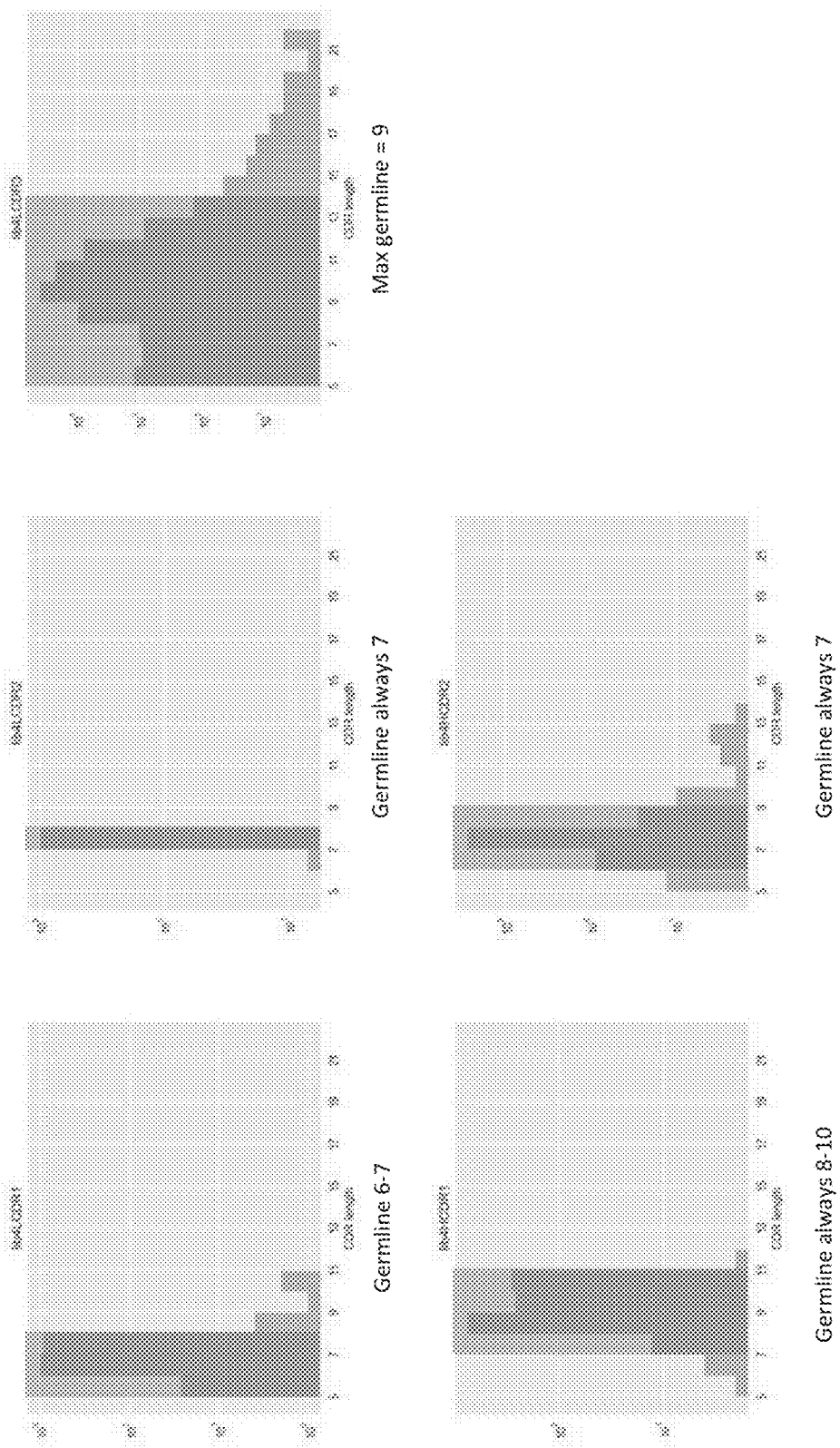
FIG. 19 includes graphs showing the length distribution of CDRs in Library 4 (using scaffold derived from necitumumab). The germline length for each CDR is indicated under each graph and the CDRs outside of the highlighted region are eliminated for anomalous length.
Figure 20:
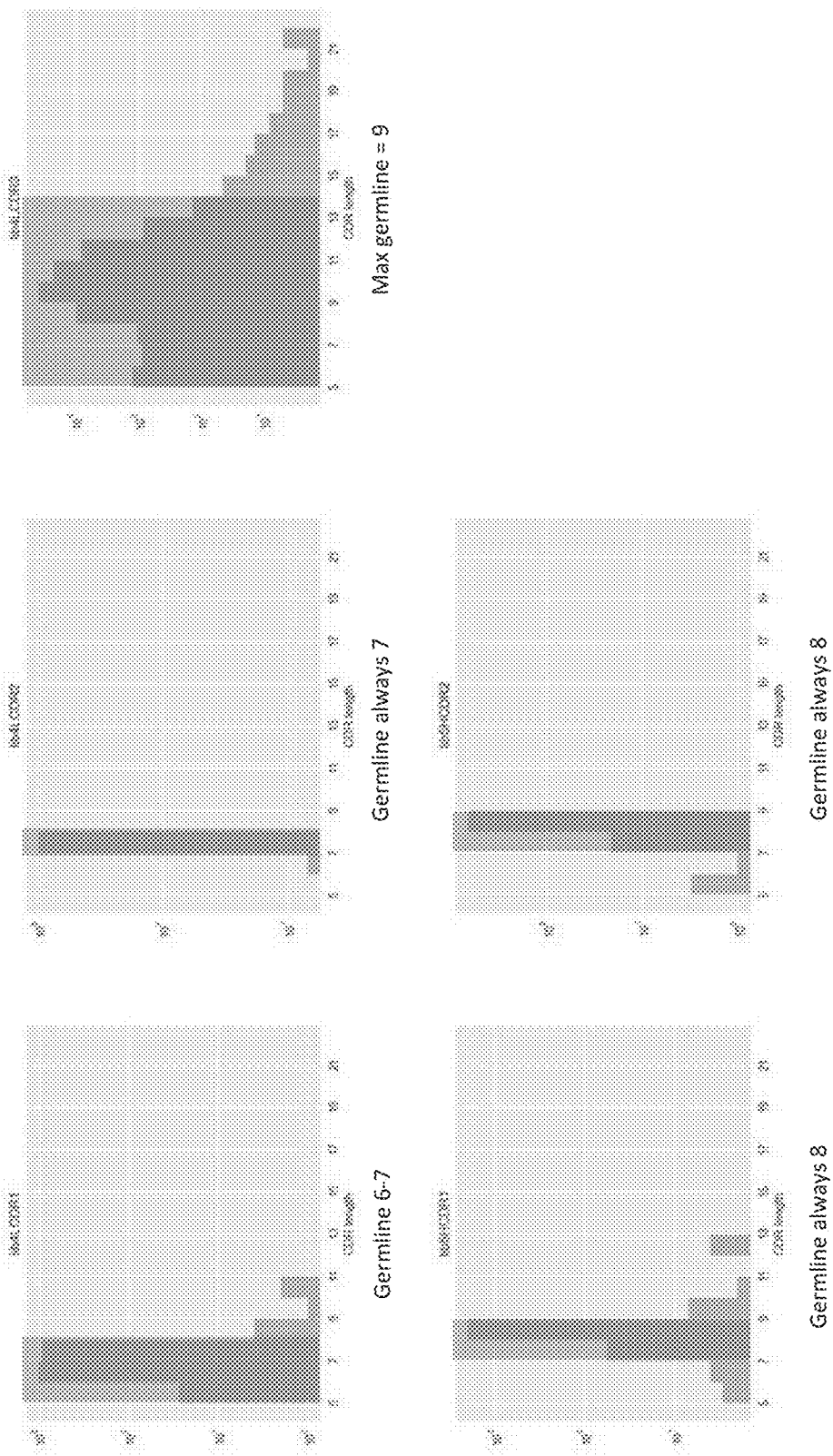
FIG. 20 includes graphs showing the length distribution of CDRs in Library 5 (using scaffold derived from anifrolumab). The germline length for each CDR is indicated under each graph and the CDRs outside of the highlighted region are eliminated for anomalous length.
Figure 21:
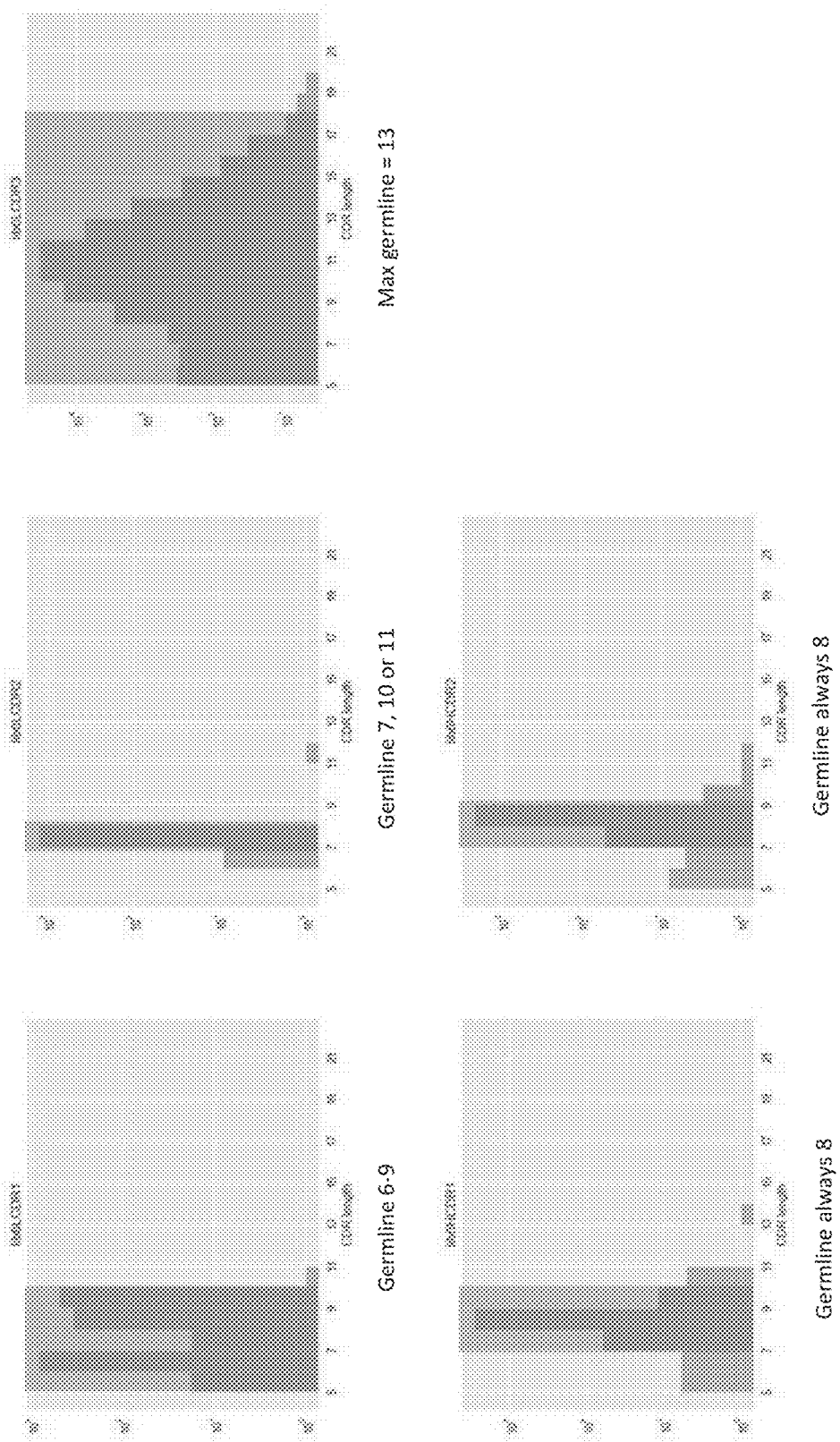
FIG. 21 includes graphs showing the length distribution of CDRs in Library 6 (using scaffold derived from evoculumab). The germline length for each CDR is indicated under each graph and the CDRs outside of the highlighted region are eliminated for anomalous length.

The use of different thresholds would be expected to yield different numbers of CDRs with different sequences as shown in FIG. 15.

Example 5: Elimination of CDRs Based on Anomalous Length

The lengths of germline CDRs are conserved, although they may vary during affinity maturation. CDRs of anomalous length are expected to reduce folding and expression of antibodies that contain them. CDRs with anomalous lengths were also computationally eliminated under the rules described in FIG. 4 and CDRs with a length outside of the pink shaded area were eliminated as shown FIGS. 16-21. The effects on the number of retained CDRs are indicated in Table 5 and Table 6. It is clear that alternative rules may be applied to the identification of naturally occurring CDRs that lack liabilities, and that as new liabilities are identified, they can be similarly eliminated. Furthermore, by carrying out next generation sequencing on CDRs experimentally selected for the presence of liabilities, such as polyreactivity or aggregation behavior, additional sequence liabilities can be identified and can be eliminated in other libraries created using this approach. As the numbers of CDRs sequenced increases, it is expected that the number of both unique CDRs, as well as the number of unique CDRs lacking liabilities will increase, so increasing the potential library diversity.

After the completion of these different informatic operations, the final number of unique CDRs identified as containing no liabilities, for each scaffold for this exemplary library is indicated in Table 3 showing both unique CDRs and CDRs including flanking scaffold oligos (in parentheses):

~3,566 (5,476) LCDR1s;
~2,972 (3,944) LCDR2s;
~218,471 (297,509) LCDR3s;
~14,340 (17,200) HCDR1s;
~11,397 (13,568) HCDR2s; and
~1,791,801 HCDR3s

TABLE 5

Number of CDRs Retained after Defined Length Restriction.

| | No length restriction | Length Restriction | Difference |
|---|---|---|---|
| Library 1 | | | |
| LCDR1 | 1,719 | 1,717 | −2 |
| LCDR2 | 1,409 | 1,406 | −3 |
| LCDR3 | 74,134 | 74,091 | −43 |
| HCDR1 | 2,878 | 2,860 | −18 |
| HCDR2 | 2,189 | 2,171 | −18 |
| Total | 82,329 | 82,245 | −84 |
| Library 2 | | | |
| LCDR1 | 122 | 103 | −19 |
| LCDR2 | 141 | 140 | −1 |
| LCDR3 | 17,920 | 17,917 | −3 |

TABLE 5-continued

Number of CDRs Retained after Defined Length Restriction.

|  | No length restriction | Length Restriction | Difference |
|---|---|---|---|
| HCDR1 | 2,335 | 2,296 | −39 |
| HCDR2 | 1,262 | 1,253 | −9 |
| Total Library 3 | 21,780 | 21,709 | −71 |
| LCDR1 | 57 | 50 | −7 |
| LCDR2 | 231 | 229 | −2 |
| LCDR3 | 32,111 | 32,092 | −19 |
| HCDR1 | 5,956 | 5,920 | −36 |
| HCDR2 | 4,569 | 4,565 | −4 |
| Total Library 4 | 42,924 | 42,856 | −68 |
| LCDR1 | 1,917 | 1,910 | −7 |
| LCDR2 | 979 | 972 | −7 |
| LCDR3 | 79,141 | 79,038 | −103 |
| HCDR1 | 1,293 | 1,285 | −8 |
| HCDR2 | 2,773 | 2,739 | −34 |
| Total Library 5 | 86,103 | 85,944 | −159 |
| HCDR1 | 1,999 | 1,979 | −20 |
| HCDR2 | 673 | 669 | −4 |
| Total Library 6 | 24,452 | 24,357 | −95 |
| LCDR1 | 1,697 | 1,696 | −1 |
| LCDR2 | 1,207 | 1,197 | −10 |
| LCDR3 | 94,383 | 94,371 | −12 |
| HCDR1 | 2,878 | 2,860 | −18 |
| HCDR2 | 2,189 | 2,171 | −18 |
| Total | 102,354 | 102,295 | −59 |

TABLE 6

Total Number of CDRs.

|  | No length restriction | Length Restriction | Difference |
|---|---|---|---|
| Total | 338,162 | 337,697 | −465 |

Example 6: Synthesis and Amplification of Oligonucleotides Corresponding to Final CDRs Oligonucleotides corresponding to those identified for HCDR1-2 and LCDR1-3 after the elimination steps as described in the above Examples were synthesized (Twist, Inc., San Francisco, CA), resulting in a total of 337,697 oligonucleotides coding for the selected CDRs. The CDR coding sequence in these oligonucleotides was flanked by 5' and 3' sequences homologous to the framework vectors, into which the CDR coding sequences were cloned. The homologous sequences were used for both amplification and insertion of the oligonucleotides into the yeast display vectors.

Figure 22K:
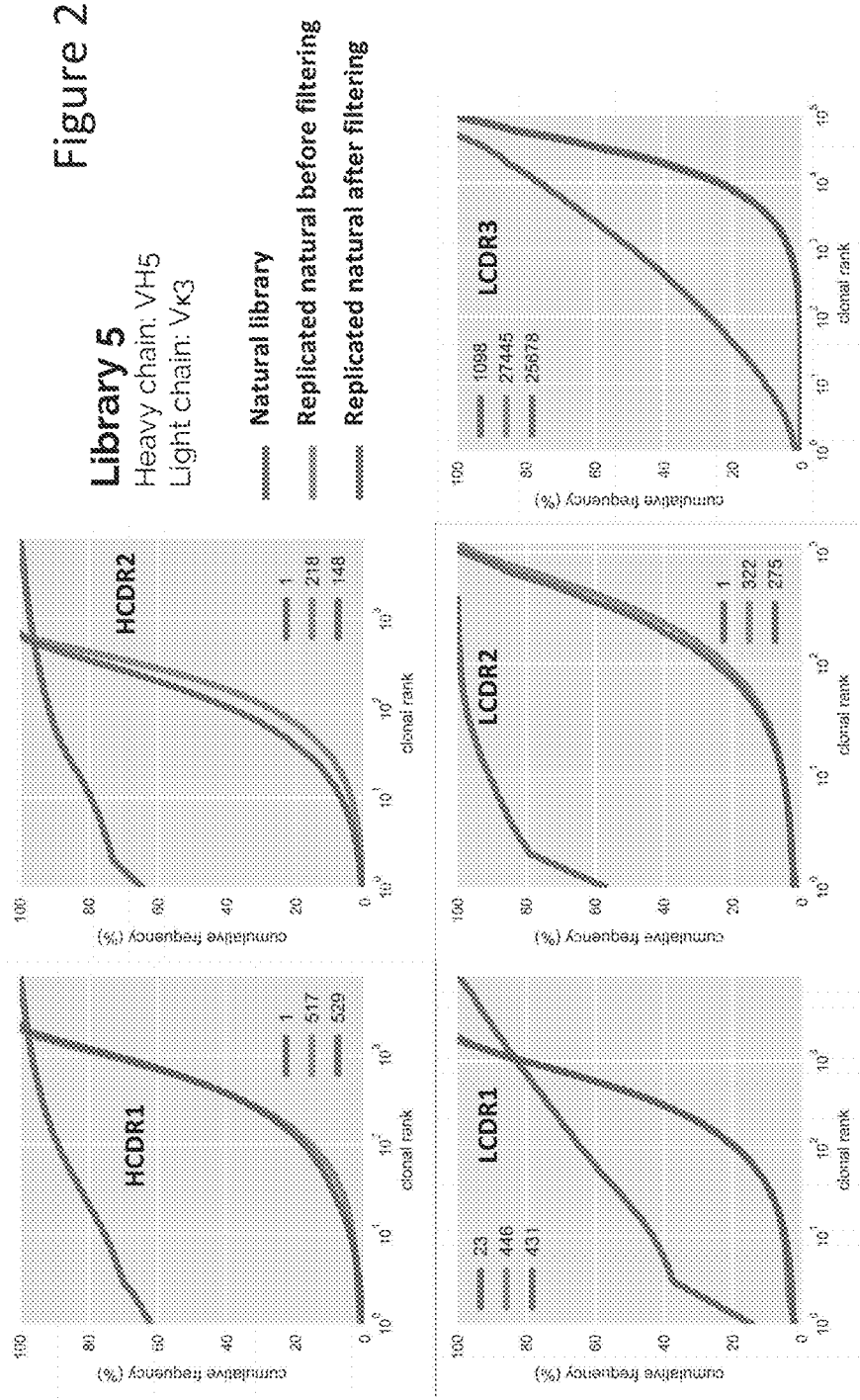

The combined pool of replicated natural CDRs amplified using primer pairs specific for each library scaffold and CDR position, cloned into the yeast display vectors described in Example 2 by homologous recombination, resulted in 30 different single CDR loop libraries (6 libraries, LCDR1-3, HCDR1-2). These were sorted for display, using a monoclonal antibody recognizing the SV5 tag by fluorescence activated cell sorting. For each of these libraries, this represents the diversity of replicated natural CDRs that are amplified using the specific primer pairs used (see below) that allow any level of display and are indicated as "Replicated natural before filtering" in FIG. 22.

FIG. 22A-F illustrates exemplary advantage of using synthetic oligonucleotides to encode HCDR1-2 and LCDR1-3 replicated natural diversity. Particularly for CDR1-2, the difference in abundance between the most and least abundant CDRs can be >300,000-fold, with the germline CDR1-2 sequences being by far the most abundant. When natural CDRs are synthesized, the distribution is always far flatter, as shown in FIGS. 22A-F, with the difference in abundance between the most and least abundant CDRs ranging from 10-200 fold, depending upon the CDR and library. The improvement in the diversity at each CDR using the approach described here is further illustrated in FIGS. 22G-L, where the cumulative distribution is indicated for each library and CDR position. The figures for each plot indicate the D50, the number of clones comprising the most abundant 50% of clones, which for all CDRs in all libraries is significantly higher for the replicated natural diversity, than for the natural diversity. In the case of HCDR3, the VDJ recombinatorial process (including addition of removal of nucleotides at the VD and DJ junctions) results in less variability in abundance between different HCDR3s.

The pool of oligonucleotides was subjected to amplification using the following primers:

For LCDR11: F-L1-LCDR1 to F-L6-LCDR1 and R-L1-LCDR1 to R-L6-LCDR1

For LCDR2: F-L1-LCDR2 to F-L6-LCDR2 and R-L1-LCDR2 to R-L6-LCDR2

For LCDR3: F-L1-LCDR3 to F-L6-LCDR3 and R-L1-LCDR3 to R-L6-LCDR3

For HCDR1: F-L1-HCDR1 to F-L1-HCDR1 and R-L1-HCDR1 to R-L1-HCDR1

For HCDR2: F-L1-HCDR2 to F-L1-HCDR2 and R-L1-HCDR2 to R-L1-HCDR2

The exemplary amplification primer sequences and assembly primer sequences are provided in Table 7 and Table 8, respectively.

TABLE 7

Exemplary Amplification Primers.

|  | Name | Sequence | Tm (° C.) | SEQ ID NO |
|---|---|---|---|---|
| 0 | F-L1-LCDR1 | GCTTCTGTTGGTGATCGTGTTACTATTACCTGTCGTGCTTCT | 77.9 | 181 |
| 1 | F-L2-LCDR1 | GTTTCTCTGGGTGAACGTGCTACCATCAACTGCAAATCTTCT | 77.9 | 182 |
| 2 | F-L3-LCDR1 | GTTACCCCAGGTGAACCAGCTTCTATTTCTTGTCGTTCTTCT | 77.9 | 183 |

TABLE 7-continued

Exemplary Amplification Primers.

| | Name | Sequence | Tm (° C.) | SEQ ID NO |
|---|---|---|---|---|
| 3 | F-L4-LCDR1 | CTGTCTCCAGGTGAACGTGCCACTCTGTCTTGTCGTGCTTCT | 81.8 | 184 |
| 4 | F-L5-LCDR1 | CTGTCTCCAGGTGAACGTGCCACTCTGTCTTGTCGTGCTTCT | 81.8 | 185 |
| 5 | F-L6-LCDR1 | GGTTCTCCAGGTCAGTCTATCACCATCTCTTGTACCGGTACC | 80.9 | 186 |
| 6 | R-L1-LCDR1 | CAGTTTTGGAGCTTTACCTGGTTTCTGCTGGTACCAAGCCAG | 79.9 | 187 |
| 7 | R-L2-LCDR1 | CAGTTTTGGTGGCTGACCTGGTTTCTGCTGGTACCAAGCCAG | 81.8 | 188 |
| 8 | R-L3-LCDR1 | CAGCTGTGGAGACTGACCTGGTTTCTGCAGGTACCAGTGCAG | 82.8 | 189 |
| 9 | R-L4-LCDR1 | CAGACGTGGAGCCTGACCTGGTTTCTGCTGGTACCAAGCCAG | 83.8 | 190 |
| 10 | R-L5-LCDR1 | CAGACGTGGAGCCTGACCTGGTTTCTGCTGGTACCAAGCCAG | 83.8 | 191 |
| 11 | R-L6-LCDR1 | CAGTTTTGGAGCTTTACCTGGGTGCTGCTGGTACCAAGAAAC | 79.9 | 192 |
| 12 | F-L1-LCDR2 | TACCAGCAGAAACCAGGTAAAGCTCCAAAACTGCTGATCTAC | 77.9 | 193 |
| 13 | F-L2-LCDR2 | TACCAGCAGAAACCAGGTCAGCCACCAAAACTGCTGATCTAC | 79.9 | 194 |
| 14 | F-L3-LCDR2 | TACCTGCAGAAACCAGGTCAGTCTCCACAGCTGCTGATCTAC | 80.9 | 195 |
| 15 | F-L4-LCDR2 | TACCAGCAGAAACCAGGTCAGGCTCCACGTCTGCTGATCTAC | 81.8 | 196 |
| 16 | F-L5-LCDR2 | TACCAGCAGAAACCAGGTCAGGCTCCACGTCTGCTGATCTAC | 81.8 | 197 |
| 17 | F-L6-LCDR2 | TACCAGCAGCACCCAGGTAAAGCTCCAAAACTGATGATCTAC | 78.9 | 198 |
| 18 | R-L1-LCDR2 | ATCGGTACCAGAACCAGAACCAGAGAAACGAGATGGAACACC | 79.9 | 199 |
| 19 | R-L2-LCDR2 | ATCGGTACCAGAACCAGAACCAGAGAAACGATCTGGAACACC | 79.9 | 200 |
| 20 | R-L3-LCDR2 | ATCGGTACCAGAACCAGAACCAGAGAAACGATCTGGAACACC | 79.9 | 201 |
| 21 | R-L4-LCDR2 | ATCGGTACCAGAACCAGAACCAGAGAAACGAGCTGGGATACC | 80.9 | 202 |
| 22 | R-L5-LCDR2 | ATCGGTACCAGAACCAGAACCAGACAGACGATCTGGGATACC | 80.9 | 203 |
| 23 | R-L6-LCDR2 | GGTGTTACCAGATTTAGAACCAGAGAAACGGTTAGAAACACC | 77.0 | 204 |
| 24 | F-L1-LCDR3 | ATCTCTTCTCTGCAGCCAGAAGATTTCGCTAACTACTACTGT | 77.0 | 205 |
| 25 | F-L2-LCDR3 | ATCTCTTCTCTGCAGGCTGAAGATGTTGCTGTTTACTACTGT | 77.0 | 206 |
| 26 | F-L3-LCDR3 | ATCTCTCGTGTTGAAGCTGAAGATGTTGGTGTTTACTACTGT | 76.0 | 207 |
| 27 | F-L4-LCDR3 | ATCTCTTCTCTGGAACCAGAAGATTTCGCTGTTTACTACTGT | 76.0 | 208 |
| 28 | F-L5-LCDR3 | ATCACCCGTCTGGAACCAGAAGATTTCGCTGTTTACTACTGT | 77.9 | 209 |
| 29 | F-L6-LCDR3 | ATCTCTGGTCTGCAGGCTGAAGATGAAGCTGATTACTACTGT | 77.9 | 210 |
| 30 | R-L1-LCDR3 | CGACCCTCCGGATTTGATTTCAACTTTGGTACCACCACCGAA | 79.9 | 211 |
| 31 | R-L6-LCDR3 | CGACCCTCCGGACAGAACGGTCAGTTTGGTACCACCACCGAA | 83.8 | 212 |
| 32 | F-L1-HCDR1 | AAAAACCAGGTGCTTCTGTTAAAGTTTCTTGTAAAGTTTCT | 72.1 | 213 |
| 33 | F-L2-HCDR1 | GTTAAACCAACCCAGACCCTGACCCTGACCTGTACCGTTTCT | 80.9 | 214 |
| 34 | F-L3-HCDR1 | GTTCAGCCAGGTGGTTCTCTGCGTCTGTCTTGTGCTGCTTCT | 81.8 | 215 |
| 35 | F-L4-HCDR1 | GTTAAACCATCTCAGACCCTGTCTCTGACCTGTACCGTTTCT | 78.9 | 216 |
| 35 | F-L5-HCDR1 | AAAAACCAGGTGAATCTCTGAAAATCTCTTGTAAAGGTTCT | 73.0 | 217 |
| 37 | F-L6-HCDR1 | AAAAACCAGGTGCTTCTGTTAAAGTTTCTTGTAAAGCTTCT | 73.0 | 218 |
| 38 | R-L1-HCDR1 | CCATTCCAGACCTTTACCTGGAGCCTGACGAACCCAGTGGAT | 81.8 | 219 |
| 39 | R-L2-HCDR1 | CCATTCCAGAGCTTTACCTGGTGGCTGACGGATCCAGTTAAC | 80.9 | 220 |
| 40 | R-L3-HCDR1 | CAGTTCCAGACCTTTACCTGGAGCCTGACGAACCCAAGACAT | 80.9 | 221 |

TABLE 7-continued

Exemplary Amplification Primers.

| | Name | Sequence | Tm (° C.) | SEQ ID NO |
|---|---|---|---|---|
| 41 | R-L4-HCDR1 | CCATTCCAGACCTTTACCTGGTGGCTGACGGATCCAAGACCA | 81.8 | 222 |
| 42 | R-L5-HCDR1 | AGATTCCAGACCTTTACCTGGAACCTGACGAACCCAAGCGAT | 79.9 | 223 |
| 43 | R-L6-HCDR1 | CCATTCCAGACCCTGACCTGGAGCCTGACGAACCCAAGAGAT | 82.8 | 224 |
| 44 | F-L1-HCDR2 | GTTCGTCAGGCTCCAGGTAAAGGTCTGGAATGGATGGGTGGT | 81.8 | 225 |
| 45 | F-L2-HCDR2 | ATCCGTCAGCCACCAGGTAAAGCTCTGGAATGGCTGGCTATG | 81.8 | 226 |
| 46 | F-L3-HCDR2 | GTTCGTCAGGCTCCAGGTAAAGGTCTGGAACTGGTTGCTTCT | 80.9 | 227 |
| 47 | F-L4-HCDR2 | ATCCGTCAGCCACCAGGTAAAGGTCTGGAATGGATCGGTTAC | 80.9 | 228 |
| 48 | F-L5-HCDR2 | GTTCGTCAGGTTCCAGGTAAAGGTCTGGAATCTATGGGTATC | 78.9 | 229 |
| 49 | F-L6-HCDR2 | GTTCGTCAGGCTCCAGGTCAGGGTCTGGAATGGATGGGTTGG | 83.8 | 230 |
| 50 | R-L1-HCDR2 | TTCGGTCATGGTAACACGACCCTGGAATTTCTGAGCGTAGAT | 78.9 | 231 |
| 51 | R-L2-HCDR2 | AGAGATGGTCAGACGAGATTTCAGAGCAGAGTTGTAAACGAT | 77.0 | 232 |
| 52 | R-L3-HCDR2 | ACGAGAGATGGTGAAACGACCTTTAACAGAATCTGGGTAGTA | 77.0 | 233 |
| 53 | R-L4-HCDR2 | AACAGACATGGTAACACGAGATTTCAGAGATGGGTTGTAATC | 76.0 | 234 |
| 54 | R-L5-HCDR2 | AGCAGAGATGGTAACCTGACCCTGGAAAGATGGAGAGTAACG | 79.9 | 235 |
| 55 | R-L6-HCDR2 | GGTGGTCATGGTACCACGACCCTGCAGTTTCTGAGCGTAGTT | 81.8 | 236 |
| 56 | F-L1-HCDR3 | CTGTCTTCTCTGAAATCTGAGGACACGGCCGTGTATTACTGT | 78.9 | 237 |
| 57 | F-L2-HCDR3 | ATGACCAACATGGATCCTGTGGACACAGCCACATATTACTGT | 77.9 | 238 |
| 58 | F-L3-HCDR3 | ATGAACTCTCTGCGTGCCGAGGACACGGCTGTGTATTACTGT | 80.9 | 239 |
| 59 | F-L4-HCDR3 | GTTAACTCTGTTACCGCCGCGGACACGGCTGTGTATTACTGT | 80.9 | 240 |
| 60 | F-L5-HCDR3 | TGGTCTTCTCTGAAAGCCTCGGACACCGCCATTTATTACTGT | 78.9 | 241 |
| 61 | F-L6-HCDR3 | CTGCGTTCTCTGCGTTCTGACGACACGGCCGTGTATTACTGT | 81.8 | 242 |
| 62 | R-JH4 | GATTGGTTTGCCGCTAGCTGAGGAGACGGTGACCAGGGTTCC | 83.8 | 243 |
| 63 | R-JH6 | GATTGGTTTGCCGCTAGCTGAGGAGACGGTGACCGTGGTCCC | 84.8 | 244 |

TABLE 8

Exemplary Assembly Primers.

| | Name | Sequences | Tm (° C.) | SEQ ID NO |
|---|---|---|---|---|
| 64 | R-L1-LCDR1-ASS | GTAGATCAGCAGTTTTGGAGCTTT | 61.8 | 245 |
| 65 | R-L2-LCDR1-ASS | GTAGATCAGCAGTTTTGGTGG | 59.4 | 246 |
| 66 | R-L3-LCDR1-ASS | GTAGATCAGCAGCTGTGGAGA | 61.3 | 247 |
| 67 | R-L4-LCDR1-ASS | GTAGATCAGCAGACGTGGAG | 60.5 | 248 |
| 68 | R-L5-LCDR1-ASS | GTAGATCAGCAGACGTGGAG | 60.5 | 249 |
| 69 | R-L6-LCDR1-ASS | GTAGATCATCAGTTTTGGAGCTTTA | 60.9 | 250 |
| 70 | F-L1-LCDR2-ASS | CTGGCTTGGTACCAGCAGAAA | 61.3 | 251 |
| 71 | F-L2-LCDR2-ASS | CTGGCTTGGTACCAGCAGAAA | 61.3 | 252 |
| 72 | F-L3-LCDR2-ASS | CTGCACTGGTACCTGCAGAAA | 61.3 | 253 |
| 73 | F-L4-LCDR2-ASS | CTGGCTTGGTACCAGCAGAAA | 61.3 | 254 |

TABLE 8-continued

Exemplary Assembly Primers.

| | Name | Sequences | Tm (° C.) | SEQ ID NO |
|---|---|---|---|---|
| 74 | F-L5-LCDR2-ASS | CTGGCTTGGTACCAGCAGAAA | 61.3 | 255 |
| 78 | F-L6-LCDR2-ASS | GTTTCTTGGTACCAGCAGCAC | 61.3 | 256 |
| 78 | R-L1-LCDR2-ASS | ACAGTAGTAGTTAGCGAAATCTTCT | 60.9 | 257 |
| 77 | R-L2-LCDR2-ASS | ACAGTAGTAAACAGCAACATCTTCA | 60.9 | 258 |
| 78 | R-L3-LCDR2-ASS | ACAGTAGTAAACACCAACATCTTCA | 60.9 | 259 |
| 78 | R-L4-LCDR2-ASS | ACAGTAGTAAACAGCGAAATCTTCT | 60.9 | 260 |
| 80 | R-L5-LCDR2-ASS | ACAGTAGTAAACAGCGAAATCTTCT | 60.9 | 261 |
| 81 | R-L6-LCDR2-ASS | ACAGTAGTAATCAGCTTCATCTTCA | 60.9 | 262 |
| 82 | F-L1-LCDR3-ASS | GGTGTTCCATCTCGTTTCTCT | 59.4 | 263 |
| 83 | F-L2-LCDR3-ASS | GGTGTTCCAGATCGTTTCTCT | 59.4 | 264 |
| 84 | F-L3-LCDR3-ASS | GGTGTTCCAGATCGTTTCTCT | 59.4 | 265 |
| 86 | F-L4-LCDR3-ASS | GGTATCCCAGCTCGTTTCTCT | 61.3 | 266 |
| 88 | F-L5-LCDR3-ASS | GGTATCCCAGATCGTCTGTCT | 61.3 | 267 |
| 87 | F-L6-LCDR3-ASS | GGTGTTTCTAACCGTTTCTCTG | 60.3 | 268 |
| 90 | R-L1-HCDR1-ASS | ACCACCCATCCATTCCAGAC | 60.5 | 269 |
| 91 | R-L2-HCDR1-ASS | CATAGCCAGCCATTCCAGAG | 60.5 | 270 |
| 92 | R-L3-HCDR1-ASS | AGAAGCAACCAGTTCCAGACC | 61.3 | 271 |
| 93 | R-L4-HCDR1-ASS | GTAACCGATCCATTCCAGACC | 61.3 | 272 |
| 94 | R-L5-HCDR1-ASS | GATACCCATAGATTCCAGACCTTT | 61.8 | 273 |
| 88 | R-L6-HCDR1-ASS | CCAACCCATCCATTCCAGAC | 60.5 | 274 |
| 96 | F-L1-HCDR2-ASS | ATCCACTGGGTTCGTCAGG | 59.5 | 275 |
| 87 | F-L2-HCDR2-ASS | GTTAACTGGATCCGTCAGCCA | 61.3 | 276 |
| 88 | F-L3-HCDR2-ASS | ATGTCTTGGGTTCGTCAGGCT | 61.3 | 277 |
| 99 | F-L4-HCDR2-ASS | TGGTCTTGGATCCGTCAGC | 59.5 | 278 |
| 100 | F-L5-HCDR2-ASS | ATCGCTTGGGTTCGTCAGGTT | 61.3 | 279 |
| 101 | F-L6-HCDR2-ASS | ATCTCTTGGGTTCGTCAGGCT | 61.3 | 280 |
| 102 | R-L1-HCDR2-ASS | ACAGTAATACACGGCCGTGTC | 61.3 | 281 |
| 103 | R-L2-HCDR2-ASS | ACAGTAATATGTGGCTGTGTCCA | 61.1 | 282 |
| 104 | R-L3-HCDR2-ASS | ACAGTAATACACAGCCGTGTC | 59.4 | 283 |
| 105 | R-L4-HCDR2-ASS | ACAGTAATACACAGCCGTGTC | 59.4 | 284 |
| 106 | R-L5-HCDR2-ASS | ACAGTAATAAATGGCGGTGTCC | 60.3 | 285 |
| 107 | R-L6-HCDR2-ASS | ACAGTAATACACGGCCGTGTC | 61.3 | 286 |
| 108 | F-L1-HCDR3-ASS | ATCTACGCTCAGAAATTCCAGG | 60.3 | 287 |
| 109 | F-L2-HCDR3-ASS | GTTTACAACTCTGCTCTGAAATCT | 60.1 | 288 |
| 110 | F-L3-HCDR3-ASS | TACTACCCAGATTCTGTTAAAGGT | 60.1 | 289 |
| 111 | F-L4-HCDR3-ASS | GATTACAACCCATCTCTGAAATCT | 60.1 | 290 |
| 112 | F-L5-HCDR3-ASS | CGTTACTCTCCATCTTTCCAG | 59.4 | 291 |
| 113 | F-L6-HCDR3-ASS | AACTACGCTCAGAAACTGCAG | 59.4 | 292 |

TABLE 8-continued

Exemplary Assembly Primers.

| Name | Sequences | Tm (° C.) | SEQ ID NO |
| --- | --- | --- | --- |
| 114 F-scfv-ASS | CGGATTGTCTTCAACCAACACAA | 61.1 | 293 |
| 115 R-scfv-ASS | CTCCTCCTGTTGAATCCAGG | 60.5 | 294 |
| 116 F-scfv | CAGTTAGATAAAAGAGGCGCG | 59.4 | 295 |
| 117 R-scfv | GCCCAGCAGTGGGTTTGG | 60.7 | 296 |
| 88 F-linker-ASS | TCCGGAGGGTCGACCATAA | 59.5 | 297 |
| 89 R-linker-ASS | GGTACCGCTCGAGGATAACTT | 61.3 | 298 |

While the diversity found in HCDR1-2 and LCDR1-3 can be covered by array-based oligonucleotide synthesis relatively easily, this may not be the case for HCDR3 in some instances, where the original diversity can easily exceed $10^8$ different HCDR3s. Even after liabilities and CDRs found fewer than 4 times may be eliminated, the number of different HCDR3s can exceed $10^7$ if NovaSeq ($3 \times 10^9$ reads) is used to assess diversity. This can be addressed either by limiting synthetic HCDR3 diversity to $<10^6$ sequences, which is tractable by array-based synthesis; or by combining synthetic HCDR1-2 and LCDR1-3 diversity with naturally diverse HCDR3 amplified from donor lymphocytes.

RNA from B lymphocytes from Leuko Paks from ten donors, comprising a total of $>10^9$ B cells, was isolated using the Miltenyi StraightFrom LeukoPak CD19 kit. cDNA was prepared using a primer annealing in the IgM constant region. HCDR3s were amplified from the cDNA using all possible combinations of the six forward primers (F-L1-HCDR3 to F1-L6-HCDR3) and the two reverse primers (R-JH4 and RJH6) described Table 7 and Table 8. This amplification appends sequences to the 5' and 3' ends homologous to the framework vectors, into which the HCDR3s are to be cloned.

Example 7: Cloning of CDRs into Single Site CDR Vectors and Selection for Functional CDRs Although natural replicated CDRs are synthesized based on criteria that should ensure their functionality (e.g., removal of liabilities), oligonucleotide synthesis may not be 100% accurate. In addition to the problem of incorrect sequences, other unidentified liabilities causing poor expression or polyreactivity may be encoded by the synthesized oligonucleotides. Selection of the functional CDRs can be an option to address this issue.

Each of the CDRs remaining from the elimination steps described above was cloned into the appropriate yeast display scaffold vector. The coding sequences of the exemplary scaffold are provided below:

```
> 1 - abrilumab
                                                          (SEQ ID NO: 139)
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTCAGCAGGCTAACTCTTTCCCATGGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTGGTTACACCCTGTCTGATCTGTCTATCCACTGGGTTCGTCAGGCTCCAGGTAAAGGTCT

GGAATGGATGGGTGGTTTCGATCCACAGGATGGTGAAACCATCTACGCTCAGAAATTCCAGGGTCGTGTT

ACCATGACCGAAGATACCTCTACCGATACCGCTTACATGGAACTGTCTTCTCTGAAATCTGAGGACACGG

CCGTGTATTACTGTGCTACCGGTTCTTCTTCTTGGTTCGATCCATGGGGTCAGGGAACCCTGGTCAC

CGTCTCCTCAgctagcggcaaaccaatcccaaacccactgctgggc

> 1a - abrilumab dLCDR1
                                                          (SEQ ID NO: 140)
cagttagataaaagaggcgcggcagcaagcggcgcgcatgccGATATCCAGATGACCCAGTCTCCATCTT CTGTTTCTGCTTCTGTTGGTGATCGTGTTACTATTACCTGTCGTGCTTCTagagaccatggccagtaagg ccggtctctCTGGCTTGGTACCAGCAGAAACCAGGTAAAGCTCCAAAACTGCTGATCTACGGTGCTTCTA
```

```
ACCTGGAATCTGGTGTTCCATCTCGTTTCTCTGGTTCTGGTTCTGGTACCGATTTCACCCTGACCATCTC

TTCTCTGCAGCCAGAAGATTTCGCTAACTACTACTGTCAGCAGGCTAACTCTTTCCCATGGACCTTCGGT

GGTGGTACCAAAGTTGAAATCAAATCCGGAGGGTCGACCATAACTTCGTATAATGTATACTATACGAAGT

TATCCTCGAGCGGTACCCAGGTTCAGCTGGTTCAGTCTGGTGCTGAAGTTAAAAAACCAGGTGCTTCTGT

TAAAGTTTCTTGTAAAGTTTCTGGTTACACCCTGTCTGATCTGTCTATCCACTGGGTTCGTCAGGCTCCA

GGTAAAGGTCTGGAATGGATGGGTGGTTTCGATCCACAGGATGGTGAAACCATCTACGCTCAGAAATTCC

AGGGTCGTGTTACCATGACCGAAGATACCTCTACCGATACCGCTTACATGGAACTGTCTTCTCTGAAATC

TGAGGACACGGCCGTGTATTACTGTGCTACCGGTTCTTCTTCTTCTTGGTTCGATCCATGGGGTCAGGGA

ACCCTGGTCACCGTCTCCTCAgctagcggcaaaccaatcccaaacccactgctgggc
```

> 1b - abrilumab dLCDR2                                                                                          (SEQ ID NO: 141)
```
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACagagaccatggccagtaaggc cggtctctGGTGTTCCATCTCGTTTCTCTGGTTCTGGTTCTGGTACCGATTTCACCCTGACCATCTCTTC

TCTGCAGCCAGAAGATTTCGCTAACTACTACTGTCAGCAGGCTAACTCTTTCCCATGGACCTTCGGTGGT

GGTACCAAAGTTGAAATCAAATCCGGAGGGTCGACCATAACTTCGTATAATGTATACTATACGAAGTTAT

CCTCGAGCGGTACCCAGGTTCAGCTGGTTCAGTCTGGTGCTGAAGTTAAAAAACCAGGTGCTTCTGTTAA

AGTTTCTTGTAAAGTTTCTGGTTACACCCTGTCTGATCTGTCTATCCACTGGGTTCGTCAGGCTCCAGGT

AAAGGTCTGGAATGGATGGGTGGTTTCGATCCACAGGATGGTGAAACCATCTACGCTCAGAAATTCCAGG

GTCGTGTTACCATGACCGAAGATACCTCTACCGATACCGCTTACATGGAACTGTCTTCTCTGAAATCTGA

GGACACGGCCGTGTATTACTGTGCTACCGGTTCTTCTTCTTCTTGGTTCGATCCATGGGGTCAGGGAACC

CTGGTCACCGTCTCCTCAgctagcggcaaaccaatcccaaacccactgctgggc
```

> 1c - abrilumab dLCDR3                                                                                          (SEQ ID NO: 142)
```
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTagagaccatggccagtaaggccggtctctTTCGGTGGTGGTACC

AAAGTTGAAATCAAATCCGGAGGGTCGACCATAACTTCGTATAATGTATACTATACGAAGTTATCCTCGA

GCGGTACCCAGGTTCAGCTGGTTCAGTCTGGTGCTGAAGTTAAAAAACCAGGTGCTTCTGTTAAAGTTTC

TTGTAAAGTTTCTGGTTACACCCTGTCTGATCTGTCTATCCACTGGGTTCGTCAGGCTCCAGGTAAAGGT

CTGGAATGGATGGGTGGTTTCGATCCACAGGATGGTGAAACCATCTACGCTCAGAAATTCCAGGGTCGTG

TTACCATGACCGAAGATACCTCTACCGATACCGCTTACATGGAACTGTCTTCTCTGAAATCTGAGGACAC

GGCCGTGTATTACTGTGCTACCGGTTCTTCTTCTTCTTGGTTCGATCCATGGGGTCAGGGAACCCTGGTC

ACCGTCTCCTCAgctagcggcaaaccaatcccaaacccactgctgggc
```

> 1d - abrilumab dHCDR1                                                                                          (SEQ ID NO: 143)
```
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTCAGCAGGCTAACTCTTTCCCATGGACCTTCGGTGGTGGTACCAA
```

```
AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTagagaccatggccagtaaggccggtctctATCCACTGGGTTCGTCAGGCTCCAGGTAAA

GGTCTGGAATGGATGGGTGGTTTCGATCCACAGGATGGTGAAACCATCTACGCTCAGAAATTCCAGGGTC

GTGTTACCATGACCGAAGATACCTCTACCGATACCGCTTACATGGAACTGTCTTCTCTGAAATCTGAGGA

CACGGCCGTGTATTACTGTGCTACCGGTTCTTCTTCTTCTTGGTTCGATCCATGGGGTCAGGGAACCCTG

GTCACCGTCTCCTCAgctagcggcaaaccaatcccaaacccactgctgggc

> 1e - abrilumab dHCDR2
                                                              (SEQ ID NO: 144)
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTCAGCAGGCTAACTCTTTCCCATGGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTGGTTACACCCTGTCTGATCTGTCTATCCACTGGGTTCGTCAGGCTCCAGGTAAAGGTCT

GGAATGGATGGGTGGTagagaccatggccagtaaggccggtctctATCTACGCTCAGAAATTCCAGGGTC

GTGTTACCATGACCGAAGATACCTCTACCGATACCGCTTACATGGAACTGTCTTCTCTGAAATCTGAGGA

CACGGCCGTGTATTACTGTGCTACCGGTTCTTCTTCTTCTTGGTTCGATCCATGGGGTCAGGGAACCCTG

GTCACCGTCTCCTCAgctagcggcaaaccaatcccaaacccactgctgggc

> 1f - abrilumab dHCDR3
                                                              (SEQ ID NO: 145)
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTCAGCAGGCTAACTCTTTCCCATGGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTGGTTACACCCTGTCTGATCTGTCTATCCACTGGGTTCGTCAGGCTCCAGGTAAAGGTCT

GGAATGGATGGGTGGTTTCGATCCACAGGATGGTGAAACCATCTACGCTCAGAAATTCCAGGGTCGTGTT

ACCATGACCGAAGATACCTCTACCGATACCGCTTACATGGAACTGTCTTCTCTGAAATCTGAGGACACGG

CCGTGTATTACTGTagagaccatggccagtaaggccggtctctGGAACCCTGGTCACCGTCTCCTCAgct agcggcaaaccaatcccaaacccactgctgggc > 2 - mepolizumab
                                                              (SEQ ID NO: 146)
cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

GCTTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT
```

-continued

ACGAAGTTATCCTCGAGCGGTACCCAGGTTACCCTGCGTGAATCTGGTCCAGCTCTGGTTAAACCAACCC
AGACCCTGACCCTGACCTGTACCGTTTCTGGTTTCTCTCTGTCTGCTTACTCTGTTAACTGGATCCGTCA
GCCACCAGGTAAAGCTCTGGAATGGCTGGCTATGATCTGGGGTGATGGTAAAATCGTTTACAACTCTGCT
CTGAAATCTCGTCTGACCATCTCTAAAGATACCTCTAAAAACCAGGTTGTTCTGACCATGACCAACATGG
ATCCTGTGGACACAGCCACATATTACTGTGCTGGTGATGGTTACTACCCATACGCTATGGATAACTGGGG
TCAGGGAACCCTGGTCACCGTCTCCTCAgctagcggcaaaccaatcccaaacccactgctgggc > 2a - mepolizumab dLCDR1 (SEQ ID NO: 147)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTAgagaccatggccagtaagg
ccggtctctCTGGCTTGGTACCAGCAGAAACCAGGTCAGCCACCAAAACTGCTGATCTACGGTGCTTCTA
CCCGTGAATCTGGTGTTCCAGATCGTTTCTCTGGTTCTGGTTCTGGTACCGATTTCACCCTGACCATCTC
TTCTCTGCAGGCTGAAGATGTTGCTGTTTACTACTGTCAGAACGTTCACTCTTTCCCATTCACCTTCGGT
GGTGGTACCAAAGTTGAAATCAAATCCGGAGGGTCGACCATAACTTCGTATAATGTATACTATACGAAGT
TATCCTCGAGCGGTACCCAGGTTACCCTGCGTGAATCTGGTCCAGCTCTGGTTAAACCAACCCAGACCCT
GACCCTGACCTGTACCGTTTCTGGTTTCTCTCTGTCTGCTTACTCTGTTAACTGGATCCGTCAGCCACCA
GGTAAAGCTCTGGAATGGCTGGCTATGATCTGGGGTGATGGTAAAATCGTTTACAACTCTGCTCTGAAAT
CTCGTCTGACCATCTCTAAAGATACCTCTAAAAACCAGGTTGTTCTGACCATGACCAACATGGATCCTGT
GGACACAGCCACATATTACTGTGCTGGTGATGGTTACTACCCATACGCTATGGATAACTGGGGTCAGGGA
ACCCTGGTCACCGTCTCCTCAgctagcggcaaaccaatcccaaacccactgctgggc > 2b - mepolizumab dLCDR2 (SEQ ID NO: 148)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTCAGTCTCTGCTGAACTCTGG
TAACCAGAAAAACTACCTGGCTTGGTACCAGCAGAAACCAGGTCAGCCACCAAAACTGCTGATCTACaga
gaccatggccagtaaggccggtctctGGTGTTCCAGATCGTTTCTCTGGTTCTGGTTCTGGTACCGATTT
CACCCTGACCATCTCTTCTCTGCAGGCTGAAGATGTTGCTGTTTACTACTGTCAGAACGTTCACTCTTTC
CCATTCACCTTCGGTGGTGGTACCAAAGTTGAAATCAAATCCGGAGGGTCGACCATAACTTCGTATAATG
TATACTATACGAAGTTATCCTCGAGCGGTACCCAGGTTACCCTGCGTGAATCTGGTCCAGCTCTGGTTAA
ACCAACCCAGACCCTGACCCTGACCTGTACCGTTTCTGGTTTCTCTCTGTCTGCTTACTCTGTTAACTGG
ATCCGTCAGCCACCAGGTAAAGCTCTGGAATGGCTGGCTATGATCTGGGGTGATGGTAAAATCGTTTACA
ACTCTGCTCTGAAATCTCGTCTGACCATCTCTAAAGATACCTCTAAAAACCAGGTTGTTCTGACCATGAC
CAACATGGATCCTGTGGACACAGCCACATATTACTGTGCTGGTGATGGTTACTACCCATACGCTATGGAT
AACTGGGGTCAGGGAACCCTGGTCACCGTCTCCTCAgctagcggcaaaccaatcccaaacccactgctgg
gc > 2c - mepolizumab dLCDR3 (SEQ ID NO: 149)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTCAGTCTCTGCTGAACTCTGG
TAACCAGAAAAACTACCTGGCTTGGTACCAGCAGAAACCAGGTCAGCCACCAAAACTGCTGATCTACGGT
GCTTCTACCCGTGAATCTGGTGTTCCAGATCGTTTCTCTGGTTCTGGTTCTGGTACCGATTTCACCCTGA
CCATCTCTTCTCTGCAGGCTGAAGATGTTGCTGTTTACTACTGTagagaccatggccagtaaggccggtc
tctTTCGGTGGTGGTACCAAAGTTGAAATCAAATCCGGAGGGTCGACCATAACTTCGTATAATGTATACT
ATACGAAGTTATCCTCGAGCGGTACCCAGGTTACCCTGCGTGAATCTGGTCCAGCTCTGGTTAAACCAAC -continued

CCAGACCCTGACCCTGACCTGTACCGTTTCTGGTTTCTCTCTGTCTGCTTACTCTGTTAACTGGATCCGT

CAGCCACCAGGTAAAGCTCTGGAATGGCTGGCTATGATCTGGGGTGATGGTAAAATCGTTTACAACTCTG

CTCTGAAATCTCGTCTGACCATCTCTAAAGATACCTCTAAAAACCAGGTTGTTCTGACCATGACCAACAT

GGATCCTGTGGACACAGCCACATATTACTGTGCTGGTGATGGTTACTACCCATACGCTATGGATAACTGG

GGTCAGGGAACCCTGGTCACCGTCTCCTCAgctagcggcaaaccaatcccaaacccactgctgggc

> 2d - mepolizumab dHCDR1

(SEQ ID NO: 150)

cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

TTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT

ACGAAGTTATCCTCGAGCGGTACCCAGGTTACCCTGCGTGAATCTGGTCCAGCTCTGGTTAAACCAACCC

AGACCCTGACCCTGACCTGTACCGTTTCTagagaccatggccagtaaggccggtctctGTTAACTGGATC

CGTCAGCCACCAGGTAAAGCTCTGGAATGGCTGGCTATGATCTGGGGTGATGGTAAAATCGTTTACAACT

CTGCTCTGAAATCTCGTCTGACCATCTCTAAAGATACCTCTAAAAACCAGGTTGTTCTGACCATGACCAA

CATGGATCCTGTGGACACAGCCACATATTACTGTGCTGGTGATGGTTACTACCCATACGCTATGGATAAC

TGGGGTCAGGGAACCCTGGTCACCGTCTCCTCAgctagcggcaaaccaatcccaaacccactgctgggc

> 2e - mepolizumab dHCDR2

(SEQ ID NO: 151)

cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

GCTTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT

ACGAAGTTATCCTCGAGCGGTACCCAGGTTACCCTGCGTGAATCTGGTCCAGCTCTGGTTAAACCAACCC

AGACCCTGACCCTGACCTGTACCGTTTCTGGTTTCTCTCTGTCTGCTTACTCTGTTAACTGGATCCGTCA

GCCACCAGGTAAAGCTCTGGAATGGCTGGCTATGagagaccatggccagtaaggccggtctctATCGTTT

ACAACTCTGCTCTGAAATCTCGTCTGACCATCTCTAAAGATACCTCTAAAAACCAGGTTGTTCTGACCAT

GACCAACATGGATCCTGTGGACACAGCCACATATTACTGTGCTGGTGATGGTTACTACCCATACGCTATG

GATAACTGGGGTCAGGGAACCCTGGTCACCGTCTCCTCAgctagcggcaaaccaatcccaaacccactgc tgggc

> 2f - mepolizumab dHCDR3

(SEQ ID NO: 152)

cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

GCTTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT

ACGAAGTTATCCTCGAGCGGTACCCAGGTTACCCTGCGTGAATCTGGTCCAGCTCTGGTTAAACCAACCC

-continued

```
AGACCCTGACCCTGACCTGTACCGTTTCTGGTTTCTCTCTGTCTGCTTACTCTGTTAACTGGATCCGTCA

GCCACCAGGTAAAGCTCTGGAATGGCTGGCTATGATCTGGGGTGATGGTAAAATCGTTTACAACTCTGCT

CTGAAATCTCGTCTGACCATCTCTAAAGATACCTCTAAAAACCAGGTTGTTCTGACCATGACCAACATGG

ATCCTGTGGACACAGCCACATATTACTGTagagaccatggccagtaaggccggtctctGGAACCCTGGTC

ACCGTCTCCTCAgctagcggcaaaccaatcccaaacccactgctgggc
```

> 3 - crenezumab
(SEQ ID NO: 153)
```
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTATCAACTCTAACGGTGGTTCTACCTACTACCCAGATTCT

GTTAAAGGTCGTTTCACCATCTCTCGTGATAACGCTAAAAACTCTCTGTACCTGCAGATGAACTCTCTGC

GTGCCGAGGACACGGCTGTGTATTACTGTGCTTCTGGTGATTACTGGGGTCAGGGGACCACGGTCACCGT

CTCCTCAgctagcggcaaaccaatcccaaacccactgctgggc
```

> 3a - crenezumab dLCDR1
(SEQ ID NO: 154)
```
cagttagataaaagaggcgcggcagcaagcggcgcgcatgccGATATCGTTATGACCCAGTCTCCACTGT CTCTGCCAGTTACCCCAGGTGAACCAGCTTCTATTTCTTGTCGTTCTTCTagagaccatggccagtaagg ccggtctctCTGCACTGGTACCTGCAGAAACCAGGTCAGTCTCCACAGCTGCTGATCTACAAAGTTTCTA

ACCGTTTCTCTGGTGTTCCAGATCGTTTCTCTGGTTCTGGTTCTGGTACCGATTTCACCCTGAAAATCTC

TCGTGTTGAAGCTGAAGATGTTGGTGTTTACTACTGTTCTCAGTCTACCCACGTTCCATGGACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTGAATCTGGTGGTGGTCTGGTTCAGCCAGGTGGTTCTCT

GCGTCTGTCTTGTGCTGCTTCTGGTTTCACCTTCTCTTCTTACGGTATGTCTTGGGTTCGTCAGGCTCCA

GGTAAAGGTCTGGAACTGGTTGCTTCTATCAACTCTAACGGTGGTTCTACCTACTACCCAGATTCTGTTA

AAGGTCGTTTCACCATCTCTCGTGATAACGCTAAAAACTCTCTGTACCTGCAGATGAACTCTCTGCGTGC

CGAGGACACGGCTGTGTATTACTGTGCTTCTGGTGATTACTGGGGTCAGGGGACCACGGTCACCGTCTCC

TCAgctagcggcaaaccaatcccaaacccactgctgggc
```

> 3b - crenezumab dLCDR2
(SEQ ID NO: 155)
```
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACagagac catggccagtaaggccggtctctGGTGTTCCAGATCGTTTCTCTGGTTCTGGTTCTGGTACCGATTTCAC

CCTGAAAATCTCTCGTGTTGAAGCTGAAGATGTTGGTGTTTACTACTGTTCTCAGTCTACCCACGTTCCA

TGGACCTTCGGTGGTGGTACCAAAGTTGAAATCAAATCCGGAGGGTCGACCATAACTTCGTATAATGTAT

ACTATACGAAGTTATCCTCGAGCGGTACCGAAGTTCAGCTGGTTGAATCTGGTGGTGGTCTGGTTCAGCC

AGGTGGTTCTCTGCGTCTGTCTTGTGCTGCTTCTGGTTTCACCTTCTCTTCTTACGGTATGTCTTGGGTT

CGTCAGGCTCCAGGTAAAGGTCTGGAACTGGTTGCTTCTATCAACTCTAACGGTGGTTCTACCTACTACC
```

-continued

CAGATTCTGTTAAAGGTCGTTTCACCATCTCTCGTGATAACGCTAAAAACTCTCTGTACCTGCAGATGAA

CTCTCTGCGTGCCGAGGACACGGCTGTGTATTACTGTGCTTCTGGTGATTACTGGGGTCAGGGGACCACG

GTCACCGTCTCCTCAgctagcggcaaaccaatcccaaacccactgctgggc

> 3c - crenezumab dLCDR3

(SEQ ID NO: 156)
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTagagaccatggccagtaaggccggtctct

TTCGGTGGTGGTACCAAAGTTGAAATCAAATCCGGAGGGTCGACCATAACTTCGTATAATGTATACTATA

CGAAGTTATCCTCGAGCGGTACCGAAGTTCAGCTGGTTGAATCTGGTGGTGGTCTGGTTCAGCCAGGTGG

TTCTCTGCGTCTGTCTTGTGCTGCTTCTGGTTTCACCTTCTCTTCTTACGGTATGTCTTGGGTTCGTCAG

GCTCCAGGTAAAGGTCTGGAACTGGTTGCTTCTATCAACTCTAACGGTGGTTCTACCTACTACCCAGATT

CTGTTAAAGGTCGTTTCACCATCTCTCGTGATAACGCTAAAAACTCTCTGTACCTGCAGATGAACTCTCT

GCGTGCCGAGGACACGGCTGTGTATTACTGTGCTTCTGGTGATTACTGGGGTCAGGGGACCACGGTCACC

GTCTCCTCAgctagcggcaaaccaatcccaaacccactgctgggc

> 3d - crenezumab dHCDR1

(SEQ ID NO: 157)
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTagagaccatggccagtaaggccggtctctATGTCTTGGGTTCGT

CAGGCTCCAGGTAAAGGTCTGGAACTGGTTGCTTCTATCAACTCTAACGGTGGTTCTACCTACTACCCAG

ATTCTGTTAAAGGTCGTTTCACCATCTCTCGTGATAACGCTAAAAACTCTCTGTACCTGCAGATGAACTC

TCTGCGTGCCGAGGACACGGCTGTGTATTACTGTGCTTCTGGTGATTACTGGGGTCAGGGGACCACGGTC

ACCGTCTCCTCAgctagcggcaaaccaatcccaaacccactgctgggc

> 3e - crenezumab dHCDR2

(SEQ ID NO: 158)
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTagagaccatggccagtaaggccggtctctTACTACCCAG

ATTCTGTTAAAGGTCGTTTCACCATCTCTCGTGATAACGCTAAAAACTCTCTGTACCTGCAGATGAACTC

-continued

TCTGCGTGCCGAGGACACGGCTGTGTATTACTGTGCTTCTGGTGATTACTGGGGTCAGGGGACCACGGTC

ACCGTCTCCTCAgctagcggcaaaccaatcccaaacccactgctgggc

> 3f - crenezumab dHCDR3
(SEQ ID NO: 159)

cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTATCAACTCTAACGGTGGTTCTACCTACTACCCAGATTCT

GTTAAAGGTCGTTTCACCATCTCTCGTGATAACGCTAAAAACTCTCTGTACCTGCAGATGAACTCTCTGC

GTGCCGAGGACACGGCTGTGTATTACTGTagagaccatggccagtaaggccggtctctGGGACCACGGTC

ACCGTCTCCTCAgctagcggcaaaccaatcccaaacccactgctgggc

> 4 - necitumumab
(SEQ ID NO: 160)

cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTCACCAGTACGGTTCTACCCCACTGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGCAGGAATCTGGTCCAGGTCTGGTTAAACCATCTCAGACCCTGTCTCTGACCT

GTACCGTTTCTGGTGGTTCTATCTCTTCTGGTGATTACTACTGGTCTTGGATCCGTCAGCCACCAGGTAA

AGGTCTGGAATGGATCGGTTACATCTACTACTCTGGTTCTACCGATTACAACCCATCTCTGAAATCTCGT

GTTACCATGTCTGTTGATACCTCTAAAAACCAGTTCTCTCTGAAAGTTAACTCTGTTACCGCCGCGGACA

CGGCTGTGTATTACTGTGCTCGTGTTTCTATCTTCGGTGTTGGTACCTTCGATTACTGGGGTCAGGGAAC

CCTGGTCACCGTCTCCTCAgctagcggcaaaccaatcccaaacccactgctgggc

> 4a - necitumumab dLCDR1
(SEQ ID NO: 161)

cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTagagaccatggccagtaagg ccggtctctCTGGCTTGGTACCAGCAGAAACCAGGTCAGGCTCCACGTCTGCTGATCTACGATGCTTCTA

ACCGTGCTACCGGTATCCCAGCTCGTTTCTCTGGTTCTGGTTCTGGTACCGATTTCACCCTGACCATCTC

TTCTCTGGAACCAGAAGATTTCGCTGTTTACTACTGTCACCAGTACGGTTCTACCCCACTGACCTTCGGT

GGTGGTACCAAAGTTGAAATCAAATCCGGAGGGTCGACCATAACTTCGTATAATGTATACTATACGAAGT

TATCCTCGAGCGGTACCCAGGTTCAGCTGCAGGAATCTGGTCCAGGTCTGGTTAAACCATCTCAGACCCT

GTCTCTGACCTGTACCGTTTCTGGTGGTTCTATCTCTTCTGGTGATTACTACTGGTCTTGGATCCGTCAG

CCACCAGGTAAAGGTCTGGAATGGATCGGTTACATCTACTACTCTGGTTCTACCGATTACAACCCATCTC

TGAAATCTCGTGTTACCATGTCTGTTGATACCTCTAAAAACCAGTTCTCTCTGAAAGTTAACTCTGTTAC

CGCCGCGGACACGGCTGTGTATTACTGTGCTCGTGTTTCTATCTTCGGTGTTGGTACCTTCGATTACTGG

GGTCAGGGAACCCTGGTCACCGTCTCCTCAgctagcggcaaaccaatcccaaacccactgctgggc

> 4b - necitumumab dLCDR2

(SEQ ID NO: 162)
cagttagataaaagaggcgcggcagcaagcggcgcgcatgccGAAATCGTTATGACCCAGTCTCCAGCTA
CCCTGTCTCTGTCTCCAGGTGAACGTGCCACTCTGTCTTGTCGTGCTTCTCAGTCTGTTTCTTCTTACCT
GGCTTGGTACCAGCAGAAACCAGGTCAGGCTCCACGTCTGCTGATCTACagagaccatggccagtaaggc
cggtctctGGTATCCCAGCTCGTTTCTCTGGTTCTGGTTCTGGTACCGATTTCACCCTGACCATCTCTTC
TCTGGAACCAGAAGATTTCGCTGTTTACTACTGTCACCAGTACGGTTCTACCCCACTGACCTTCGGTGGT
GGTACCAAAGTTGAAATCAAATCCGGAGGGTCGACCATAACTTCGTATAATGTATACTATACGAAGTTAT
CCTCGAGCGGTACCCAGGTTCAGCTGCAGGAATCTGGTCCAGGTCTGGTTAAACCATCTCAGACCCTGTC
TCTGACCTGTACCGTTTCTGGTGGTTCTATCTCTTCTGGTGATTACTACTGGTCTTGGATCCGTCAGCCA
CCAGGTAAAGGTCTGGAATGGATCGGTTACATCTACTACTCTGGTTCTACCGATTACAACCCATCTCTGA
AATCTCGTGTTACCATGTCTGTTGATACCTCTAAAAACCAGTTCTCTCTGAAAGTTAACTCTGTTACCGC
CGCGGACACGGCTGTGTATTACTGTGCTCGTGTTTCTATCTTCGGTGTTGGTACCTTCGATTACTGGGGT
CAGGGAACCCTGGTCACCGTCTCCTCAgctagcggcaaaccaatcccaaacccactgctgggc > 4c - necitumumab dLCDR3

(SEQ ID NO: 163)
cagttagataaaagaggcgcggcagcaagcggcgcgcatgccGAAATCGTTATGACCCAGTCTCCAGCTA
CCCTGTCTCTGTCTCCAGGTGAACGTGCCACTCTGTCTTGTCGTGCTTCTCAGTCTGTTTCTTCTTACCT
GGCTTGGTACCAGCAGAAACCAGGTCAGGCTCCACGTCTGCTGATCTACGATGCTTCTAACCGTGCTACC
GGTATCCCAGCTCGTTTCTCTGGTTCTGGTTCTGGTACCGATTTCACCCTGACCATCTCTTCTCTGGAAC
CAGAAGATTTCGCTGTTTACTACTGTagagaccatggccagtaaggccggtctctTTCGGTGGTGGTACC
AAAGTTGAAATCAAATCCGGAGGGTCGACCATAACTTCGTATAATGTATACTATACGAAGTTATCCTCGA
GCGGTACCCAGGTTCAGCTGCAGGAATCTGGTCCAGGTCTGGTTAAACCATCTCAGACCCTGTCTCTGAC
CTGTACCGTTTCTGGTGGTTCTATCTCTTCTGGTGATTACTACTGGTCTTGGATCCGTCAGCCACCAGGT
AAAGGTCTGGAATGGATCGGTTACATCTACTACTCTGGTTCTACCGATTACAACCCATCTCTGAAATCTC
GTGTTACCATGTCTGTTGATACCTCTAAAAACCAGTTCTCTCTGAAAGTTAACTCTGTTACCGCCGCGGA
CACGGCTGTGTATTACTGTGCTCGTGTTTCTATCTTCGGTGTTGGTACCTTCGATTACTGGGGTCAGGGA
ACCCTGGTCACCGTCTCCTCAgctagcggcaaaccaatcccaaacccactgctgggc > 4d - necitumumab dHCDR1

(SEQ ID NO: 164)
cagttagataaaagaggcgcggcagcaagcggcgcgcatgccGAAATCGTTATGACCCAGTCTCCAGCTA
CCCTGTCTCTGTCTCCAGGTGAACGTGCCACTCTGTCTTGTCGTGCTTCTCAGTCTGTTTCTTCTTACCT
GGCTTGGTACCAGCAGAAACCAGGTCAGGCTCCACGTCTGCTGATCTACGATGCTTCTAACCGTGCTACC
GGTATCCCAGCTCGTTTCTCTGGTTCTGGTTCTGGTACCGATTTCACCCTGACCATCTCTTCTCTGGAAC
CAGAAGATTTCGCTGTTTACTACTGTCACCAGTACGGTTCTACCCCACTGACCTTCGGTGGTGGTACCAA
AGTTGAAATCAAATCCGGAGGGTCGACCATAACTTCGTATAATGTATACTATACGAAGTTATCCTCGAGC
GGTACCCAGGTTCAGCTGCAGGAATCTGGTCCAGGTCTGGTTAAACCATCTCAGACCCTGTCTCTGACCT
GTACCGTTTCTagagaccatggccagtaaggccggtctctTGGTCTTGGATCCGTCAGCCACCAGGTAAA
GGTCTGGAATGGATCGGTTACATCTACTACTCTGGTTCTACCGATTACAACCCATCTCTGAAATCTCGTG
TTACCATGTCTGTTGATACCTCTAAAAACCAGTTCTCTCTGAAAGTTAACTCTGTTACCGCCGCGGACAC
GGCTGTGTATTACTGTGCTCGTGTTTCTATCTTCGGTGTTGGTACCTTCGATTACTGGGGTCAGGGAACC
CTGGTCACCGTCTCCTCAgctagcggcaaaccaatcccaaacccactgctgggc -continued > 4e - necitumumab dHCDR2
(SEQ ID NO: 165)
cagttagataaaagaggcgcggcagcaagcggcgcgcatgccGAAATCGTTATGACCCAGTCTCCAGCTA
CCCTGTCTCTGTCTCCAGGTGAACGTGCCACTCTGTCTTGTCGTGCTTCTCAGTCTGTTTCTTCTTACCT
GGCTTGGTACCAGCAGAAACCAGGTCAGGCTCCACGTCTGCTGATCTACGATGCTTCTAACCGTGCTACC
GGTATCCCAGCTCGTTTCTCTGGTTCTGGTTCTGGTACCGATTTCACCCTGACCATCTCTTCTCTGGAAC
CAGAAGATTTCGCTGTTTACTACTGTCACCAGTACGGTTCTACCCCACTGACCTTCGGTGGTGGTACCAA
AGTTGAAATCAAATCCGGAGGGTCGACCATAACTTCGTATAATGTATACTATACGAAGTTATCCTCGAGC
GGTACCCAGGTTCAGCTGCAGGAATCTGGTCCAGGTCTGGTTAAACCATCTCAGACCCTGTCTCTGACCT
GTACCGTTTCTGGTGGTTCTATCTCTTCTGGTGATTACTACTGGTCTTGGATCCGTCAGCCACCAGGTAA
AGGTCTGGAATGGATCGGTTACagagaccatggccagtaaggccggtctctGATTACAACCCATCTCTGA
AATCTCGTGTTACCATGTCTGTTGATACCTCTAAAAACCAGTTCTCTCTGAAAGTTAACTCTGTTACCGC
CGCGGACACGGCTGTGTATTACTGTGCTCGTGTTTCTATCTTCGGTGTTGGTACCTTCGATTACTGGGGT
CAGGGAACCCTGGTCACCGTCTCCTCAgctagcggcaaaccaatcccaaacccactgctgggc > 4f - necitumumab dHCDR3
(SEQ ID NO: 166)
cagttagataaaagaggcgcggcagcaagcggcgcgcatgccGAAATCGTTATGACCCAGTCTCCAGCTA
CCCTGTCTCTGTCTCCAGGTGAACGTGCCACTCTGTCTTGTCGTGCTTCTCAGTCTGTTTCTTCTTACCT
GGCTTGGTACCAGCAGAAACCAGGTCAGGCTCCACGTCTGCTGATCTACGATGCTTCTAACCGTGCTACC
GGTATCCCAGCTCGTTTCTCTGGTTCTGGTTCTGGTACCGATTTCACCCTGACCATCTCTTCTCTGGAAC
CAGAAGATTTCGCTGTTTACTACTGTCACCAGTACGGTTCTACCCCACTGACCTTCGGTGGTGGTACCAA
AGTTGAAATCAAATCCGGAGGGTCGACCATAACTTCGTATAATGTATACTATACGAAGTTATCCTCGAGC
GGTACCCAGGTTCAGCTGCAGGAATCTGGTCCAGGTCTGGTTAAACCATCTCAGACCCTGTCTCTGACCT
GTACCGTTTCTGGTGGTTCTATCTCTTCTGGTGATTACTACTGGTCTTGGATCCGTCAGCCACCAGGTAA
AGGTCTGGAATGGATCGGTTACATCTACTACTCTGGTTCTACCGATTACAACCCATCTCTGAAATCTCGT
GTTACCATGTCTGTTGATACCTCTAAAAACCAGTTCTCTCTGAAAGTTAACTCTGTTACCGCCGCGGACA
CGGCTGTGTATTACTGTagagaccatggccagtaaggccggtctctGGAACCCTGGTCACCGTCTCCTCA
gctagcggcaaaccaatcccaaacccactgctgggc > 5 - anifrolumab
(SEQ ID NO: 167)
cagttagataaaagaggcgcggcagcaagcggcgcgcatgccGAAATCGTTCTGACCCAGTCTCCAGGTA
CCCTGTCTCTGTCTCCAGGTGAACGTGCCACTCTGTCTTGTCGTGCTTCTCAGTCTGTTTCTTCTTCTTT
CCTGGCTTGGTACCAGCAGAAACCAGGTCAGGCTCCACGTCTGCTGATCTACGGTGCTTCTTCTCGTGCT
ACCGGTATCCCAGATCGTCTGTCTGGTTCTGGTTCTGGTACCGATTTCACCCTGACCATCACCCGTCTGG
AACCAGAAGATTTCGCTGTTTACTACTGTCAGCAGTACGATTCTTCTGCTATCACCTTCGGTGGTGGTAC
CAAAGTTGAAATCAAATCCGGAGGGTCGACCATAACTTCGTATAATGTATACTATACGAAGTTATCCTCG
AGCGGTACCGAAGTTCAGCTGGTTCAGTCTGGTGCTGAAGTTAAAAAACCAGGTGAATCTCTGAAAATCT
CTTGTAAAGGTTCTGGTTACATCTTCACCAACTACTGGATCGCTTGGGTTCGTCAGGTTCCAGGTAAAGG
TCTGGAATCTATGGGTATCATCTACCCAGGTGATTCTGATATCCGTTACTCTCCATCTTTCCAGGGTCAG
GTTACCATCTCTGCTGATAAATCTATCACCACCGCTTACCTGCAGTGGTCTTCTCTGAAAGCCTCGGACA
CCGCCATTTATTACTGTGCTCGTCACGATATCGAAGGTTTCGATTACTGGGGTCGTGGAACCCTGGTCAC
CGTCTCCTCAgctagcggcaaaccaatcccaaacccactgctgggc > 5a - anifrolumab dLCDR1
(SEQ ID NO: 168)
cagttagataaaagaggcgcggcagcaagcggcgcgcatgccGAAATCGTTCTGACCCAGTCTCCAGGTA -continued CCCTGTCTCTGTCTCCAGGTGAACGTGCCACTCTGTCTTGTCGTGCTTCTagagaccatggccagtaagg ccggtctctCTGGCTTGGTACCAGCAGAAACCAGGTCAGGCTCCACGTCTGCTGATCTACGGTGCTTCTT

CTCGTGCTACCGGTATCCCAGATCGTCTGTCTGGTTCTGGTTCTGGTACCGATTTCACCCTGACCATCAC

CCGTCTGGAACCAGAAGATTTCGCTGTTTACTACTGTCAGCAGTACGATTCTTCTGCTATCACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTCAGTCTGGTGCTGAAGTTAAAAAACCAGGTGAATCTCT

GAAAATCTCTTGTAAAGGTTCTGGTTACATCTTCACCAACTACTGGATCGCTTGGGTTCGTCAGGTTCCA

GGTAAAGGTCTGGAATCTATGGGTATCATCTACCCAGGTGATTCTGATATCCGTTACTCTCCATCTTTCC

AGGGTCAGGTTACCATCTCTGCTGATAAATCTATCACCACCGCTTACCTGCAGTGGTCTTCTCTGAAAGC

CTCGGACACCGCCATTTATTACTGTGCTCGTCACGATATCGAAGGTTTCGATTACTGGGGTCGTGGAACC

CTGGTCACCGTCTCCTCAgctagcggcaaaccaatcccaaacccactgctgggc

> 5b - anifrolumab dLCDR2  (SEQ ID NO: 169)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACagagaccatggccagtaa ggccggtctctGGTATCCCAGATCGTCTGTCTGGTTCTGGTTCTGGTACCGATTTCACCCTGACCATCAC

CCGTCTGGAACCAGAAGATTTCGCTGTTTACTACTGTCAGCAGTACGATTCTTCTGCTATCACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTCAGTCTGGTGCTGAAGTTAAAAAACCAGGTGAATCTCT

GAAAATCTCTTGTAAAGGTTCTGGTTACATCTTCACCAACTACTGGATCGCTTGGGTTCGTCAGGTTCCA

GGTAAAGGTCTGGAATCTATGGGTATCATCTACCCAGGTGATTCTGATATCCGTTACTCTCCATCTTTCC

AGGGTCAGGTTACCATCTCTGCTGATAAATCTATCACCACCGCTTACCTGCAGTGGTCTTCTCTGAAAGC

CTCGGACACCGCCATTTATTACTGTGCTCGTCACGATATCGAAGGTTTCGATTACTGGGGTCGTGGAACC

CTGGTCACCGTCTCCTCAgctagcggcaaaccaatcccaaacccactgctgggc

> 5c - anifrolumab dLCDR3  (SEQ ID NO: 170)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTagagaccatggccagtaaggccggtctctTTCGGTGGTGGT

ACCAAAGTTGAAATCAAATCCGGAGGGTCGACCATAACTTCGTATAATGTATACTATACGAAGTTATCCT

CGAGCGGTACCGAAGTTCAGCTGGTTCAGTCTGGTGCTGAAGTTAAAAAACCAGGTGAATCTCTGAAAAT

CTCTTGTAAAGGTTCTGGTTACATCTTCACCAACTACTGGATCGCTTGGGTTCGTCAGGTTCCAGGTAAA

GGTCTGGAATCTATGGGTATCATCTACCCAGGTGATTCTGATATCCGTTACTCTCCATCTTTCCAGGGTC

AGGTTACCATCTCTGCTGATAAATCTATCACCACCGCTTACCTGCAGTGGTCTTCTCTGAAAGCCTCGGA

CACCGCCATTTATTACTGTGCTCGTCACGATATCGAAGGTTTCGATTACTGGGGTCGTGGAACCCTGGTC

ACCGTCTCCTCAgctagcggcaaaccaatcccaaacccactgctgggc

> 5d - anifrolumab dHCDR1  (SEQ ID NO: 171)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTagagaccatggccagtaaggccggtctctATCGCTTGGGTTCGTCAGGTTCCAGGT

AAAGGTCTGGAATCTATGGGTATCATCTACCCAGGTGATTCTGATATCCGTTACTCTCCATCTTTCCAGG

GTCAGGTTACCATCTCTGCTGATAAATCTATCACCACCGCTTACCTGCAGTGGTCTTCTCTGAAAGCCTC

GGACACCGCCATTTATTACTGTGCTCGTCACGATATCGAAGGTTTCGATTACTGGGGTCGTGGAACCCTG

GTCACCGTCTCCTCAgctagcggcaaaccaatcccaaacccactgctgggc

> 5e - anifrolumab dHCDR2    (SEQ ID NO: 172)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTGGTTACATCTTCACCAACTACTGGATCGCTTGGGTTCGTCAGGTTCCAGGTAAAGG

TCTGGAATCTATGGGTATCagagaccatggccagtaaggccggtctctCGTTACTCTCCATCTTTCCAGG

GTCAGGTTACCATCTCTGCTGATAAATCTATCACCACCGCTTACCTGCAGTGGTCTTCTCTGAAAGCCTC

GACACCGCCATTTATTACTGTGCTCGTCACGATATCGAAGGTTTCGATTACTGGGGTCGTGGAACCCTG

GTCACCGTCTCCTCAgctagcggcaaaccaatcccaaacccactgctgggc

> 5f - anifrolumab dHCDR3    (SEQ ID NO: 173)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTGGTTACATCTTCACCAACTACTGGATCGCTTGGGTTCGTCAGGTTCCAGGTAAAGG

TCTGGAATCTATGGGTATCATCTACCCAGGTGATTCTGATATCCGTTACTCTCCATCTTTCCAGGGTCAG

GTTACCATCTCTGCTGATAAATCTATCACCACCGCTTACCTGCAGTGGTCTTCTCTGAAAGCCTCGGACA

CCGCCATTTATTACTGTagagaccatggccagtaaggccggtctctGGAACCCTGGTCACCGTCTCCTCA gctagcggcaaaccaatcccaaacccactgctgggc > 6 - evolocumab    (SEQ ID NO: 174)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

-continued

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTGGTTACACCCTGACCTCTTACGTATCTCTTGGGTTCGTCAGGCTCCAGGTCA

GGGTCTGGAATGGATGGGTTGGGTTTCTTTCTACAACGGTAACACCAACTACGCTCAGAAACTGCAGGGT

CGTGGTACCATGACCACCGATCCATCTACCTCTACCGCTTACATGGAACTGCGTTCTCTGCGTTCTGACG

ACACGGCCGTGTATTACTGTGCTCGTGGTTACGGTATGGATGTTTGGGGTCAGGGGACCACGGTCACCGT

CTCCTCAgctagcggcaaaccaatcccaaacccactgctgggc

> 6a - evolocumab dLCDR1
(SEQ ID NO: 175)

cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCagagaccatggccagtaaggccg gtctctGTTTCTTGGTACCAGCAGCACCCAGGTAAAGCTCCAAAACTGATGATCTACGAAGTTTCTAACC

GTCCATCTGGTGTTTCTAACCGTTTCTCTGGTTCTAAATCTGGTAACACCGCTTCTCTGACCATCTCTGG

TCTGCAGGCTGAAGATGAAGCTGATTACTACTGTAACTCTTACACCTCTACCTCTATGGTTTTCGGTGGT

GGTACCAAACTGACCGTTCTGTCCGGAGGGTCGACCATAACTTCGTATAATGTATACTATACGAAGTTAT

CCTCGAGCGGTACCGAAGTTCAGCTGGTTCAGTCTGGTGCTGAAGTTAAAAAACCAGGTGCTTCTGTTAA

AGTTTCTTGTAAAGCTTCTGGTTACACCCTGACCTCTTACGGTATCTCTTGGGTTCGTCAGGCTCCAGGT

CAGGGTCTGGAATGGATGGGTTGGGTTTCTTTCTACAACGGTAACACCAACTACGCTCAGAAACTGCAGG

GTCGTGGTACCATGACCACCGATCCATCTACCTCTACCGCTTACATGGAACTGCGTTCTCTGCGTTCTGA

CGACACGGCCGTGTATTACTGTGCTCGTGGTTACGGTATGGATGTTTGGGGTCAGGGGACCACGGTCACC

GTCTCCTCAgctagcggcaaaccaatcccaaacccactgctgggc

> 6b - evolocumab dLCDR2
(SEQ ID NO: 176)

cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCCTTCTGATGTTGGTGGTTACAA

CTCTGTTTCTTGGTACCAGCAGCACCCAGGTAAAGCTCCAAAACTGATGATCTACagagaccatggccag taaggccggtctctGGTGTTTCTAACCGTTTCTCTGGTTCTAAATCTGGTAACACCGCTTCTCTGACCAT

CTCTGGTCTGCAGGCTGAAGATGAAGCTGATTACTACTGTAACTCTTACACCTCTACCTCTATGGTTTTC

GGTGGTGGTACCAAACTGACCGTTCTGTCCGGAGGGTCGACCATAACTTCGTATAATGTATACTATACGA

AGTTATCCTCGAGCGGTACCGAAGTTCAGCTGGTTCAGTCTGGTGCTGAAGTTAAAAAACCAGGTGCTTC

TGTTAAAGTTTCTTGTAAAGCTTCTGGTTACACCCTGACCTCTTACGGTATCTCTTGGGTTCGTCAGGCT

CCAGGTCAGGGTCTGGAATGGATGGGTTGGGTTTCTTTCTACAACGGTAACACCAACTACGCTCAGAAAC

TGCAGGGTCGTGGTACCATGACCACCGATCCATCTACCTCTACCGCTTACATGGAACTGCGTTCTCTGCG

TTCTGACGACACGGCCGTGTATTACTGTGCTCGTGGTTACGGTATGGATGTTTGGGGTCAGGGGACCACG

GTCACCGTCTCCTCAgctagcggcaaaccaatcccaaacccactgctgggc

> 6c - evolocumab dLCDR3
(SEQ ID NO: 177)

cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTagagaccatggccagtaaggccggtctctTTCGGTGGT

-continued

```
GGTACCAAACTGACCGTTCTGTCCGGAGGGTCGACCATAACTTCGTATAATGTATACTATACGAAGTTAT

CCTCGAGCGGTACCGAAGTTCAGCTGGTTCAGTCTGGTGCTGAAGTTAAAAAACCAGGTGCTTCTGTTAA

AGTTTCTTGTAAAGCTTCTGGTTACACCCTGACCTCTTACGGTATCTCTTGGGTTCGTCAGGCTCCAGGT

CAGGGTCTGGAATGGATGGGTTGGGTTTCTTTCTACAACGGTAACACCAACTACGCTCAGAAACTGCAGG

GTCGTGGTACCATGACCACCGATCCATCTACCTCTACCGCTTACATGGAACTGCGTTCTCTGCGTTCTGA

CGACACGGCCGTGTATTACTGTGCTCGTGGTTACGGTATGGATGTTTGGGGTCAGGGGACCACGGTCACC

GTCTCCTCAgctagcggcaaaccaatcccaaacccactgctgggc
```

> 6d - evolocumab dHCDR1  
(SEQ ID NO: 178)
```
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTagagaccatggccagtaaggccggtctctATCTCTTGGGTTCGTCAGGCTCCA

GGTCAGGGTCTGGAATGGATGGGTTGGGTTTCTTTCTACAACGGTAACACCAACTACGCTCAGAAACTGC

AGGGTCGTGGTACCATGACCACCGATCCATCTACCTCTACCGCTTACATGGAACTGCGTTCTCTGCGTTC

TGACGACACGGCCGTGTATTACTGTGCTCGTGGTTACGGTATGGATGTTTGGGGTCAGGGGACCACGGTC

ACCGTCTCCTCAgctagcggcaaaccaatcccaaacccactgctgggc
```

> 6e - evolocumab dHCDR2  
(SEQ ID NO: 179)
```
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTGGTTACACCCTGACCTCTTACGGTATCTCTTGGGTTCGTCAGGCTCCAGGTCA

GGGTCTGGAATGGATGGGTTGGagagaccatggccagtaaggccggtctctAACTACGCTCAGAAACTGC

AGGGTCGTGGTACCATGACCACCGATCCATCTACCTCTACCGCTTACATGGAACTGCGTTCTCTGCGTTC

TGACGACACGGCCGTGTATTACTGTGCTCGTGGTTACGGTATGGATGTTTGGGGTCAGGGGACCACGGTC

ACCGTCTCCTCAgctagcggcaaaccaatcccaaacccactgctgggc
```

> 6f - evolocumab dHCDR3  
(SEQ ID NO: 180)
```
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG
```

```
TTTCTTGTAAAGCTTCTGGTTACACCCTGACCTCTTACGGTATCTCTTGGGTTCGTCAGGCTCCAGGTCA

GGGTCTGGAATGGATGGGTTGGGTTTCTTTCTACAACGGTAACACCAACTACGCTCAGAAACTGCAGGGT

CGTGGTACCATGACCACCGATCCATCTACCTCTACCGCTTACATGGAACTGCGTTCTCTGCGTTCTGACG

ACACGGCCGTGTATTACTGTAgagaccatggccagtaaggccggtctctGGGACCACGGTCACCGTCTCC

TCAgctagcggcaaaccaatcccaaacccactgctgggc
```

Sequences 1-6 refer to the coding sequence of the exemplary scaffolds as indicated and sequences 1a-1f, 2a-2f, 3a-3f, 4a-4f, 5a-5f, and 6a-6f refer to sequences in which cloning sites were inserted flanking the corresponding CDRs of each exemplary scaffold as indicated.

Figure 24:
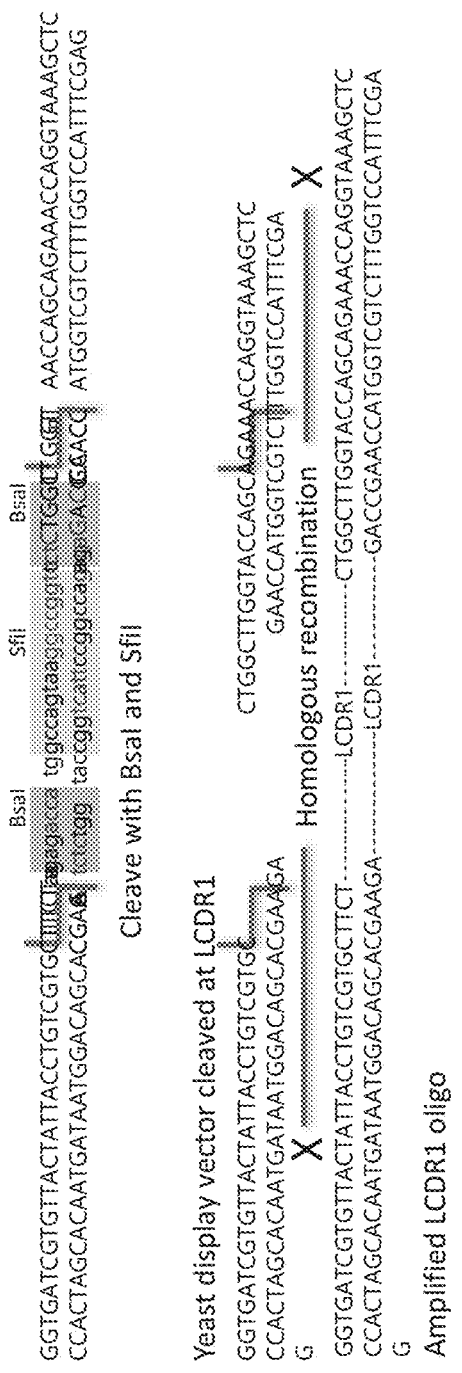
FIG. 24 is a diagram showing an exemplary process of inserting oligonucleotides encoding LC CDR1 s into a yeast display vector. Nucleic acid sequences representing part of a yeast display vector to be cleaved with BsaI and SfiI correspond to SEQ ID NOs: 103-104 (from top to bottom). Sequences of the cleaved vector (middle) correspond to SEQ ID NOs: 105-108 (labeled from top to bottom then left to right). Sequences of the amplified LCDR1 oligo (middle) correspond to SEQ ID NOs: 109-112 (labeled top to bottom then left to right). Homologous recombination produces the amplified LCDR1 inserted into the yeast display vector (bottom), which corresponds to SEQ ID NOs: 113-116 (labeled top to bottom then left to right).
Figure 25A:
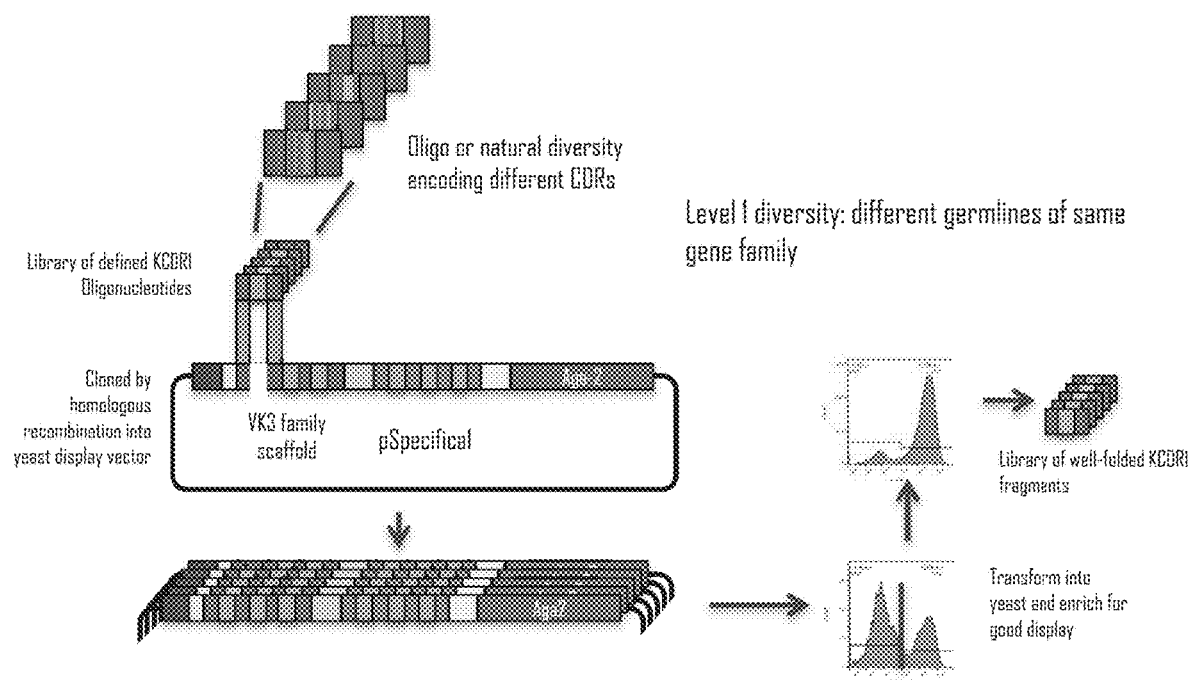
FIG. 25A is a diagram illustrating an exemplary process of isolating well expressed antibody CDRs by sorting yeast displaying single CDR loop libraries after cloning, using VK chains comprising functional KCDR1 as an example.
Figure 25B:
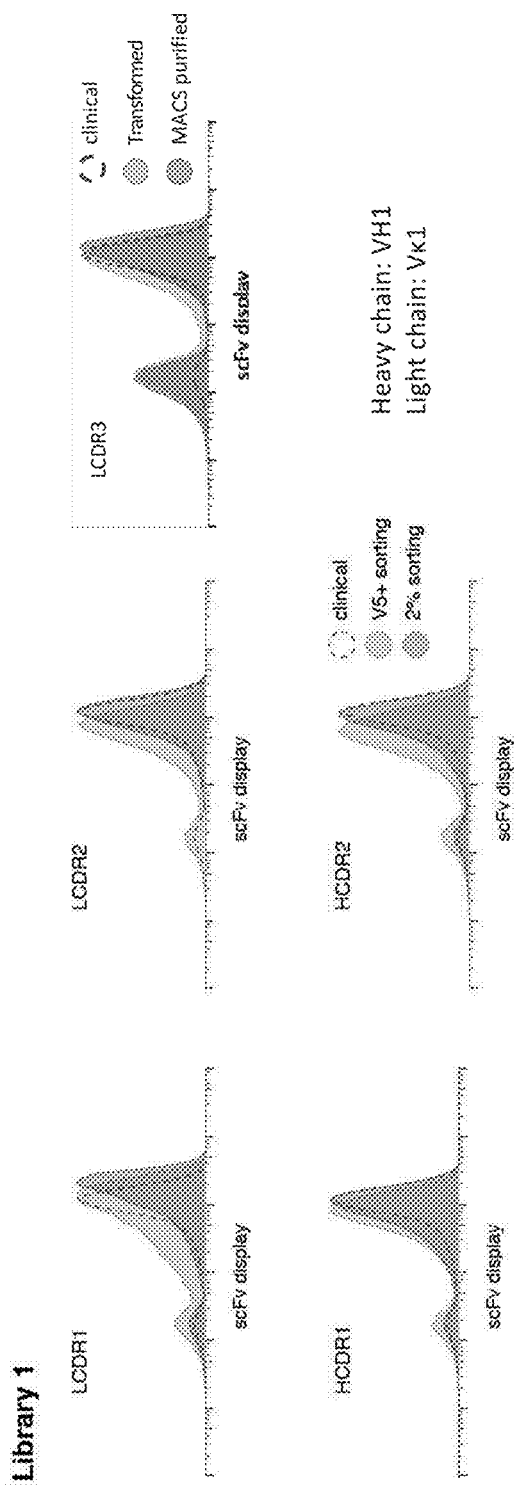
FIGS. 25B-25G illustrate the results of applying the exemplary process of isolating displayed single CDR loop libraries for each of the CDR (HCDR1-1, LCDR1-3) libraries displayed in yeast. The X axis indicates the level of antibody display, while the Y axis indicates the number of clones at each particular display level. For all histograms the display level of the clinical candidate is shown as a dotted blue line. For LCDR1-2 and HCDR1-2, fluorescence activated cell sorting was used to sort the most fluorescent 2% of yeast, corresponding to yeast displaying the most highly expressed antibodies. The display levels for the SV5 sorted (blue plot) and the most fluorescent 2% (red plot) are shown. For LCDR3, magnetic activated cell sorting was used to sort yeast displaying the most highly expressed antibodies. The transformed yeast clones (blue plot) are compared to the magnetic activated cell sorted yeast clones (red).
Figure 25C:
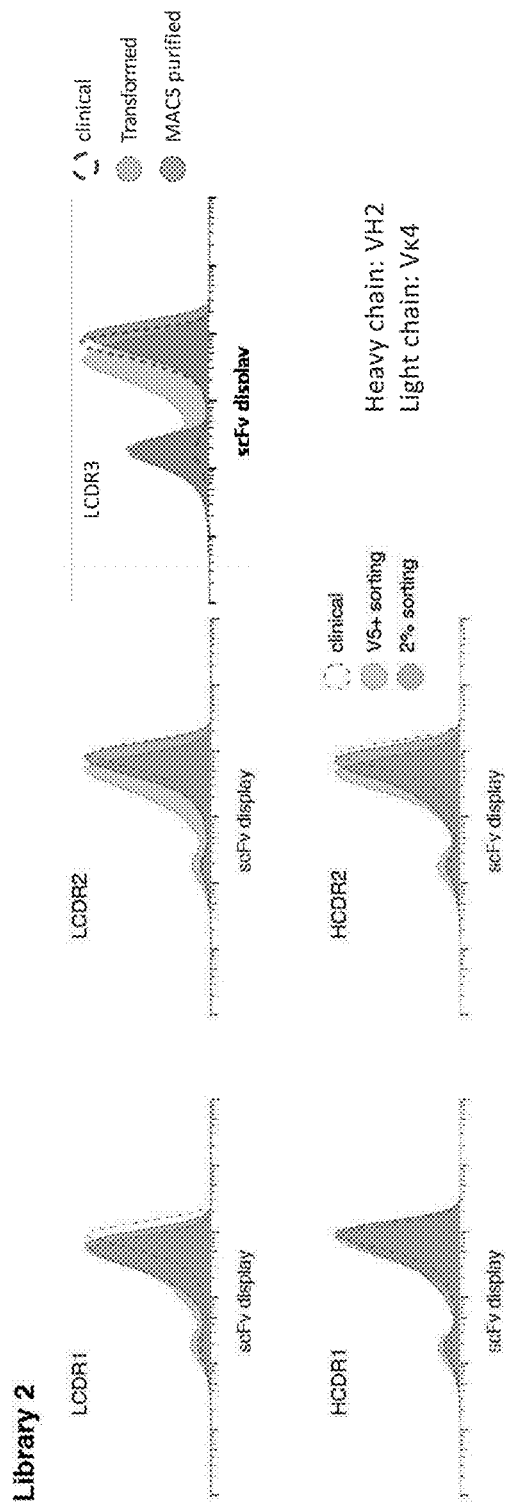
Figure 25D:
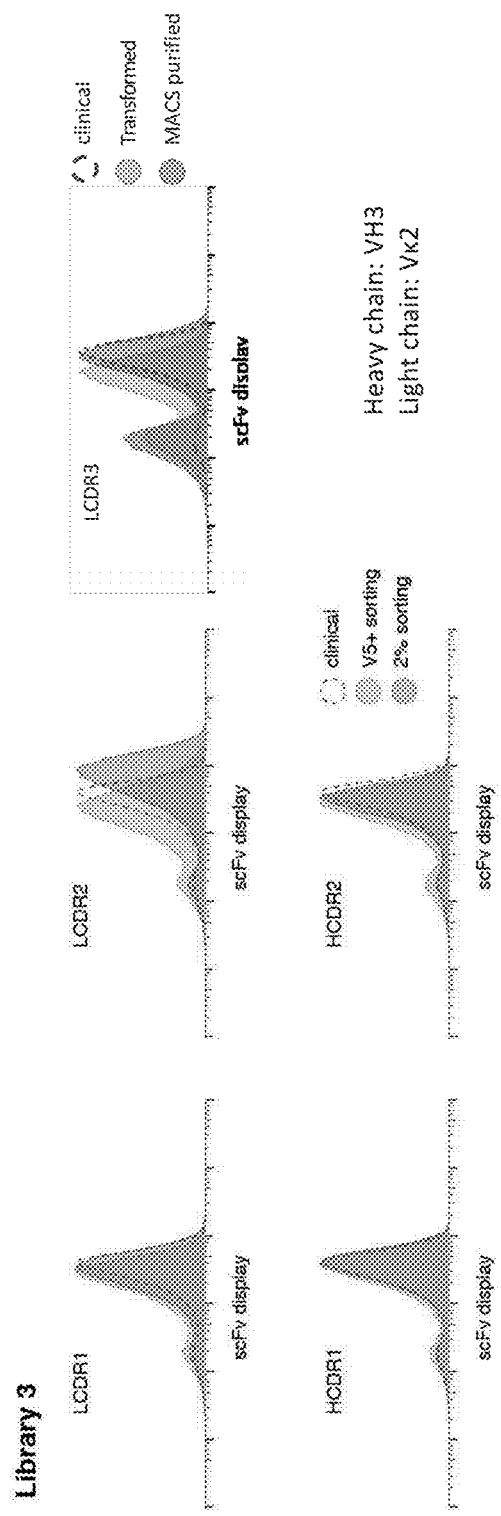
Figure 25E:
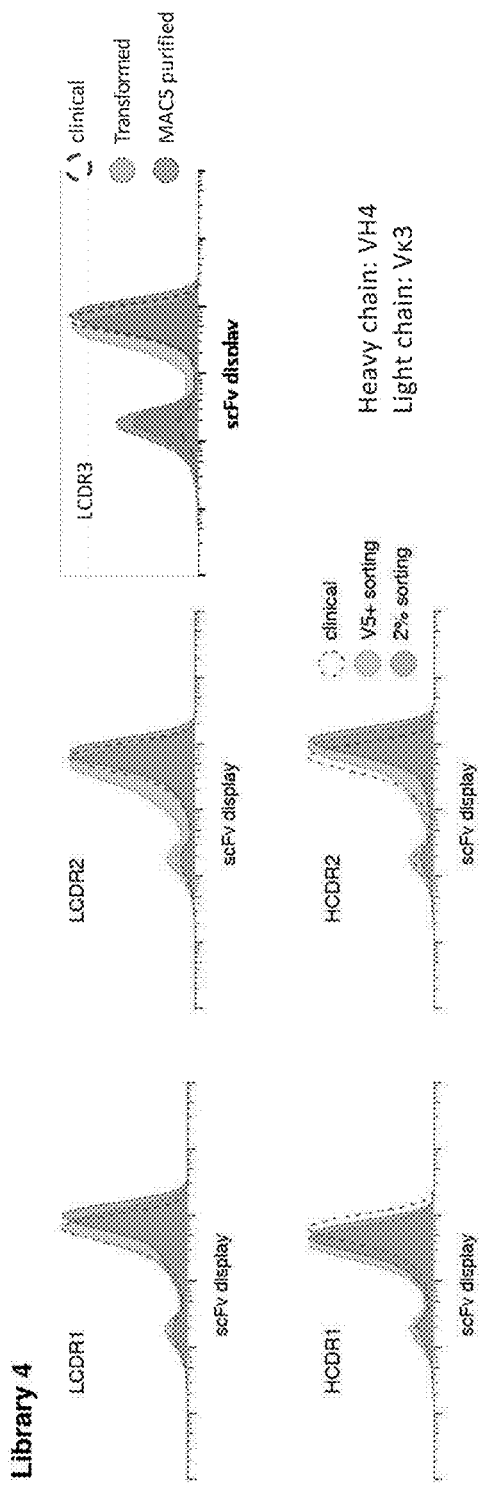
Figure 25F:
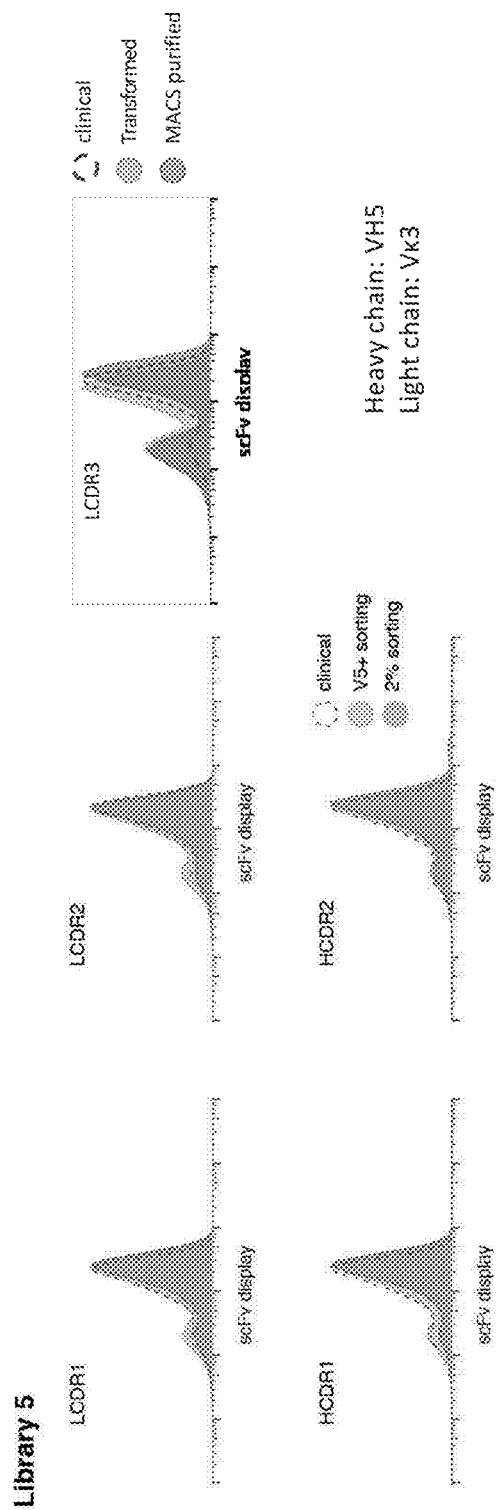
Figure 25G:
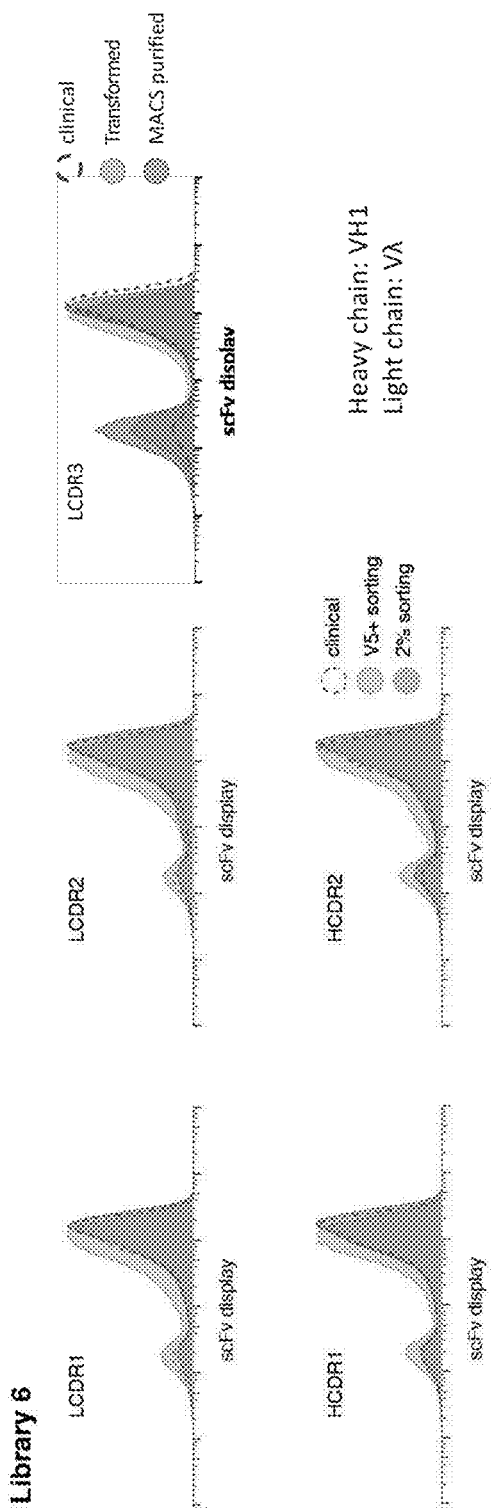

Using LCDR1 of library 1 as an example, the LCDR1 scaffold vector was digested with BsaI and SfiI leaving a gap at the site of LCDR1, as shown in FIG. 24. The cleaved vector and the collection of LCDR1 oligonucleotides were then transformed into yeast. Inside yeast cells, homologous recombination between the vector and the LCDR1 oligonucleotides results in insertion of the LCDR1 oligonucleotides into the LCDR1 scaffold vector. The entire population of LCDR1 yeast scaffold vectors carrying each of the LCDR1 oligonucleotides identified above constitutes a LCDR1 yeast display library (FIG. 25). For the LCDR1 scaffold vector, all portions of the VH and VL domains are constant except for the LCDR1 that is assessed. Selection for functional LCDR1 was carried out by sorting for display (i.e., expression). After the display of the scFv is induced, the yeast cells are stained with fluorescent-labelled antibody that detects scFv display (using the mAb recognizing the SV5 tag). For CDR1-2 libraries, the populations are analyzed by flow cytometry and sorted by fluorescence activated cell sorting by gating the top 2% most fluorescent cells among the positive population—this ensures the enrichment for CDRs that promote high levels of display. In FIGS. 22A-L, the population after this stringent 2% sorting is indicated as "Replicated natural after filtering". At least a 10-fold number of cells is sorted as compared to the theoretical diversity to ensure recovery of all possible clones. For LCDR3, after scFv display induction and staining with fluorescent-labelled antibody that detects the scFv display (SV5), the positive population (scFv displaying) is purified using MACS (magnetic-activated cell sorting) employing magnetic nanoparticles that recognize the primary antibody (SV5) used. The higher the level of the scFv display, the higher the probability of the cell binding the nanoparticles—especially when competition is employed by having a number of cells that far exceeds the binding capacity of the nanoparticles, thus, enriching for well displaying sequences, analogously to fluorescence activated cell sorting of the most fluorescent 2% for the CDR1-2 described above. The MACS technique is preferentially employed for LCDR3 due to the capacity of purifying a large number of cells in a short span of time, since the theoretical diversity of the LCDR3 is several fold higher than CDR1-2.

Figure 23:
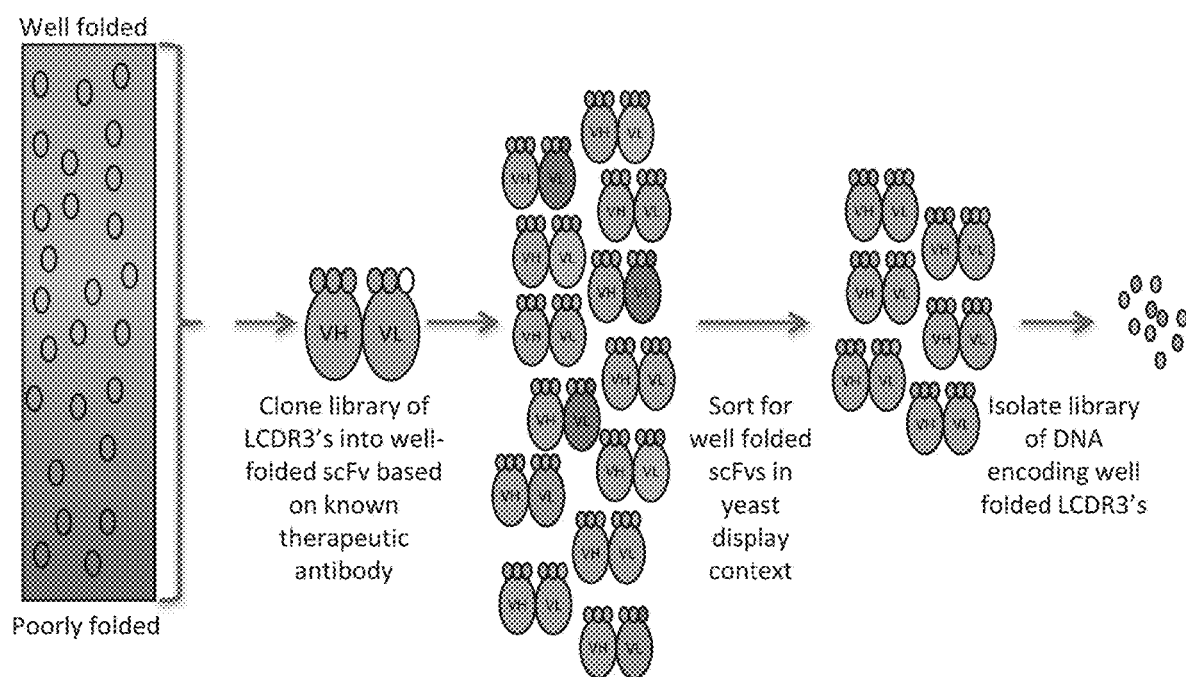
FIG. 23 is a diagram illustrating an exemplary process for selecting for functional CDRs, for example, well folded LC CDR3s.

Although scFvs are used in this example for yeast display, the format of CDR-specific scaffold vectors can be VH, VL, scFv, Fab or full-length immunoglobulin, the requirement being that display can be carried out. By sorting libraries of single CDRs cloned into well folded scaffolds, those CDRs that contain stop codons, frameshifts, or are poorly expressed or polyreactive may be eliminated. Effective display on the yeast surface has been previously correlated with improved stability and folding in diverse proteins (Cherf, G. M. and J. R. Cochran (2015). "Applications of Yeast Surface Display for Protein Engineering." Methods Mol Biol 1319: 155-175; Pavoor, T. V., et al., (2012). "An enhanced approach for engineering thermally stable proteins using yeast display." Protein engineering, design & selection: PEDS 25(10): 625-630; Pepper, L. R., et al., (2008). "A decade of yeast surface display technology: where are we now?" Comb Chem High Throughput Screen 11(2): 127-134; Xu, L., et al., (2013). "Rapid optimization and prototyping for therapeutic antibody-like molecules." *MAbs* 5(2): 237-254). After each CDR library is sorted, a collection of well expressed, non-polyreactive CDRs is obtained by isolating DNA from yeast cells expressing well folded CDRs. Schematic illustrations of how functional CDR libraries are cloned and sorted are shown in FIGS. 23-25. The non-filtered and filtered libraries for the 6 different scaffolds are show in FIGS. 25B-G: the populations are analyzed by flow cytometry and expression levels (x axis) are represented as a histogram. The analysis shows a clear improvement after enrichment (top 2% by fluorescence activated cell sorting for CDRs 1-2, and magnetic activated cell sorting for LCDR3), with most libraries showing display levels exceeding that of the original clinical candidate from which the scaffolds were generated.

In the examples provided here, we have sorted for improved expression levels. However, a similar approach can be taken using any selective method that distinguishes yeast displaying antibodies with desirable properties (e.g. high expression, low polyreactivity, good developability) from yeast displaying antibodies with undesirable properties (e.g. low expression, high polyreactivity, poor developability). For example, to select antibodies with reduced polyreactivity, clones displaying antibodies (scFvs, Fabs, IgGs, or other antibody fragment) that do not bind to polyspecificity reagents would be selected. Examples of such polyspecificity reagents include those described in (Hotzel, I. et al. A strategy for risk mitigation of antibodies with fast clearance. *MAbs* 4, 753-760, doi:10.4161/mabs.22189 (2012); Xu, Y. et al. Addressing polyspecificity of antibodies selected from an in vitro yeast presentation system: a FACS-based, high-throughput selection and analytical tool. *Protein Eng Des Sel* 26, 663-670, doi:10.1093/protein/gzt047 (2013); Kelly, R. L. et al. Chaperone proteins as single component reagents to assess antibody nonspecificity. *MAbs* 9, 1036-1040, doi: 10.1080/19420862.2017.1356529 (2017).)

Example 8: Assembly of Full Length scFv Library

Figure 26:
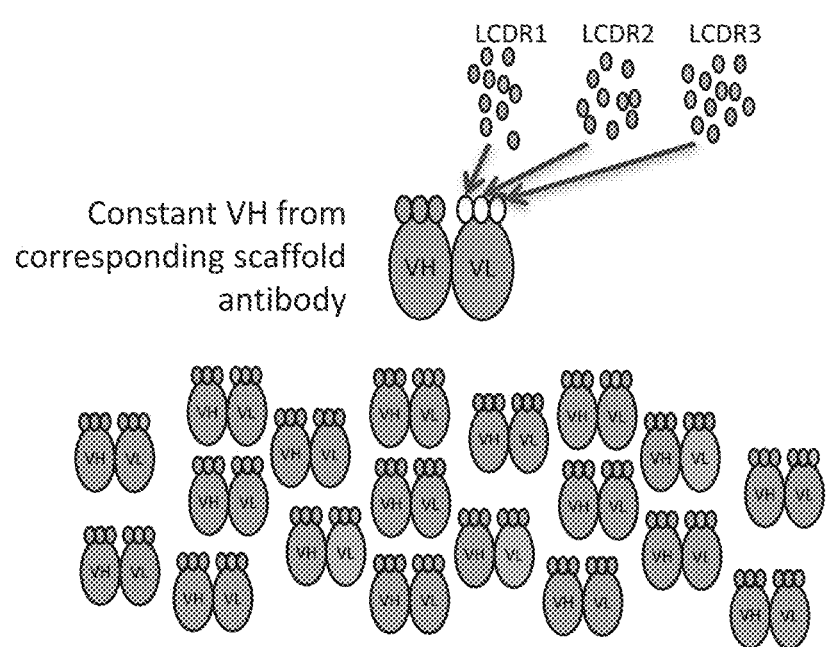
FIG. 26 is a diagram illustrating the pairing between a constant VH chain and VL chains with diversity in LC CDRs to select functional antibodies.
Figure 27:
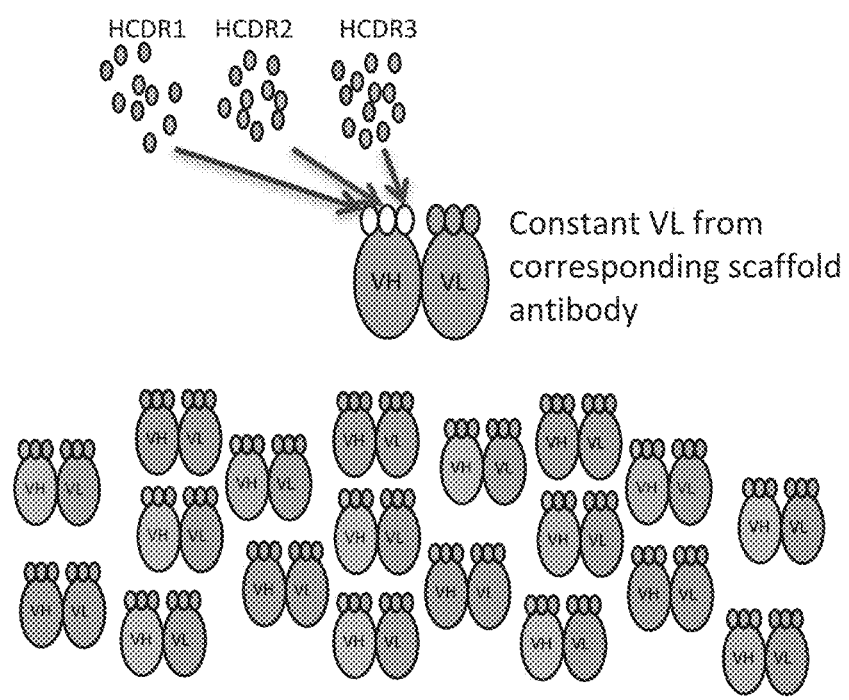
FIG. 27 is a diagram illustrating pairing between a constant VL chain and VH chains with diversity in VH CDRs for selection of functional antibodies.
Figure 28:
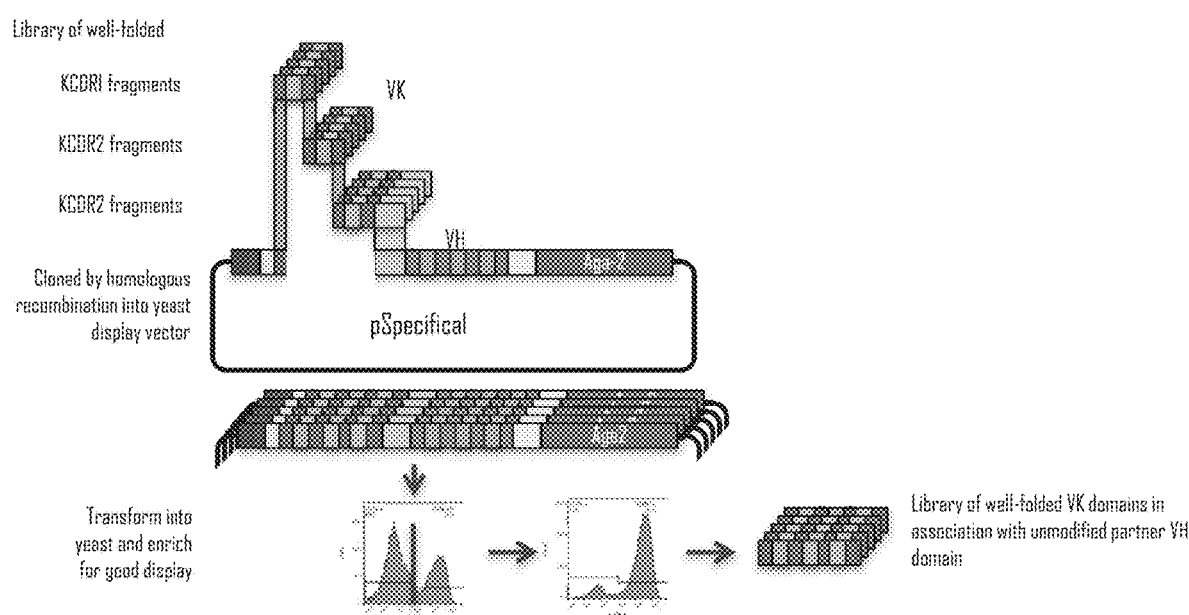
FIG. 28 is a diagram illustrating construction of an exemplary antibody library comprising VL chains having well-folded LC CDRs selected via yeast display and unmodified VH domains.
Figure 29:
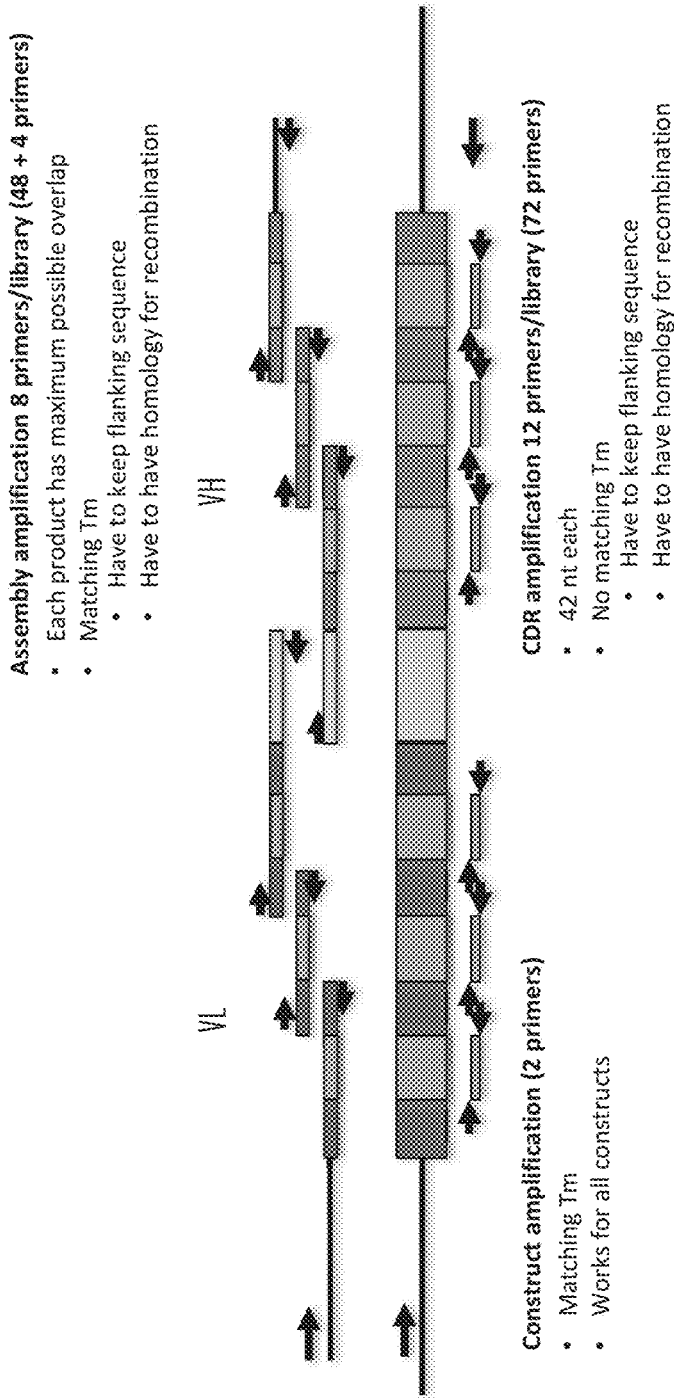
FIG. 29 is a diagram illustrating an exemplary process of amplifying and assembling VH and VL CDRs into a preselected VH or VL scaffold.
Figure 30:
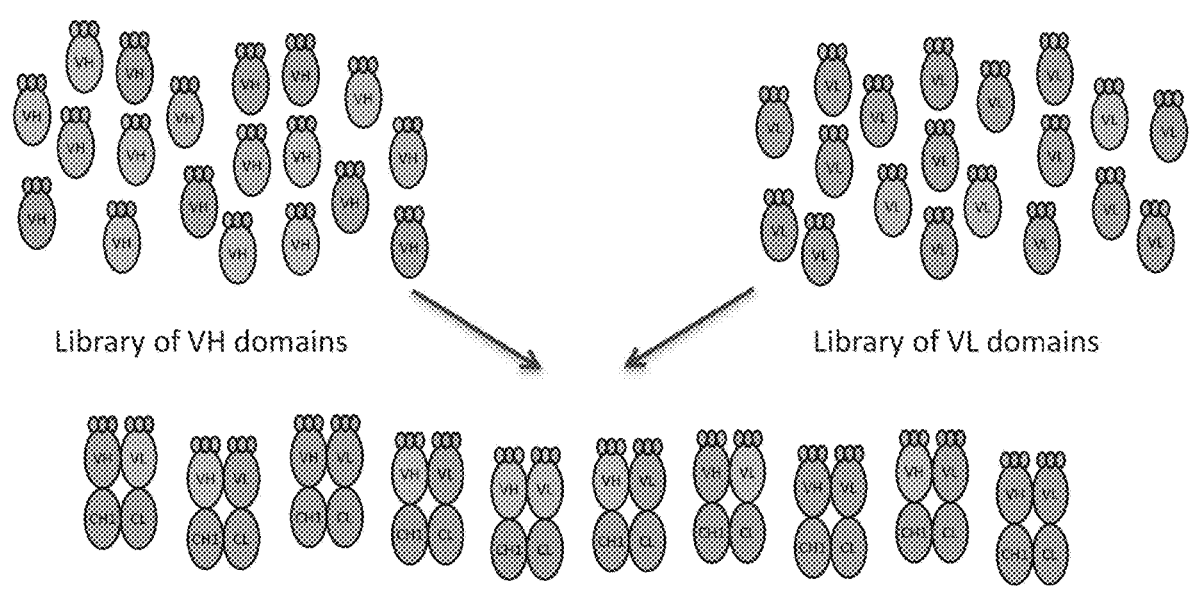
FIG. 30 is a diagram illustrating construction of an exemplary Fab antibody library via combining a library of VH domains and a library of VL domains.
Figure 31:
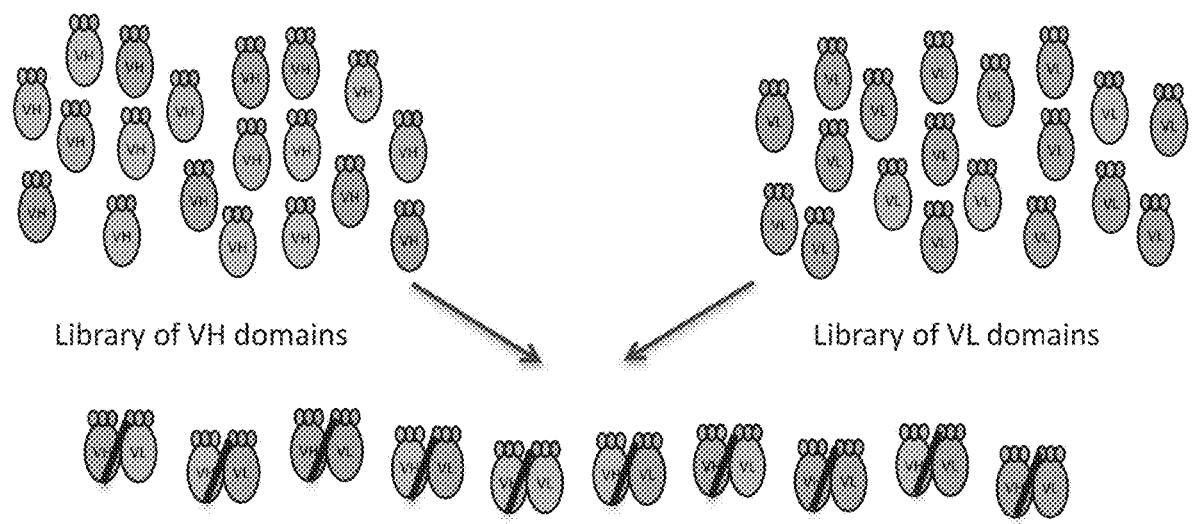
FIG. 31 is a diagram illustrating construction of an exemplary scFv antibody library via combining a library of VH domains and a library of VL domains.
Figure 32:
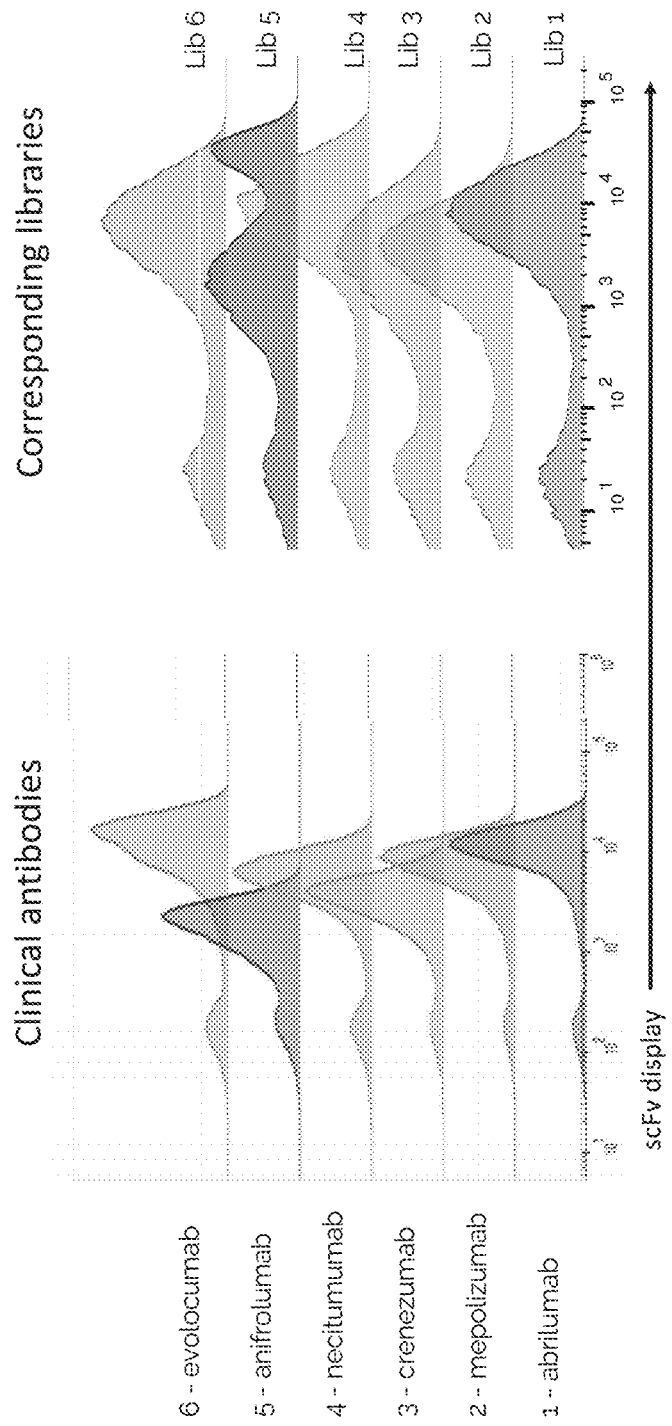
FIG. 32 is a flow plot of scFvs corresponding to the clinical candidates used as scaffolds compared to the corresponding libraries. The double peak for library 5 is thought to be due to the presence of a smaller truncated product, which was eliminated in the final phage display libraries.

Once each individual CDR library was screened for expression and developability, the VH and VL CDRs were assembled into full length VH or VL domains. Individual CDRs in VL and VH were amplified with the flanking sequence using the primers described in Table 7 and Table 8. This was carried out as illustrated in FIGS. 29-31, with the VH and VL first assembled from their constituent CDR fragments and flanking framework regions, and then combined into complete scFvs or Fabs. An alternative approach would be to assemble each full length VH or VL within the context of their non-modified VL or VH partner chains as illustrated in FIGS. 26-28. This alternative approach would allow sorting (by FACS or MACS) for VH or VL libraries that are functional within the context of their unmodified partner chains. However, we found that the direct assembly of complete scFvs directly from libraries of filtered CDRs led to highly functional scFv libraries without the need for this intermediate step, as illustrated in FIG. 32, which shows that the peak display level of scFvs derived from the clinical antibodies used as scaffolds is similar to that for the corresponding libraries, except that the distribution of library display levels is broader than that of the clinical candidate antibodies used as scaffolds, and includes some scFvs that are displayed better than the parental clinical scaffold scFv.

followed by chromatography to remove contaminants. The backbone was ligated to the scFv/Fab library using T4 DNA ligase overnight at 16° C. The ligation was purified and electrotransformed into electrocompetent *E. coli* TG1 cells. The transformed cells were plated out on agar plates containing carbenicillin and glucose to select for bacteria that received the plasmid. Analysis of the scFv libraries by PacBio sequencing revealed >90% open reading frames (Table 9), and essentially no clone duplication (Table 10).

TABLE 9

Percentage of open reading frames in scFv libraries as assessed by PacBio sequencing.

| Library | sequences analyzed | correct frame | ORFs | ORF % |
|---|---|---|---|---|
| Lib1 | 6,510 | 6,103 | 6,050 | 93% |
| Lib2 | 5,699 | 5,403 | 5,355 | 94% |
| Lib3 | 7,012 | 6,623 | 6,583 | 94% |
| Lib4 | 9,168 | 8,660 | 8,613 | 94% |
| Lib5 | 7,640 | 7,282 | 7,242 | 95% |
| Lib6 | 5,378 | 5,027 | 5,005 | 93% |

TABLE 10

Analysis of library diversity by PacBio.

| library | No. reads | Full-Length | | HCDR3 + LCDR3 | | HCDR3 | | LCDR3 | | HCDR2 | | LCDR2 | | HCDR1 | | LCDR1 | |
|---|---|---|---|---|---|---|---|---|---|---|---|---|---|---|---|---|---|
| | | No. | % | No. | % | No. | % | No. | % | No. | % | No. | % | No. | % | No. | % |
| 1 | 6000 | 5998 | 99.97 | 5998 | 99.97 | 5851 | 97.52 | 5679 | 94.65 | 1786 | 29.77 | 2224 | 37.07 | 2158 | 35.97 | 1328 | 22.13 |
| 2 | 5265 | 5258 | 99.87 | 5258 | 99.87 | 4740 | 90.03 | 4675 | 88.79 | 1927 | 36.60 | 1796 | 34.11 | 2267 | 43.06 | 481 | 9.14 |
| 3 | 6496 | 6493 | 99.95 | 6493 | 99.95 | 6300 | 96.98 | 5828 | 89.72 | 3077 | 47.37 | 1329 | 20.46 | 3676 | 56.59 | 438 | 6.74 |
| 4 | 8423 | 8420 | 99.96 | 8420 | 99.96 | 8137 | 96.60 | 7965 | 94.56 | 2538 | 30.13 | 1355 | 16.09 | 2525 | 29.98 | 1399 | 16.61 |
| 5 | 7030 | 7029 | 99.99 | 7015 | 99.79 | 6457 | 91.85 | 6263 | 89.09 | 1780 | 25.32 | 1873 | 26.64 | 2684 | 38.18 | 2090 | 29.73 |
| 6 | 4899 | 4898 | 99.98 | 4898 | 99.98 | 4735 | 96.65 | 4725 | 96.45 | 1639 | 33.46 | 1148 | 23.43 | 1833 | 37.42 | 1545 | 31.54 |

The functional antibody library can be assembled within the context of different display vectors, including phage, yeast or mammalian display vectors.

Example 9: Cloning into a Phage Display Vector (pDAN5)

Once the scFv or Fab libraries were assembled, they were ligated into a phage display vector, such as pDAN5 to explore their functionality. This vector contains a cloning site upstream of the g3 of the filamentous phage, comprised by the restriction enzyme sites for BssHII and NheI. The scFv/Fabs created in Example 8 were amplified with flanking primers containing the BssHII restriction site upstream of the light chain and the NheI downstream of the heavy chain. The PCR product was then digested with the same enzymes to generate cohesive ends. The pDAN5 plasmid was cultivated in *E. coli*, extracted by alkaline lysis and purified by cesium chloride/ethidium bromide gradient. The plasmid was digested with the same enzymes and the backbone purified by agarose gel electrophoresis extraction Example 10: Creation of Bacteriophage Particles, Including Western Blot The transformed bacteria were cultivated in a shaking flask containing liquid 2×YT media+carbenicillin+glucose (the glucose is to inhibit scFv/Fab expression) at 37° C. until an OD600 nm of 0.5 was reached. The bacteria were superinfected with M13KO7 helper phage (at a multiplicity of infection of 5) for 30 min at 37° C. without shaking. The bacteria were centrifuged, the media removed and replaced with 2×YT media+carbenicillin+kanamycin and cultivated for 16 h at 25° C. in a shaker incubator.

Figure 33:
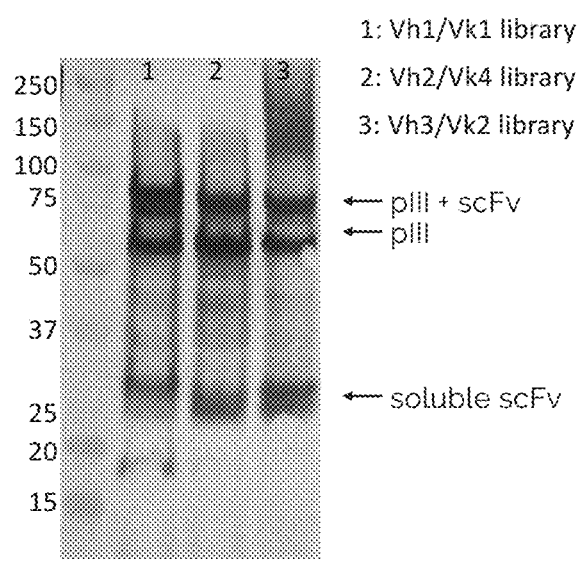
FIG. 33 shows a western blot of libraries 1-3 with the pIII and the scFv-pIII bands indicated.

To recover the phage particles, the cultures were centrifuged to separate the bacteria and the supernatant, where the phage is found. The supernatant was mixed with a 20% PEG 8000+2.5 M NaCl solution at a 5:1 ratio. This causes the phage to precipitate, allowing them to be harvested by centrifugation. The supernatant was discarded and the phage pellet was resuspended in a PBS solution. The display of the scFv/Fab by the phage was assessed by SDS-PAGE+western blot using an antibody that specifically recognizes the expression tag (SV5) as show in FIG. 33.

Figure 34:
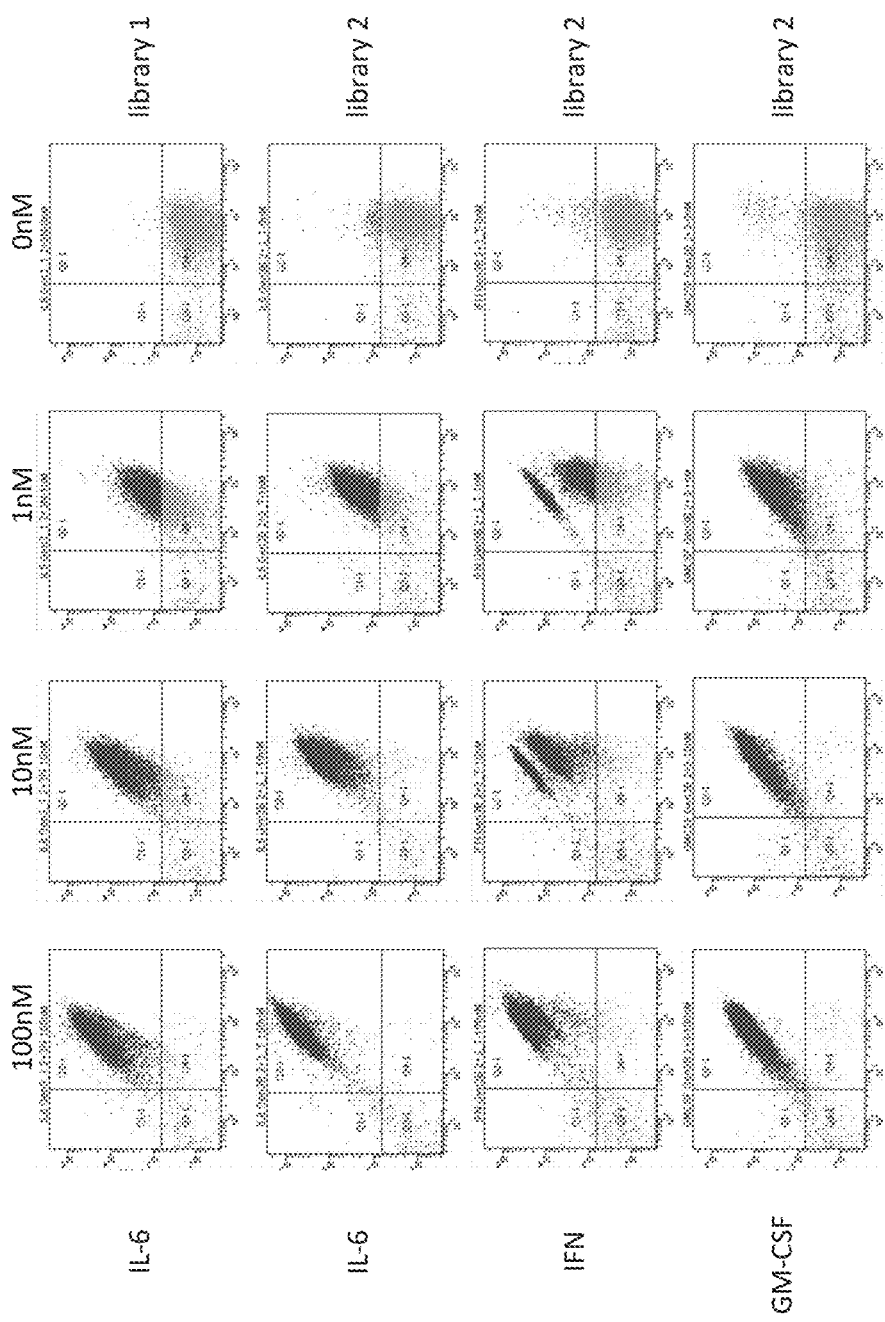
FIG. 34 shows binding of antibodies displayed on yeast binding to targets against which they were selected at different concentrations. Display on yeast followed two rounds of selection by phage display, and two rounds of yeast display. Library 1 and Library 2 represent two different libraries created using the same LCDR1-3 and HCDR1-2 diversity, and HCDR3 diversity from different donors.

Example 11: Antibody Selection by Combined Phage and Yeast Display Using the Library After construction and phage particle production, the library was screened against targets of interest. While selection can be carried out using phage display alone (Sblattero, D. & Bradbury, A. Exploiting recombination in single bacteria to make large phage antibody libraries. *Nat Biotechnol* 18, 75-80 (2000)), we prefer to combine phage and yeast display technologies (Ferrara, F. et al. Using phage and yeast display to select hundreds of monoclonal antibodies: application to antigen 85, a tuberculosis biomarker. *PLoS One* 7, e49535 (2012)). $10^{12}$ phage particles displaying the scFv library were used in two rounds of selection against the biotinylated recombinant human antigens of clinical interest—interleukin 6, interferon alpha, and GM-CSF—using the Kingfisher magnetic bead system: $2 \times 10^7$ streptavidin-conjugated magnetic beads (Dynabeads M-280) coated with the biotinylated proteins (100-400 nM) were washed, coated with the antigen, incubated with the phage particles and washed again to remove non-binders. Phage particles were then eluted by reducing the pH and infecting F' pilus-carrying bacteria (Ominmax-2T1, Thermo Fisher Scientific) . The phages were propagated, and the selection cycle reiterated. After two rounds of phage enrichment, the scFvs were PCR amplified and transferred to an N-terminal yeast display system by homologous recombination (pSpec yeast display vector), in which the scFv is displayed fused to the N terminus of Aga-2. The transformed yeast was then induced for scFv display by adding galactose to the culture media. The induced yeast minilibraries were then used for another two to three rounds of enrichment against the biotinylated recombinant human antigens by fluorescence activated cell sorting. Up to 10,000 yeast cells with positive antigen binding signal were sorted and propagated in each round. Target concentration in the first sorting round was 100 nM, reduced to 10 nM and then 1 nM. After these rounds of phage and yeast sorting enrichment the recovered populations was analyzed by flow cytometry to test for binding against the antigens in decreasing concentration of antigen and in the absence of the antigen to check for non-specific binding to secondary reagents (FIG. 34). Results show that the library can successfully yield high affinity binders to all antigens tested.

Example 12: Affinity Determination of Selected Antibodies

Affinity determination of antibodies selected from the naïve library using the phage+yeast display protocol described in Example 11, was performed following the approaches described herein. Binding affinity of the antibody variants thus obtained to various targets (e.g., GM-CSF, IFN-a 2A and IL-6) was examined using a Carterra LSA machine. Briefly, supernatants from yeast expressing scFv-Fc fusions from selections against GM-CSF, IFN-a 2A and IL-6 were immobilized on a Carterra LSA HC200M chip with anti-human Fc. The chips were activated with 1:1:1 100 mM MES pH 5.5, 100 mM S—NHS, 400 mM EDC (all reconstituted in MES 5.5), and 100 µL of each were mixed in a vial immediately before running the assay. The polyclonal goat anti-human IgG was immobilized for 10-minute at 50 µg/mL followed by 7-minute deactivation with 1 M Ethanolamine pH 8.5.

Figure 37:
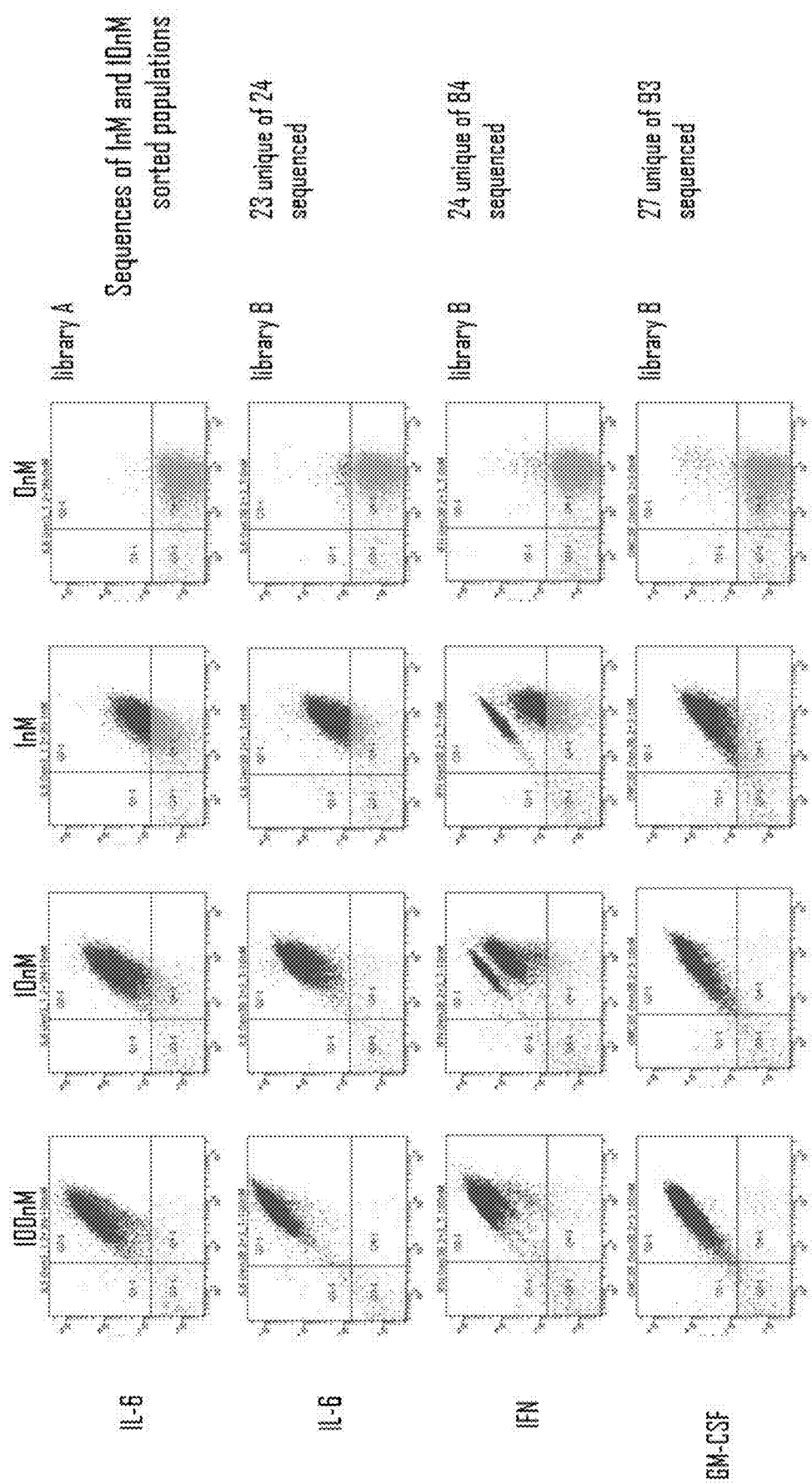
FIG. 37 includes diagrams showing clones binding to the indicated antigens at various concentrations (100 nM, 10 nM, 1 nm, or 0 nM) isolated from Library A or Library B.

The scFv-Fc supernatants were diluted two or three fold into HBSTE buffer and cycled for 12 minutes across the anti-Fc surface. Antigens were tested in a three-fold dilution series starting at 6 nM for IFN-2A and 167 nM for IL-6/GM-SCF. The antigen samples were tested from lowest to highest concentration. FIG. 37.

Data was processed using a floated Rmax parameter for the IFN-2A and GM-SCF clones that did not dissociate fully between binding cycles; some of the data were also fit using a bulk shift parameter.

Figure 38A:
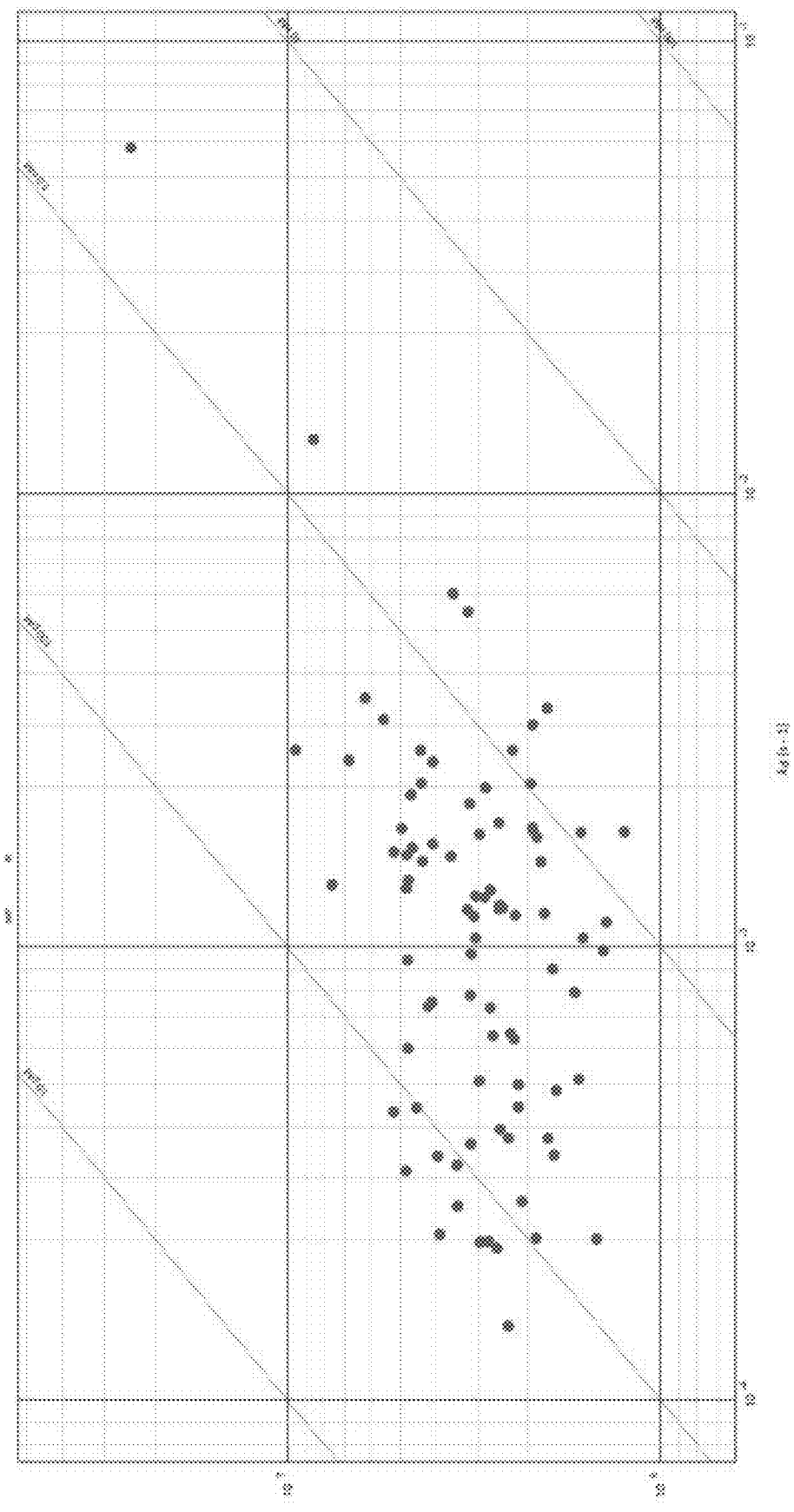
Figure 38C:
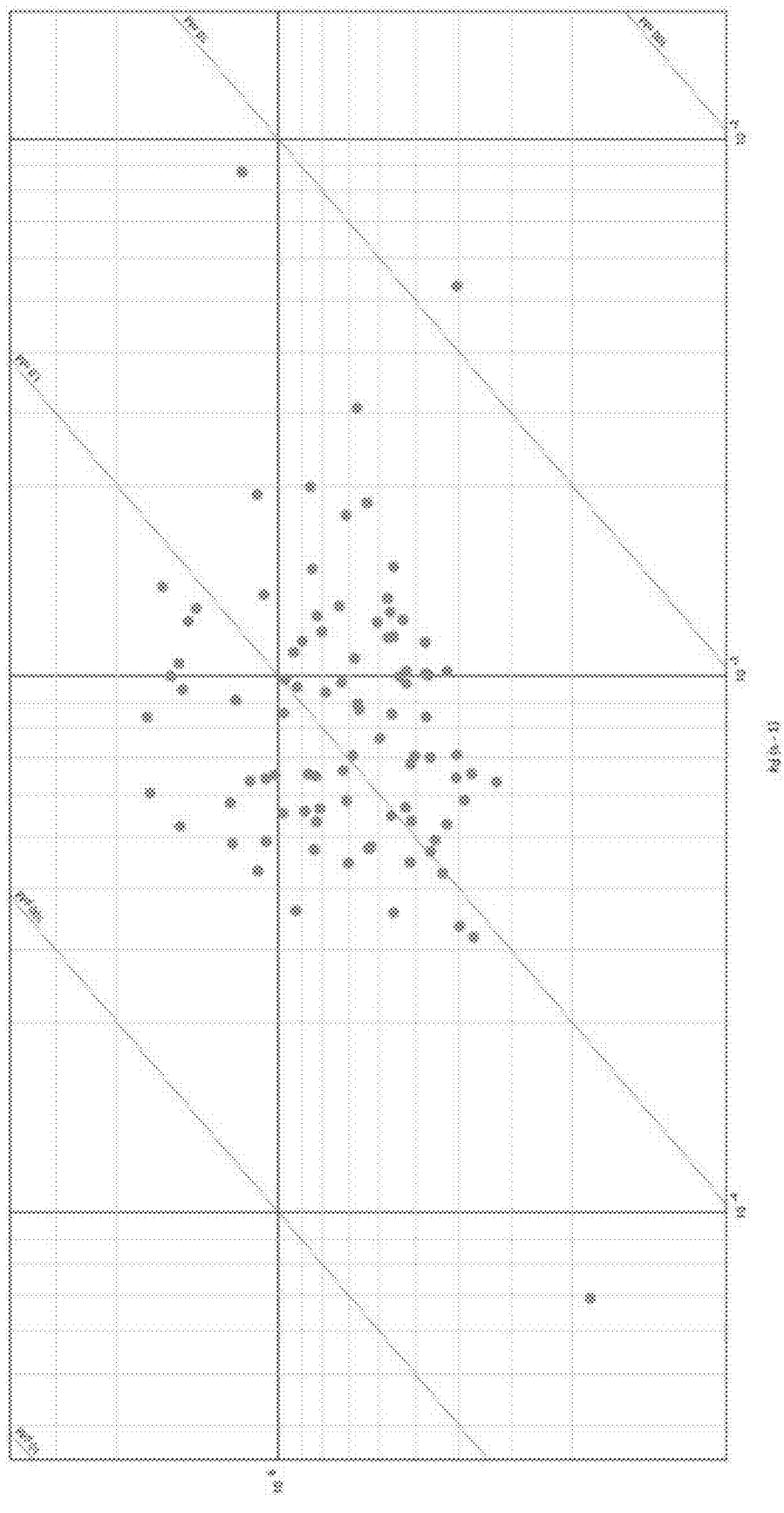

As shown in FIGS. 38A-38C, the affinities of antibodies selected directly from the library, constructed as described in Examples 1-10, are shown to be extremely potent, with many subnanomolar antibodies having been selected.

Figure 39:
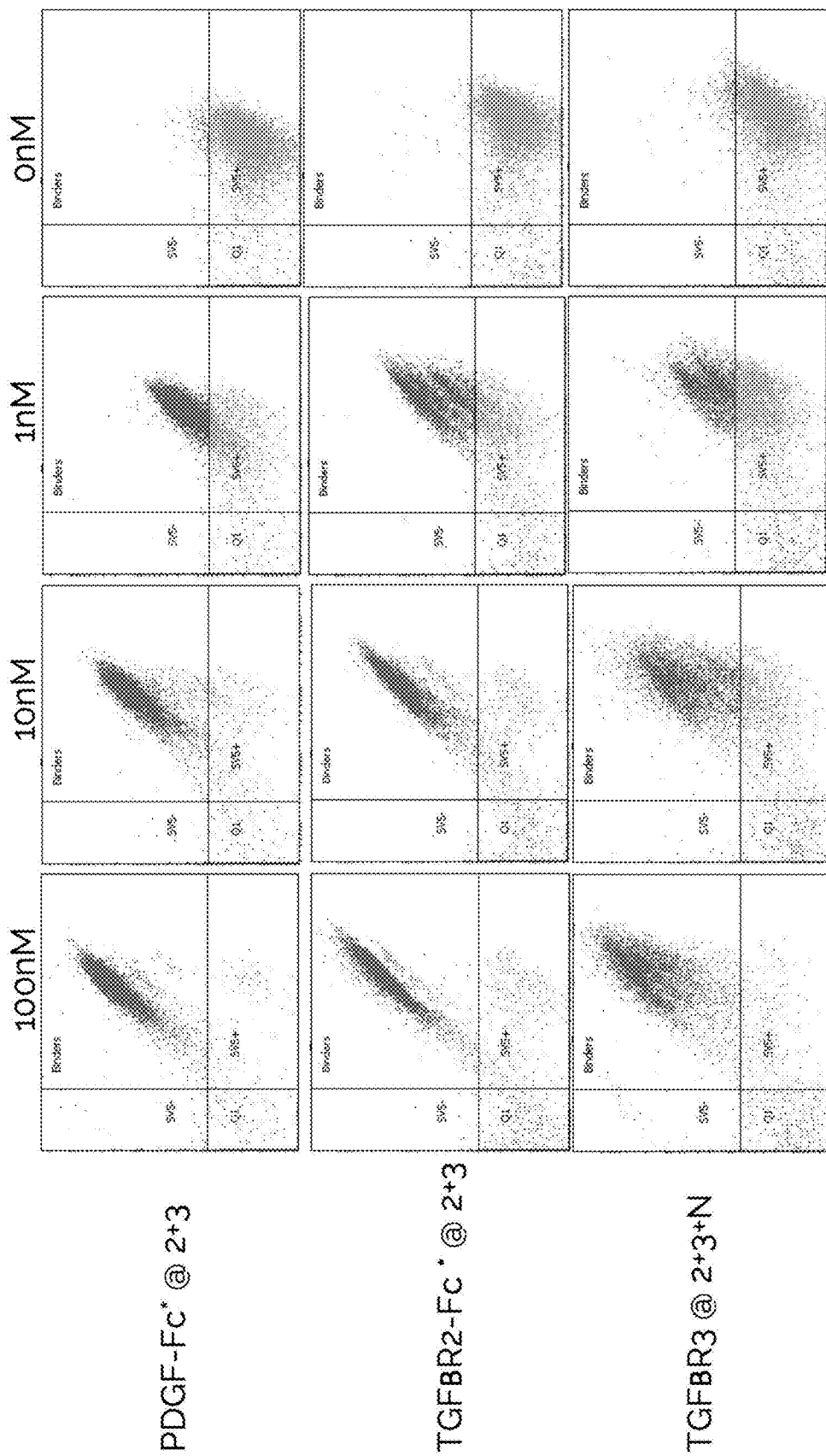
FIG. 39 is a diagram showing isolation of antibodies with high binding affinity to additional antigens, PDGF, TGFBR2, and TGFBR3, from the libraries disclosed herein.

Antibodies to additional targets, including PDGF, TGFBR2, and TGFBR3, were explored using this approach and similar results were observed. FIG. 39.

Example 13: Antibody Maturation

To select an optimized VL and VH pair and assemble the CDRs into a mature antibody, the following approach can be used. First, the VH is kept in unmodified form while the VLs in the LCDR libraries are shuffled. The remaining functional VLs are assembled with the unmodified VH and the formed antibodies are tested for functionality (FIG. 35). Likewise, the VL is kept unmodified and the VHs comprising synthetic HCDR1/2 and natural HCDR3 in the VH library is shuffled. Each of the remaining functional VH can be assembled with the unmodified VH and the newly formed antibodies are tested for their functions (FIG. 36).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for producing an antibody library, the method comprising: providing:
   (a) a first plurality of nucleic acids encoding amino acid sequences of one or more naturally occurring human antibody heavy chain CDR1 fragments,
   (b) a second plurality of nucleic acids encoding amino acid sequences of one or more naturally occurring human antibody heavy chain CDR2 fragments,
   (c) a third plurality of nucleic acids encoding amino acid sequences of one or more naturally occurring human antibody heavy chain CDR3 fragments,
   (d) a nucleic acid gene encoding amino acid sequences of an antibody heavy chain variable domain comprising a heavy chain CDR1 region, a heavy chain CDR2 region, and a heavy chain CDR3 region,
   (e) a fourth plurality of nucleic acids encoding amino acid sequences of one or more naturally occurring human antibody light chain CDR1 fragments,
   (f) a fifth plurality of nucleic acids encoding amino acid sequences of one or more naturally occurring human antibody light chain CDR2 fragments,
   (g) a sixth plurality of nucleic acids encoding amino acid sequences of one or more naturally occurring human antibody light chain CDR3 fragments, and
   (h) a nucleic acid gene encoding amino acid sequences of an antibody light chain variable domain comprising a light chain CDR1 region, a light chain CDR2 region, and a light chain CDR3 region;
   inserting the first plurality of nucleic acids, the second plurality of nucleic acids, and the third plurality of nucleic acids into the heavy chain CDR1 region, the heavy chain CDR2 region, and the heavy chain CDR3 region, respectively, of the gene encoding the antibody heavy chain variable domain, thereby producing a population of nucleic acids encoding an antibody heavy chain variable domain library;
   inserting the fourth plurality of nucleic acids, the fifth plurality of nucleic acids, and the sixth plurality of nucleic acids into the light chain CDR1 region, the light chain CDR2 region, and the light chain CDR3 region, respectively, of the gene encoding the antibody light chain variable domain, thereby producing a population of nucleic acids encoding an antibody light chain variable domain library; and
   combining the population of nucleic acids encoding the antibody heavy chain variable domain library to the population of nucleic acids encoding an antibody light chain variable domain library, thereby producing an antibody library;
   wherein the library comprises nucleic acids encoding amino acid sequences of a heavy chain framework region 1, a heavy chain framework region 2, a heavy chain framework region 3, and a heavy chain framework region 4;
   wherein the library comprises nucleic acids encoding amino acid sequences of a light chain framework region 1, a light chain framework region 2, a light chain framework region 3, and a light chain framework region 4; and
   a plurality of nucleic acids encoding a population of heavy chain domains comprising one or more CDR1s, one or more CDR2s, and one or more CDR3s located at the CDR1 region, the CDR2 region, and the CDR3 region of a heavy chain gene, respectively;
   wherein at least 90% of the one or more heavy chain CDR1s and at least 90% of the one or more heavy chain CDR2s are free of amino acid sequence liabilities, wherein the amino acid sequence liabilities are: (i) a glycosylation site comprising the motif NXS, NXT, or NXC, in which X represents any naturally occurring amino acid residue except for proline; (ii) a deamidation site comprising the motif of NG, NS, NT, NN, NA, NH, ND, NQ, NF, NW or NY; (iii) an isomerization site comprising the motif of DT, DH, DS, DG, DN, DR, DY or DD; (iv) any cysteines; (v) net charge greater than 1; (vi) a tripeptide motif containing at least two residues with aromatic side chains comprising F, H, W or Y; (vii) a poly specificity site comprising the motif GG, GGG, RR, VG, W, WV, WW, WWW, YY, or WXW, in which X represents any amino acid residue; (viii) a protease sensitive or hydrolysis prone site comprising the motif of DX, in which X is P, G, S, V, Y, F, Q, K, L, or D; (ix) an integrin binding site comprising RGD, RYD, LDV, or KGD; (x) a lysine glycation site comprising KE, EK, or ED; (xi) a metal catalyzed fragmentation site comprising the motif of HS, SH, KT, HXS, or SXH, in which X represents any amino acid residue; (xii) a polyspecificity aggregation site comprising a motif of $X_1X_2X_3$, wherein each of $X_1$, $X_2$, and $X_3$ is independently selected from the group consisting of F, I, L, V, W and Y; (xiii) a streptavidin binding motif comprises the motif HPQ, EPDW (SEQ ID NO: 49), PWXWL (SEQ ID NO: 50), in which X represents any amino acid residue, GDWVFI (SEQ ID NO: 51), or PWPWLG (SEQ ID NO: 52); (xiv) one or more arginine residues; (xv) a hydrophobic CDR sequence; and/or (xvi) a CDR mutation that reduces binding to protein A said CDR mutation comprising any mutation in the last amino acid of the CDR2, according to the IMGT definition, to A, G, C, D, E, F, G, H, I, L, M, N, P, Q, S, V, W or Y;
   wherein at least 90% of the one or more heavy chain CDR1s, at least 90% of the one or more heavy chain CDR2s, and at least 90% of the one or more heavy chain CDR3s are free of non-functional members; wherein functional members are well folded and can form well folded scFvs or Fabs;
   wherein at least two of the heavy chain framework regions 1, 2, 3, and 4 are from a human, humanized or partially humanized heavy chain germline sequence;
   wherein each heavy chain framework region and/or light chain framework region can contain up to five amino acid substitutions, and
   wherein the nucleic acid sequences encoding the amino acid sequences of the one or more heavy chain CDR3s are from heavy chain CDR3s of human donor lymphocytes.

2. The method of claim 1, wherein the antibody heavy chain variable domain framework 1, framework 2, framework 3, framework 4 are from a human or humanized VH3-23 (DP-47) sequence.

3. The method of claim 1, wherein the antibody light chain variable domain framework 1, framework 2, framework 3, framework 4 are from a human or humanized kappa VK1-39 sequence.

4. The method of claim 1, wherein the antibody library is a fragment antigen-binding (Fab) library.

5. The method of claim 1, wherein the antibody library is a single-chain variable fragment (scFv) library.

6. The method of claim 1, wherein the first plurality of nucleic acids, the second plurality of nucleic acids, the third plurality of nucleic acids, the fourth plurality of nucleic acids, the fifth plurality of nucleic acids and the sixth plurality of nucleic acids is produced by a process comprising:
  (a) obtaining amino acid sequences of the heavy chain CDR1 regions, heavy chain CDR2 regions, light chain CDR1 regions, light chain CDR2 regions, and light chain CDR3 regions of a population of naturally-occurring human antibodies,
  (b) excluding from (a) the heavy chain CDR1 amino acid sequences, the heavy chain CDR2 amino acid sequences, the light chain CDR1 amino acid sequences, light chain CDR2 amino acid sequences, and the light chain CDR3 amino acid sequences that comprise any one or all of (i) to (xiv) to obtain sequence liability-free heavy chain CDR1 sequences, sequence liability-free heavy chain CDR2 sequences, sequence liability-free light chain CDR1 sequences, sequence liability-free light chain CDR2 sequences, and sequence liability-free light chain CDR3 sequences; and
  (c) synthesizing the first plurality of nucleic acids that encode the sequence liability-free heavy chain CDR1 regions, the second plurality of nucleic acids that encode the sequence liability-free heavy chain CDR2 regions, the fourth plurality of nucleic acids that encode the sequence liability-free light chain CDR1 regions, the fifth plurality of nucleic acids that encode the sequence liability-free light chain CDR2 regions, and the sixth plurality of nucleic acids that encode the sequence liability-free light chain CDR3 regions.

7. The method of claim 6, wherein the third plurality of nucleic acids is produced by a process comprising: (a) amplifying the heavy chain CDR3 regions from a population of human B cells; and (b) combining the third plurality of nucleic acids that encode the human heavy chain CDR3 regions obtained in (a) with the remaining CDRs.

8. The method of claim 6, wherein the processes for producing the first plurality of nucleic acids, the second plurality of nucleic acids, and the third plurality of nucleic acids further comprise isolating functional members from the sequence liability-free heavy chain CDR1 and CDR2 regions, and from the CDR3 regions, wherein:
  (i) the functional members of the sequence liability-free heavy chain CDR1 and CDR2 regions or the functional members of the CDR3 regions are isolated by expressing antibodies comprising the sequence liability-free heavy chain CDR1 and CDR2 regions, and the CDR3 regions in host cells in a manner that the antibodies are displayed on surface of the host cells, isolating the host cells that display antibodies on their surfaces, and isolating the CDR1, CDR2, and CDR3 regions in the displayed antibodies, which are functional members of the CDR1, CDR2, and CDR3 regions; or
  (ii) the functional members of the sequence liability-free heavy chain CDR1 and CDR2 regions, and the CDR3 regions are isolated by expressing human antibodies comprising the sequence liability-free heavy chain CDR1 and CDR2 regions, and the CDR3 regions in fusion with a folding reporter, which optionally is B lactamase or green fluorescent protein, or fragments thereof, to obtain members with improved folding.

* * * * *

UNITED STATES PATENT AND TRADEMARK OFFICE
CERTIFICATE OF CORRECTION

PATENT NO. : 12,359,346 B2
APPLICATION NO. : 18/592456
DATED : July 15, 2025
INVENTOR(S) : Andrew Raymon Morton Bradbury et al.

Page 1 of 1

It is certified that error appears in the above-identified patent and that said Letters Patent is hereby corrected as shown below:

In the Claims

Column 164, Claim 1, Line 12:
Replace "poly specificity" with: --polyspecificity--

Column 164, Claim 1, Line 24:
Replace "X.sub.1X.sub.2X.sub.3" with: --$X_1X_2X_3$--

Column 164, Claim 1, Lines 24-25:
Replace "X.sub.1, X.sub.2, and X.sub.3" with: --$X_1$, $X_2$, and $X_3$--

Column 164, Claim 1, Line 27:
Replace "comprises" with: --comprising--

Column 164, Claim 1, Line 33:
Replace "protein A said" with: --protein A, said--

Column 164, Claim 2, Line 55:
Replace "3, framework" with: --3, and framework--

Column 164, Claim 3, Line 59:
Replace "3, framework" with: --3, and framework--

Column 165, Claim 6, Line 12:
Replace "light chain CDR2 amino acid sequences" with: --the light chain CDR2 amino acid sequences--

Signed and Sealed this
Twenty-third Day of September, 2025

John A. Squires
*Director of the United States Patent and Trademark Office*